United States Patent
Behrouzian et al.

(10) Patent No.: US 9,163,221 B2
(45) Date of Patent: Oct. 20, 2015

(54) FATTY ALCOHOL FORMING ACYL REDUCTASES (FARS) AND METHODS OF USE THEREOF

(71) Applicant: Codexis, Inc., Redwood City, CA (US)

(72) Inventors: Behnaz Behrouzian, Sunnyvale, CA (US); Louis Clark, San Francisco, CA (US); Yihui Zhu, Redwood City, CA (US); Michael Clay, Menlo Park, CA (US); Kristian Karlshoej, Santa Clara, CA (US)

(73) Assignee: CODEXIS, INC., Redwood City, CA (US)

( * ) Notice: Subject to any disclaimer, the term of this patent is extended or adjusted under 35 U.S.C. 154(b) by 37 days.

(21) Appl. No.: 14/040,550

(22) Filed: Sep. 27, 2013

(65) Prior Publication Data

US 2014/0093929 A1    Apr. 3, 2014

Related U.S. Application Data

(63) Continuation of application No. 13/171,138, filed on Jun. 28, 2011, now Pat. No. 8,574,878.

(60) Provisional application No. 61/359,211, filed on Jun. 28, 2010.

(51) Int. Cl.

| C12P 7/04 | (2006.01) |
|---|---|
| C12N 1/20 | (2006.01) |
| C12N 1/00 | (2006.01) |
| C11D 3/00 | (2006.01) |
| C07H 21/02 | (2006.01) |
| C07C 51/00 | (2006.01) |
| C07C 35/04 | (2006.01) |
| C07C 1/00 | (2006.01) |
| C07K 1/00 | (2006.01) |
| C12N 9/02 | (2006.01) |
| C07C 1/22 | (2006.01) |
| C10G 3/00 | (2006.01) |
| C11D 3/20 | (2006.01) |
| C12N 9/04 | (2006.01) |

(52) U.S. Cl.
CPC ............... *C12N 9/0008* (2013.01); *C07C 1/22* (2013.01); *C10G 3/00* (2013.01); *C10G 3/40* (2013.01); *C11D 3/2003* (2013.01); *C12N 9/0006* (2013.01); *C12P 7/04* (2013.01); *C07K 2319/00* (2013.01); *C07K 2319/036* (2013.01); *C10G 2300/1011* (2013.01); *C10G 2400/04* (2013.01); *C11D 3/2013* (2013.01); *C11D 3/2031* (2013.01)

(58) Field of Classification Search
CPC ............... C07C 1/22; C07K 2319/00; C07K 2319/036; C10G 3/00; C10G 3/40; C10G 2300/1011; C10G 2400/04; C11D 3/2003; C11D 3/2031; C11D 3/2013; C12N 9/0008; C12N 9/0006; C12P 7/04

USPC ......... 435/157, 252.3, 252.33, 254.11, 254.2; 510/392; 536/23.2, 23.1; 554/161; 568/840; 585/639, 733; 530/350

See application file for complete search history.

(56) References Cited

U.S. PATENT DOCUMENTS

| 5,370,996 | A  | 12/1994 | Metz et al. |
|---|---|---|---|
| 6,828,475 | B1 | 12/2004 | Metz et al. |
| 8,216,815 | B2 | 7/2012 | McDaniel et al. |
| 8,574,878 | B2* | 11/2013 | Behrouzian et al. .......... 435/157 |
| 8,633,002 | B2* | 1/2014 | Roessler et al. ............. 435/155 |
| 2003/0097686 | A1 | 5/2003 | Knauf et al. |
| 2009/0148918 | A1 | 6/2009 | Trimbur et al. |
| 2010/0154293 | A1 | 6/2010 | Hom et al. |
| 2010/0203614 | A1 | 8/2010 | Wahlen et al. |
| 2011/0000125 | A1 | 1/2011 | McDaniel et al. |
| 2012/0165562 | A1 | 6/2012 | Hattendorf et al. |

FOREIGN PATENT DOCUMENTS

| WO | 2009/140695 A1 | 11/2009 |
|---|---|---|
| WO | 2011/008535 A1 | 1/2011 |
| WO | 2011/019858 A1 | 2/2011 |
| WO | 2007/136762 A2 | 7/2012 |

OTHER PUBLICATIONS

Aarts et al., "The Arabidopsis Male Sterility 2 protein shares similarity with reductases in elongation/condensation complexes," The Plant Journal, 1997, 12(3):615-623.

Broun et al., "Catalytic plasticity of fatty acid modification enzymes underlying chemical diversity of plant lipids." Science, 1998, vol. 282, pp. 1315-1317.

Crameri et al., "Improved Green Fluorescent Protein by Molecular Evolution Using DNA Shuffling," Nature Biotechnology, 1996, vol. 14, pp. 315-319.

Devos et al., "Practical limits of function prediction," Proteins: Structure, Function, and Genetics, 2000, vol. 41, pp. 98-107.

Doan et al.; "Functional expression of live Arabidopsis fatty acyl-CoA, reductase genes in *Escherichia coli*"; 2009, Journal of Plant Physiology, vol. 166, pp. 787-796.

GenBank Direct Submission EDM49836, "Putative dehydrogenase domain of multifunctional non-ribosomal peptide synthetases and related enzyme [Marinobacter algicola DG 893]," Jul. 24, 2007, http://www.ncbi.nim.nih.gov/protein/EDM49636, Retrieved from the internet Jan. 31, 2012, 2 pages.

(Continued)

*Primary Examiner* — Ganapathirama Raghu

(74) *Attorney, Agent, or Firm* — Kilpatrick Townsend & Stockton LLP

(57) ABSTRACT

The present disclosure provides methods useful for producing fatty alcohol compositions from recombinant host cells. The disclosure further provides variant fatty acyl-CoA reductase (FAR) enzymes, polynucleotides encoding the variant FAR enzymes, and vectors and host cells comprising the same.

29 Claims, 2 Drawing Sheets

(56) References Cited

OTHER PUBLICATIONS

Metz et al., "Purification of a Jojoba Embryo Fatty Acyl-Coenzyme A Reductase and Expression of its cDNA in High Erucic Acid Rapeseed," Plant Physiology, 2000, vol. 122, pp. 635-644.

Minshull et al., "Protein evolution by molecular breeding," Current Opinion in Chemical Biology, 1999, 3:284-290.

Moto et al, "Pheromone gland-specific fatty-acyl reductase of the silkmoth, *Bombyx mori*," Proc. Natl. Acad. Sci USA, 2003, vol. 100(16), pp. 9156-9161.

Reiser et al., "Isolation of Mutants of *Acinetobacter calcoaceticus* Deficient in Wax Ester Synthesis and Complementation of One Mutation with a Gene Encoding a Fatty Acyl Coenzyme A Reductase," J. Bacteriol., 1997, vol. 179(9), pp. 2969-2975.

Seffernick et al., "Melamine deaminase and Atrazine chlorohydrolase: 98 percent identical but functionally different," J. Bacteriol., 2001, vol. 183(8), pp. 2405-2410.

Steen et al.; "Microbial production of fatty-acid-derived fuels and chemicals from plant biomass", 2010, Nature, vol. 463, pp. 559-563.

Teerawanichpan et al.; "Fatty Acyl-CoA Reductase and Wax Synthase from *Eugiena gracilis* in the Biosynthesis of Medium-Chain Wax Esters"; 2010, Lipids, vol. 45, pp. 263-273.

Wahlen et al., "Purification, Characterization, and Potential Bacterial Wax Production Rold of an NADPH-Dependent Fatty Aldehyde Reductase from *Marinobacter aquaeolei* VT8," Applied and Environmental Microbiology, 2009, vol. 75(9), 2758-2764; p. 2759.

Whisstock et al., "Prediction of protein function from protein sequence," Q. Rev. Biophysics, 2003, vol. 36(3), pp. 307-340.

Witkowski et al., "Conversion of b-ketoacyl synthase to a Malonyl Docarboxyiase by replacement of the active cysteine with glutamine," Biochemistry, 1999, Vol. 38, pp. 11643-11650.

Zhang et al., "Directed evolution of a fucosidase from a galactosidase by DNA shuffling and screening," Proc. Natl. Acad. Sci. USA, Apr. 1997, vol. 94, pp. 4504-4509.

\* cited by examiner

Fig. 2

```
                    1                                                           60
SEQ ID 2      (1)   MATQQQQNGASASG-VLEQLRGKHVLITGTTGFLGKVVLEKLIRTVPDIGGIHLLIRGNK
SEQ ID 5      (1)   MAIQQVHHADTSSSKVLGQLRGKRVLITGTTGFLGKVVLERLIRAVPDIGAIYLLIRGNK
Consensus     (1)   MA QQ    A SAS  VL QLRGK VLITGTTGFLGKVVLEKLIR VPDIGAIHLLIRGNK
                    61                                                          120
SEQ ID 2     (60)   RHPAARERFLNEIASSSVFERLRHDDNEAFETFLEERVHCITGEVTESRFGLTPERFRAL
SEQ ID 5     (61)   RHPDARSRFLEEIATSSVFDRLREABSEGEDAFLEERIHCVTGEVTEAGFGIGQEDYRKL
Consensus    (61)   RHP AR RFL EIASSSVFDRLR  D EAFD FLEERIHCITGEVTEA FGI   E FR L
                    121                                                         180
SEQ ID 2    (120)   AGQVDAFINSAASVNFREELDKALKINTLCLENVAALAELNSAMAVIQVSTCYVNGKNSG
SEQ ID 5    (121)   ATELDAVINSAASVNFREELDKALAINTLCLRNIAGMVDLNPKLAVIQVSTCYVNGMNSG
Consensus   (121)   A  LDA INSAASVNFREELDKAL INTLCL NIAAL DLN   LAVIQVSTCYVNG NSG
                    181                                                         240
SEQ ID 2    (180)   QITESVIKPAGESIPRSTDGYYEIEELVHLLQDKISDVKARYSGKVLEKKLVDLGIREAN
SEQ ID 5    (181)   QVTESVIKPAGEAVPRSPDGFYEIEELVRLLQDKIEDVQARYSGKVLERKLVDLGIREAN
Consensus   (181)   QITESVIKPAGEAIPRS DGFYEIEELV LLQDKI DV ARYSGKVLEKKLVDLGIREAN
                    241                                                         300
SEQ ID 2    (240)   NYGWSDTYTFTKWLGEQLLMKALSGRSLTIVRPSIIESALEEPSPGWIEGVKVADAIILA
SEQ ID 5    (241)   RYGWSDTYTFTKWLGEQLLMKALNGRTLELLRPSIIESALEEPAPGWIEGVKVADAIILA
Consensus   (241)    YGWSDTYTFTKWLGEQLLMKAL GRSLTILRPSIIESALEEPAPGWIEGVKVADAIILA
                    301                                                         360
SEQ ID 2    (300)   YAREKVSLFPGKRSCTIDVIPVDLVANSTILSLAEALSGSGQRRIYQCCSGGSNPTSLCK
SEQ ID 5    (301)   YAREKVTLFPGKRSGTIDVIPVDLVANSIILSLAEALGEPGRRRIYQCCSGGNPISLGE
Consensus   (301)   YAREKVSLFPGKRSGIIDVIPVDLVANSIILSLAEAL   G RRIYQCCSGG NPISLG
                    361                                                         420
SEQ ID 2    (360)   FIDYLMAEAKTNYAAYDQLFYRRPIKPEVAVNRKIFDVVVGGMRVPLSIAGKAMRLAGQN
SEQ ID 5    (361)   FIDHLMAESKANYAAYDHLFYRQPSKPFLAVNRALFDLVISGVRLPLSLTDRVLKLLGNS
Consensus   (361)   FIDHLMAEAK NYAAYD LFYR PSKPFLAVNR LFDLVI GMRLPLSI  K LKL GN
                    421                                                         480
SEQ ID 2    (420)   RELKVLKNLDTTRSLATIFGFYTAPDYIFRNDSLMALASRMGELDRVLEPVDARQIDWQL
SEQ ID 5    (421)   RDLKMLRNLDTTQSLATIFGFYTAPDYIFRNDELMALANRMGEVDKGLEPVDARLIDWEL
Consensus   (421)   RDLKMLKNLDTT SLATIFGFYTAPDYIFRND LMALA RMGELDK LFPVDAR IDW L
                    481                                   514
SEQ ID 2    (480)   YLCKIHLGGLNRYALKERKLYSLRAADTRKKAA-
SEQ ID 5    (481)   YLRKIHLAGLNRYALKERKVYSLKTARQRKKAA-
Consensus   (481)   YL KIHLAGLNRYALKERKLYSLK A  RKKAA
```

FATTY ALCOHOL FORMING ACYL REDUCTASES (FARS) AND METHODS OF USE THEREOF

CROSS-REFERENCES TO RELATED APPLICATIONS

This application is a continuation of U.S. application Ser. No. 13/171,138, filed Jun. 28, 2011, now issued as U.S. Pat. No. 8,574,878, which claims benefit of priority of U.S. Provisional Application No. 61/359,211, filed Jun. 28, 2010, the entire content of each of which is incorporated herein by reference.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 90834-888301_ST 25.TXT, created on Nov. 20, 2013, 51,866 bytes, machine format IBM-PC, MS-Windows operating system, is hereby incorporated by reference.

BACKGROUND OF THE INVENTION

Reliance on petroleum-derived fuels has depleted the supply of natural resources and has required increased reliance on imported gasoline and diesel products. In addition, the burning of petroleum-based fuels has increased the amount of greenhouse gasses (e.g., carbon dioxide and methane) in the atmosphere that is contributing to the gradual warming of the earth's climate.

Fuels, such as biodiesel, that are made from animal or vegetable products burn cleaner than petroleum-derived fuels and do not produce a net increase in greenhouse gases. Furthermore, they are a sustainable energy source and have the potential to reduce the United States' reliance on imported petroleum-based products. However, there is a concern that using land to produce fuel crops rather than food crops will contribute to world hunger.

Fatty acids are the principal component of cell membranes and are used by nearly all organisms as a primary source of energy storage. Fatty alcohols are the reduction products of fatty acids and, like fatty acids, can be produced enzymatically by cultured cells. Fatty alcohols can be reacted with acids to form ester compositions similar to those present in biodiesel fuel, or reduced to form kerosene-like compositions, or hydrocarbon compositions similar to petrodiesel. Enzymes that convert fatty acyl-thioester substrates (e.g., fatty acyl-CoA or fatty acyl-ACP) to fatty alcohols are commonly referred to as fatty alcohol forming acyl-CoA reductases or fatty acyl reductases ("FARs").

PCT Publication No. WO 2007/136762 discloses genetically engineered microorganisms for the production of fatty acid derivatives and methods of their use.

U.S. Pat. No. 5,370,996 and Metz et al., 2000, *Plant Physiology* 122:635-644 disclose isolation and characterization of a fatty acyl reductase (FAR) enzyme from the desert shrub *Simmondsia chinensis*, more commonly known as jojoba.

Moto et al., 2003, *Proc. Nat'l Acad. Sci USA* 100(16): 9156-9161 discloses the isolation and characterization of a FAR enzyme from the silk moth *Bombyx mori*.

Reiser et al., 1997, *J. Bacteriol.* 179(9):2969-2975 discloses the isolation and characterization of a fatty acyl CoA reductase enzyme from the wax ester producing bacterium *Acinetobacter calcoaceticus* that reduces a fatty acyl-CoA substrate with chain lengths from C14 to C22 to the corresponding fatty aldehyde, requiring a dehydrogenase enzyme for conversion of the fatty aldehyde to the fatty alcohol.

In theory, these FAR enzymes could be expressed in heterologous hosts as a means of producing a non-petroleum-based, renewable source of fatty alcohol or derivative compositions for use in biofuels. However, when expressed in heterologous hosts such as *E. coli* and yeast, the yields of fatty alcohols obtained are insufficient for certain applications. In addition, at most, only a small fraction of fatty alcohols produced are secreted by the microorganisms, increasing substantially the cost of purification.

Accordingly, there is a need in the art for enzymes such as FAR enzymes that can be used efficiently to produce fatty alcohols for use in industrial applications such as but not limited to applications in the chemical industry (e.g., household detergents, including laundry detergents in liquid and powder form, hard surface cleaners, dishwashing liquids, and the like; lubricants and solvents; industrial cleaners; and surfactants), in the food industry, in the personal care industry (e.g., in soaps, cosmetics, shampoos, and gels), in the medical industry, and in the fuels industry (e.g., in diesel fuels).

BRIEF SUMMARY OF THE INVENTION

In one aspect, the invention provides recombinant fatty alcohol forming acyl-CoA reductase (FAR) variants that exhibit improved properties. In some embodiments, a FAR variant is capable of producing at least about 1.5 times more fatty alcohol than a wild-type FAR polypeptide (e.g., a FAR polypeptide comprising SEQ ID NO:2 or SEQ ID NO:5). In some embodiments, a FAR variant is capable of producing an improved fatty alcohol profile as compared to a wild-type FAR polypeptide. In some embodiments, the invention relates to improved fatty alcohol forming acyl-CoA reductase (FAR) polypeptides capable of producing at least about 1.5 times more fatty alcohol than a wild-type FAR polypeptide comprising SEQ ID NO:2 and/or producing an improved fatty alcohol profile as compared to a wild-type FAR polypeptide comprising SEQ ID NO:2 when assayed under the same conditions. In some embodiments, the improved fatty alcohol forming acyl-CoA reductase (FAR) polypeptides are capable of producing at least about 1.5 times more fatty alcohol than a wild-type FAR polypeptide comprising SEQ ID NO:5 and/or producing an improved fatty alcohol profile as compared to a wild-type FAR polypeptide comprising SEQ ID NO:5 when assayed under the same conditions. In some embodiments a cell (e.g., *E. coli*) expressing the improved FAR produces at least 2-fold, at least 3-fold, at least 4-fold, at least 5-fold, at least 6-fold, at least 7-fold, at least 8-fold, at least 9-fold, or at least 10-fold more fatty alcohol than a wild-type FAR polypeptide (e.g., a FAR polypeptide comprising SEQ ID NO:2 or SEQ ID NO:5).

In some embodiments, the amount and/or profile of fatty alcohols produced is measured by determining and/or quantifying the fatty alcohols produced by a microorganism that expresses a FAR polypeptide (e.g., a wild-type FAR polypeptide or a FAR variant as described here). In some embodiments, the microorganism is a bacteria (e.g., *E. coli*) or a yeast (e.g., a *Yarrowia* or a *Saccharomyces cerevisiae*).

In some embodiments, the invention relates to a fatty alcohol forming acyl-CoA reductase (FAR) variant that has at least 70% (or at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%) sequence identity to SEQ ID NO:2, wherein the variant comprises a substitution at one or more positions selected from position 134, position 138, position 511, position 510, position 2, position 140, position 421, and position 458, wherein the position is numbered with reference to SEQ ID NO:2, and wherein a cell in which the FAR variant is expressed produces more fatty alcohol than a corresponding cell of the same type in which the wild-type FAR from which the FAR variant is derived is expressed. In some embodiments, the cell expressing the FAR variant produces at least 1.5, at least 2, at least 3, at least 4, at least 5, at least 6, at least 7, at least 8, at least 9, or at least 10 times more fatty alcohol than the corresponding cell of the same type which expresses the wild-type FAR from which the FAR variant is derived. In some embodiments, the cell is a bacteria cell (e.g., *E. coli*). In some embodiments the cell is a yeast cell (e.g., a *Yarrowia* or a *Saccharomyces cerevisiae* cell). In some embodiments, the wild-type FAR is *Marinobacter algicola* FAR having the amino acid sequence of SEQ ID NO:2. In some embodiments, the wild-type FAR is *Marinobacter aquaeolei* FAR having the amino acid sequence of SEQ ID NO:5.

In some embodiments, the invention relates to a fatty alcohol forming acyl-CoA reductase (FAR) variant that has at least 70% (or at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%) sequence identity to SEQ ID NO:2, wherein the variant comprises a substitution at one or more positions selected from position 14, position 18, position 63, position 65, position 104, position 128, position 134, position 174, position 177, position 224, position 226, position 227, position 244, position 283, position 306, position 351, position 364, position 365, position 370, position 376, position 377, position 389, position 404, position 406, position 433, or position 487, and wherein a cell in which the FAR variant is expressed produces more fatty alcohol than a corresponding cell of the same type in which the wild-type FAR from which the FAR variant is derived is expressed. In some embodiments, the cell expressing the FAR variant produces at least 1.5, at least 2, at least 3, at least 4, at least 5, at least 6, at least 7, at least 8, at least 9, or at least 10 times more fatty alcohol than the corresponding cell of the same type which expresses the wild-type FAR from which the FAR variant is derived. In some embodiments, the cell is a yeast cell (e.g., a *Yarrowia* or a *Saccharomyces cerevisiae*) or a bacterial cell (e.g., *E. coli*). In some embodiments, the wild-type FAR is *Marinobacter algicola* FAR having the amino acid sequence of SEQ ID NO:2. In some embodiments, the wild-type FAR is *Marinobacter aquaeolei* FAR having the amino acid sequence of SEQ ID NO:5.

In some embodiments, a FAR variant comprises at least about 70% (or at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%) sequence identity to SEQ ID NO:2 or SEQ ID NO:5 and comprises an amino acid substitution at one or more positions selected from A2, T3, Q4, Q5, Q6, Q7, N8, G9, A10, A12, G14, E17, Q18, K22, V24, L33, I42, G50, L54, R60, H61, P62, A63, R65, L69, E71, A73, S74, S76, V77, H83, E87, T91, L93, H98, T101, G102, V104, S107, G110, L111, T112, P113, R115, R117, A120, G121, Q122, A125, N128, S132, N134, E137, E138, D140, A142, K144, L148, E151, V153, N160, A162, N174, N177, Q180, V185, I186, P188, T197, D198, E202, E204, E205, V207, L209, D212, K213, V217, R220, K224, L226, E227, K229, R236, E237, S244, D245, T246, L257, K260, A261, S263, G264, S266, I269, S283, I287, E288, V290, A295, A299, E303, V305, S306, V318, I328, L330, S331, L332, A333, S339, G340, Q341, R342, G350, G351, K359, L364, M365, A366, T370, A374, D376, Q377, Y380, R381, T384, A389, D396, V397, V398, V399, G400, G401, R403, V404, P405, L406, A409, G410, A412, M413, A416, Q418, E421, N427K, D429, T430, S432, S433, T436, I437, F440, A443, P444, Y446, S452, S458, R459, L463, D464, V466, A472, Q474, L479, I484, G487, N490, E496, K498, L499, Y500, S501, L502, A504, A505, D506, T507, R508, K509, K510, A511, and A512, wherein the position is numbered with reference to SEQ ID NO:2. In some embodiments, the variant comprises one or more amino acid substitutions selected from A2D/F/G/H/I/P/N/Q/T/V/W, T3R, Q4R, Q5S, Q6P, Q7N, N8K/S, G9D/F, A10T, A12T/V, G14N/R/V/W, E17D, Q18I, K22E, V24I, L33V, I42L, G50S/V, L54P, R60H, H61R, P62S, A63R/Y, R65G/Q/Y, L69E/Q, E71K, A73K/V, S74K/P, S76K/N/R, V77A/I, H83R, E87G/V, T91I/R, L93V, H98P/R, T101L, G102C, V104I/M, S107C/L/W, G110D, L111S, T112A, P113D/L, R115A/H, R117D, A120V, G121H/S, Q122R, A125V, N128H, S132G, N134K/R/S, E137L, E138L/Q, D140C, A142V, K144Q, L148E, E151L, V153I, N160S, A162T, N174C, N177Q/R/T, Q180H/R, V185A/I, I186A/GN, P188A/I/M/S, T197P, D198Q, E202G, E204G, E205G/P, V207I/L, L209K/N, D212R, K213R, V217L, R220C, K224R, L226A/M, E227A/G/H/R/T, K229R, R236K, E237L, S244A/F/G/H/P, D245N, T246A, L257K, K260R/T, A261D, S263P, G264S, S266A, I269T, S283E/F/K/M/T/V, I287L, E288Q, V290I, A295T/V, A299T, E303G, V305I, S306F/H/N/W, V318I, I328T, L330V, S331V, L332S, A333T, S339G/V, G340P/S/V, Q341K, R342L, G350S, G351C, K359L, L364F/I, M365N, A366T/V, T370A/I, A374K/Y, D376P, Q377C/K/Y, Y380K/N/R, R381C, T384R, A389I/L/M/V, D396G, V397I/L, V398Y, V399T, G400A/L, G401A/C/I/L/S/V, R403C/S, V404A, P405A/C/F/G/L/S/V/W, L406Y, A409V/W/Y, G410A/C/H/N/Q/R/S, A412C/F/M/V, M413L/R, A416L/V, Q418I/R/V/Y, E421I/L/N/P/R/S/V/Y, N427K, D429E/K/N/Q/R, T430H/I/R, R432C/Q, S433F/H/K/L/N/W, T436D/K/Q, I437V, F440L, A443T, P444S, Y446H, S452A/G/N, S458G/L/M/Q, R459H, L463E/T, D464G, V466E/Q/R, A472V, Q474R, L479Q, I484V, G487R/S/T/Y, N490S, E496A, K498A, L499A/H/I/N/P/R/S, Y500C/G/H/L/N/P/Q/R/S/W, S501 G/R, L502A/P/Q/R/S, A504G/R, A505K, D506G/S, T507A/G/P/R/S, R508D/G/H, K509D/E/G/H/N/R/S/Y, K510A/D/G/P/S/Y, A511G/I/K/P/Q/R/S/T, and A512K/S/T.

In some embodiments, a variant as described herein is encoded by a polynucleotide that hybridizes at high stringency to the complement of SEQ ID NOs: 1, 3, 4, 13, or 14 and comprises one or more amino acid substitutions as described herein.

In some embodiments, the variant comprises at least about 70% (or at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%) sequence identity to SEQ ID NO:2 or SEQ ID NO:5 and comprises an amino acid substitution relative to SEQ ID NO:2 at one or more positions selected from position 134, position 138, position 188, position 458, and position 511, wherein the position is numbered with reference to SEQ ID NO:2. In some embodiments, the variant comprises an amino acid substitution at one or more positions selected from N134, E138, P188, S458, and A511.

In some embodiments, the variant comprises one or more amino acid substitutions selected from N134R, E138O, P188S, S458Q, and A511T.

In some embodiments, the variant comprises at least about 70% (or at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%) sequence identity to SEQ ID NO:2 or SEQ ID NO:5 and comprises an amino acid substitution relative to SEQ ID NO:2 at one or more positions selected from position 303, position 401, position 405, position 412, position 416, position 418, position 458, position 502, position 508, and position 509, wherein the position is numbered with reference to SEQ ID NO:2. In some embodiments, the variant comprises an amino acid substitution at one or more positions selected from E303, G401, P405, A412, A416, Q418, S458, L502, R508, and K509. In some embodiments, the variant comprises one or more amino acid substitutions selected from E303G, G401A/L/S/V, P405A/C/F/I/V, A412V, A416L, Q418I/V, S458Q, L502S, R508G/H, and K509D/H.

In some embodiments, the variant comprises at least about 70% (or at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%) sequence identity to SEQ ID NO:2 or SEQ ID NO:5 and comprises an amino acid substitution relative to SEQ ID NO:2 at one or more positions selected from position 22, position 87, position 209, position 264, position 401, position 416, position 500, position 508, and position 509, wherein the position is numbered with reference to SEQ ID NO:2. In some embodiments, the variant comprises an amino acid substitution at one or more positions selected from K22, E87, L209, G264, G401, A416, Y500, R508, and K509. In some embodiments, the variant comprises one or more amino acid substitutions selected from K22R, E87G, L209K/L/N, G264S, G401V, A416L, Y500D, R508D/G, and K509D/H/N/Y.

In some embodiments, the variant comprises at least about 70% (or at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%) sequence identity to SEQ ID NO:2 or SEQ ID NO:5 and comprises an amino acid substitution relative to SEQ ID NO:2 at one or more positions selected from N134, E138, P188, P405, Q418, and A511, wherein the position is numbered with reference to SEQ ID NO:2. In some embodiments, the variant comprises one or more amino acid substitutions selected from N134S, E138Q, P188S, P405V, Q418V, and A511T. In some embodiments, the variant has the amino acid sequence of SEQ ID NO:6, the sequence of Variant 370 described in Table 2.

In some embodiments, the variant comprises at least about 70% (or at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%) sequence identity to SEQ ID NO:2 or SEQ ID NO:5 and comprises an amino acid substitution relative to SEQ ID NO:2 at one or more positions selected from N134, E138, P188, L209, P405, Q418, S458, L502, R508, K509, and A511, wherein the position is numbered with reference to SEQ ID NO:2. In some embodiments, the variant comprises one or more amino acid substitutions selected from N134S, E138Q, P188S, L209K, P405V, Q418V, S458Q, L502S, R508D, K509D, and A511T. In some embodiments, the variant has the amino acid sequence of SEQ ID NO:7, the sequence of Variant 391 described in Table 2. In some embodiments, the variant comprises at least about 70% (or at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%) sequence identity to the amino acid sequence of SEQ ID NO:7 and further comprises one or more amino acid substitutions selected from G14R/V, Q18I, A63R, R65G, V104I/M, N128H, S134R, N174C, N177T, K224R, L226M, E227R, S244P, S283F/M, S306W, G351C, L364I, M365N, T370I, D376P, Q377K, A389I, V404A, L406Y, S433K, or G487R. In some embodiments, the variant comprises the amino acid sequence of SEQ ID NO:7 and further comprises one or more amino acid substitutions selected from G14R/V, Q18I, A63R, R65G, V104I/M, N128H, S134R, N174C, N177T, K224R, L226M, E227R, S244P, S283F/M, S306W, G351C, L364I, M365N, T370I, D376P, Q377K, A389I, V404A, L406Y, S433K, or G487R.

In some embodiments, the variant comprises at least about 70% (or at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%) sequence identity to SEQ ID NO:2 or SEQ ID NO:5 and comprises an amino acid substitution relative to SEQ ID NO:2 at one or more positions selected from N134, E138, P188, Q377, P405, Q418, S458, L502, R508, K509, and A511, wherein the position is numbered with reference to SEQ ID NO:2. In some embodiments, the variant comprises one or more amino acid substitutions selected from N134S, E138Q, P188S, Q377K, P405V, Q418V, S458Q, L502S, R508D, K509D, and A511T. In some embodiments, the variant has the amino acid sequence of SEQ ID NO:8, the sequence of Variant 436 described in Table 2.

In some embodiments, the variant comprises at least about 70% (or at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%) sequence identity to SEQ ID NO:2 or SEQ ID NO:5 and comprises an amino acid substitution relative to SEQ ID NO:2 at one or more positions selected from N134, E138, P188, P405, Q418, S433, S458, L502, R508, K509, and A511, wherein the position is numbered with reference to SEQ ID NO:2. In some embodiments, the variant comprises an amino acid substitution at one or more positions selected from N134S, E138Q, P188S, P405V, Q418V, S433K, S458Q, L502S, R508D, K509D, and A511T. In some embodiments, the variant has the amino acid sequence of SEQ ID NO:9, the sequence of Variant 438 described in Table 2. In some embodiments, the variant comprises at least about 70% (or at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%) sequence identity to the amino acid sequence of SEQ ID NO:9 and further comprises one or more amino acid substitutions selected from G14R/V, Q18I, A63R, R65G, V104I/M, N128H, S134R, N174C, N177T, K224R, L226M, E227R, S244P, S283F/M, S306W, G351C, L364I, M365N, T370I, D376P, Q377K, A389I, V404A, L406Y, S433K, or G487R. In some embodiments, the variant comprises the amino acid sequence of SEQ ID NO:9 and further comprises one or more amino acid substitutions selected from G14R/V, Q18I, A63R, R65G, V104I/M, N128H, S134R, N174C, N177T, K224R, L226M, E227R, S244P, S283F/M, S306W, G351C, L364I, M365N, T370I, D376P, Q377K, A389I, V404A, L406Y, S433K, or G487R.

In some embodiments, the variant comprises at least about 70% (or at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%) sequence identity to SEQ ID NO:2 or SEQ ID NO:5 and comprises an amino acid substitution relative to SEQ ID NO:2 at one or more positions selected from N128, N134, E138, N174, P188, L226, G351, P405, Q418, S433, S458, L502, 8508, K509, and A511, wherein the position is numbered with reference to SEQ ID NO:2. In some embodiments, the variant comprises one or more amino acid substitutions selected from N128H, N134S, E138Q, N174C, P188S, L226M, G351C, P405V, Q418V, S433K, S458Q, L502S, R508D, K509D, and A511T. In some embodiments, the variant has the amino acid sequence of SEQ ID NO:10, the sequence of Variant 547 described in Table 2.

In some embodiments, the variant comprises at least about 70% (or at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%) sequence identity to SEQ ID NO:2 or SEQ ID NO:5 and comprises an amino acid substitution relative to SEQ ID NO:2 at one or more positions selected from Q18, A63, R65, N128, N134, E138, P188, P405, Q418, S433, S458, G487, L502, R508, K509, and A511, wherein the position is numbered with reference to SEQ ID NO:2. In some embodiments, the variant comprises one or more amino acid substitutions selected from Q18I, A63R, R65G, N128H, N134S, E138Q, P188S, P405V, Q418V, S433K, S458Q, G487R, L502S, R508D, K509D, and A511 T. In some embodiments, the variant has the amino acid sequence of SEQ ID NO:11, the sequence of Variant 555 described in Table 2.

In some embodiments, the variant comprises at least about 70% (or at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%) sequence identity to SEQ ID NO:2 or SEQ ID NO:5 and comprises an amino acid substitution relative to SEQ ID NO:2 at one or more positions selected from Q18, N128, N134, E138, N174, N177, P188, L226, G351, P405, Q418, S433, S458, L502, 8508, K509, and A511, wherein the position is numbered with reference to SEQ ID NO:2. In some embodiments, the variant comprises one or more amino acid substitutions selected from Q18I, N128H, N134S, E138Q, N174C, N177T, P188S, L226M, G351C, P405V, Q418V, S433K, S458Q, L502S, R508D, K509D, and A511T. In some embodiments, the variant has the amino acid sequence of SEQ ID NO:12, the sequence of Variant 556 described in Table 2.

In some embodiments, the variant comprises at least about 70% (or at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%) sequence identity to SEQ ID NO:2 or SEQ ID NO:5 and has one or more amino acid substitution sets selected from the amino acid substitution sets listed in Table 2 or Table 5.

In some embodiments, a FAR variant comprises at least about 70% (or at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%) sequence identity to SEQ ID NO:5 and comprises an amino acid substitution relative to SEQ ID NO:5 at one or more positions selected from A2, Q4, Q5, H8, A9, A45, P63, R66, E72, A74, S77, E88, A108, G111, G113, D116, N135, D141, Q181, D199, E205, E238, A374, A375, P406, D411, R412, D422, D430, S434, 1438, N459, E497, Y501, S502, L503, T505, Q508, R509, K510, K511, A512, and A513, wherein the position is numbered with reference to SEQ ID NO:5. In some embodiments, the variant comprises one or more amino acid substitutions selected from A2F/G/H/P/Q/T, Q4I, Q5F/N, H8K/N, A9L, A45V, P63Q/S, R66N, E72Q/S, A74L, S77G, E88Q, A108C/L/R, G111S, G113A, D116A/E, N135K, D141C/G, Q181D, D199G, E205G/R, E238C, A374V, A375Q/Y, P406S, D411R, R412H, D422A, D430K, S434F/K/W, I438V, N459G/Q, E497F/Y, Y501G/P/S/W, S502G, L503Q/R/S, T505K/R, Q508G/S, R509A/D, K510G, K511C/D/G, A512G/K/P/Q/S/T, and A513L/Y.

In some embodiments, a variant as described herein is encoded by a polynucleotide that hybridizes at high stringency to the complement of SEQ ID NOs:1, 3, 4, 13, or 14 and comprises one or more amino acid substitutions as described herein.

In some embodiments, the invention relates to improved FAR polypeptides comprising an amino acid sequence that is at least 85% identical to SEQ ID NO:2 and includes at least one substitution of an amino acid residue compared to a wild type FAR having at least 85% sequence identity to SEQ ID NO:2, wherein the improved FAR is capable of producing 1.5 times more fatty alcohol than the corresponding wild-type when assayed under the same conditions.

In some embodiments, the improved FAR polypeptide comprises an amino acid sequence that is at least 80% (also at least 85%, also at least 90% and also at least 95%) identical to SEQ ID NO:2 and includes substitutions at one or more of positions 2, 134, 138, 188, 405 and 511 relative to SEQ ID NO: 2. In some embodiments, the substitution of the amino acid residue at position 2 is H, T, D, F, V, G, Q, P or I; the substitution of the amino acid residue at position 134 is R, K, or S; the substitution of the amino acid residue at position 138 is Q or L; the substitution of the amino acid residue at position 188 is S; the substitution of the amino acid residue at position 405 is V, S, F, G, C, L, S, A, or W; and the substitution of the amino acid residue at position 511 is T, P, G, S, K, Q, or R. In other embodiments, the improved FAR includes substitutions at each of positions 2, 134, 138, 188, 405 and 511 relative to SEQ ID NO:2. In some embodiments the improved FAR includes substitutions at the combination of positions 134, 138, 188 and 511 relative to SEQ ID NO:2.

In some embodiments, the improved FAR is a functional fragment of an improved full-length FAR enzyme.

In another aspect, the invention relates to an isolated polynucleotide comprising a sequence encoding an improved FAR polypeptide encompassed by the invention. In some embodiments, the polynucleotide is a codon optimized polynucleotide.

In another aspect, the invention relates to a vector which comprises said polynucleotides and optionally one or more control sequences such as a promoter capable of mediating expression of the polynucleotide encoding the improved FAR polypeptides in a host microorganism.

In another aspect, the invention relates to a recombinant microorganism comprising the vector and/or polynucleotide encoding an improved FAR polypeptide encompassed by the invention. In some embodiments, the microorganism is an *E. coli* or a yeast (e.g., a *Yarrowia* or a *Saccharomyces cerevisiae*).

In yet another aspect, the invention relates to a host cell comprising a recombinant polynucleotide sequence encoding a fatty alcohol forming acyl-CoA reductase (FAR) variant. In some embodiments, the host cell comprises a FAR variant that has at least 70% (or at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%) sequence identity to SEQ ID NO:2, wherein the variant comprises a substitution at one or more positions selected from position 134, position 138, position 511, position 510, position 2, position 140, position 421, and position 458, wherein the position is numbered with reference to SEQ ID NO:2, with the proviso that the FAR variant does not have the sequence of SEQ ID NO:5. In some embodiments, the FAR variant comprises a substitution at one or more of positions 134, 138, and 511, wherein the position is numbered with reference to SEQ ID NO:2, and wherein the amino acid at position 134 is lysine, arginine, or serine; the amino acid at position 138 is leucine or glutamine; and/or the amino acid at position 511 is glycine, isoleucine, lysine, proline, glutamine, arginine, serine, or threonine. In some embodiments, the FAR variant further comprises a substitution at one or both of positions 510 and 2, wherein the position is numbered with reference to SEQ ID NO:2, and wherein the amino acid at position 510 is alanine, aspartic acid, glycine, proline, serine, or tyrosine; and/or the amino acid at position 2 is aspartic acid, phenylalanine, glycine, histidine, isoleucine, asparagine, proline, glutamine, threonine, valine, or tryptophan. In some embodiments, the FAR variant further comprises a substitution at one or more of positions 140, 421, and 458, wherein the position is numbered with reference to SEQ ID NO:2, and wherein the amino acid at position 140 is cysteine; the amino acid at position 421 is isoleucine, leucine, asparagine, proline, arginine, serine, valine, or tyrosine; and/or the amino acid at position 458 is glycine, leucine, methionine, or glutamine. In some embodiments, the FAR variant further comprises a substitution at one or more of positions 188, 405, and 418, wherein the position is numbered with reference to SEQ ID NO:2, and wherein the amino acid at position 188 is alanine, isoleucine, methionine, or serine; the amino acid at position 405 is alanine, cysteine, phenylalanine, glycine, leucine, serine, valine, or tryptophan; and/or the amino acid at position 418 is isoleucine, arginine, valine, or tyrosine.

In some embodiments, the host cell comprises a FAR variant comprising at least 95% sequence identity to SEQ ID NO:5. In some embodiments, the host cell comprises a FAR variant comprising at least 95% sequence identity to SEQ ID NO:5 and comprises a substitution at position 135, position 139, and position 512, numbered with reference to SEQ ID NO:5.

In some embodiments, the host cell comprises a FAR variant that has at least 70% (or at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%) sequence identity to SEQ ID NO:2, wherein the variant comprises a substitution at one or more positions selected from position 14, position 18, position 63, position 65, position 104, position 128, position 134, position 174, position 177, position 224, position 226, position 227, position 244, position 283, position 306, position 351, position 364, position 365, position 370, position 376, position 377, position 389, position 404, position 406, position 433, or position 487, with the proviso that the FAR variant does not have the sequence of SEQ ID NO:5. In some embodiments, the substitution or substitutions are selected from G14R/V, Q18I, A63R, R65G, V104I/M, N128H, S134R, N174C, N177T, K224R, L226M, E227R, S244P, S283F/M, S306W, G351C, L364I, M365N, T370I, D376P, Q377K, A389I, V404A, L406Y, S433K, or G487R.

In some embodiments, the host cell comprises a FAR variant that has the amino acid sequence of any of SEQ ID NOs:6, 7, 8, 9, 10, 11, or 12. In some embodiments, the host cell comprises a FAR variant that comprises the amino acid sequence of any of SEQ ID NOs:6, 7, 8, 9, 10, 11, or 12 and further comprises a substitution at one or more positions selected from position 14, position 18, position 63, position 65, position 104, position 128, position 134, position 174, position 177, position 224, position 226, position 227, position 244, position 283, position 306, position 351, position 364, position 365, position 370, position 376, position 377, position 389, position 404, position 406, position 433, and position 487. In some embodiments, the substitution or substitutions are selected from G14R/V, Q18I, A63R, R65G, V104I/M, N128H, S134R, N174C, N177T, K224R, L226M, E227R, S244P, S283F/M, S306W, G351C, L364I, M365N, T370I, D376P, Q377K, A389I, V404A, L406Y, S433K, or G487R.

In one aspect, a FAR variant protein, vectors and cells comprising a nucleic acid encoding the FAR variant protein, cells expressing the FAR variant protein, and fatty alcohol products obtained from the cells are provided, where the FAR variant protein has 100% identity to SEQ: ID NO:2 except for the substitutions present in any individual FAR variant selected from variant numbers 1-629 in Table 2. In other embodiments, the FAR variant protein has 100% identity to SEQ: ID NO:2 except for (1) the substitutions present in any individual FAR variant selected from variant numbers 1-629 in Table 2 and (2) one, two, three, four, five, six, seven, eight, nine, ten, eleven or twelve additional substitutions, e.g., 1-5, 2-6, 4-8, 5-12 substitutions (which optionally are conservative substitutions).

In one aspect, a FAR variant protein, vectors and cells comprising a nucleic acid encoding the FAR variant protein, cells expressing the FAR variant protein, and fatty alcohol products obtained from the cells are provided, where the FAR variant protein has 100% identity to SEQ: ID NO:5 except for the substitutions present in any individual FAR variant selected from variant numbers 1-629 in Table 5. In other embodiments, the FAR variant protein has 100% identity to SEQ: ID NO:5 except for (1) the substitutions present in any individual FAR variant selected from variant numbers 1-629 in Table 5 and (2) one, two, three, four, five, six, seven, eight, nine, ten, eleven or twelve additional substitutions, e.g., 1-5, 2-6, 4-8, 5-12 substitutions (which optionally are conservative substitutions).

In some embodiments, the host cell is a yeast or a bacterium. In some embodiments, the host cell is *E. coli*, a *Yarrowia* species, or a *Saccharomyces* species.

In some embodiments, the host cell produces more fatty alcohol than a corresponding cell of the same type expressing a wild-type FAR from which the FAR variant is derived. In some embodiments, the host cell produces at least 1.5, at least 2, at least 3, at least 4, at least 5, at least 6, at least 7, at least 8, at least 9, or at least 10 times more fatty alcohol than the corresponding cell of the same type which expresses the wild-type FAR from which the FAR variant is derived. In some embodiments, at least 90% of the fatty alcohol produced is C10-C18. In some embodiments, at least 90% of the fatty alcohol produced is C12-C16 fatty alcohols. In some embodiments, at least 30% of the fatty alcohol produced is C12-C14 fatty alcohols. In some embodiments, at least 55% of the fatty alcohol produced is C16-C18 fatty alcohols. In some embodiments, at least 90% of the fatty alcohol produced is C14-C18 fatty alcohols. In some embodiments, the host cell produces a fatty alcohol profile comprising an increased amount of C16:1 (cis $\Delta^9$-1-hexadecenol) fatty alcohol and a decreased amount of C18:1 (cis $\Delta^{11}$-1-octadecenol) fatty alcohol relative to a corresponding cell of the same type expressing a wild-type FAR from which the FAR variant is derived. In some embodiments, at least 5 g/L of recoverable fatty alcohols are produced. In some embodiments, at least 15 g/L of recoverable fatty alcohols are produced.

In still another aspect, the invention relates to method of producing fatty alcohols comprising culturing a host cell as described herein in a culture medium under conditions in which the fatty alcohols are produced. In some embodiments, the fatty alcohols are secreted into the culture medium. In some embodiments, the fatty alcohols are recovered (e.g., from the host cell or from the culture medium). In some embodiments, the method further comprises the step of isolating the fatty alcohols from the culture medium. In some embodiments, at least 5 g/L of recoverable fatty alcohols are produced. In some embodiments, at least 15 g/L of recoverable fatty alcohols are produced.

In still another aspect, the invention relates to methods of producing fatty alcohol compositions comprising culturing a microorganism (e.g., *E. coli*) comprising a polynucleotide encoding an improved FAR polypeptide according to the invention in a suitable culture medium, allowing expression of the polynucleotide and production of the fatty alcohols. In some embodiments at least 5.0 g/L (e.g., at least 10.0 g/L, at least 15 g/L, at least 20 g/L, at least 25 g/L, at least 30 g/L, at least 35 g/L, at least 40 g/L, at least 45 g/L, or at least 50 g/L) of fatty alcohols are recovered from the microorganism and/or culture. In some embodiments the fatty alcohols produced by the recombinant microorganism are further isolated from the culture.

In yet another aspect, the invention relates to compositions comprising and/or derived from the fatty alcohol composition produced by the methods of the invention. In some embodiments, the fatty alcohol compositions produced by the methods encompassed by the invention, or a fraction thereof, are further reduced to yield an alkane composition. In some embodiments the fatty alcohol composition produced by the methods encompassed by the invention are esterified yielding fatty esters. In some embodiments, the fatty alcohol compositions produced by the methods encompassed by the invention, or a fraction thereof, are modified to produce fatty esters. In some embodiments, the fatty alcohols are subjected to reduction or esterification to produce a diesel fuel component.

In yet another aspect, the invention provides methods of producing a detergent composition, the method comprising combining the fatty alcohols produced by the methods described herein, or a fraction thereof, with a detergent component selected from sodium carbonate, a complexation agent, zeolites, a protease, a lipase, amylase, carboxymethyl cellulose, optical brighteners, colorants and perfumes, thereby producing the detergent composition. In another aspect, the invention relates to detergent compositions produced by a method described herein.

In still another aspect, the invention provides methods of producing a fuel composition, the method comprising reducing or esterifying the fatty alcohols produced by a method described herein, or a fraction thereof, to yield the fuel composition. In some embodiments, a method of producing fuel comprises (a) producing fatty alcohols according to a method described herein, and (b) subjecting the fatty alcohols, or a fraction thereof, to one or more chemical reactions to generate alkanes, whereby fuel is produced. In some embodiments, the fatty alcohols comprise at least 90% C14-C18 fatty alcohols. In some embodiments, the fatty alcohols comprise less than 1% C18:0 fatty alcohols. In another aspect, the invention relates to fuel compositions produced by a method described herein.

In a first embodiment, the present invention relates to an improved fatty alcohol forming acyl-CoA reductase (FAR) polypeptide capable of producing at least about 1.5 times more fatty alcohol than a wild-type FAR polypeptide comprising SEQ ID NO:2 when assayed under the same conditions.

In a second embodiment, the present invention relates to an improved fatty alcohol forming acyl-CoA reductase (FAR) polypeptide comprising an amino acid sequence that is at least 80% identical to SEQ ID NO:2 and includes at least one substitution of an amino acid residue compared to wild-type FAR having at least 80% sequence identity to SEQ ID NO:2, wherein the improved FAR is capable of producing 1.5 times more fatty alcohol than the corresponding wild-type when assayed under the same conditions.

In a third embodiment, the present invention relates to the FAR polypeptide of the first or second embodiments, which comprises an amino acid sequence that is at least 90% identical to SEQ ID NO:2.

In a fourth embodiment, the present invention relates to the FAR polypeptide of the first or second embodiments, which comprises an amino acid sequence that is at least 90% identical to SEQ ID NO:2 and includes substitutions at one or more of positions 2, 134, 138, 188, 405 and 511 relative to SEQ ID NO:2.

In a fifth embodiment, the present invention relates to the FAR polypeptide of the first or second embodiments, which comprises an amino acid sequence that is at least 95% identical to SEQ ID NO:2 and includes substitutions at one or more of positions 2, 134, 138, 188, 405 and 511 relative to SEQ ID NO:2.

In a sixth embodiment, the present invention relates to the FAR polypeptide of the fourth embodiment in which the amino acid residue at position 2 is H, T, D, F, V, G, Q, P or I; the amino acid residue at position 134 is R, K, or S; the amino acid residue at position 138 is Q or L; the amino acid residue at position 188 is S; the amino acid residue at position 405 is V, S, F, G, C, L, S, A, or W; and the amino acid residue at position 511 is T, P, G, S, K, Q, or R.

In a seventh embodiment, the present invention relates to the FAR polypeptide of the fourth embodiment which includes substitutions at each of positions 2, 134, 138, 188, 405, and 511 relative to SEQ ID NO:2.

In an eighth embodiment, the present invention relates to the FAR polypeptide of the fourth embodiment which includes substitutions at each of positions 134, 138, 188, and 511 relative to SEQ ID NO:2.

In a ninth embodiment, the present invention relates to the FAR polypeptide of the eighth embodiment in which the substitution at position 134 is S; the substitution at position 138 is Q; the substitution at position 199 is S; and the substitution at position 511 is T.

In a tenth embodiment, the present invention relates to the FAR polypeptide of the fourth embodiment which comprises one to five additional substitutions at positions other than positions 2, 134, 138, 188, 405, and 511 relative to SEQ ID NO:2.

In an eleventh embodiment, the present invention relates to the FAR polypeptide of the tenth embodiment in which the additional substitutions are selected from the substitutions in Table 2.

In a twelfth embodiment, the present invention relates to the FAR polypeptide of the first or second embodiments which is a polypeptide selected from the variant polypeptides in Table 2.

In a thirteenth embodiment, the present invention relates to the FAR polypeptide of any of the first through twelfth embodiments which is a functional fragment.

In a fourteenth embodiment, the present invention relates to an isolated polynucleotide comprising a sequence encoding a FAR polypeptide according to any one of the first through thirteenth embodiments.

In a fifteenth embodiment, the present invention relates to an expression vector comprising a nucleic acid sequence encoding a FAR polypeptide according to any one of the first through thirteenth embodiments operably linked to a control sequence suitable for effecting expression in a host cell.

In a sixteenth embodiment, the present invention relates to the expression vector of the fifteenth embodiment in which the control sequence is a promoter.

In a seventeenth embodiment, the present invention relates to the expression vector of the sixteenth embodiment which is suitable for effecting expression in a bacterium, yeast, algae or filamentous fungi.

In an eighteenth embodiment, the present invention relates to the expression vector of the seventeenth embodiment which is suitable for effecting expression in an *E. coli*.

In a nineteenth embodiment, the present invention relates to the expression vector of the seventeenth embodiment which is suitable for effecting expression in *Saccharomyces cerevisiae*.

In a twentieth embodiment, the present invention relates to the expression vector of the sixteenth embodiment which is suitable for effecting expression in a *Yarrowia* sp.

In a twenty-first embodiment, the present invention relates to a microorganism engineered to express a FAR polypeptide according to any one of the first through thirteenth embodiments.

In a twenty-second embodiment, the present invention relates to the microorganism of the twenty-first embodiment which is an *E. coli*.

In a twenty-third embodiment, the present invention relates to the microorganism of the twenty-first embodiment which is a *Yarrowia*.

In a twenty-fourth embodiment, the present invention relates to the microorganism of the twenty-first embodiment which is a *Saccharomyces cerevisiae*.

In a twenty-fifth embodiment, the present invention relates to a method of producing a fatty alcohol composition comprising culturing a microorganism according to any one of the twenty-first through twenty-fourth embodiments in a suitable culture medium, in which the fatty alcohol composition is produced.

In a twenty-sixth embodiment, the present invention relates to the method of the twenty-fifth embodiment, in which at least 5 g/L of recoverable fatty alcohols are produced.

In a twenty-seventh embodiment, the present invention relates to the method of the twenty-sixth embodiment, in which at least 15 g/L of recoverable fatty alcohols are produced.

In a twenty-eighth embodiment, the present invention relates to the method according to the twenty-fifth through twenty-seventh embodiments, which further comprises the step of isolating the fatty alcohols from the culture.

In a twenty-ninth embodiment, the present invention relates to the fatty alcohol composition produced by the method of the twenty-fifth through twenty-eighth embodiments.

In a thirtieth embodiment, the present invention relates to a method of producing an alkane composition comprising culturing a microorganism according to any one of the twenty-first through twenty-fourth embodiments in a suitable culture medium in which a fatty alcohol composition is produced and reducing the fatty alcohol composition to yield an alkane composition.

In a thirty-first embodiment, the present invention relates to the alkane composition produced by the method of the thirtieth embodiment.

In a thirty-second embodiment, the present invention relates to a method of producing a fatty ester composition comprising culturing a microorganism according to any one of the twenty-first through twenty-fourth embodiments in a suitable culture medium in which a fatty alcohol composition is produced, exposing the fatty alcohol composition to esterification to produce a fatty ester composition.

In a thirty-third embodiment, the present invention relates to the fatty alcohol composition produced by the method of the thirty-second embodiment.

These and other embodiments of the invention are more fully described herein below.

BRIEF DESCRIPTION OF THE DRAWINGS

FIG. 2 depicts a sequence alignment of the wild-type FAR enzyme of *Marinobacter algicola* strain DG893 (SEQ ID NO:2) and the wild-type FAR enzyme of *Marinobacter aquaeolei* (SEQ ID NO:5).

DETAILED DESCRIPTION OF THE INVENTION

I. Definitions

Figure 1:
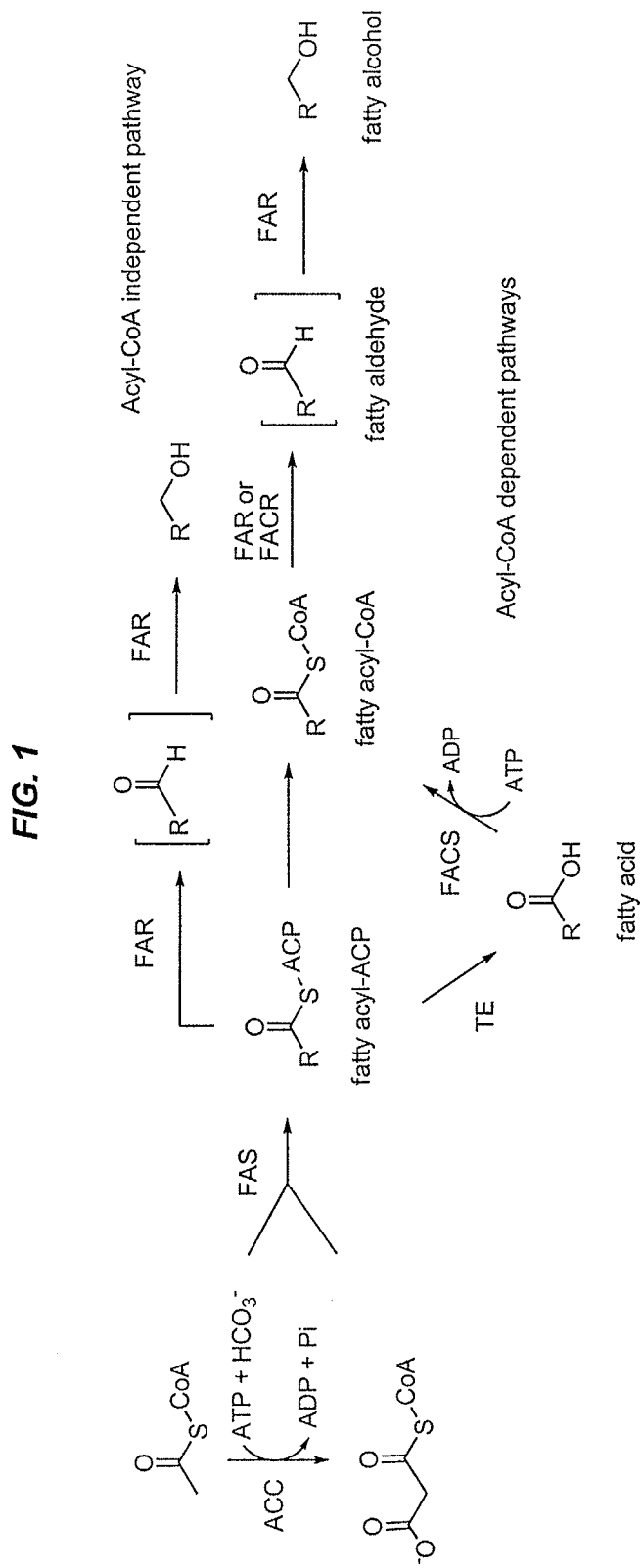
FIG. 1 depicts biosynthetic pathways for fatty alcohol production via (a) an acyl-CoA dependent pathway utilizing fatty acyl-ACP and fatty acyl-CoA intermediates and (b) an acyl-CoA independent pathway utilizing fatty acyl-ACP intermediates but not a fatty acyl-CoA intermediate, wherein "R" as used in the compound formulas is a C7 to C23 saturated, unsaturated, linear, branched or cyclic hydrocarbon chain.

Unless defined otherwise, all technical and scientific terms used herein generally have the same meaning as commonly understood by one of ordinary skill in the art to which this invention pertains. Generally, the nomenclature used herein and the laboratory procedures of cell culture, molecular genetics, organic chemistry, analytical chemistry and nucleic acid chemistry described below are those well known and commonly employed in the art. It is noted that the indefinite articles "a" and "an" and the definite article "the" are used in the present application to mean one or more unless the context clearly dictates otherwise. Further, the term "or" is used in the present application to mean the disjunctive "or" and the conjunctive "and".

Abbreviations: "FAR" denotes fatty acyl reductase or fatty alcohol forming acyl-CoA reductase; "ACP" denotes acyl carrier protein; "CoA" denotes coenzyme A; "TE" denotes thioesterase; "FAS" denotes fatty acid synthase; "FACR" denotes fatty acyl-CoA reductase; "FACS" denotes fatty acyl-CoA synthase (synthetase) and acyl-CoA synthase (synthetase) as used interchangeably herein; and "ACC" denotes acetyl-CoA carboxylase. Amino acids are designated using the one-letter symbols recommended by the IUPAC-IUB Biochemical Nomenclature Commission.

"Fatty alcohol forming acyl-CoA reductase," "fatty acyl reductase" and "FAR", are used interchangeably herein to refer to an enzyme that catalyzes the reduction of a fatty acyl-CoA, a fatty acyl-ACP, or other fatty acyl thioester complex to a fatty alcohol, in a reaction linked to the oxidation of NAD(P)H to NAD(P)$^+$, as shown in the following Scheme 1:

Scheme 1

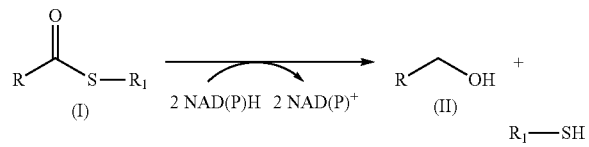

wherein "R" represents a C7 to C23 saturated, unsaturated, linear, branched or cyclic hydrocarbon chain, and "$R_1$" represents CoA, ACP or other fatty acyl thioester substrates. CoA is a non-protein acyl carrier group factor (or moiety) involved in the synthesis and oxidation of fatty acids. "ACP" is a polypeptide or protein subunit of fatty acid synthase used in the synthesis of fatty acids. In some embodiments, a fatty aldehyde intermediate may be produced in the reaction depicted in Scheme 1.

FARs are distinct from FACRs. FACRs reduce fatty acyl-CoA intermediates only to fatty aldehydes and require an additional oxidoreductase enzyme to generate the corresponding fatty alcohol.

"Fatty aldehyde" as used herein refers to a saturated or unsaturated aliphatic aldehyde and reference is made to FIG. 1, wherein R is as defined above.

The term "fatty acid" as used herein refers to a compound of formula III:

wherein "R" is as defined above. Saturated or unsaturated fatty acids can be described as "Ca:b", wherein "a" is an integer that represents the total number of carbon atoms and "b" is an integer that refers to the number of double bonds in the carbon chain.

The term "fatty alcohol" as used herein refers to an aliphatic alcohol of the formula R—OH, where R is as defined above. Saturated or unsaturated fatty alcohols can also be described using the nomenclature "Ca:b" or, alternatively "Ca:b-OH", wherein "a" is an integer that represents the total number of carbon atoms in the fatty alcohol and "b" is an integer that refers to the number of double bonds in the carbon chain. In some embodiments, a fatty alcohol produced according to the methods disclosed herein is a C8-C24 saturated or unsaturated fatty alcohol (i.e., a C8, C9, C10, C11, C12, C13, C14, C15, C16, C17, C18, C19, C20, C21, C22, or C24 fatty alcohol). In some embodiments, one or more of the following fatty alcohols is produced: 1-octanol (C8:0), 1-decanol (C10:0), 1-dodecanol (012:0), 1-tetradecanol (C14:0), 1-hexadecanol (C16:0), 1-octadecanol (C18:0), 1-icosanol (C20:0), 1-docosanol (C22:0), 1-tetracosanol (024:0), cis $\Delta^9$-1-hexadecenol (C16:1), and cis $\Delta^{11}$-1-octadecenol (C18:1). It is understood that, unless otherwise specified, a reference to a "Cx fatty alcohol" includes both saturated and unsaturated fatty alcohols having "x" carbon atoms.

Unsaturated fatty acids or fatty alcohols can be referred to as "cis $\Delta^x$" or "trans $\Delta^x$", wherein "cis" and "trans" refer to the carbon chain configuration around the double bond and "x" indicates the number of the first carbon of the double bond, wherein carbon 1 is the carboxylic acid carbon of the fatty acid or the carbon bound to the —OH group of the fatty alcohol.

The terms "fatty acyl-thioester" and "fatty acyl-thioester complex" refer to a compound of formula (I), in which a fatty acyl moiety is covalently linked via a thioester linkage to a carrier moiety. Fatty acyl-thioesters are substrates for the improved FAR polypeptides described herein.

The term "fatty acyl-CoA" refers to a compound of formula (I), wherein $R_1$ is Coenzyme A.

The term "fatty acyl-ACP" refers to a compound of formula (I) wherein $R_1$ is acyl carrier protein.

The term "fatty acid synthase (FAS)" refers to an enzyme or enzyme complex that catalyzes the conversion of acetyl-CoA and malonyl-CoA to fatty acyl-ACP as set forth in the following Scheme 2:

Scheme 2

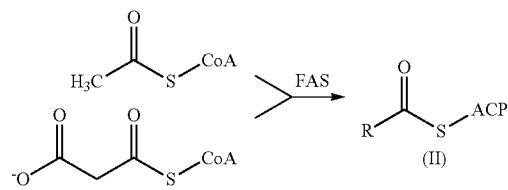

wherein ACP is a protein which comprises a covalently attached phosphopantetheine moiety. In certain embodiments, the FAS is composed of more than one distinct enzymatic activity. In various embodiments, the distinct enzymatic activities reside in separate polypeptides. In some embodiments, the separate polypeptides form one or more protein complexes.

The term "acyl-ACP thioesterase (TE)" refers to an enzyme that catalyzes the cleavage of acyl-ACP to form a fatty acid, as shown in the following Scheme 3, wherein R has the same meaning as set forth above:

Scheme 3

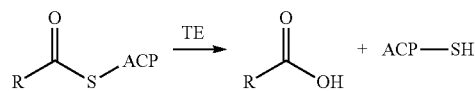

The term "fatty acyl-CoA synthetase" or "acyl-CoA synthetase" or "FACS" are used interchangeably herein to refer to an enzyme that catalyzes the formation of a covalent complex between the acyl portion of the fatty acid and CoA as shown in the following Scheme 4, wherein R has the same meaning as set forth above:

Scheme 4

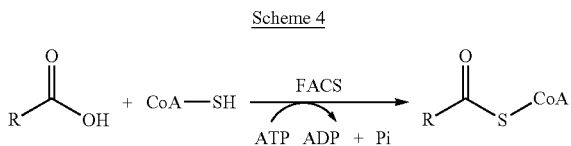

The term "acetyl-CoA carboxylase (ACC)" refers to an enzyme that catalyzes the conversion of acetyl-CoA to malonyl-CoA as shown in the following Scheme 5:

Scheme 5

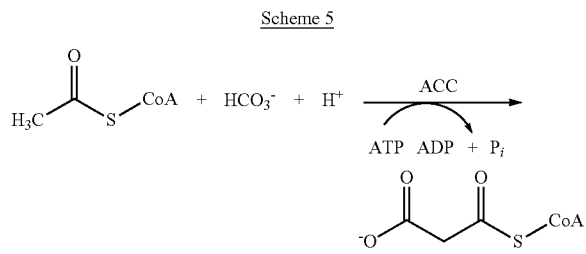

The term "acyl-CoA dehydrogenase (ACD)" refers an enzyme that catalyzes the introduction of a trans double-bond between C2 and C3 of an acyl-CoA thioester substrate as shown in the following Scheme 6:

Scheme 6

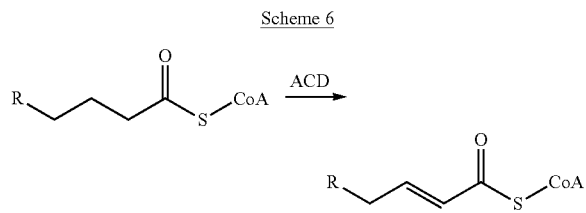

The phrase "acyl-CoA independent pathway" refers to the production of fatty alcohols by the direct enzymatic conversion of fatty acyl-ACP substrates to fatty alcohols and does not involve the use of free fatty acids or fatty acyl-CoA intermediates. This biosynthetic pathway differs from a) the fatty acyl-CoA dependent pathway which converts fatty acyl-ACP directly to fatty acyl CoA via an acyl-transfer reaction, such as in yeast, and b) the fatty acyl-CoA dependent pathway which converts fatty acyl-ACP to fatty acyl-CoA via a free fatty acid intermediate, such as in bacteria. See FIG. 1.

The acyl-CoA independent pathway has the advantage of bypassing the step of forming a fatty acyl-CoA substrate from free fatty acid, which requires the use of ATP. Therefore, the acyl-CoA independent pathway may use less energy than the acyl-CoA dependent pathway that utilizes a free fatty acid intermediate.

"Conversion" refers to the enzymatic conversion of the substrate to the corresponding product.

"Naturally-occurring" or "wild-type" refers to the form found in nature. For example, a naturally occurring or wild-type polypeptide or polynucleotide sequence is a sequence present in an organism that can be isolated from a source in nature and which has not been intentionally modified by human manipulation. A wild-type organism or cell refers to an organism or cell that has not been intentionally modified by human manipulation.

The term "wild-type fatty alcohol forming acyl-CoA reductase" or "wild-type FAR," as used herein, refers to a naturally-occurring FAR polypeptide that is produced in nature. In some embodiments, a wild-type FAR is produced by a gammaproteobacteria, including but not limited to strains of *Marinobacter, Oceanobacter*, and *Hahella*. Naturally occurring FAR polypeptides are described, for example, in US patent publication 2011/0000125, incorporated by reference herein. In some embodiments, a wild-type FAR is a naturally-occurring FAR polypeptide that is produced by the *Marinobacter algicola* strain DG893 (SEQ ID NO:2). In some embodiments, a wild-type FAR is a naturally-occurring FAR polypeptide that is produced by the *Marinobacter aquaeolei* strain VT8 (SEQ ID NO:5)'. FARs that are not wild-type can be denoted "recombinant" FARs, whether prepared using recombinant techniques or by chemical synthesis.

The terms "improved FAR polypeptides" and "FAR variants" are used interchangeably to refer to improved full length FAR enzymes having substitutions at one or more positions relative to a wild type FAR enzyme. and functional (or "biologically active") fragments thereof. In one embodiment, "improved FAR polypeptides" comprise at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO:2 and also the functional fragments of said improved full length FAR enzymes. "Improved FAR polypeptides" can also refer to polypeptides comprising at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 5, and functional fragments thereof.

"Variant" means an improved FAR polypeptide or polynucleotide encoding an improved FAR polypeptide comprising one or more modifications relative to a wild-type FAR polypeptide such as wild-type FAR from *Marinobacter* species, or the wild-type polynucleotide such as substitutions, insertions, and/or deletions of one or more amino acid residues or of one or more specific nucleotides or codons in the polypeptide or polynucleotide.

The terms "modifications" and "mutations," when used in the context of substitutions, deletions, insertions and the like with respect to polynucleotides and polypeptides, are used interchangeably herein and refer to changes that are introduced by genetic manipulation to create variants from a wild-type sequence.

"Deletion" refers to modification to a polypeptide by removal of one or more amino acids from the reference polypeptide. Deletions can comprise removal of 1 or more amino acids, 2 or more amino acids, 5 or more amino acids, 10 or more amino acids, 15 or more amino acids, or 20 or more amino acids, up to 10% of the total number of amino acids, or up to 20% of the total number of amino acids making up the reference enzyme while retaining enzymatic activity and/or retaining the improved properties of an engineered enzyme. Deletions can be directed to the internal portions and/or terminal portions of the polypeptide. In various embodiments, the deletion can comprise a continuous segment or can be discontinuous. The term "deletion" is also used to refer to a DNA modification in which one or more nucleotides or nucleotide base-pairs have been removed, as compared to the corresponding reference, parental or "wild type" DNA.

"Insertion" refers to modification to a polypeptide by addition of one or more amino acids to the reference polypeptide. In some embodiments, the modification comprises insertions of one or more amino acids to the naturally occurring polypeptide as well as insertions of one or more amino acids to other modified polypeptides. Insertions can be in the internal portions of the polypeptide, or to the carboxy or amino terminus. Insertions as used herein include fusion proteins as is known in the art. The insertion can be a contiguous segment of amino acids or separated by one or more of the amino acids in the naturally occurring polypeptide. The term "insertion" is also used to refer to a DNA modification in which or more nucleotides or nucleotide base-pairs have been inserted, as compared to the corresponding reference, parental or "wild type" DNA.

"Different from" or "differs from" with respect to a designated reference sequence refers to difference of a given amino acid or polynucleotide sequence when aligned to the reference sequence. Generally, the differences can be determined when the two sequences are optimally aligned. Differences include modifications such as insertions, deletions, or substitutions of amino acid residues in comparison to the reference sequence.

A polynucleotide or polypeptide that is "derived from" a particular organism refers to a wild-type polynucleotide or polypeptide that originates in the organism. The expression "derived from" can also be used in the context of mutant or variant polynucleotides and polypeptides. In this context, the particular mutant is said to be "derived from" the wild-type sequence from which it was engineered or to which its sequence is compared. For example, in some embodiments, an improved FAR enzymes described herein can be said to be "derived from" the wild-type FAR enzyme of SEQ ID NO:2 or SEQ ID NO:5. In some embodiments a polypeptide sequence of an engineered FAR is at least 90%, sometimes at least 95%, sometimes at least 96%, sometimes at least 97%, and sometimes at least 98% identical to the naturally occurring homolog from which it was derived. In some embodiments a polypeptide sequence of an engineered FAR has 100% identity with the naturally occurring homolog, except at a position or set of positions specified (relative to SEQ ID NO:2) in Table 2, below (i.e., corresponding to one of Variants 1-629.

"Percentage of sequence identity," "percent identity" and "percentage homology" are used interchangeably herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence (which may also contain gaps to optimize the alignment) for alignment of the two sequences. The percentage may be calculated by determining the number of positions at which the identical nucleic acid base or amino acid residue occurs in both sequences to yield the number of matched positions, dividing the number of matched positions by the total number of positions in the window of comparison (including positions where one of the sequences has a gap(s) and multiplying the result by 100 to yield the percentage of sequence identity. For example, a polypeptide with an amino acid sequence matching SEQ ID NO:2 at 491 positions, with one gap, would have 491/512=95.9% identity to SEQ ID NO:2. Similarly, a FAR variant that has 475 residues (i.e., less than full-length) and matches SEQ ID NO:2 at 460 positions would have 460/475=96.8% identity. Those of skill in the art appreciate that there are many established algorithms available to align two sequences and that different methods may give slightly different results.

Alignment of sequences for comparison can be conducted, e.g., by the local homology algorithm of Smith and Waterman, 1981, Adv. Appl. Math. 2:482, by the homology alignment algorithm of Needleman and Wunsch, 1970, J. Mol. Biol. 48:443, by the search for similarity method of Pearson and Lipman, 1988, Proc. Natl. Acad. Sci. USA 85:2444, by computerized implementations of these algorithms (GAP, BESTFIT, FASTA, and TFASTA in the GCG Wisconsin Software Package), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)). The Clustral (Chenna R., Sugawara H., Koike T., Lopez R., Gibson T. J., Higgins D. G., Thompson J. D., (2003) Multiple sequence alignment with the Clustral series of programs, Nucleic Acids Res., 31, 3497-3500.) and T-Coffee (T-COFFEE: A novel method for multiple sequence alignments. Notredame, Higgins, Heringa, JMB 302 (205-217) 2000 software packages may also be used to align sequences.

Examples of algorithms that are suitable for determining percent sequence identity and sequence similarity are the BLAST and BLAST 2.0 algorithms, which are described in Altschul et al., 1990, J. Mol. Biol. 215: 403-410 and Altschul et al., 1977, Nucleic Acids Res. 3389-3402, respectively. Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff and Henikoff, 1989, Proc Natl Acad Sci USA 89:10915). Exemplary determination of sequence alignment and % sequence identity can employ the BESTFIT or GAP programs in the GCG Wisconsin Software package (Accelrys, Madison Wis.), using default parameters provided.

"Reference sequence" refers to a defined sequence used as a basis for a sequence comparison. A reference sequence may be a subset of a larger sequence, for example, a segment of a full-length gene or polypeptide sequence. Generally, a reference sequence is at least 20 nucleotide or amino acid residues in length, at least 25 residues in length, at least 50 residues in length, at least 100 residues in length or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptide are typically performed by comparing sequences of the two polynucleotides over a "comparison window" to identify and compare local regions of sequence similarity.

"Comparison window" refers to a conceptual segment of at least about 20 contiguous nucleotide positions or amino acids residues wherein a sequence may be compared to a reference sequence of at least 20 contiguous nucleotides or amino acids and wherein the portion of the sequence in the comparison window may comprise additions or deletions (i.e., gaps) of 20 percent or less as compared to the reference sequence (which does not comprise additions or deletions) for optimal alignment of the two sequences. The comparison window can be longer than 20 contiguous residues, and includes, optionally 30, 40, 50, 100, or longer windows.

Nucleic acids "hybridize" when they associate, typically in solution. Nucleic acids hybridize due to a variety of well-characterized physico-chemical forces, such as hydrogen bonding, solvent exclusion, base stacking and the like. As used herein, the term "stringent hybridization wash conditions" in the context of nucleic acid hybridization experiments, such as Southern and Northern hybridizations, are sequence dependent, and are different under different environmental parameters. An extensive guide to the hybridization of nucleic acids is found in Tijssen (1993) "Laboratory Techniques in biochemistry and Molecular Biology—Hybridization with Nucleic Acid Probes," Part I, Chapter 2 (Elsevier, New York), which is incorporated herein by reference. For polynucleotides of at least 100 nucleotides in length, low to very high stringency conditions are defined as follows: prehybridization and hybridization at 42° C. in 5×SSPE, 0.3% SDS, 200 μg/ml sheared and denatured salmon sperm DNA, and either 25% formamide for low stringencies, 35% formamide for medium and medium-high stringencies, or 50% formamide for high and very high stringencies, following standard Southern blotting procedures. For polynucleotides of at least 100 nucleotides in length, the carrier material is finally washed three times each for 15 minutes using 2×SSC, 0.2% SDS at least at 50° C. (low stringency), at least at 55° C. (medium stringency), at least at 60° C. (medium-high stringency), at least at 65° C. (high stringency), and at least at 70° C. (very high stringency).

"Codon optimized" refers to changes in the codons of the polynucleotide encoding a protein to those preferentially used in a particular organism such that the encoded protein is efficiently expressed in the organism. Although the genetic code is degenerate in that most amino acids are represented by several codons, called "synonyms" or "synonymous" codons, it is well known that codon usage by particular organisms is nonrandom and biased towards particular codon triplets. This codon usage bias may be higher in reference to a given gene, genes of common function or ancestral origin, highly expressed proteins versus low copy number proteins, and the aggregate protein coding regions of an organism's genome. In some embodiments, the polynucleotides encoding enzymes may be codon optimized for optimal production from the host organism selected for expression.

"Preferred, optimal, high codon usage bias codons" refers interchangeably to codons that are used at higher frequency in the protein coding regions than other codons that code for the same amino acid. The preferred codons may be determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof. Codons whose frequency increases with the level of gene expression are typically optimal codons for expression. A variety of methods are known for determining the codon frequency (e.g., codon usage, relative synonymous codon usage) and codon preference in specific organisms, including multivariate analysis, for example, using cluster analysis or correspondence analysis, and the effective number of codons used in a gene (See GCG Codon Preference, Genetics Computer Group Wisconsin Package; CodonW, John Peden, University of Nottingham; McInerney, J. 0, 1998, Bioinformatics 14:372-73; Stenico et al., 1994, Nucleic Acids Res. 222437-46; Wright, F., 1990, Gene 87:23-29). Codon usage tables are available for a growing list of organisms (see for example, Wada et al., 1992, Nucleic Acids Res. 20:2111-2118; Nakamura et al., 2000, Nucl. Acids Res. 28:292; Duret, et al., supra; Henaut and Danchin, "*Escherichia coli* and *Salmonella*," 1996, Neidhardt, et al. Eds., ASM Press, Washington D.C., p. 2047-2066). The data source for obtaining codon usage may rely on any available nucleotide sequence capable of coding for a protein. These data sets include nucleic acid sequences actually known to encode expressed proteins (e.g., complete protein coding sequences-CDS), expressed sequence tags (ESTs), or predicted coding regions of genomic sequences (see for example, Mount, D., Bioinformatics: Sequence and Genome Analysis, Chapter 8, Cold Spring Harbor Laboratory Press, Cold Spring Harbor, N.Y., 2001; Uberbacher, E. C., 1996, Methods Enzymol. 266:259-281; Tiwari et al., 1997, Comput. Appl. Biosci. 13:263-270).

In describing the various variants and amino acid substitutions of the present invention, the nomenclature described below is adapted for ease of reference. In all cases the accepted IUPAC single letter or triple letter amino acid abbreviations are employed. IUPAC single letter amino acid abbreviations are as follows: alanine (A); cysteine (C); aspartic acid (D); glutamic acid (E); phenylalanine (F); glycine (G); histidine (H); isoleucine (I); lysine (K); leucine (L); methionine (M); asparagine (N); proline (P); glutamine (Q); arginine (R); serine (S); threonine (T); valine (V); tryptophan (W); and tyrosine (Y). For amino acid substitutions the following nomenclature is used: [Original amino acid, position, substituted amino acid]. As a non-limiting example, for a variant polypeptide described with reference to SEQ ID NO:2, "A2V" indicates that in the variant polypeptide, the alanine at position 2 of the reference sequence is replaced by valine, with amino acid position being determined by optimal alignment of the variant sequence with SEQ ID NO:2. Similarly, "A512K/S/T" describes three variants: a variant in which the alanine at position 512 of the reference sequence is replaced by lysine, a variant in which the alanine at position 512 of the reference sequence is replaced by serine, and a variant in which the alanine at position 512 of the reference sequence is replaced by threonine. In some embodiments, an amino acid (or base) may be called "X," by which is meant any amino acid (or base). For example, X2D/F/G/H/I/P/N/Q/T/V/W can refer to a substitution in a FAR homolog in which the residue (X) at the position in the homolog corresponding to position 2 of a specified sequence (e.g., SEQ ID NO:2) is substituted so that the residue at position 2 is any of D, F, G, H, I, P, N, Q, T, V, and W.

The term "amino acid substitution set" or "substitution set" refers to a group of amino acid substitutions. A substitution set can have 1, 2, 3, 4, 5, 6, 7, 8, 9, 10, 11, 12, 13, 14, 15, or more amino acid substitutions. In some embodiments, a substitution set refers to the set of amino acid substitutions that is present in any of the variant FAR polypeptides listed in Table 2, Table 4, and/or Table 5. For example, the substitution set for Variant 370 (Table 2) consists of the amino acid substitutions N134S, E138Q, P188S, P405V, Q418V, and A511T.

"Conservative" amino acid substitutions or mutations refer to the interchangeability of residues having similar side chains, and thus typically involves substitution of the amino acid in the polypeptide with amino acids within the same or similar defined class of amino acids. However, as used herein, conservative mutations do not include substitutions from a hydrophilic to hydrophilic, hydrophobic to hydrophobic, hydroxyl-containing to hydroxyl-containing, or small to small residue, if the conservative mutation can instead be a substitution from an aliphatic to an aliphatic, non-polar to non-polar, polar to polar, acidic to acidic, basic to basic, aromatic to aromatic, or constrained to constrained residue. Further, as used herein, A, V, L, or I can be conservatively mutated to either another aliphatic residue or to another non-polar residue. In some embodiments, conservatively substituted variations of the FAR polypeptides of the present invention include substitutions of less than 10%, less than 5%, less than 2% and sometimes less than 1% of the amino acids of the polypeptide sequence, with a conservatively selected amino acid of the same conservative substitution group. The addition of sequences which do not alter the encoded activity of an FAR polynucleotide, such as the addition of a non-functional or non-coding sequence, is considered a conservative variation of the polynucleotide. Table 1 below shows exemplary conservative substitutions.

TABLE 1

Conservative Substitutions

| Residue | Possible Conservative Mutations |
|---|---|
| A, L, V, I | Other aliphatic (A, L, V, I) |
| | Other non-polar (A, L, V, I, G, M) |
| G, M | Other non-polar (A, L, V, I, G, M) |
| D, E | Other acidic (D, E) |
| K, R | Other basic (K, R) |
| P, H | Other constrained (P, H) |
| N, Q, S, T | Other polar (N, Q, S, T) |
| Y, W, F | Other aromatic (Y, W, F) |
| C | None |

In some embodiments, there may be at least 1, at least 2, at least 3, at least 4, at least 5, at least 6, at least 7, at least 8, at least 9, at least 10, at least 15, at least 20, at least 25, at least 30, at least 35, or at least 40 conservative substitutions.

"Non-conservative substitution" refers to substitution or mutation of an amino acid in the polypeptide with an amino acid with significantly differing side chain properties. Non-conservative substitutions may use amino acids between, rather than within, the defined groups listed above. In one embodiment, a non-conservative mutation affects (a) the structure of the peptide backbone in the area of the substitution (e.g., proline for glycine) (b) the charge or hydrophobicity, or (c) the bulk of the side chain.

"Functional fragment" as used herein refers to a polypeptide that has an amino-terminal and/or carboxy-terminal deletion and/or internal deletion, but where the remaining amino acid sequence is identical to the corresponding positions in the sequence to which it is being compared (e.g., a full-length FAR variant of the invention) and that retains substantially all of the activity of the full-length polypeptide. Improved functional fragments can comprise up to 60%, 65%, 70%, 75%, 80%, 85%, 90%, 95%, 96%, 97%, 98%, and 99% of the improved full-length FAR enzyme.

An "endogenous" polynucleotide, gene, promoter or polypeptide refers to any polynucleotide, gene, promoter or polypeptide that originates in a particular host cell. A polynucleotide, gene, promoter or polypeptide is not endogenous to a host cell if it has been removed from the host cell, subjected to laboratory manipulation, and then reintroduced into a host cell.

A "heterologous" polynucleotide, gene, promoter or polypeptide refers to any polynucleotide, gene, promoter or polypeptide that is introduced into a host cell that is not normally present in that cell, and includes any polynucleotide, gene, promoter or polypeptide that is removed from the host cell and then reintroduced into the host cell.

"Inactive" or "inactivated" in reference to a gene refers to a gene having at least one function that is impaired. Genes can be inactivated in a variety of ways known in the art, including but not limited to insertion of a mobile genetic element (e.g., a transposon); deletion of all or part of the gene, such that the gene product is not made, or is truncated and is non-functional; mutation of the gene such that the gene product is not made, or is truncated and is non-functional; deletion or mutation of one or more control elements that control expression of the gene such that the gene product is not made; and the like. In certain embodiments genes can be inactivated by methods other than genetic modification, for example, by gene silencing at the transcriptional level or at the post-transcriptional level using for example RNAi.

"Recombinant host cell" refers to a cell into which has been introduced a heterologous polynucleotide, gene, promoter, e.g., an expression vector, or to a cell having a heterologous polynucleotide or gene integrated into the genome.

"Control sequence" is defined herein to include all components, which are necessary or advantageous for the expression of a polypeptide of the present disclosure. Each control sequence may be native or foreign to the nucleic acid sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide.

"Operably linked" and "operably associated" are defined herein as a configuration in which a control sequence is appropriately placed at a position relative to the coding sequence of the DNA sequence such that the control sequence directs the expression of a polynucleotide and/or polypeptide.

"Promoter sequence" is a nucleic acid sequence that is recognized by a host cell for expression of the coding region. The control sequence may comprise an appropriate promoter sequence. The promoter sequence contains transcriptional control sequences, which mediate the expression of the polypeptide. The promoter may be any nucleic acid sequence which shows transcriptional activity in the host cell of choice including mutant, truncated, and hybrid promoters, and may be obtained from genes encoding extracellular or intracellular polypeptides either endogenous or heterologous to the host cell.

The term "expression" includes any step involved in the production of the polypeptide including, but not limited to, transcription, post-transcriptional modification, translation, post-translational modification, and secretion.

The terms "transform" or "transformation," as used in reference to a cell, means a cell has a non-native nucleic acid sequence integrated into its genome or as an episome (e.g., plasmid) that is maintained through multiple generations.

The term "culturing" refers to growing a population of microbial cells under suitable conditions in a liquid or solid medium. In particular embodiments, culturing refers to the fermentative bioconversion of a substrate to an end product.

The term "recoverable," as used in reference to producing a composition (e.g., fatty alcohols) by a method of the present invention, refers to the amount of composition which can be isolated from the reaction mixture yielding the composition according to methods known in the art.

The term "fuel component," as used herein, refers to any compound or mixture of compounds that is used to formulate a fuel composition.

II. Introduction

The present invention relates to, among other things, variant FAR enzymes and functional fragments thereof with improved properties, polynucleotides encoding the variant FAR enzymes, recombinant microorganisms comprising a nucleic acid encoding an improved FAR polypeptide, microorganisms capable of expressing the improved FAR polypeptides, processes for producing fatty alcohols and other compositions derived therefrom using the improved FAR polypeptides, and the resultant compositions.

Wild-type FAR polypeptides have been described in WO 2011/008535 (published 20 Jan. 2011), incorporated by reference herein for all purposes. Certain FAR enzymes isolated from genera of the class of marine bacteria such as gammaproteobacteria found in seawater (and particularly FARs obtained from strains of *Marinobacter* and *Oceanobacter* or taxonomic equivalents thereof) are capable of generating high yields of fatty alcohols when genes encoding these enzymes are expressed in heterologous cells. For example, *Marinobacter* species algicola (strain DG893) possesses FAR enzymes which are capable of producing more than 100-fold more total fatty alcohol than FAR enzymes from *B. mori*, when expressed in an *E. coli* host. It has now been discovered that FAR enzymes containing mutations in their polypeptide sequences, such as one or more amino acid substitutions, have improved properties as compared to their wild-type counterparts.

SEQ ID NO:2 is the wild-type FAR from *Marinobacter algicola* (strain DG893) and is described in WO 2011/008535 (published 20 Jan. 2011), which is incorporated herein by reference for all purposes. SEQ ID NO:13 is the polynucleotide sequence encoding SEQ ID NO:2. SEQ ID NO:1 is a polynucleotide sequence encoding the wild-type FAR protein from *Marinobacter algicola* strain DG893 (SEQ ID NO: 2) that is codon optimized for expression in *E. coli*. SEQ ID NO:3 is a polynucleotide sequence encoding SEQ ID NO:2 that is codon optimized for expression in *Yarrowia lipolytica*. SEQ ID NO:5 is the wild-type FAR from *Marinobacter aquaeolei* VT8, which is also described in WO 2011/008535. SEQ ID NO:4 is a polynucleotide sequence encoding the wild-type FAR protein from *Marinobacter aquaeolei* VT8 (SEQ ID NO:5) that is codon optimized for expression.

Amino acid sequence identity between SEQ ID NO:2 and SEQ ID NO:5 is 78%. See FIG. 2.

In one aspect, the disclosure provides the improved FAR polypeptides per se. In another aspect, it can be seen that substitutions introduced at numerous different amino acid (also referred to herein as "residue") positions within the wild-type FAR of SEQ ID NO:2 yield improved FAR polypeptides capable of catalyzing increased production of fatty alcohols as compared to the wild-type FAR (see Table 2). Depending upon the position mutated, single amino acid changes at specified positions give rise to 2-fold or greater increases in fatty alcohol production.

In one aspect the invention relates to FAR polypeptides with at least about 70% sequence identity with SEQ ID NO:2 (wild-type *M. algicola* FAR) and with one or more of the specified substitutions; these polypeptides exhibit improved characteristics and/or properties as described herein. In some embodiments, a FAR polypeptide shows at least about 75% (e.g., at least 80%, at least 85%, at least 90%, at least 91%, at least 92%, at least 93%, at least 94%, at least 95%, at least 96%, at least 97%, at least 98% and at least 99%) sequence identity with the wild-type FAR of SEQ ID NO:2 and also includes one or more of the specified substitutions will exhibit improved characteristics and/or properties as described herein. In another aspect, the invention relates to FAR polypeptides that comprise an amino acid sequence encoded by a nucleic acid that hybridizes under stringent conditions over substantially the entire length of a nucleic acid corresponding to SEQ ID NO:1, SEQ ID NO:3, or SEQ ID NO:13. In some embodiments the FAR variant is derived from a *Marinobacter* species other than *Marinobacter algicola*.

In a related aspect, the invention describes FAR variants showing at least about 70% (e.g., at least 75%, at least 80%, at least 85%, at least 90%, at least 91%, at least 92%, at least 93%, at least 94%, at least 95%, at least 96%, at least 97%, at least 98% or at least 99%) sequence identity with SEQ ID NO:5 (wild-type *M. aquaeolei* FAR) and comprising substitutions disclosed herein (see, e.g., Tables 4 and 5). These FAR variants exhibit improved characteristics and/or properties as described herein. In some embodiments the FAR variant is derived from a *Marinobacter* species other than *Marinobacter aquaeolei*.

III. Improved Properties of Far Variants

In one aspect, the invention provides FAR variants having improved properties over a wild-type FAR enzyme (e.g., SEQ ID NO:2 or 5) or over a reference sequence. For example, a cell expressing a FAR variant of the invention may have increased fatty alcohol production compared to a cell expressing a wild-type FAR (also referred to herein as a "control cell"), and/or the fatty alcohols produced may have a different fatty alcohol profile than the fatty alcohols produced by the control cell. Improved properties of FAR variants include, but are not limited to, increased total fatty alcohol production; increased production of fatty alcohols at a specified culture pH (e.g., pH 3.5, 4, 4.5, 5, 5.5, 6, 6.5, 7, 7.5, or 8) or over a broader pH range (e.g., pH 3.5-7); increased production of fatty alcohols at a specified culture temperature (e.g., 30° C., 37° C., or 40° C.), or over a broader temperature range (e.g., 30° C.-42° C.); and changes in fatty alcohol profile as compared to a wild-type FAR. For example, a cell expressing the improved FAR may have a fatty alcohol profile that includes a higher percentage of total long chain fatty alcohols (e.g., C16-C18) or including a higher percentage of shorter chain fatty alcohols (e.g., C12-C14). It will be understood that reference to a FAR variant "with increased fatty alcohol production" and/or producing differential fatty acid profiles refers to fatty alcohol production by a host cell expressing the FAR variant (e.g., host cells into which a recombinant polynucleotide encoding the FAR variant has been introduced). In some embodiments the host cell is a yeast or bacteria. In some embodiments, the host cell is E. coli, which has proved particularly useful for production of fatty alcohols using the FAR variants disclosed herein.

Fatty Alcohol Production

In some embodiments, the FAR variants (or improved FAR polypeptides) of the invention, when expressed in a recombinant host cell, produce (i.e., yield) an increased amount of fatty alcohols as compared to a wild-type FAR having the sequence of SEQ ID NO:2 and/or a wild-type FAR having the sequence SEQ ID NO:5. In some embodiments, a FAR variant of the present invention has at least about 70% (or at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%) sequence identity to SEQ ID NO:2 or SEQ ID NO:5 and comprises one or more amino acid substitutions as described herein (e.g., one or more amino acid substitutions or amino acid substitution sets listed in Table 2, Table 4, or Table 5), wherein a cell in which the FAR variant is expressed produces at least 1.5 times more fatty alcohol than a corresponding cell of the same type which expresses the wild-type FAR from which the FAR variant is derived under the same conditions. In some embodiments, the fatty alcohol production of a host cell (e.g., E. coli) expressing a FAR variant and a corresponding host cell of the same type expressing the wild-type FAR from which the FAR variant is derived is measured under the same culture medium conditions (e.g., using LB or M9YE medium), the same temperature conditions (e.g., at 30° C. or at 37° C.), and the same time conditions (e.g., for 24 hours). In some embodiments the host cell (e.g., E. coli) expressing the FAR variant produces at least 2-fold, at least 3-fold, at least 4-fold, at least 5-fold, at least 6-fold, at least 7-fold, at least 8-fold, at least 9-fold, or at least 10-fold more fatty alcohols as compared to the corresponding host cell of the same type expressing the wild-type FAR from which the FAR variant is derived.

In some embodiments, the improved FAR polypeptides of the invention are capable of producing more fatty alcohol than a wild-type polypeptide corresponding to SEQ ID NO:2 when the polynucleotide encoding the improved FAR polypeptide as described herein is expressed in a host cell.

Fatty alcohol production is measured in a host cell, such as an E. coli host cell or a yeast (e.g., Yarrowia or Saccharomyces) host cell. See Examples 2, 4, and 6 below. In some embodiments, the improved FAR polypeptide of the invention is capable of producing more fatty alcohol than a wild-type polypeptide corresponding to SEQ ID NO:2 when the polynucleotide encoding the improved FAR polypeptide is expressed in E. coli and cultured under the same conditions. In some embodiments, the improved FAR polypeptide of the invention is capable of producing more fatty alcohol than a wild-type polypeptide corresponding to SEQ ID NO:2 when the polynucleotide encoding the improved FAR polypeptide is expressed in a yeast and cultured under the same conditions. In one embodiment, the yeast is Yarrowia lipolytica. In one embodiment, the yeast is Saccharomyces cerevisiae.

In some embodiments, the improved FAR polypeptide of the invention is capable of producing more fatty alcohol than a wild-type polypeptide corresponding to SEQ ID NO: 2 when total fatty alcohol production is determined. "Total fatty alcohol," as used herein, refers to the intracellular and secreted amount of fatty alcohol. In some embodiments, the improved FAR polypeptide of the invention is capable of producing more fatty alcohol than a wild-type polypeptide corresponding to SEQ ID NO:2 when secreted fatty alcohol production is determined. "Secreted fatty alcohol," as used herein, refers to the extracellular fatty alcohol.

Fatty alcohol content can be measured using art known methods, such as methods described herein below. In some embodiments, the improved FAR polypeptide of the invention is capable of producing more fatty alcohol than a wild-type polypeptide corresponding to SEQ ID NO:2 when fatty alcohol production is determined by gas chromatography. In some embodiments, all fatty alcohols that are produced (e.g., all secreted fatty alcohols or total fatty alcohol) can be measured. In certain embodiments, total fatty alcohol production or secreted fatty alcohol production is determined by measuring production of representative fatty alcohols C14:0 (1-tetradecanol), C16:1 (cis $\Delta^9$-1-hexadecenol), C16:0 (1-hexadecanol), C18:1 (cis $\Delta^{11}$-1-octadecenol), and C18:0 (1-octadecanol) produced.

Fatty Alcohol Profile

In some embodiments, the FAR variants of the invention produce fatty alcohol profiles that differ from the fatty alcohol profiles produced by wild-type FAR. In some embodiments, a FAR variant of the present invention has at least about 70% (or at least about 75%, at least about 80%, at least about 85%, at least about 90%, at least about 91%, at least about 92%, at least about 93%, at least about 94%, at least about 95%; at least about 96%, at least about 97%, at least about 98%, or at least about 99%) sequence identity to SEQ ID NO:2 or SEQ ID NO:5 and comprises one or more amino acid substitutions as described herein (e.g., one or more amino acid substitutions or amino acid substitution sets listed in Table 2, Table 4, or Table 5), wherein a cell in which the FAR variant is expressed produces a fatty alcohol profile that differs from the fatty alcohol profile that is produced by a corresponding cell of the same type expressing the wild-type FAR from which the FAR variant derived. when cultured under the same conditions. For example, a cell (e.g., E. coli) expressing the FAR variant may produce a higher percentage of a particular fatty alcohol than the cell expressing the wild-type (e.g., a higher percentage of C14:0 or C16:1); or produce a lower percentage of a particular fatty alcohol than the cell expressing the wild-type (e.g., a lower percentage of C18:1); or produces a higher percentage of a range of fatty alcohols than the cell expressing the wild-type (such as a higher percentage of C10-C16 fatty alcohols). Generally, the fatty alcohol profiles produced by a host cell (e.g., E. coli) expressing a FAR variant and by a corresponding host cell of the same type expressing the wild-type FAR from which the FAR variant is derived are measured by culturing the cells under the same conditions, e.g, the same culture medium conditions (e.g., using LB or M9YE medium), the same temperature conditions (e.g., at 30° C. or at 37° C.), and for the same culture period conditions (e.g., culture for 24 hours).

A fatty alcohol profile refers to the chain length distribution in a composition containing fatty alcohols, or the chain length distribution of fatty alcohols produced by a cell. In some embodiments, the fatty alcohol profile contains saturated fatty alcohols, unsaturated fatty alcohols, or a mixture of saturated and unsaturated fatty alcohols. The degree of unsaturation and position within a chain can also vary. For example, a fatty alcohol may have 1, 2, 3, or more double bonds. Additionally, two fatty alcohols with the same chain length may each have a single double bond but at different positions. In some embodiments, the relative proportions of C14:0 (1-tetradecanol), C16:1 (cis $\Delta^9$-1-hexadecenol), C16:0

(1-hexadecanol), C18:1 (cis $\Delta^{11}$-1-octadecenol), and C18:0 (1-octadecanol) are measured to determine fatty alcohol profile. Fatty alcohol profiles can be measured using art known methods, such as methods described herein below.

The fatty alcohol profiles produced by FAR variants of the present invention are beneficial for various purposes, including but not limited to fuel compositions, detergent compositions, and cosmetic compositions. As is known in the art and described hereinbelow, fatty alcohols or fatty alcohol derivatives of specified chain length(s) are particularly useful in particular applications. Non-limiting examples include, for example, fatty alcohols or fatty alcohol derivatives having a chain length of C12-C14, which may be used in household care products; fatty alcohols or fatty alcohol derivatives having a chain length of C12-C18, which may be used in fuel compositions; and fatty alcohols or fatty alcohol derivatives having a chain length of C16-C18, which may be used in personal care products.

As described in Example 3 and Table 3, below, fatty alcohol profile is affected by the FAR variant selected, the background strain, and culture conditions (e.g., temperature). For example, the fatty alcohol profile of FAR variant number 436 includes 19% C14:0 when expressed in E. coli BW25113-ΔtorR at 30° C., and 38% C14:0 when expressed in E. coli W3110-ΔfhuA at 37° C. Accordingly, fatty alcohol profiles that are produced by the methods of the present invention can be influenced by adjusting conditions such as the FAR variant used, temperature, and background strain.

In some embodiments, the fatty alcohol compositions produced by the methods described herein have a fatty alcohol profile comprising at least about 60%, at least about 65%, at least about 70%, at least about 75%, at least about 80%, at least about 85%, at least about 90%, or at least about 95% C10-C18 fatty alcohols. In some embodiments, the fatty alcohol compositions produced by the methods described herein have a fatty alcohol profile comprising at least about 60%, at least about 65%, at least about 70%, at least about 75%, at least about 80%, at least about 85%, at least about 90%, or at least about 95% C10-C14 fatty alcohols. In some embodiments, the fatty alcohol compositions produced by the methods described herein have a fatty alcohol profile comprising at least about 60%, at least about 65%, at least about 70%, at least about 75%, at least about 80%, at least about 85%, at least about 90%, or at least about 95% C12-C16 fatty alcohols. In some embodiments, the fatty alcohol compositions produced by the methods described herein have a fatty alcohol profile comprising at least about 60%, at least about 65%, at least about 70%, at least about 75%, at least about 80%, at least about 85%, at least about 90%, or at least about 95% C14-C16 fatty alcohols. In some embodiments, the fatty alcohol compositions produced by the methods described herein have a fatty alcohol profile comprising at least about 60%, at least about 65%, at least about 70%, at least about 75%, at least about 80%, at least about 85%, at least about 90%, or at least about 95% C14-C18 fatty alcohols. In some embodiments, the fatty alcohol compositions produced by the methods described herein have a fatty alcohol profile comprising at least about 60%, at least about 65%, at least about 70%, at least about 75%, at least about 80%, at least about 85%, at least about 90%, or at least about 95% C16-C18 fatty alcohols. In some embodiments, the fatty alcohol compositions produced by the methods described herein have a fatty alcohol profile comprising less than about 20%, less than about 15%, less than about 10%, or less than about 5% 018 fatty alcohols.

In some embodiments, the fatty alcohol compositions produced by the methods described herein have a fatty alcohol profile comprising a mixture of 1-tetradecanol (C14:0), 1-hexadecanol (C16:0), 1-octadecanol (C18:0), cis $\Delta^9$-1-hexadecenol (C16:1), and/or cis $\Delta^{11}$-1-octadecenol (C18:1) fatty alcohols. In some embodiments, the fatty alcohol profile comprises at least about 10%, at least about 15%, at least about 20%, at least about 25%, at least about 30%, at least about 35%, at least about 40%, at least about 45%, at least about 50%, at least about 55%, at least about 60% or more of C14:0 fatty alcohol. In some embodiments, the fatty alcohol profile further comprises at least about 20%, at least about 25%, at least about 30%, at least about 35%, at least about 40%, at least about 45%, at least about 50%, at least about 55%, at least about 60%, at least about 65%, or more of C16:1 fatty alcohol. In some embodiments, the fatty alcohol profile further comprises at least about 10%, at least about 15%, at least about 20%, at least about 25%, at least about 30%, at least about 35%, at least about 40%, at least about 45%, at least about 50% or more of C16:0 fatty alcohol. In some embodiments, the fatty alcohol profile further comprises up to about 5%, up to about 10%, up to about 15%, up to about 20%, or up to about 25% of C18:1 fatty alcohol.

In some embodiments, the fatty alcohol composition further comprises one or more of another C8-C20 fatty alcohol, for example, 1-octanol (C8:0), 1-decanol (C10:0), 1-dodecanol (C12:0), 1-heptadecanol (C17:0), 1-octadecanol (C18:0), or 1-icosanol (C20:0).

In some embodiments, the fatty alcohol composition has a fatty alcohol profile comprising a mixture of 1-tetradecanol (C14:0), 1-hexadecanol (C16:0), 1-octadecanol (C18:0), cis $\Delta^9$-1-hexadecenol (C16:1), and/or cis $\Delta^{11}$-1-octadecenol (C18:1) fatty alcohols in the following proportions (where the total percentage of fatty alcohols is 100%): about 10%-30% C14:0, about 30%-45% C16:1, about 30%-20% C16:0, and about 30%-5% C18:1. In some embodiments, the fatty alcohol composition has a fatty alcohol profile comprising a mixture of 1-tetradecanol (C14:0), 1-hexadecanol (C16:0), 1-octadecanol (C18:0), cis $\Delta^9$-1-hexadecenol (C16:1), and/or cis $\Delta^{11}$-1-octadecenol (C18:1) fatty alcohols in the following proportions: about 15%-35% C14:0, about 35%-45% C16:1, about 30%-15% C16:0, and about 20%-5% 018:1. In some embodiments, the fatty alcohol composition has a fatty alcohol profile comprising a mixture of 1-tetradecanol (C14:0), 1-hexadecanol (C16:0), 1-octadecanol (C18:0), cis $\Delta^9$-1-hexadecenol (C16:1), and/or cis $\Delta^{11}$-1-octadecenol (C18:1) fatty alcohols in the following proportions: about 20%-30% C14:0, about 35%-25% C16:1, about 30%-40% C16:0, and about 15%-5% C18:1. In some embodiments, the fatty alcohol composition has a fatty alcohol profile comprising a mixture of 1-tetradecanol (C14:0), 1-hexadecanol (C16:0), 1-octadecanol (C18:0), cis $\Delta^9$-1-hexadecenol (C16:1), and/or cis $\Delta^{11}$-1-octadecenol (018:1) fatty alcohols in the following proportions: about 20%-40% C14:0, about 30%-40% C16:1, about 30%-20% C16:0, and about 20%-0% C18:1. In some embodiments, the fatty alcohol composition has a fatty alcohol profile comprising a mixture of 1-tetradecanol (C14:0), 1-hexadecanol (C16:0), 1-octadecanol (C18:0), cis $\Delta^9$-1-hexadecenol (C16:1), and/or cis $\Delta^{11}$-1-octadecenol (C18:1) fatty alcohols in the following proportions: about 15%-30% C14:0, about 40%-45% C16:1, about 20%-25% C16:0, and about 25%-0% C18:1. In some embodiments, the fatty alcohol composition has a fatty alcohol profile comprising a mixture of 1-tetradecanol (C14:0), 1-hexadecanol (C16:0), 1-octadecanol (C18:0), cis $\Delta^9$-1-hexadecenol (C16:1), and/or cis $\Delta^{11}$-1-octadecenol (C18:1) fatty alcohols in the following proportions: about 25%-30% C14:0, about 40%-45% C16:1, about 25%-20% C16:0, and about 10%-5% C18:1. In some embodiments, the fatty alcohol composition has a fatty alcohol profile comprising a mixture of 1-tetradecanol (C14:0), 1-hexadecanol (C16:0), 1-octadecanol (C18:0), cis $\Delta^9$-1-hexadecenol (C16:1), and/or cis $\Delta^{11}$-1-octadecenol (C18:1) fatty alcohols in the following proportions: about 20%-30% C14:0, about 35%-40% C16:1, about 35%-25% C16:0, and about 10%-5% C18:1. In some embodiments, the fatty alcohol composition has a profile that further comprises less than 5%, less than 4%, less than 3%, less than 2%, or less than 1% of C18:0.

In some embodiments, the fatty alcohol compositions produced by the methods described herein have a fatty alcohol profile comprising an increased amount of C14:0 (1-tetradecanol), an increased amount of C16:1 (cis $\Delta^9$-1-hexadecenol), a decreased amount of C16:0 (1-hexadecanol), and/or a decreased amount of C18:1 (cis $\Delta^{11}$-1-octadecenol) relative to a wild-type FAR from which the FAR variant is derived (e.g., SEQ ID NO:2). In some embodiments, the fatty alcohol composition has a fatty alcohol profile comprising at least 5%, at least 10%, at least 15%, at least 20%, at least 25%, at least 30%, at least 35%, at least 40%, at least 45%, at least 50%, at least 55%, at least 60%, at least 70%, at least 80%, at least 90%, at least 100%, at least 150%, at least 200%, at least 250%, at least 300%, at least 400%, at least 500% or more C14:0; at least 5%, at least 10%, at least 15%, at least 20%, at least 25%, at least 30%, at least 35%, at least 40%, at least 45%, at least 50% or more C16:1; at least 5%, at least 10%, at least 15%, at least 20%, at least 25%, at least 30%, at least 35%, at least 40%, at least 45%, at least 50% or less C16:0; and at least 5%, at least 10%, at least 15%, at least 20%, at least 25%, at least 30%, at least 35%, at least 40%, at least 45%, at least 50%, at least 55%, at least 60%, at least 70%, at least 80%, at least 90% or less C18:1 relative to the wild-type FAR from which the FAR variant is derived.

In some embodiments, the fatty alcohol compositions produced by the methods described herein have a fatty alcohol profile comprising an increased amount of C14:0 (1-tetradecanol), an increased amount of C16:1 (cis $\Delta^9$-1-hexadecenol), an increased amount of C16:0 (1-hexadecanol), and/or a decreased amount of C18:1 (cis $\Delta^{11}$-1-octadecenol) relative to a wild-type FAR from which the FAR variant is derived (e.g., SEQ ID NO:2). In some embodiments, the fatty alcohol composition has a fatty alcohol profile comprising at least 5%, at least 10%, at least 15%, at least 20%, at least 25%, at least 30%, at least 35%, at least 40%, at least 45%, at least 50%, at least 55%, at least 60%, at least 70%, at least 80%, at least 90%, at least 100%, at least 150%, at least 200%, at least 250%, at least 300%, at least 400%, at least 500% or more C14:0; at least 5%, at least 10%, at least 15%, at least 20%, at least 25%, at least 30%, at least 35%, at least 40%, at least 45%, at least 50% or more C16:1; at least 5%, at least 10%, at least 15%, at least 20%, at least 25%, at least 30%, at least 35%, at least 40%, at least 45%, at least 50% or more C16:0; and at least 5%, at least 10%, at least 15%, at least 20%, at least 25%, at least 30%, at least 35%, at least 40%, at least 45%, at least 50%, at least 55%, at least 60%, at least 70%, at least 80%, at least 90% or less C18:1 relative to the wild-type FAR from which the FAR variant is derived.

In some embodiments, the fatty alcohol compositions produced by the methods described herein have a fatty alcohol profile comprising an increased amount of C14:0 (1-tetradecanol), a decreased amount of C16:1 (cis $\Delta^9$-1-hexadecenol), an increased amount of C16:0 (1-hexadecanol), and/or a decreased amount of C18:1 (cis $\Delta^{11}$-1-octadecenol) relative to a wild-type FAR from which the FAR variant is derived (e.g., SEQ ID NO:2). In some embodiments, the fatty alcohol composition has a fatty alcohol profile comprising at least 5%, at least 10%, at least 15%, at least 20%, at least 25%, at least 30%, at least 35%, at least 40%, at least 45%, at least 50%, at least 55%, at least 60%, at least 70%, at least 80%, at least 90%, at least 100%, at least 150%, at least 200%, at least 250%, at least 300%, at least 400%, at least 500% or more C14:0; at least 5%, at least 10%, at least 15%, at least 20%, at least 25%, at least 30%, at least 35%, at least 40%, at least 45%, at least 50% or less C16:1; at least 5%, at least 10%, at least 15%, at least 20%, at least 25%, at least 30%, at least 35%, at least 40%, at least 45%, at least 50% or more C16:0; and at least 5%, at least 10%, at least 15%, at least 20%, at least 25%, at least 30%, at least 35%, at least 40%, at least 45%, at least 50%, at least 55%, at least 60%, at least 70%, at least 80%, at least 90% or less C18:1 relative to the wild-type FAR from which the FAR variant is derived.

Fatty Alcohol Measurements

FAR fatty alcohol production and fatty alcohol profiles (i.e., chain length distribution) can be measured can be determined by methods described in the Examples section (e.g., Examples 2-4) and/or using any other methods known in the art. Fatty alcohol production by an organism or culture expressing a FAR variant can be described as an absolute quantity (e.g., moles/liter of culture) or as a fold-improvement over production by an organism or culture expressing a reference FAR sequence (e.g., a wild-type FAR or a different FAR variant).

Fatty alcohol production and/or fatty alcohol profiles by a microorganism expressing a FAR polypeptide can be measured, for example, using gas chromatography. In general, cells expressing a FAR variant are cultured, total or secreted fatty alcohols are isolated, and fatty alcohol amount and/or content is measured.

Any number of assays can be used to determine whether a host cell expressing a FAR variant as described herein produces an increased amount of fatty alcohols (e.g., at least 1.5 times more fatty alcohols) compared to a corresponding cell of the same type expressing a wild-type FAR, and/or whether a host cell expressing a FAR variant as described herein produces a different fatty alcohol profile compared to a corresponding cell of the same type expressing a wild-type FAR, including exemplary assays described herein. In one exemplary assay, fatty alcohols produced by productive E. coli strains are collected by extraction of 0.5 mL E. coli whole culture (culture medium plus cells) expressing a FAR variant using 1 mL of isopropanol:methyl t-butyl ether (MTBE) (4:6 ratio). The extraction mixture is allowed to shake for 2 hours at room temperature. The extraction mixture is then centrifuged, the upper organic phase transferred into a vial and analyzed by the gas chromatography (GC) equipped with flame ionization detector (FID) and DB-5MS column (length 30 m, I.D. 0.32 mm, film 0.25 um), starting at 150° C., and increasing the temperature at a rate of 25° C./min to 246° C., then holding for 1.81 min.

Fatty alcohol production by a host cell expressing a FAR variant can also be compared to a comparable cell ("control cell") expressing a reference sequence, such as a wild-type FAR or a different FAR variant. Typically the FARs of the host and control cells are under control of the same promoter and the cells are maintained under the same conditions. For illustration, fatty alcohol production can be measured in E. coli (e.g., strain E. coli BW25113), using FARs under the control of the same promoter (e.g., the lac promoter), where the cells are cultured at 37° C. and fatty alcohol produced after 24 hours of culture are measured.

Fatty alcohol profiles (i.e., chain length distribution) can be determined, for example, using gas chromatography and/or mass spectroscopy. In an exemplary assay, fatty alcohols are produced as described above and the identification of individual fatty alcohols is performed by comparison to commercial standards (Sigma Chemical Company, 6050 Spruce St. Louis, Mo. 63103). The identity of the peaks can also be confirmed by running the samples through a gas chromatography (GC) equipped with mass spectrometer (MS) as needed.

IV. Far Variants

In one aspect, the sequences of the improved FAR polypeptides described herein include one or more mutations (e.g. substitutions) as compared to SEQ ID NO:2), such that the resulting FAR variant polypeptide has improved characteristics and/or properties as compared to the wild-type FAR, such as, for example, increased fatty alcohol production. In a related aspect, the invention provides a recombinant FAR variant comprising one or more mutations (e.g. substitutions) as compared to a wild-type FAR polypeptide from *M. aquaeolei* (SEQ ID NO:5), Substitutions that yield increased fatty alcohol production under these conditions are described herein. These substitutions can be used singly or in any combinations. In some embodiments, a FAR variant comprises a single substitution set, e.g., a substitution set of any of Tables 2, 4, or 5. In some embodiments, a FAR variant comprises two or more substitution sets. As is apparent from Table 2, combinations of substitutions can be selected so as to provide fatty alcohol production under the conditions specified that is anywhere from about 1.5-fold greater than that of the wild-type FAR of SEQ ID NO:2 to more than four-fold greater. In some embodiments, combinations of substitutions can be selected so as to provide fatty alcohol production under the conditions specified that is at least about 1.5-fold, about 2-fold, about 3-fold, about 4-fold, about 5-fold, about 6-fold, about 7-fold, about 8-fold, about 9-fold, or about 10-fold greater than that of the wild-type FAR (e.g., SEQ ID NO:2 or SEQ ID NO:5).

Improved or increased fatty alcohol production of a FAR variant relative to a reference polypeptide can be detected by comparing fatty alcohol production by host cells expressing the FAR variant to fatty alcohol production by host cells (of the same type) expressing the reference protein (which may be a wild-type or variant FAR) or a host cell not expressing exogenous FAR. It will be understood by those of skill that it is desirable that the only parameter varied between the cells is the FAR being expressed (e.g., a wild-type FAR or a FAR variant). Thus, for example, the FAR variant and reference polypeptide will be encoded by polynucleotides with the same sequence except at codons corresponding to substitutions (typically a sequence that is codon optimized for the cell type) and will be controlled by the same promoter, and cells expressing the polypeptides will be cultured under the same conditions. Improved or increased fatty alcohol production of a cell expressing a FAR variant relative to a cell not expressing an exogenous FAR may also be measured.

For bacterial host cells, such as *E. coli*, exemplary assay conditions are described in Examples 2, 3, and 4. In one approach, *E. coli* are transformed with an expression cassette comprising a sequence encoding the FAR variant or the reference protein (e.g., wild-type FAR, such as FAR Maa or FAR Maq) and an operably linked promoter. The cells may be stably transformed. The promoter may be constitutive or inducible. The lac promoter may be used. The cells are grown in medium (e.g., M9YE medium containing 0.5-5% glucose; Dunny, G. M., and Clewell, D. B., 1975. *J. Bacteriol.* 124: 784-790) and any appropriate selection agents (see Examples). In one approach the cells are cultured for a period of time (e.g., 18 hours or 24 hours) and fatty alcohol production is assayed. Typically, total fatty alcohol is assayed, but the amount of fatty alcohol secreted into the medium may be assayed if desired. In some embodiments, the promoter is inducible. For example. cells may be grown (e.g., to an $OD_{600}$ of 0.6-0.8), at which point expression of the heterologous FAR gene is induced (e.g., by addition of IPTG to a 1 mM final concentration when the lac promoter is used). Incubation is continued for 24 hours at 30° (alternatively 37° C. or 40° C.) and fatty alcohol production is assayed.

It will be apparent that the same assays may be used to assess FAR activity of functionally active fragments of FAR variants.

It has been discovered that certain substitutions, both singly and in various combinations, yield improvements in fatty alcohol production compared to the wild-type FAR (see Tables 2 and 4). These substitutions may include 1, 2, 3, 4, 5, 6, 7, 8, 9, 10, 15, 20 or more than 20 substitutions. In some embodiments, the improved FAR polypeptides of the invention differ from SEQ ID NO:2 in up to 20 residues. In some embodiments, the improved FAR polypeptides of the invention differ from SEQ ID NO:5 in up to 20 residues. In some embodiments, the improved FAR polypeptides differ from SEQ ID NO:2, or differ from SEQ ID NO:5, in up to 15 residues, sometimes in up to 12 residues, and sometimes in up to 10 residues.

As shown in Table 2, it can be seen that substitutions introduced at numerous different amino acid (also referred to herein as "residue") positions in the wild-type FAR of SEQ ID NO:2 yield improved FAR polypeptides capable of producing increased yields of total fatty acid as compared to this wild-type FAR. Similarly, as shown in Table 4, substitutions in SEQ ID NO:5 increase fatty alcohol yield. Single amino acid changes at specified positions give rise to 2-fold or greater increases in fatty alcohol production.

Accordingly, in some embodiments, the improved FAR polypeptide of the invention contains at least one amino acid substitution relative to SEQ ID NO:2 and is capable of producing at least about 1.5-fold more fatty alcohol than a wild-type FAR corresponding to SEQ ID NO:2 when assayed under the same conditions. In some embodiments, the improved FAR polypeptide is capable of producing at least about 1.5 more fatty alcohol than a wild-type FAR consisting of SEQ ID NO:2 when assayed under the same conditions. In some embodiments, the improved FAR polypeptide of the invention contains at least one amino acid substitution relative to SEQ ID NO:5 and is capable of producing at least about 1.5-fold more fatty alcohol than a wild-type FAR corresponding to SEQ ID NO:5 when assayed under the same conditions.

While single substitutions are beneficial, it can be seen from the examples (e.g., Tables 2, 4, and 5) that combinations of substitutions can yield further benefit. Thus, combinations of substitutions can be selected to yield improved FAR enzymes capable of producing specified levels of total fatty alcohol when cultured under the conditions described herein (e.g., in Example 4). For example, improved FAR polypeptides can be readily designed that yield from 1.5, 1.8, 2.0, 2.2, 2.4, 2.6, 2.8, 3.0, 3.2, 3.4, 3.6, 3.8, 4.0, 4.5 or even higher-fold increases in total fatty alcohol compared to the wild-type FAR of SEQ ID NO:2. For example, in some embodiments, FAR variants can be readily designed that produce about 1.5, 1.8, 2.0, 2.2, 2.4, 2.6, 2.8, 3.0, 3.2, 3.4, 3.6, 3.8, 4.0, 4.5, 5.0, 5.5, 6.0, 6.5, 7.0, 7.5, 8.0, 8.5, 9.0, 9.5, 10.0 or even higher-fold increases in total fatty alcohol compared to the wild-type FAR of SEQ ID NO:2 or SEQ ID NO:5.

Accordingly, in some embodiments, a FAR variant of the present invention contains at least two, at least three, at least four, at least five, or more amino acid substitutions relative to wild-type FAR (e.g., SEQ ID NO:2 or SEQ ID NO:5) and is capable of producing at least about 1.5-fold, at least about 2-fold, at least about 3-fold, at least about 4-fold, at least about 5-fold, at least about 6-fold, at least about 7-fold, at least about 8-fold, at least about 9-fold, or at least about 10-fold more fatty alcohol than the wild-type FAR (e.g., SEQ ID NO:2 or SEQ ID NO:5). In some embodiments, the improved FAR polypeptide contains at least two amino acid substitutions relative to SEQ ID NO:2 (or SEQ ID NO:5) and is capable of producing at least about 1.5-fold, at least about 2.0-fold, at least about 2.5-fold, at least about 3.0-fold, at least about 3.5-fold, at least about 4.0-fold more fatty alcohol than a wild-type FAR corresponding to SEQ ID NO:2 (or SEQ ID NO:5) when assayed under the same conditions. In some embodiments, the improved FAR polypeptide contains at least three amino acid substitutions relative to SEQ ID NO:2 (or SEQ ID NO:5) and is capable of producing at least about 1.5-fold, at least about 2.0-fold, at least about 2.5-fold, at least about 3.0-fold, at least about 3.5-fold, at least about 4.0-fold more fatty alcohol than a wild-type FAR corresponding to SEQ ID NO:2 (or SEQ ID NO:5) when assayed under the same conditions. In some embodiments, the improved FAR polypeptide contains at least four amino acid substitutions relative to SEQ ID NO:2 (or SEQ ID NO:5) and is capable of producing at least about 1.5-fold, at least about 2.0-fold, at least about 2.5-fold, at least about 3.0-fold, at least about 3.5-fold, at least about 4.0-fold more fatty alcohol than a wild-type FAR corresponding to SEQ ID NO:2 (or SEQ ID NO:5) when assayed under the same conditions. In some embodiments, the improved FAR polypeptide contains at least five amino acid substitutions relative to SEQ ID NO:2 (or SEQ ID NO:5) and is capable of producing at least about 1.5-fold, at least about 2.0-fold, at least about 2.5-fold, at least about 3.0-fold, at least about 3.5-fold, at least about 4.0-fold more fatty alcohol than a wild-type FAR corresponding to SEQ ID NO:2 (or SEQ ID NO:5) when assayed under the same conditions.

In some embodiments, a FAR variant comprises at least about 70% (or at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%) sequence identity to SEQ ID NO:2 and comprises an amino acid substitution relative to SEQ ID NO:2 at one or more positions selected from A2, T3, Q4, Q5, Q6, Q7, N8, G9, A10, A12, G14, E17, Q18, K22, V24, L33, I42, G50, L54, R60, H61, P62, A63, R65, L69, E71, A73, S74, S76, V77, H83, E87, T91, L93, H98, T101, G102, V104, S107, G110, L111, T112, P113, R115, R117, A120, G121, Q122, A125, N128, S132, N134, E137, E138, D140, A142, K144, L148, E151, V153, N160, A162, N174, N177, Q180, V185, I186, P188, T197, D198, E202, E204, E205, V207, L209, D212, K213, V217, R220, K224, L226, E227, K229, R236, E237, S244, D245, T246, L257, K260, A261, S263, G264, S266, I269, S283, I287, E288, V290, A295, A299, E303, V305, S306, V318, I328, L330, S331, L332, A333, S339, G340, Q341, R342, G350, G351, K359, L364, M365, A366, T370, A374, D376, Q377, Y380, R381, T384, A389, D396, V397, V398, V399, G400, G401, R403, V404, P405, L406, A409, G410, A412, M413, A416, Q418, E421, N427K, D429, T430, R432, S433, T436, I437, F440, A443, P444, Y446, S452, S458, R459, L463, D464, V466, A472, 0474, L479, I484, G487, N490, E496, K498, L499, Y500, S501, L502, A504, A505, D506, T507, 8508, K509, K510, A511, and A512, wherein the position is numbered with reference to SEQ ID NO:2. In some embodiments, the variant comprises one or more amino acid substitutions selected from A2D/F/G/H/I/P/N/Q/T/V/W, T3R, Q4R, Q5S, Q6P, Q7N, N8K/S, G9D/F, A10T, A12T/V, G14N/R/V/W, E17D, Q18I, K22E, V24I, L33V, I42L, G50S/V, L54P, R60H, H61R, P62S, A63R/Y, R65G/Q/Y, L69E/Q, E71K, A73K/V, S74K/P, S76K/N/R, V77A/I, H83R, E87G/V, T91I/R, L93V, H98P/R, T101L, G102C, V104I/M, S107C/L/W, G110D, L111S, T112A, P113D/L, R115A/H, R117D, A120V, G121H/S, Q122R, A125V, N128H, S132G, N134K/R/S, E137L, E138L/Q, D140C, A142V, K144Q, L148E, E151L, V153I, N160S, A162T, N174C, N177Q/R/T, Q180H/R, V185A/I, I186A/G/Y, P188A/I/M/S, T197P, D198Q, E202G, E204G, E205G/P, V207I/L, L209K/N, D212R, K213R, V217L, R220C, K224R, L226A/M, E227A/G/H/R/T, K229R, R236K, E237L, S244A/F/G/H/P, D245N, T246A, L257K, K260R/T, A261D, S263P, G264S, S266A, I269T, S283E/F/K/M/T/V, I287L, E288Q, V290I, A295T/V, A299T, E303G, V305I, S306F/H/N/W, V318I, I328T, L330V, S331V, L332S, A333T, S339G/V, G340P/S/V, Q341K, R342L, G350S, G351C, K359L, L364F/I, M365N, A366T/V, T370A/I, A374K/Y, D376P, Q377C/K/Y, Y380K/N/R, R381C, T384R, A389I/L/M/V, D396G, V397I/L, V398Y, V399T, G400A/L, G401A/C/I/L/S/V, R403C/S, V404A, P405A/C/F/G/L/S/V/W, L406Y, A409V/W/Y, G410A/C/H/N/Q/R/S, A412C/F/M/V, M413L/R, A416L/V, Q418I/R/V/Y, E421I/L/N/P/R/S/V/Y, N427K, D429E/K/N/Q/R, T430H/I/R, R432C/Q, S433F/H/K/L/N/W, T436D/K/Q, I437V, F440L, A443T, P444S, Y446H, S452A/G/N, S458G/L/M/Q, R459H, L463E/T, D464G, V466E/Q/R, A472V, Q474R, L479Q, I484V, G487R/S/T/Y, N490S, E496A, K498A, L499A/H/I/N/P/R/S, Y500C/G/H/L/N/P/Q/R/S/W, S501G/R, L502A/P/Q/R/S, A504G/R, A505K, D506G/S, T507A/G/P/R/S, R508D/G/H, K509D/E/G/H/N/R/S/Y, K510A/D/G/P/S/Y, A511G/I/K/P/Q/R/S/T, and A512K/S/T.

In some embodiments, a FAR variant comprises at least about 70% (or at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%) sequence identity to SEQ ID NO:2 and comprises a substitution relative to SEQ ID NO:2 at one or more positions selected from position 2, position 134, position 138, position 140, position 421, position 458, position 510, and position 511, wherein the position is numbered with reference to SEQ ID NO:2. The residues at positions 2, 134, 138, 140, 421, 458, 510, and 511 have been identified by the inventors as being important for fatty alcohol production, as shown in the Examples below. As shown below and in FIG. 2, positions 2, 134, 138, 140, 421, 458, 510, and 511 of SEQ ID NO:2 correspond to positions 2, 135, 139, 141, 422, 459, 511, and 512, respectively, of SEQ ID NO:5. In some embodiments, the amino acid residue at position 2 relative to SEQ ID NO:2 is alanine (A2); the amino acid residue at position 134 relative to SEQ ID NO:2 is asparagine (N134); the amino acid residue at position 138 relative to SEQ ID NO:2 is glutamic acid (E138); the amino acid residue at position 140 relative to SEQ ID NO:2 is aspartic acid (D140); the amino acid residue at position 421 relative to SEQ ID NO:2 is glutamic acid (E421); the amino acid residue at position 458 relative to SEQ ID NO:2 is serine (S458); the amino acid residue at position 510 relative to SEQ ID NO:2 is lysine (K510); and the amino acid residue at position 511 relative to SEQ ID NO:2 is alanine (A511). In some embodiments, a FAR variant comprises an amino acid substitution at residue A2 that is selected from aspartic acid, phenylalanine, glycine, histidine, isoleucine, asparagine, proline, glutamine, threonine, valine, or tryptophan (A2D/F/G/H/I/N/P/Q/T/V/W). In some embodiments, a FAR variant comprises an amino acid substitution at residue N134 that is selected from lysine, arginine, or serine (N134K/R/S). In some embodiments, a FAR variant comprises an amino acid substitution at residue E138 that is selected from leucine or glutamine (E138L/Q). In some embodiments, a FAR variant comprises an amino acid substitution at residue D140 that is cysteine (D140C). In some embodiments, a FAR variant comprises an amino acid substitution at residue E421 that is selected from isoleucine, leucine, asparagine, proline, arginine, serine, valine, or tyrosine (E421I/L/N/P/R/S/V/Y). In some embodiments, a FAR variant comprises an amino acid substitution at residue S458 that is selected from glycine, leucine, methionine, or glutamine (S458G/L/M/Q). In some embodiments, a FAR variant comprises an amino acid substitution at residue K510 that is selected from alanine, aspartic acid, glycine, proline, serine, or tyrosine (K510A/D/G/P/S/Y). In some embodiments, a FAR variant comprises an amino acid substitution at residue A511 that is selected from glycine, isoleucine, lysine, proline, glutamine, arginine, serine, or threonine (A511G/I/K/P/Q/R/S/T).

It is notable that positions 511 of SEQ ID NO:2 and 512 of SEQ ID NO:5 are very close to the carboxy-terminus of the FAR protein. Indeed, substitutions at one or more of residues 501-511 (numbered accoding to SEQ ID NO:2) are found in many FAR variants that support increased fatty alcohol production, and substitutions at 501, 502, 504, 507, 509, 510, and 511 were found in both *M. algicola* FAR and *M. aquaeolei* FAR (see Table 4A). These residues are in the "Sterile" pfam domain (see, e.g., the website pfam.sanger.ac.uk/). Further, without intending to be bound by a particular mechanism, the C-termini of *M algicola* FAR and *M. aquaeolei* FAR (RK-KAA and RKKAA) are characterized by the motif +++HH where "+" is a positively charged amino acid (e.g., K, R) and "H" is a hydrophobic amino acid (e.g., A, I, L, F, V, P and G). Thus, in one aspect a FAR variant of the invention has at least about 75%, at least about 80%, at least about 85%, at least about 90%, at least about 93%, at least about 95%, at least about 97%, and at least about 98% identity to a wild-type FAR (e.g., SEQ ID NO: 2 and/or SEQ ID NO: 5) and comprises a C-terminal amino acid sequence that is not the +++HH motif.

In some embodiments, the FAR variant further comprises a substitution relative to SEQ ID NO:2 at one or more of position 188, position 405, and position 418, wherein the positions are numbered with reference to SEQ ID NO:2. The residues at positions 188, 405, and 418 have been identified by the inventors as being important for fatty alcohol production, as shown in the Examples below. As shown below and in FIG. 2, positions 188, 405, and 418 of SEQ ID NO:2 correspond to positions 189, 406, and 419, respectively, of SEQ ID NO:5. In some embodiments, the amino acid residue at position 188 relative to SEQ ID NO:2 is proline (P188); the amino acid residue at position 405 relative to SEQ ID NO:2 is proline (P405); and the amino acid residue at position 418 relative to SEQ ID NO:2 is glutamine (Q418). In some embodiments, a FAR variant comprises an amino acid substitution at residue P188 that is selected from alanine, isoleucine, methionine, or serine (P188A/I/M/S). In some embodiments, a FAR variant comprises an amino acid substitution at residue P405 that is selected from alanine, cysteine, phenylalanine, glycine, leucine, serine, valine, or tryptophan (P405A/C/F/G/L/S/V/W). In some embodiments, the FAR variant comprises an amino acid substitution at residue Q418 that is selected from isoleucine, arginine, valine, and tyrosine (Q418I/R/V/Y).

In some embodiments, improved FAR polypeptides comprise at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% identity to the wild-type FAR of SEQ ID NO:2, that include substitutions at one or more of positions 2, 134, 138, 188, 405, 418 and 511 when aligned to SEQ ID NO:2. As shown below and in FIG. 2, positions 2, 134, 138, 188, 405, and 418 correspond to positions 2, 135, 139, 189, 406, and 419, respectively, of SEQ ID NO:5. In some embodiments, the substitution at position 2 is H, T, D, F, V, G, Q, P or I (particularly G, F, Q and D); the substitution at position 134 is R, K or S (particularly S); the substitution at position 138 is Q or L (particularly Q); the substitution at position 188 is S; the substitution at position 405 is any amino acid; preferably V, S, F, G, C, L, S, A, W (particularly an aliphatic amino acid); the substitution at position 418 is V, R, I or Y; and the substitution at position 511 is any amino acid and particularly T, P, G, S, K, Q or R, and more particularly T and Q. In some embodiments the improved FAR will comprises a sequence comprising at least 85%, at least 90%, at least 95%, and at least 97% sequence identity to SEQ ID NO: 2 and a substitution at position 134 and 511 when aligned with SEQ ID NO: 2. In some embodiments, the improved FAR enzyme will comprise additional substitutions at one or more positions 303, 401, 416, 499, 505, 508, 509, 510 when aligned to SEQ ID NO:2. In some particular embodiments such optional additional substitutions include one or more of the following substitutions (relative to SEQ ID NO:2): 303G, 401 (aliphatic amino acid or S); 418 (aliphatic amino acid or R; preferably I or V), 416 (V or L; preferably L), 499 (R, P, S, H, N, I, or A), 505K, 508G and 509 (G, H, E, R, D, S or N) and 510 (S, D or Y).

In some embodiments, the improved FAR polypeptides comprise at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% identity to the wild-type FAR of SEQ ID NO:2, that include substitutions at one or more of positions A2, N134, E138, P188, P405, Q418 and A511 when aligned to SEQ ID NO:2. In some embodiments, the substitution at position 2 is H, T, D, F, V, G, Q, P or I (particularly G, F, Q and D); the substitution at position 134 is R, K or S (particularly S); the substitution at position 138 is Q or L (particularly Q); the substitution at position 188 is S; the substitution at position 405 is any amino acid; preferably V, S, F, G, C, L, S, A, W (particularly an aliphatic amino acid); the substitution at position Q418 is V, R, I or Y; and the substitution at position A511 is any amino acid and particularly T, P, G, S, K, Q or R, and more particularly T and Q. In some embodiments the improved FAR will comprises a sequence comprising at least 85%, at least 90%, at least 95%, and at least 97% sequence identity to SEQ ID NO:2 and a substitution at position N134 and A511 when aligned with SEQ ID NO: 2. In some embodiments, the improved FAR enzyme will comprise additional substitutions at one or more of positions E303, G401, A416, L499, L502, A505, R508, K509, and K510 when aligned to SEQ ID NO:2. In some particular embodiments such optional additional substitutions include one or more of the following substitutions (relative to SEQ ID NO:2): E303G, G401 (aliphatic amino acid or S); Q418 (aliphatic amino acid or R; preferably I or V), A416 (V or L; preferably L), L499 (R, P, S, H, N, I, or A), L502 (S, Q, A, R, or P), A505K, R508G and K509 (G, H, E, R, D, S or N) and 510 (S, D or Y). The additional substitutions may also be selected from any of the substitutions in Table 2.

In some embodiments, the improved FAR polypeptide comprises a sequence having at least 75%, at least 80%, at least 85%, at least 90%, at least 91%, at least 92%, at least 93%, at least 94%, at least 95%, at least 96%, at least 97%, at least 98%, or at least 99% sequence identity to sequence SEQ ID NO:2 and a substitution at position 511. In particular embodiments, the improved FAR polypeptide comprises an amino acid substitution at position 511: T, P, G, S, K, Q, or R relative to SEQ ID NO:2.

In some embodiments, the improved FAR polypeptide comprises the following amino acid substitutions relative to SEQ ID NO:2: position N134: R, K or S; position E138: Q or L; position P188: S: and position A511: T, P, G, S, K, Q and R. In other particular embodiments, the improved FAR enzyme comprises the following amino acid substitutions relative to SEQ ID NO:2; position 134: S; position 138: L; position 188: S; and position 511: T.

In some embodiments, the improved FAR polypeptide comprises the following amino acid substitution relative to SEQ ID NO:2: a) position 134 and position 188 and particularly position 134 is S and position 188 is S; b) position 134, position 138 and position 188, and particularly position 134 is S; position 138 is Q; and position 188 is S; c) position 188 and position 511, and particularly position 188 is S and position 511 is T; d) position 134, position 138, position 188, position 405 and position 511 and particularly 134 is S; 138 is Q; 188 is S; 405 is V and 511 is T. The improved FAR polypeptide may include further substitutions such as 1, 2, 3, 4, 5, 6, 7 or more substitutions relative to SEQ ID NO:2. The one or more substitutions may be selected from positions 2, 303, 401, 416, 418, 499, 502, 505, 508, or 509 relative to SEQ ID NO:2, and more particularly 2 (D, V, F, T, N, H, W, P, I, Q, or G), 303 (G), 401 (V, I, L, S, or A) 412 (V, F or C), 416 (L or V), 418 (R, V, I, or Y), 499 (R, P, S, H, N, I, or A), 502 (S, Q, A, R, or P), 505 (K), 508 (G, H or D), or 509 (D, H, S, E, G, N, R or Y) relative to SEQ ID NO:2.

In some embodiments, the improved FAR polypeptide comprises an amino acid substitution at one or more positions corresponding to position 2, 134, 140, 107, 237, 410, 421, 429, 433, 458, 499, 502, 504, 509, or 511 of SEQ ID NO:2 or a sequence having at least 75%, at least 80%, at least 85%, at least 90%, at least 93%, at least 95%, at least 97%, or at least 98% identity with SEQ ID NO:2 and optionally at least 1, at least 2, at least 3, at least 4, at least 5, at least 6, at least 7, or at least 8 further substitutions.

In some embodiments, a FAR variant comprises at least about 70% (or at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%) sequence identity to SEQ ID NO:5 and comprises an amino acid substitution relative to SEQ ID NO:5 at one or more positions selected from A2, Q4, Q5, H8, A9, A45, P63, R66, E72, A74, S77, E88, A108, G111, G113, D116, N135, D141, Q181, D199, E205, E238, A374, A375, P406, D411, R412, D422, D430, S434, I438, N459, E497, Y501, S502, L503, T505, Q508, R509, K510, K511, A512, and A513, wherein the position is numbered with reference to SEQ ID NO:5. In some embodiments, the variant comprises one or more amino acid substitutions selected from A2F/G/H/P/Q/T, Q4I, Q5F/N, H8K/N, A9L, A45V, P63Q/S, R66N, E72Q/S, A74L, S77G, E88Q, A108C/L/R, G111S, G113A, D116A/E, N135K, D141C/G, Q181D, D199G, E205G/R, E238C, A374V, A375Q/Y, P406S, D411R, R412H, D422A, D430K, S434F/K/W, I438V, N459G/Q, E497F/Y, Y501 G/P/S/W, S502G, L503Q/R/S, T505K/R, Q508G/S, R509A/D, K510G, K511C/D/G, A512G/K/P/Q/S/T, and A513L/Y.

In some embodiments, a variant as described herein is encoded by a polynucleotide that hybridizes at high stringency to the complement of SEQ ID NOs:1, 3, 4, 13 or 14 and comprises one or more amino acid substitutions as described herein.

In some embodiments, a FAR variant comprising any of the mutations described herein (e.g., any of the FAR variants in Tables 2, 4, and 5 as well as any variants that comprise an amino acid substitution set provided in Table 2, Table 4, or Table 5) comprises at least at least 75%, at least 80%, at least 85%, at least 90%, at least 91%, at least 92%, at least 93%, at least 94%, at least 95%, at least 96%, at least 97%, at least 98%, or at least 99% identity to a wild-type FAR produced by *M. algicola* (e.g., SEQ ID NO:2). In some embodiments, a FAR variant comprising any of the mutations described herein (e.g., any of the FAR variants in Tables 2, 4, and 5 as well as any variants that comprise an amino acid substitution set provided in Table 2, Table 4, or Table 5) comprises at least at least 75%, at least 80%, at least 85%, at least 90%, at least 91%, at least 92%, at least 93%, at least 94%, at least 95%, at least 96%, at least 97%, at least 98%, or at least 99% identity to a wild-type FAR produced by *M. aquaeolei* (e.g., SEQ ID NO:5).

Any of the improved FAR polypeptides as described herein may also include one or more additional substitutions, or one or more insertions or deletions, in addition to the specified substitutions described herein. It is expected that FAR polypeptides having at least about 75% (e.g., at least 80%, at least 85%, at least 90%, at least 91%, at least 92%, at least 93%, at least 94%, at least 95%, at least 96%, at least 97%, at least 98%, or at least 99%) sequence identity with the wild-type FAR of SEQ ID NO:2 or SEQ ID NO:5 and also having one or more of the specified substitutions will exhibit improved characteristics and/or properties as described herein.

In some embodiments, the improved FAR polypeptides may have less than about 99%, less than about 98%, less than about 97%, less than about 96%, less than about 95%, less than about 93%, less than about 90%, or less than about 85% sequence identity to SEQ ID NO:2 or SEQ ID NO:5.

Residue positions which have been found to be important to total fatty alcohol yield, and which provide significant increases when used in various different combinations, include residue positions corresponding to positions 134, 138, 188 and 511 of SEQ ID NO:2. The wild-type residues at these positions may be substituted by any one of the other naturally encoded amino acids. In some embodiments, the substitutions at these positions are, independently of one another, selected from the following: position 134: R, K or S (preferably S); position 138: Q or L (preferably L); position. 188: S; and position 511: T, P, G, S, K, Q, or R (preferably T).

In some embodiments, the improved FAR polypeptides contain an amino acid substitution at position 134 relative to SEQ ID NO:2. In some embodiments, the improved FAR polypeptide contains an amino acid R, K, or S at position N134 relative to SEQ ID NO:2.

In some embodiments, the improved FAR polypeptides contain an amino acid substitution at position 138 relative to SEQ ID NO:2. In some embodiments, the improved FAR polypeptide contains an amino acid 0 or L at position E138 relative to SEQ ID NO:2.

In some embodiments, the improved FAR polypeptides contain an amino acid substitution at position P188 relative to SEQ ID NO:2. In some embodiments, the improved FAR polypeptide contains an amino acid S at position 188 relative to SEQ ID NO:2.

In some embodiments, the improved FAR polypeptides contain an amino acid substitution at position P405 relative to SEQ ID NO:2. In some embodiments, the improved FAR polypeptide contains an amino acid V, S, F, G, C, L, S, A, or W at position 405 relative to SEQ ID NO:2.

In some embodiments, the improved FAR polypeptides contain an amino acid substitution at position A511 relative to SEQ ID NO:2. In some embodiments, the improved FAR polypeptide contains an amino acid T, P, G, S, K, Q, or R at position 511 relative to SEQ ID NO:2. In preferred embodiments, the polypeptide contains the amino acid T at position 511 relative to SEQ ID NO:2.

In some embodiments, the polypeptide contains substitutions for at least two of positions N134, E138, P188 and A511 relative to SEQ ID NO:2. In other embodiments, the polypeptide contains substitutions for at least three of positions N134, E138, P188 and A511 relative to SEQ ID NO:2. In other embodiments, the polypeptide contains substitutions for all four of positions 134, 138, 188 and 511 relative to SEQ ID NO:2. In these embodiments, wherein the polypeptide comprises substitutions for at least two, at least three, or all four, of positions 134, 138, 188 and 511 relative to SEQ ID NO:2, the substitutions may independently be selected from the following: position 134: R, K or S (preferably S); position 138: Q or L (preferably L); position 188: S; and position 511: T, P, G, S, K, Q, or R (preferably T).

In preferred embodiments, the improved FAR polypeptide of the invention contains the following amino acid substitutions relative to SEQ ID NO:2: position 134: R, K or S; position 138: Q or L; position 188: S; and position 511: T, P, G, S, K, Q, R.

In other preferred embodiments, the improved FAR polypeptide of the invention contains the following amino acid substitutions relative to SEQ ID NO:2: position 134: S; position 138: L; position 188: S; and position 511:T.

One or more additional substitutions may also be beneficial. For example, it has been found that including one or more additional substitutions at residue positions corresponding to residue positions 303, 401, 405, 416, 418, 505, 508 and 509 of SEQ ID NO:2 yield beneficial increases in fatty alcohol yield. When such additional substitutions are included in an improved FAR enzyme, the wild-type residue may be mutated to any one of the other naturally encoded amino acids. In some embodiments, the substitutions at these positions are, independently of one another, selected from the following: position 303:G; position 401:aliphatic amino acid (e.g., V, L, A I) or S (preferably aliphatic amino acid); position 405:aliphatic amino acid, G, C or F (preferably aliphatic amino acid); position 416: aliphatic amino acid (preferably V or L); position 418: aliphatic amino acid, R or Y (preferably Y); position 505: basic amino acid (preferably K); position 508: G, H (preferably H); position 509: G, H, E, R, D, S, or N (preferably D).

In some embodiments, the improved FAR polypeptides have amino acid sequences corresponding to SEQ ID NO:2 that include the following substitutions (relative to SEQ ID NO:2): N134 (S or R), E138Q, P188S and A511 (G, K, R or T), and optionally 1, 2, 3, 4, 5, 6, 7, 8, 9, 10, or more additional substitutions at any other residue position. Specific exemplary embodiments of this class of improved FAR polypeptides include variant Nos: 211, 216, 238-264, and 266-423 of Table 2.

In some embodiments, a FAR variant comprises at least about 70% (or at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%) sequence identity to SEQ ID NO:2 and comprises a substitution relative to SEQ ID NO:2 at one or more positions selected from K22, E87, N134, E138, P188, L209, G264, E303, G401, P405, A412, A416, Q418, S458, Y500, L502, 8508, K509, and A511, wherein the position is numbered with reference to SEQ ID NO:2. Substitutions at positions K22, E87, N134, E138, P188, L209, G264, E303, G401, P405, A412, A416, Q418, S458, Y500, L502, R508, K509, and A511, as numbered with reference to a wild-type *M. algicola* FAR polypeptide (e.g., SEQ ID NO:2), were identified by the inventors as being beneficial for increasing fatty alcohol production or increasing production of a particular fatty alcohol profile.

Certain FAR variants of the present invention have an amino acid sequence that includes at least one amino acid substitution at one or more amino acid residues selected from N134, E138, P188, S458, and A511, wherein the amino acid residues are numbered with reference to SEQ ID NO:2. Amino acid substitutions at one or more of these positions are predicted to be beneficial substitutions for increasing fatty alcohol production or increasing production of a particular fatty alcohol profile. In some embodiments, a FAR variant of the present invention has an amino acid sequence that comprises at least about 70% (or at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%) sequence identity to SEQ ID NO:2 and comprises one or more amino acid substitutions selected from N134R, E138Q, P188S, S458Q, and A511T, wherein the position is numbered with reference to SEQ ID NO:2, which are predicted to be beneficial substitutions for increasing fatty alcohol production.

Certain FAR variants of the present invention have an amino acid sequence that includes at least one amino acid substitution at one or more amino acid residues selected from E303, G401, P405, A412, A416, Q418, S458, L502, R508, and K509, wherein the amino acid residues are numbered with reference to SEQ ID NO:2. Amino acid substitutions at one or more of these positions are predicted to be beneficial substitutions for increasing fatty alcohol production or increasing production of a particular fatty alcohol profile. In some embodiments, a FAR variant of the present invention has an amino acid sequence that comprises at least about 70% (or at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%) sequence identity to SEQ ID NO:2 and comprises one or more amino acid substitutions selected from E303G, G401A/L/S/V, P405A/C/F/L/V, A412V, A416L, Q418I/V, S458Q, L502S, R508G/H, and K509D/H, wherein the position is numbered with reference to SEQ ID NO:2, which are predicted to be beneficial substitutions for increasing fatty alcohol production.

Certain FAR variants of the present invention have an amino acid sequence that includes at least one amino acid substitution at one or more amino acid residues selected from K22, E87, L209, G264, G401, A416, Y500, R508, and K509, wherein the amino acid residues are numbered with reference to SEQ ID NO:2. Amino acid substitutions at one or more of these positions are predicted to be beneficial substitutions for increasing fatty alcohol production or increasing production of a particular fatty alcohol profile. In some embodiments, a FAR variant of the present invention has an amino acid sequence that comprises at least about 70% (or at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%) sequence identity to SEQ ID NO:2 and comprises one or more amino acid substitutions selected from K22R, E87G, L209K/L/N, G264S, G401V, A416L, Y500D, R508D/G, and K509D/H/N/Y, wherein the position is numbered with reference to SEQ ID NO:2, which are predicted to be beneficial substitutions for increasing fatty alcohol production.

Functional Fragments of FAR Variants

Skilled artisans will appreciate that oftentimes, the full length sequence of an enzyme is not required for enzymatic activity. Therefore, "functional fragments" of the various improved FAR enzymes described herein are also contemplated and included in the disclosure. Improved FAR enzymes and functional fragments thereof are sometimes referred to herein as "improved FAR polypeptides." The enzymatic activity of functional fragments may be measured as described in the Examples hereinbelow.

In some embodiments the functional fragments comprise at least 85%, at least 90%, at least 95%, and at least 98% of the corresponding improved full-length FAR enzyme. In many instances, functional fragments, like the improved full-length FAR enzyme from which they are derived, will produce 1.5-fold or higher total fatty alcohol than the wild-type FAR of SEQ ID NO:2, when assayed under the same conditions. In some embodiments, the improved FAR polypeptide of the invention is from about 350 to about 550 amino acids in length, e.g., from about 350 to about 400 amino acids in length. In some embodiments, the improved FAR polypeptide of the invention is from 400 to 550 amino acids in length, such as from 400 to 500, from 450 to 500, from 500 to 550, from 500 to 525, or from 505 to 515 amino acids in length.

In some embodiments, regions of one or both termini, such as, for example, from about 1 to about 10; 1 to about 15; or 1 to about 20 residues at one or both termini, may be removed without significantly deleteriously affecting the activity of the enzyme. Such deletions can often times be made internally without detrimental effect. In instances of multifunctional, multi-domain enzymes, entire domains can be removed without deleteriously affecting a desired enzymatic activity.

Exemplary Substitutions in *Marinobacter* Algicola FAR Homologs

In another aspect, the present invention provides FAR proteins that are variants of naturally occurring FAR enzymes of marine proteobacteria species other than *Marinobacter algicola* (strain DG893) which comprise a substitution or modification at at least one position corresponding to a substitution of a *M. algicola* FAR variant described herein, and which have improved properties relative to the naturally occurring FAR enzyme.

In particular, analogous substitutions may be made in marine gammaproteobacteria with significant sequence similarity to *Marinobacter algicola* (strain DG893). For example, analogous substitutions may be made in other species of *Marinobacter* including but not limited to *M. algicola, M. aquaeolei, M. arcticus, M. actinobacterium*, and *M. lipolyticus*; species of *Oceanobacter* including but not limited to *Oceanobacter* sp. Red65 (renamed *Bermanella marisrubi*), *Oceanobacter* strain WH099, and *O. kriegii*; and species of *Hahella* including but not limited to *H. chejuensis* and equivalent species thereof.

Improved FAR polypeptides may also be derived from FAR enzymes identified from wild-type organisms using multiple sequence alignments using Hidden Markov Models ("HMMs"), which identify proteins in compiled protein family databases that share common domains with previously-identified suitable FAR enzymes. See, e.g., the website pfam-.sanger.ac.uk/. In certain embodiments, the HMMs are used to identify NAD binding domains and/or sterile domains.

It is within the ability of one of ordinary skill in the art to identify other examples of structurally homologous proteins. The present invention provides variants of these and other FAR proteins in which substitutions are made at residues corresponding to those identified herein in the *M. algicola* FAR protein.

To produce FAR homologs with improved properties, the sequences of the wild-type *M. algicola* FAR and the FAR homolog (e.g., a *M. aquaeolei* FAR protein) can be aligned in a pairwise manner as described supra. Based on the alignment, a residue in a position in the homolog that corresponds, based on the alignment, with a specified position in *M. algicola* FAR is identified. For example, analogous substitutions in wild-type *M. aquaeolei* FAR to those substitutions described in Table 2 can be made by aligning the wild-type *M. algicola* FAR protein (e.g., SEQ ID NO:2) with the wild-type *M. aquaeolei* FAR protein (e.g., SEQ ID NO:5) (see, e.g., FIG. 2). Analogous substitutions in *M. aquaeolei* FAR are described herein in Example 8.

Thus, in some embodiments, the present invention provides a recombinant FAR variant comprising at least about 70% (or at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%) sequence identity to SEQ ID NO:2 and comprising one or more amino acid substitutions selected from X2D/F/G/H/I/P/N/Q/T/V/W, X3R, X4R, X5S, X6P, X7N, X8K/S, X9D/F, X10T, X12T/V, X14N/R/V/W, X17D, X18I, X22E, X24I, X33V, X42L, X50S/V, X54P, X60H, X61R, X62S, X63R/Y, X65G/Q/Y, X69E/Q, X71K, X73K/V, X74K/P, X76K/N/R, X77A/I, X83R, X87G/V, X91I/R, X93V, X98P/R, X101L, X102C, X104I/M, X107C/L/W, X110D, X111S, X112A, X113D/L, X115A/H, X117D, X120V, X121H/S, X122R, X125V, X128H, X132G, X134K/R/S, X137L, X138L/Q, X140C, X142V, X144Q, X148E, X151L, X153I, X160S, X162T, X174C, X177Q/R/T, X180H/R, X185A/I, X186A/G/Y, X188A/I/M/S, X197P, X198Q, X202G, X204G, X205G/P, X207I/L, X209K/N, X212R, X213R, X217L, X220C, X224R, X226A/M, X227A/G/H/R/T, X229R, X236K, X237L, X244A/F/G/H/P, X245N, X246A, X257K, X260R/T, X261D, X263P, X264S, X266A, X269T, X283E/F/K/M/T/V, X287L, X288Q, X290I, X295T/V, X299T, X303G, X305I, X306F/H/N/W, X318I, X328T, X330V, X331V, X332S, X333T, X339G/V, X340P/S/V, X341K, X342L, X350S, X351C, X359L, X364F/I, X365N, X366T/V, X370A/I, X374K/Y, X376P, X377C/K/Y, X380K/N/R, X381C, X384R, X389I/L/M/V, X396G, X397I/L, X398Y, X399T, X400A/L, X401A/C/I/L/S/V, X403C/S, X404A, X405A/C/F/G/L/S/V/W, X406Y, X409V/W/Y, X410A/C/H/N/Q/R/S, X412C/F/M/V, X413L/R, X416L/V, X418I/R/V/Y, X421I/L/N/P/R/S/V/Y, X427K, X429E/K/N/Q/R, X430H/I/R, X432C/Q, X433F/H/K/L/N/W, X436D/K/Q, X437V, X440L, X443T, X444S, X446H, X452A/G/N, X458G/L/M/Q, X459H, X463E/T, X464G, X466E/Q/R, X472V, X474R, X479Q, X484V, X487R/S/T/Y, X490S, X496A, X498A, X499A/H/I/N/P/R/S, X500C/G/H/L/N/P/Q/R/S/W, X501G/R, X502A/P/Q/R/S, X504G/R, X505K, X506G/S, X507A/G/P/R/S, X508D/G/H, X509D/E/G/H/N/R/S/W, X510A/D/G/P/S/Y, X511G/I/K/P/Q/R/S/T, and X512K/S/T, wherein the position is numbered with reference to a wild-type *M. algicola* FAR (e.g., SEQ ID NO:2), and wherein the FAR variant exhibits increased fatty alcohol production relative to the wild-type FAR homolog from which the FAR variant is derived and/or exhibits an improved fatty alcohol profile relative to the wild-type FAR from which the FAR variant is derived. In some embodiments, the FAR variant produces an increased amount of fatty alcohols as compared to the wild-type FAR. In some embodiments, the FAR variant produces an increased amount of an aggregate of the fatty alcohols C14:0 (1-tetradecanol), C16:1 (cis Δ⁹-1-hexadecenol), C16:0 (1-hexadecanol), C18:1 (cis Δ¹¹-1-octadecenol), and C18:0 (1-octadecanol) as compared to the wild-type FAR. In some embodiments, the FAR variant produces a fatty alcohol profile that differs from the fatty alcohol profiles produced by the wild-type FAR. In some embodiments, the FAR variant produces a fatty alcohol profile having an increased amount of C16:1 (cis Δ⁹-1-hexadecenol) and a decreased amount of C18:1 (cis Δ¹¹-1-octadecenol) as compared to the wild-type FAR. In some embodiments, the fatty alcohol profile produced by the FAR variant further comprises an increased amount of C14:0 (1-tetradecanol) as compared to the wild-type FAR. In some embodiments, the fatty alcohol profile produced by the FAR variant further comprises a decreased amount of C16:0 (1-hexadecanol) as compared to the wild-type FAR.

In some embodiments, the present invention relates to a method of making FAR variants having increased fatty alcohol production and/or an improved fatty alcohol profile relative to wild-type FAR. In some embodiments, the method comprises:

(a) identifying a sequence that comprises at least about 70% (or at least about 75%, at least about 80%, at least about 85%, at least about 90%, at least about 95%, at least about 96%, at least about 97%, at least about 98%, or at least about 99%) sequence identity to SEQ ID NO:2 (alternatively, SEQ ID NO:5);

(b) aligning the identified sequence with the sequence of SEQ ID NO:2 (alternatively, SEQ ID NO:5); and (c) substituting one or more amino acid residues from the identified sequence, wherein the substitutions are made at one or more positions corresponding to positions selected from A2, T3, Q4, Q5, Q6, Q7, N8, G9, A10, A12, G14, E17, Q18, K22, V24, L33, I42, G50, L54, R60, H61, P62, A63, R65, L69, E71, A73, S74, S76, V77, H83, E87, T91, L93, H98, T101, G102, V104, S107, G110, L111, T112, P113, R115, R117, A120, G121, Q122, A125, N128, S132, N134, E137, E138, D140, A142, K144, L148, E151, V153, N160, A162, N174, N177, Q180, V185, I186, P188, T197, D198, E202, E204, E205, V207, L209, D212, K213, V217, I220, K224, L226, E227, K229, R236, E237, S244, D245, T246, L257, K260, A261, S263, G264, S266, I269, S283, I287, E288, V290, A295, A299, E303, V305, S306, V318, I328, L330, S331, L332, A333, S339, G340, 0341, R342, G350, G351, K359, L364, M365, A366, T370, A374, D376, Q377, Y380, R381, T384, A389, D396, V397, V398, V399, G400, G401, R403, V404, P405, L406, A409, G410, A412, M413, A416, Q418, E421, N427K, D429, T430, R432, S433, T436, I437, F440, A443, P444, Y446, S452, S458, R459, L463, D464, V466, A472, Q474, L479, I484, G487, N490, E496, K498, L499, Y500, S501, L502, A504, A505, D506, T507, R508, K509, K510, A511, and A512, wherein the positions are numbered with reference to SEQ ID NO:2.

In some embodiments, step (c) of the method comprises making one or more amino acid substitutions selected from A2D/F/G/H/I/P/N/Q/T/V/W, T3R, Q4R, Q5S, Q6P, Q7N, N8K/S, G9D/F, A10T, A12T/V, G14N/R/V/W, E17D, Q18I, K22E, V24I, L33V, I42L, G50S/V, L54P, R60H, H61R, P62S, A63R/Y, R65G/Q/Y, L69E/Q, E71K, A73K/V, S74K/P, S76K/N/R, V77A/I, H83R, E87G/V, T91I/R, L93V, H98P/R, T101L, G102C, V104I/M, S107C/L/W, G110D, L111S, T112A, P113D/L, R115A/H, R117D, A120V, G121H/S, Q122R, A125V, N128H, S132G, N134K/R/S, E137L, E138L/Q, D140O, A142V, K144Q, L148E, E151L, V153I, N160S, A162T, N174C, N177Q/R/T, Q180H/R, V185A/I, I186A/GN, P188A/I/M/S, T197P, D198Q, E202G, E204G, E205G/P, V207I/L, L209K/N, D212R, K213R, V217L, R220C, K224R, L226A/M, E227A/G/H/R/T, K229R, R236K, E237L, S244A/F/G/H/P, D245N, T246A, L257K, K260R/T, A261D, S263P, G264S, S266A, I269T, S283E/F/K/M/T/V, I287L, E288Q, V290I, A295T/V, A299T, E303G, V305I, S306F/H/N/W, V318I, I328T, L330V, S331V, L332S, A333T, S339G/V, G340P/S/V, Q341K, R342L, G350S, G351C, K359L, L364F/I, M365N, A366T/V, T370A/I, A374K/Y, D376P, Q377C/K/Y, Y380K/N/R, R381C, T384R, A389I/L/M/V, D396G, V397I/L, V398Y, V399T, G400A/L, G401A/C/I/L/S/V, R403C/S, V404A, P405A/C/F/G/L/S/V/W, L406Y, A409V/W/Y, G410A/C/H/N/Q/R/S, A412C/F/MN, M413L/R, A416L/V, Q418I/R/V/Y, E421I/L/N/P/R/S/V/Y, N427K, D429E/K/N/Q/R, T430H/I/R, R432C/Q, S433F/H/K/L/N/W, T436D/K/Q, I437V, F440L, A443T, P444S, Y446H, S452A/G/N, S458G/L/M/Q, R459H, L463E/T, D464G, V466E/Q/R, A472V, Q474R, L479Q, I484V, G487R/S/T/Y, N490S, E496A, K498A, L499A/H/I/N/P/R/S, Y500C/G/H/L/N/P/Q/R/S/W, S501G/R, L502A/P/Q/R/S, A504G/R, A505K, D506G/S, T507A/G/P/R/S, R508D/G/H, K509D/E/G/H/N/R/S/Y, K510A/D/G/P/S/Y, A511G/I/K/P/Q/R/S/T, and A512K/S/T.

In some embodiments, the method further comprises determining whether the one or more amino acid substitutions increase fatty alcohol production and/or an improved fatty alcohol profile in comparison to the wild-type FAR from which the FAR variant is derived.

*M. aquaeolei* FAR Variants

In a related aspect FAR variants derived from *M. aquaeolei* FAR (SEQ ID NO:5) are provided. Tables 4, 4A, and 5 show exemplary substitutions and substitution sets. In one aspect, the invention provides a FAR variant comprising at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to SEQ ID NO:5 and comprising a substitution at a substitution position (or set of positions) disclosed in Tables 4, 4A, or 5. These variants are sometimes referred to as "FAR Maq variants." It will be appreciated, as noted above, that position 512 of SEQ ID NO:5 corresponds to position 511 of SEQ ID NO:2 and that SEQ ID NO:5 and SEQ ID NO:2 share 78% sequence identity. Accordingly, FAR maq variants can be viewed as a subgenus of FAR variants of the invention to which all disclosure herein is applicable.

In some embodiments, a FAR variant comprises at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to SEQ ID NO:5 and comprises a substitution relative to SEQ ID NO:5 at one or more positions selected from position 2, position 135, position 139, position 141, position 422, position 459, position 511, and position 512, wherein the position is numbered with reference to SEQ ID NO:5. In some embodiments, the amino acid residue in the FAR variant at position 2 relative to SEQ ID NO:5 is alanine (A2); the amino acid residue at position 135 relative to SEQ ID NO:5 is asparagine (N135); the amino acid residue at position 135 relative to SEQ ID NO:5 is glutamic acid (E139); the amino acid residue at position 141 relative to SEQ ID NO:5 is aspartic acid (D141); the amino acid residue at position 422 relative to SEQ ID NO:5 is aspartic acid (D422); the amino acid residue at position 459 relative to SEQ ID NO:5 is asparagine (N459); the amino acid residue at position 511 relative to SEQ ID NO:5 is lysine (K511); and the amino acid residue at position 512 relative to SEQ ID NO:5 is alanine (A512). In some embodiments, a FAR variant comprises an amino acid substitution at residue A2 that is selected from aspartic acid, phenylalanine, glycine, histidine, isoleucine, asparagine, proline, glutamine, threonine, valine, or tryptophan (A2D/F/G/H/I/N/P/Q/T/V/W). In some embodiments, a FAR variant comprises an amino acid substitution at residue N135 that is selected from lysine, arginine, or serine (N135K/R/S). In some embodiments, a FAR variant comprises an amino acid substitution at residue E139 that is selected from leucine or glutamine (E139L/Q). In some embodiments, a FAR variant comprises an amino acid substitution at residue D141 that is cysteine (D141C). In some embodiments, a FAR variant comprises an amino acid substitution at residue D422 that is selected from isoleucine, leucine, asparagine, proline, arginine, serine, valine, or tyrosine (D422I/L/N/P/R/S/V/Y). In some embodiments, a FAR variant comprises an amino acid substitution at residue N459 that is selected from glycine, leucine, methionine, or glutamine (N459G/L/M/Q). In some embodiments, a FAR variant comprises an amino acid substitution at residue K511 that is selected from alanine, aspartic acid, glycine, proline, serine, or tyrosine (K511A/D/G/P/S/Y). In some embodiments, a FAR variant comprises an amino acid substitution at residue A512 that is selected from glycine, isoleucine, lysine, proline, glutamine, arginine, serine, or threonine (A512G/I/K/P/Q/R/S/T). In some embodiments, a FAR variant comprises 100% amino acid sequence identity to SEQ ID NO:5 except for amino acid substitutions at one or more of positions A2, N135, E139, D141, D422, N459, K511, and A512 as numbered with reference to SEQ ID NO:5.

In some embodiments, the FAR variant further comprises a substitution relative to SEQ ID NO:5 at one or more of position 189, position 406, and position 419, wherein the positions are numbered with reference to SEQ ID NO:5. In some embodiments, the amino acid residue at position 189 relative to SEQ ID NO:5 is proline (P189); the amino acid residue at position 406 relative to SEQ ID NO:5 is proline (P406); and the amino acid residue at position 419 relative to SEQ ID NO:2 is asparagine (N419). In some embodiments, a FAR variant comprises an amino acid substitution at residue P189 that is selected from alanine, isoleucine, methionine, or serine (P189A/I/M/S). In some embodiments, a FAR variant comprises an amino acid substitution at residue P406 that is selected from alanine, cysteine, phenylalanine, glycine, leucine, serine, valine, or tryptophan (P406A/C/F/G/L/S/V/W). In some embodiments, the FAR variant comprises an amino acid substitution at residue N419 that is selected from isoleucine, arginine, valine, and tyrosine (N419I/R/V/Y). In some embodiments, a FAR variant comprises 100% amino acid sequence identity to SEQ ID NO:5 except for amino acid substitutions at one or more of positions A2, N135, E139, D141, P189, P406, N419, D422, N459, K511, and A512 as numbered with reference to SEQ ID NO:5.

FAR Maq variants of the invention as described herein may have any of the improved properties disclosed hereinabove, such as increased total fatty alcohol production, increased production of fatty alcohols at a specified culture pH or over an increased pH range, or changes in fatty alcohol profile as compared to a wild-type FAR.

FAR Maq variants of the invention may comprise a substitution or substitution set exemplified in Tables 4 or 5. For example, FAR Maq Variant No. 5 (see Table 4) has a threonine (substituted for alanine) at position 2, and alanine (substituted for glycine) at position 113 (numbered with reference to SEQ ID NO:5). More broadly, FAR Maq variants of the invention may comprise a substitution at a position or set of positions exemplified in Table 4 or Table 5. As a non-limiting example, FAR Maq Variant No. 5 (see Table 4) has a substitution for alanine at position 2 and a substitution for glycine at position 113 (wherein the positions are numbered with reference to SEQ ID NO:5), and accordingly a particular FAR Maq variant of the invention may comprise a substitution at position 2 (i.e., any residue other than alanine) and at position 113 (i.e., any residue other than glycine), and optionally any other substitutions as described herein, e.g., as described in Table 4 or Table 5.

Increased Thermotolerance

As described in the examples, screening of some FAR variants included culture at elevated temperature (e.g., 37° C. or 40° C., rather than 30° C.). See, e.g., Table 2. In these experiments a number of substitutions were identified that may increase the thermotolerance of a FAR polypeptide (i.e., allow the polypeptide to retain activity at elevated temperatures). Alternatively, these substitutions may shift the temperature optimum of the variant from a lower temperature to a higher temperature.

For example, the following substitutions to variant 391 resulted in increased activity at 37° C.: G14R/V, V104I/M, S134R, E227R, S244P, S283M, S306W, L364I, T370I, D376P, Q377K, A389I, and S433K, numbered with reference to SEQ ID NO:2. It is believed that introducing substitutions into one or more of positions G14, V104, S134, E227, S244, S283, S306, L364, T370, D376, Q377, A389, and S433, numbered with reference to SEQ ID NO:2, into any of Variants 1-629 of Table 2, or into corresponding positions in any of Variants 1-629 of Table 5, will result in improved activity when the host cell (e.g., E. coli) is incubated at an elevated temperature (e.g., 37° C.). For example, it is believed that introducing one or more of the following substitutions into any of Variants 1-629 of Table 2, or equivalent substitutions into any of Variants 1-629 of Table 5, will result in improved activity when the host cell (e.g., E. coli) is incubated at an elevated temperature (e.g., ≥37° C.): G14R/V, V104I/M, S134R, E227R, S244P, S283M, S306W, L364I, T370I, D376P, Q377K, A389I, or S433K.

For example, the following substitution sets to variant 438 resulted in increased activity at 40° C.: Q18I, A63R, R65G, N128H, S134R, N174C, N177T, K224R, L226M, S283F, G351C, M365N, V404A, L406Y, K433S, and G487R, numbered with reference to SEQ ID NO:2. It is believed that introducing substitutions into one or more of positions Q18, A63, R65, N128, S134, N174, N177, K224, L226, S283, G351, M365, V404, L406, K433, or G487, numbered with reference to SEQ ID NO:2 into any of Variants 1-629 of Table 2, or into corresponding positions in any of Variants 1-629 of Table 5, will result in improved activity when the host cell (e.g., E. coli) is incubated at an elevated temperature (e.g., 40° C.). For example, it is believed that introducing one or more of the following substitutions into any of Variants 1-629 of Table 2, or equivalent substitutions into any of Variants 1-629 of Table 5, will result in improved activity when the host cell (e.g., E. coli) is incubated at an elevated temperature (e.g., 40° C.): Q18I, A63R, R65G, N128H, S134R, N174C, N177T, K224R, L226M, S283F, G351C, M365N, V404A, L406Y, K433S, or G487R.

Generation of FAR Variants

A FAR variant of the present invention can be subject to further modification to generate new polypeptides that retain the specific substitutions that characterize the variant and which may have desirable properties. For example, a polynucleotide encoding a FAR with an improved property can be subjected to additional rounds of mutagenesis to generate polypeptides that retain the properties of the parent or exhibit further improvements in the desired enzyme or enzyme properties.

Methods for generating variant libraries of polynucleotides encoding modified polypeptides are well known in the art. For example, mutagenesis and directed evolution methods can be readily applied to polynucleotides encoding the FAR polypeptide of SEQ ID NO: 2 to generate variant libraries that can be expressed, screened, and assayed using the methods described herein: Mutagenesis and directed evolution methods are well known in the art. See, e.g., Ling, et al., "Approaches to DNA mutagenesis: an overview," Anal. Biochem., 254(2):157-78 (1997); Dale, et al., "Oligonucleotide-directed random mutagenesis using the phosphorothioate method," Methods Mol. Biol., 57:369-74 (1996); Smith, "In vitro mutagenesis," Ann. Rev. Genet., 19:423-462 (1985); Botstein, et al., "Strategies and applications of in vitro mutagenesis," Science, 229:1193-1201 (1985); Carter, "Site-directed mutagenesis," Biochem. J., 237:1-7 (1986); Kramer, et al., "Point Mismatch Repair," Cell, 38:879-887 (1984); Wells, et al., "Cassette mutagenesis: an efficient method for generation of multiple mutations at defined sites," Gene, 34:315-323 (1985); Minshull, et al., "Protein evolution by molecular breeding," Current Opinion in Chemical Biology, 3:284-290 (1999); Christians, et al., "Directed evolution of thymidine kinase for AZT phosphorylation using DNA family shuffling," Nature Biotechnology, 17:259-264 (1999); Crameri, et al., "DNA shuffling of a family of genes from diverse species accelerates directed evolution," Nature, 391: 288-291; Crameri, et al., "Molecular evolution of an arsenate detoxification pathway by DNA shuffling," Nature Biotechnology, 15:436-438 (1997); Zhang, et al., "Directed evolution of an effective fucosidase from a galactosidase by DNA shuffling and screening," Proceedings of the National Academy of Sciences, U.S.A., 94:45-4-4509; Crameri, et al., "Improved green fluorescent protein by molecular evolution using DNA shuffling," Nature Biotechnology, 14:315-319 (1996); Stemmer, "Rapid evolution of a protein in vitro by DNA shuffling," Nature, 370:389-391 (1994); Stemmer, "DNA shuffling by random fragmentation and reassembly: In vitro recombination," Proceedings of the National Academy of Sciences, U.S.A., 91:10747-10751 (1994); WO 95/22625; WO 97/0078; WO 97/35966; WO 98/27230; WO 00/42651; WO 01/75767; and WO 2009/152336, all of which are incorporated herein by reference.

V. Polynucleotides and Expression Systems Encoding Far Variants

In another aspect, the present invention provides polynucleotides encoding the FAR variants as described herein. The polynucleotide can be a DNA or RNA, and can be single-stranded or double-stranded. The polynucleotide may be operably linked to one or more heterologous regulatory or control sequences that control gene expression to create a recombinant polynucleotide capable of expressing the polypeptide. Expression constructs containing a heterologous polynucleotide encoding the engineered FAR variant can be introduced into appropriate host cells to express the FAR variant.

In some embodiments, the FAR variant is generated from a wild-type FAR cDNA sequence (e.g., a wild-type M. algicola FAR cDNA sequence of SEQ ID NO:1 or SEQ ID NO:3 or a wild-type M. aquaeolei FAR cDNA sequence of SEQ ID NO:4) or the portion thereof comprising the open reading frame, with changes made as required at the codons corresponding to substitutions (residues mutated relative to the wild-type sequence as described herein, for example at any of Tables 2, 4, or 5). In addition, one or more "silent" nucleotide changes can be incorporated. These changes may affect cellobiohydrolase activity in a variety of ways. For example, without intending to be bound by a particular mechanism, silent mutations may increase the stability of mRNAs encoding the variant protein.

The availability of a polypeptide sequence of a specific improved FAR polypeptide provides a description of all polynucleotides capable of encoding that enzyme or fragment because of the known correspondence between amino acids and the genetic code. For most orgamisms the genetic code is "Amino Acid (one letter code) [codons]": phenylalanine (F) [TTT, TTC]; leucine (L) [TTA, TTG, CTT, CTC, CTA, CTG]; isoleucine (I) [ATT, ATC, ATA]; methionine (M) [ATG]; valine (V) [TGG, GTC, GTA, GTG]; serine (S) [TCT, TCC, TCA, TCG, AGT, AGC]; proline (P) [CCT, CCC, CCA, CCG]; threonine (T) [ACT, ACC, ACA, ACG]; alanine (A) [GCT, GCC, GCA, GCG]; tyrosine (Y) [TAT, TAC]; histidine (H) [CAT, CAC]; glutamine (Q) [CAA, CAG]; asparagine (N) [AAT, AAC]; lysine (K) AAA, AAG]; aspartic acid (D) [GAT, GAC]; glutamic acid (E) [GAA, GAG]; cysteine (C) [TGT, TGC]; tryptophan (W) [TGG]; arginine (R) [CGT, CGC, CGA, CGG, AGA, AGG]; and glycine (G) [GGT, GGC, GGA, GGG]. In certain embodiments, the degeneracy of the genetic code is used to produce a large number of polynucleotides that encode the improved FAR polypeptides described herein. In some embodiments, the polynucleotides that encode the improved FAR polypeptides described herein are codon optimized for expression in specific microorganisms. In particular embodiments, the polynucleotides that encode the improved FAR polypeptides described herein are codon optimized for expression in bacteria, yeast or filamentous fungi. In some embodiments, the polynucleotides are codon optimized for expression in oleaginous yeast. In other specific embodiments, the polynucleotides are codon optimized for expression in E. coli, S. cerevisiae or Y. lipolytica. Codon schemes and/or methods for determining codon schemes optimized for particular microorganisms of interest are well known (see, e.g., the references cited with the definition of "preferred, optimal high, codon usage bias codons"; see also the website www.kazusa.or.jp/codon/).

A variety of methods are known for determining the codon frequency (e.g., codon usage, relative synonymous codon usage) and codon preference in specific organisms, including multivariate analysis, for example, using cluster analysis or correspondence analysis, and the effective number of codons used in a gene (see GCG CodonPreference, Genetics Computer Group Wisconsin Package; Codon W, John Peden, University of Nottingham; McInerney, J. O, 1998, Bioinformatics 14:372-73; Stenico et al., 1994, Nucleic Acids Res. 222437-46; Wright, F., 1990, Gene 87:23-29; Wada et al., 1992, Nucleic Acids Res. 20:2111-2118; Nakamura et al., 2000, Nucl. Acids Res. 28:292; Henaut and Danchin, "Escherichia coli and Salmonella," 1996, Neidhardt, et al. Eds., ASM Press, Washington D.C., p. 2047-2066, all of which are incorporated herein be reference). The data source for obtaining codon usage may rely on any available nucleotide sequence capable of coding for a protein. These data sets include nucleic acid sequences actually known to encode expressed proteins (e.g., complete protein coding sequences-CDS), expressed sequence tags (ESTs), or predicted coding regions of genomic sequences (see for example, Mount, D.,

*Bioinformatics: Sequence and Genome Analysis*, Chapter 8, Cold Spring Harbor Laboratory Press, Cold Spring Harbor, N.Y., 2001; Uberbacher, E. C., 1996, *Methods Enzymol.* 266: 259-281; Tiwari et al., 1997, *Comput. Appl. Biosci.* 13:263-270, all of which are incorporated herein by reference).

In some embodiments, the present invention provides a method for making an improved FAR polynucleotide variant, wherein the method comprises introducing one or more mutations into a polynucleotide encoding a FAR which comprises at least 70% (at least 75%, at least 80%, at least 85%, at least 90%, at least 93%, or at least 95%) sequence identity to the amino acid sequence of SEQ ID NO:2 or a functional fragment thereof to produce a modified polynucleotide, wherein the modification is selected from the group consisting of a substitution, a deletion, and an insertion; transforming a host cell with the modified polynucleotide; and screening the transformed host cell for an improvement in a desired phenotype relative to a corresponding transformed host cell comprising a polynucleotide encoding a wild-type FAR having at least 70% (at least 75%, at least 80%, at least 85%, at least 90%, at least 93%, at least 95%) sequence identity to the amino acid sequence of SEQ ID NO:2 or a functional fragment thereof. Exemplary phenotypes include improved fatty alcohol production, total and/or secreted fatty alcohol composition, and/or alteration of the fatty alcohol composition (including, but not limited to, an increase in the amount of C18 fatty alcohols compared to the amount of C14 fatty alcohols comprising the composition, an increased amount of C14-C16 fatty alcohols produced, or a profile comprising one or more of an increased amount of C16:1 (cis $\Delta^9$-1-hexadecenol), and a decreased amount of C18:1 (cis $\Delta^{11}$-1-octadecenol), an increased amount of C14:0 (1-tetradecanol), and a decreased amount of C16:0 (1-hexadecanol) as compared to wild-type FAR). Accordingly, in some embodiments the invention relates to a polynucleotide sequence that encodes an improved FAR polypeptide wherein the polynucleotide is selected from the group consisting of a polynucleotide that encodes a fatty acyl reductase (FAR) polypeptide comprising a sequence that is at least 75%, at least 80%, at least 85%, at least 90%, at least 95% or at least 97% identical to SEQ ID NO:2 and said improved FAR polypeptide comprising one or more substitutions. In some embodiments, the one or more substitutions comprise an amino acid substitution set listed in Table 2, Table 4, or Table 5. In some embodiments, the one or more substitutions comprise a substitution at any one of positions 2, 134, 138, 188, 405, 511 or combinations thereof when aligned to SEQ ID NO:2.

In some embodiments, the polynucleotide encodes a full-length improved FAR polypeptide wherein the corresponding full-length FAR enzyme has at least 80% (e.g., at least 85%, at least 90%, at least 91%, at least 92%, at least 93%, at least 94%, at least 95%, at least 96%, at least 97%, at least 98% or at least 99%) sequence identity with the wild-type FAR of SEQ ID NO:2 and also includes one or more of the specified substitutions as described herein (see, e.g., Section II supra). In some embodiments, the improved FAR comprises an amino acid sequence encoded by a nucleic acid that hybridizes under stringent conditions over substantially the entire length of a nucleic acid corresponding to SEQ ID NO:1, SEQ ID NO:3, or SEQ ID NO:4.

In some embodiments, the polynucleotide encoding an improved FAR polypeptide will have at least 90%, at least 93%, at least 94%, at least 95%, at least 96%, at least 97% or at least 98% sequence identity to nucleic acid sequences of SEQ ID NO:1, SEQ ID NO:3, or SEQ ID NO:4.

Certain silent mutations have also been identified in polynucleotides encoding the improved FAR polypeptides which appear to confer the property of increased fatty alcohol production in transformed *E. coli* cells as compared to wild-type *M. algicola* DG893 FAR (see Table 2). The silent mutations include: t6a, t6g, t6c, t9c, t9g, t27c, a30g, a51g, a81t, a147t, c171t, t174c, t180c, t226a, a237g, g243a, a318g, c321g, c321a, a336c, t339g, t363c, c402t, t459c, a474g, a540g, t564g, a615g, g627t, t628c, a633g, g681a, g711a, t792c, t834c, t870c, t927c, t967c, c994t, t1026c, t1149c, c1173t, t1203c, t1236g, t1248c, g1263a, g1272a, c1281t, t1287c, g1290c, t1297a, c1299g, t1326c, t1357c, c1366t, t1372a, t1374g, t1398c, t1410c, t1413c, t1435c, t1461g, g1485a, g1497t, t1501a, t1504c, t1515g, t1515a, t1521c, t1524c, a1527g, and t1533c (where nucleotide position is determined by alignment with SEQ ID NO:1).

Polynucleotide Synthesis

Polynucleotides encoding FAR polypeptides can be prepared using methods that are well known in the art. Typically, oligonucleotides of up to about 40 bases are individually synthesized, then joined (e.g., by enzymatic or chemical ligation methods, or polymerase-mediated methods) to form essentially any desired continuous sequence. For example, polynucleotides of the present invention can be prepared by chemical synthesis using, for example, the classical phosphoramidite method described by Beaucage, et al., 1981, *Tetrahedron Letters*, 22:1859-69, or the method described by Matthes, et al., 1984, *EMBO J.* 3:801-05, both of which are incorporated herein by reference. These methods are typically practiced in automated synthetic methods. According to the phosphoramidite method, oligonucleotides are synthesized, e.g., in an automatic DNA synthesizer, purified, annealed, ligated and cloned in appropriate vectors.

In addition, essentially any nucleic acid can be custom ordered from any of a variety of commercial sources, such as The Midland Certified Reagent Company (Midland, Tex.), The Great American Gene Company (Ramona, Calif.), ExpressGen Inc. (Chicago, Ill.), Operon Technologies Inc. (Alameda, Calif.), and many others.

Polynucleotides may also be synthesized by well-known techniques as described in the technical literature. See, e.g., Carruthers, et al., 1982, *Cold Spring Harbor Symp. Quant. Biol.*, 47:411-18 and Adams et al., 1983, *J. Am. Chem. Soc.* 105:661, both of which are incorporated herein by reference. Double stranded DNA fragments may then be obtained either by synthesizing the complementary strand and annealing the strands together under appropriate conditions, or by adding the complementary strand using DNA polymerase with an appropriate primer sequence.

General texts that describe molecular biological techniques which are useful herein, including the use of vectors, promoters, protocols sufficient to direct persons of skill through in vitro amplification methods, including the polymerase chain reaction (PCR) and the ligase chain reaction (LCR), and many other relevant methods, include Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (2nd Ed.), Vol. 1-3, Cold Spring Harbor Laboratory, Cold Spring Harbor, N.Y., 1989 ("Sambrook") and *Current Protocols in Molecular Biology*, F. M. Ausubel et al., eds., Current Protocols, a joint venture between Greene Publishing Associates, Inc. and John Wiley & Sons, Inc., (supplemented through 2009) ("Ausubel"), all of which are incorporated herein by reference. Reference is made to Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36-47; *The Journal Of NIH Research* (1991) 3, 81-94; (Kwoh et al. (1989) *Proc. Natl. Acad. Sci. USA* 86, 1173; Guatelli et al. (1990) *Proc. Natl. Acad. Sci. USA* 87, 1874; Lomeli et al. (1989) *J. Clin. Chem* 35, 1826; Landegren et al., (1988) *Science* 241, 1077-1080; Van Brunt (1990) *Biotechnology* 8, 291-294; Wu and Wallace, (1989) *Gene* 4, 560; Barringer et al. (1990) *Gene* 89, 117, and Sooknanan and Malek (1995) *Biotechnology* 13: 563-564, all of which are incorporated herein by reference. Methods for cloning in vitro amplified nucleic acids are described in Wallace et al., U.S. Pat. No. 5,426,039, which is incorporated herein by reference.

Vectors

The present invention further provides DNA constructs and vectors comprising polynucleotides encoding the improved FAR polypeptides for expression in heterologous recombinant host cells. In certain embodiments, the DNA constructs and vectors comprise a polynucleotide sequence that encodes any one of the improved FAR polypeptides as disclosed above. In certain embodiments, the DNA constructs and vectors comprise a polynucleotide sequence as encompassed by the invention and disclosed herein above. In certain embodiments, the DNA constructs and vectors comprise a polynucleotide sequence that encodes an improved FAR polypeptide herein, wherein the improved FAR is a full-length FAR. In other embodiments, the DNA constructs and vectors comprise a polynucleotide sequence that encodes an improved FAR polypeptide, wherein the improved FAR is a functional fragment of an improved full-length FAR enzyme. In certain embodiments, the polynucleotides encoding improved FAR polypeptides for expression in heterologous recombinant host cells as described herein are operably linked to a promoter, and optionally, to other control sequences.

In a particular aspect the present invention provides an expression vector comprising a FAR polynucleotide operably linked to a heterologous promoter. Expression vectors of the present invention may be used to transform an appropriate host cell to permit the host to express the FAR protein. Methods for recombinant expression of proteins in bacteria, yeast, and other organisms are well known in the art, and a number expression vectors are available or can be constructed using routine methods.

A recombinant expression vector can be any vector, e.g., a plasmid or a virus, which can be manipulated by recombinant DNA techniques to facilitate expression of an improved FAR polypeptide in a recombinant host cell. In certain embodiments, the expression vectors is stably integrated into the chromosome of the recombinant host cell and comprises one or more heterologous genes operably linked to one or more control sequences useful for production of an improved FAR polypeptide. In other embodiments, the expression vector is an extrachromosomal replicative DNA molecule, e.g., a linear or closed circular plasmid, that is found either in low copy number (e.g., from about 1 to about 10 copies per genome equivalent) or in high copy number (e.g., more than about 10 copies per genome equivalent).

Expression vectors which, in certain embodiments, are useful for expressing improved FAR enzymes as disclosed herein are commercially available, e.g., from Sigma-Aldrich Chemicals, St. Louis, Mo. and Stratagene, LaJolla, Calif. In some embodiments, examples of suitable expression vectors are plasmids which are derived from pBR322 (Gibco BRL), pUC (Gibco BRL), pREP4, pCEP4 (Invitrogen) or pPoly (Lathe et al., 1987, *Gene* 57:193-201).

In certain embodiments, the present disclosure provides a plasmid for expression of heterologous genes in E. coll. Expression vector pCK11900, which comprises a P15A origin of replication (P15A ori), lac a CAP binding site, a lac promoter, a T7 ribosomal binding site (T7g10 RBS) and a chloramphenicol resistance gene (camR). This expression vector is depicted in FIG. 3 of U.S. Patent Publication No. 2006/0195947, which is incorporated herein by reference in its entirety.

In certain embodiments, the present disclosure provides a replicating plasmid for expression of heterologous genes in *Yarrowia*, and particularly in *Y. lipolytica*.

In some embodiments, expression vectors as described herein are adapted for overexpression of genes encoding enzymes other than improved FAR polypeptides that are directly involved in fatty acid biosynthesis. In particular embodiments, the overexpressed gene encodes a protein selected from a fatty acid synthase (FAS), an acyl-ACP thioesterase (TE), a fatty acyl-CoA synthase (FACS) and an acetyl-CoA carboxylase (ACC). In some embodiments, the expression vector encoding the improved FAR enzyme and the expression vector encoding a second enzyme (e.g., an FAS, TE, FACS or ACC) are separate nucleic acids. In other embodiments, the improved FAR enzyme and the second enzyme are encoded on the same expression vector, and expression of each enzyme is independently regulated by a different promoter.

In various embodiments, an expression vector optionally contains a ribosome binding site (RBS) for translation initiation, and a transcription terminator, such as PinII. The vector also optionally includes appropriate sequences for amplifying expression, e.g., an enhancer.

Promoters

Suitable promoters include constitutive promoters, regulated promoters, and inducible promoters. Appropriate promoter sequences can be obtained from genes encoding extracellular or intracellular polypeptides which are either endogenous or heterologous to the host cell. Methods for the isolation, identification and manipulation of promoters of varying strengths are available in or readily adapted from the art. See, e.g., Nevoigt et al. (2006) *Appl. Environ. Microbiol.* 72:5266-5273, the disclosure of which is herein incorporated by reference in its entirety.

In certain embodiments, the DNA constructs and vectors comprising a polynucleotide encoding an improved FAR polypeptides are suitable for expression in bacteria. For bacterial host cells, suitable promoters for directing transcription of the nucleic acid constructs of the present disclosure, include the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, *Bacillus megaterium* promoters, and prokaryotic beta-lactamase gene (Villa-Kamaroff et al., *Proc. Natl Acad. Sci. USA* 75: 3727-3731(1978)), as well as the tac promoter (DeBoer et al., *Proc. Natl Acad. Sci. USA* 80: 21-25(1993)). Additional promoters include trp promoter, phage lambda PL, T7 promoter, promoters found at PromEC and the like. Promoters suitable for use in the present disclosure are described in "Useful proteins from recombinant bacteria" in *Scientific American* 242:74-94 (1980); and in Sambrook et al (2001) *Molecular Cloning: A Laboratory Manual*, 3$^{rd}$ ed., Cold Spring Harbor Laboratory Press, New York.

In various embodiments, the DNA constructs and vectors comprising polynucleotides encoding an improved FAR polypeptide are suitable for expression in yeast. In certain embodiments, the DNA constructs and vectors comprising the polynucleotides encoding an improved FAR are suitable for expression in oleaginous yeast, such as but not limited to *Yarrow lipolytica*. In certain embodiments the promoter is a *Y. lipolytica* promoter.

In certain embodiments, the DNA constructs and vectors comprising the polynucleotides encoding an improved FAR polypeptide are suitable for expression in yeast, such as but not limited to *S. cerevisiae*. For yeast host cells, suitable promoters for directing transcription of the nucleic acid constructs of the present disclosure are known to the skilled artisan and include, but are not limited to, an enolase (ENO-1_gene) promoter, a galactokinase (GAL1) promoter, an alcohol dehydrogenase/glyceraldehyde-3-phosphate dehydrogenase (ADH2/GAP) promoter, a translation elongation factor EF-1 alpha (TEF1) promoter as well as those described by Romanos et al. (1992) *Yeast* 8:423-488. In other embodiments, promoters include the TEF1 promoter and an RPS7 promoter.

In various embodiments, the DNA constructs and vectors comprising polynucleotides encoding an improved FAR polypeptide are suitable for expression in filamentous fungal host cells. For these cells, suitable promoters for directing the transcription of the nucleic acid constructs of the present disclosure include promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof. Examples of suitable promoters useful for directing the transcription of the nucleotide constructs of the present invention in a filamentous fungal host cell are promoters such as cbh1, cbh2, egl1, egl2, pepA, hfb1, hfb2, xyn1, amy, and glaA (Nunberg et al., Mol. Cell Biol., 4:2306-2315 (1984), Boel et al., EMBO J 3:1581-1585 ((1984) and EPA 137280).

Other Regulatory Elements

In various embodiments, the polynucleotides useful for expressing heterologous FAR enzymes in recombinant host cells are operably linked to other control sequences, including but not limited to, a transcription terminator sequence, a signal sequence that when translated directs the expressed polypeptide into the secretory pathway of the recombinant host cell, and a polyadenylation sequence (eukaryotes). The choice of appropriate control sequences for use in the polynucleotide constructs of the present disclosure is within the skill in the art and in various embodiments is dependent on the recombinant host cell used and the desired method of recovering the fatty alcohol compositions produced.

In various embodiments, the expression vector includes one or more selectable markers, which permit easy selection of transformed cells. Selectable markers for use in a host organism as described herein include, but are not limited to, genes that confers antibiotic resistance (e.g., ampicillin, kanamycin, chloramphenicol or tetracycline resistance) to the recombinant host organism that comprises the vector.

VI. Host Cells Comprising Far Variants

In some embodiments, the present invention provides a method for producing a recombinant host cell, wherein the method comprises: (a) providing a nucleic acid construct of the present invention, wherein the nucleic acid construct comprises polynucleotide encoding an improved FAR polypeptide as described herein; and (b) transforming a host cell with the nucleic acid construct to produce a recombinant cell. In some embodiments, the host cell is a bacterial cell. In some embodiments, the host cell is a yeast cell. The transformed or transfected host cell is cultured in a suitable nutrient medium under conditions permitting the expression of the FAR enzyme. The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection).

Host Cells

The recombinant host cells or microorganisms of the present invention generally comprise a polynucleotide, such as one of the polynucleotides described above, encoding an improved FAR polypeptide. Suitable host microorganisms include, but are not limited to, bacteria, yeast, filamentous fungi and algae. In certain embodiments, the yeast is an oleaginous yeast. In certain embodiments, microorganisms useful as recombinant host cells are wild-type microorganisms.

In various embodiments, microorganisms useful as recombinant host cells are genetically modified. As used herein, "genetically modified" microorganisms include microorganisms having one or more endogenous genes removed, microorganisms having one or more endogenous genes with reduced expression compared to the parent or wild-type microorganism, or microorganisms having one or more genes overexpressed compared to the parent or wild-type microorganism. In certain embodiments, the one or more genes that are overexpressed are endogenous to the microorganism. In some embodiments, the one or more genes that are overexpressed are heterologous to the microorganism.

In certain embodiments, the genetically modified microorganism comprises an inactivated or silenced endogenous gene that codes for a protein involved in the biosynthesis of fatty acyl-CoA substrates. In particular embodiments, the inactive or silenced gene encodes a fatty acyl-ACP thioesterase or a fatty acyl-CoA synthetase (FACS).

In certain embodiments, the genetically modified microorganism overexpresses a gene that encodes one or more proteins other than an improved FAR enzyme. In various embodiments, the one or more overexpressed proteins increase the rate at which the recombinant cell produces the acyl-thioester FAR substrate, e.g., the compound of formula (I) shown above. In some embodiments, the one or more overexpressed genes encodes a protein directly involved in fatty acid biosynthesis. In particular embodiments, the one or more overexpressed genes encode a protein selected from a fatty acid synthase (FAS), an acyl-ACP thioesterase (TE), a fatty acyl-CoA synthase (FACS) and an acetyl-CoA carboxylase (ACC). In some embodiments, the overexpressed gene is endogenous to the microorganism. In other embodiments, the overexpressed gene is heterologous to the microorganism.

Prokaryotic Host Cells

In some embodiments, the host cell is a prokaryotic cell. Suitable prokaryotic cells include gram positive, gram negative and gram-variable bacterial cells. In certain embodiments, host cells include, but are not limited to, species of a genus selected from the group consisting of *Agrobacterium, Alicyclobacillus, Anabaena, Anacystis, Acinetobacter, Acidothermus, Arthrobacter, Azobacter, Bacillus, Bifidobacterium, Brevibacterium, Butyrivibrio, Buchnera, Campestris,*

Camplyobacter, Clostridium, Corynebacterium, Chromatium, Coprococcus, Cyanobacteria, Escherichia, Enterococcus, Enterobacter, Erwinia, Fusobacterium, Faecalibacterium, Francisella, Flavobacterium, Geobacillus, Haemophilus, Helicobacter, Klebsiella, Lactobacillus, Lactococcus, llyobacter, Micrococcus, Microbacterium, Mesorhizobium, Methylobacterium, Methylobacterium, Mycobacterium, Neisseria, Pantoea, Pseudomonas, Prochlorococcus, Rhodobacter, Rhodopseudomonas, Rhodopseudomonas, Roseburia, Rhodospirillum, Rhodococcus, Scenedesmun, Streptomyces, Streptococcus, Synnecoccus, Saccharomonospora, Staphylococcus, Serratia, Salmonella, Shigella, Thermoanaerobacterium, Tropheryma, Tularensis, Temecula, The rmosynechococcus, Thermococcus, Ureaplasma, Xanthomonas, Xylella, Yersinia and Zymomonas. In particular embodiments, the host cell is a species of a genus selected from the group consisting of Agrobacterium, Arthrobacter, Bacillus, Clostridium, Corynebacterium, Escherichia, Erwinia, Geobacillus, Klebsiella, Lactobacillus, Mycobacterium, Pantoea, Rhodococcus, Streptomyces and Zymomonas.

In certain embodiments, the recombinant host cell is an industrial bacterial strain. Numerous bacterial industrial strains are known and suitable for use in the methods disclosed herein. In some embodiments, the bacterial host cell is a species of the genus Bacillus, e.g., B. thuringiensis, B. anthracis, B. megaterium, B. subtilis, B. lentus, B. circulars, B. pumilus, B. lautus, B. coagulans, B. brevis, B. firmus, B. alkaophius, B. licheniformis, B. clausii, B. stearothermophilus, B. halodurans and B. amyloliquefaciens. In particular embodiments, the host cell is a species of the genus Bacillus and is selected from the group consisting of B. subtilis, B. pumilus, B. licheniformis, B. clausii, B. stearothermophilus, B. megaterium and B. amyloliquefaciens.

In some embodiments the bacterial host cell is a species of the genus Erwinia, e.g., E. uredovora, E. carotovora, E. ananas, E. herbicola, E. punctata or E. terreus.

In other embodiments the bacterial host cell is a species of the genus Pantoea, e.g., P. citrea or P. agglomerans.

In still other embodiments, the bacterial host cell is a species of the genus Streptomyces, e.g., S. ambofaciens, S. achromogenes, S. avermitilis, S. coelicolor, S. aureofaciens, S. aureus, S. fungicidicus, S. griseus or S. lividans.

In further embodiments, the bacterial host cell is a species of the genus Zymomonas, e.g., Z. mobilis or Z lipolytica.

In further embodiments, the bacterial host cell is a species of the genus Rhodococcus, e.g. R. opacus.

In particular embodiments, the bacterial host cell is a species of the genus Escherichia, e.g., E. coli. In certain embodiments, the E. coli is a wild-type bacterium. In various embodiments, the wild-type E. coli bacterial strain useful in the processes described herein is selected from, but not limited to, strain W3110, strain MG1655 and strain BW25113. In other embodiments, the E. coli is genetically modified. Examples of genetically modified E. coli useful as recombinant host cells include, but are not limited to, genetically modified E. coli found in the Keio Collection, available from the National BioResource Project at NBRP E. coli, Microbial Genetics Laboratory, National Institute of Genetics 1111 Yata, Mishima, Shizuoka, 411-8540.

In particular embodiments, the genetically modified E. coli comprises an inactivated or silenced endogenous fadD gene, which codes for an acyl-CoA synthetase protein. In other embodiments the genetically modified E. coli comprises an inactivated of silenced endogenous fadK gene, which codes for an endogenous short-chain acyl-CoA synthetase. In still other embodiments, the genetically modified E. coli comprises an inactivated or silenced endogenous fadD gene and an inactivated or silenced endogenous fadK gene. In other embodiments, the genetically modified E. coli comprises an endogenous fadD gene that has reduced expression compared to the parent or wild-type strain. In various embodiments, the genetically modified E. coli comprises an endogenous fadK gene that has reduced expression compared to the parent or wild-type strain.

Yeast Host Cells

In certain embodiments, the recombinant host cell is a yeast. In various embodiments, the yeast host cell is a species of a genus selected from the group consisting of Candida, Hansenula, Saccharomyces, Schizosaccharomyces, Pichia, Kluyveromyces, and Yarrowia. In particular embodiments, the yeast host cell is a species of a genus selected from the group consisting of Saccharomyces, Candida, Pichia and Yarrowia.

In various embodiments, the yeast host cell is selected from the group consisting of Hansenula polymorpha, Saccharomyces cerevisiae, Saccaromyces carlsbergensis, Saccharomyces diastaticus, Saccharomyces norbensis, Saccharomyces kluyveri, Schizosaccharomyces pombe, Pichia pastoris, Pichia finlandica, Pichia trehalophila, Pichia ferniemtans, lssatchenkia orientalis, Pichia kodamae, Pichia membranaefaciens, Pichia opuntiae, Pichia thermotolerans, Pichia salictaria, Pichia quercuum, Pichia pijperi, Pichia stipitis, Pichia methanolica, Pichia angusta, Kluyveromyces lactis, Candida albicans, Candida krusei, Candida ethanolic and Yarrowia lipolytica and synonyms or taxonomic equivalents thereof.

In certain embodiments, the yeast host cell is a wild-type cell. In various embodiments, the wild-type yeast cell strain is selected from, but not limited to, strain BY4741, strain FL100a, strain INVSC1, strain NRRL Y-390, strain NRRL Y-1438, strain NRRL YB- 1952, strain NRRL Y-5997, strain NRRL Y-7567, strain NRRL Y-1532, strain NRRL YB-4149and strain NRRL Y-567. In other embodiments, the yeast host cell is genetically modified. Examples of genetically modified yeast useful as recombinant host cells include, but are not limited to, genetically modified yeast found in the Open Biosystems collection found at the website www.openbiosystems.com/GeneExpression/Yeast/YKO/. See Winzeler et al. (1999) Science 285:901-906.

In other embodiments, the recombinant host cell is an oleaginous yeast. Oleaginous yeast are organisms that accumulate lipids such as tri-acylglycerols. Examples of oleaginous yeast include, but are not limited to, organisms selected from the group consisting of Yarrowia lipolytica, Yarrowia paralipolytica, Candida revkaufi, Candida pulcherrima, Candida tropicalis, Candida utilis, Candida curvata D, Candida curvata R, Candida diddensiae, Candida boldinii, Rhodotorula glutinous, Rhodotorula graminis, Rhodotorula mucilaginosa, Rhodotorula minuta, Rhodotorula bacarum, Rhodosporidium toruloides, Cryptococcus (terricolus) albidus var. albidus, Cryptococcus laurentii, Trichosporon pullans, Trichosporon cutaneum, Trichosporon cutancum, Trichosporon pullulans, Lipomyces starkeyii, Lipomyces lipoferus, Lipomyces tetrasporus, Endomycopsis vernalis, Hansenula ciferri, Hansenula saturnus, and Trigonopsis variables. In particular embodiments, the oleaginous yeast is Y. lipolytica. In certain embodiments, Yarrowia lipolytica strains include, but are not limited to, DSMZ 1345, DSMZ 3286, DSMZ 8218, DSMZ 70561, DSMZ 70562, and DSMZ 21175.

In certain embodiments, the oleaginous yeast is a wild-type organism. In other embodiments, the oleaginous yeast is genetically modified.

In yet other embodiments, the recombinant host cell is a filamentous fungus. In certain embodiments, the filamentous fungal host cell is a species of a genus selected from the group consisting of *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora, Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Trametes, Tolypocladium, Trichoderma, Verticillium, Volvariella*, and teleomorphs, synonyms or taxonomic equivalents thereof.

In some embodiments, the filamentous fungal host cell is an *Aspergillus* species, a *Chrysosporium* species, a *Corynascus* species, a *Fusarium* species, a *Humicola* species, a *Myceliophthora* species, a *Neurospora* species, a *Penicillum* species, a *Tolypocladium* species, a *Tramates* species, or *Trichoderma* species. In other embodiments, the *Trichoderma* species is selected from *T. longibrachiatum, T. viride, Hypocrea jecorina* and *T. reesei*; the *Aspergillus* species is selected from *A. awamori, A. funigatus, A. japonicus, A. nidulans, A. niger, A. aculeatus, A. foetidus, A. oryzae, A. sojae*, and *A. kawachi*; the *Chrysosporium* species is *C. lucknowense*; the *Fusarium* species is selected from *F. graminum, F. oxysporum* and *F. venenatum*; the *Myceliophthora* species is *M. thermophilia*; the *Neurospora* species is *N. crassa*; the *Humicola* species is selected from *H. insolens, H. grisea*, and *H. lanuginosa*; the *Penicillum* species is selected from *P. purpurogenum, P. chtysogenum*, and *P. verruculosum;* the *Thielavia* species is *T. terrestris*; and the *Trametes* species is selected from *T. villosa* and *T. versicolor*.

In some embodiments, the filamentous fungal host is a wild-type organism. In other embodiments, the filamentous fungal host is genetically modified.

In certain particular embodiments, recombinant host cells for use in the methods described herein are derived from strains of *Escherichia coli, Bacillus, Saccharomyces, Streptomyces* and *Yarrowia*.

In certain embodiments the host cell is a *Yarrowia* cell, such as a *Y. lipolytica* cell.

Cells which are useful in the practice of the present disclosure include prokaryotic and eukaryotic cells which are readily accessible from a number of culture collections and other sources, e.g., the American Type Culture Collection (ATCC), Deutsche Sammlung von Mikroorganismen and Zellkulturen GmbH (DSMZ) (German Collection of Microorganisms and Cell Culture), Centraalbureau Voor Schimmelcultures (CBS), and Agricultural Research Service Patent Culture Collection, Northern Regional Research Center (NRRL). *Yarrowia lipolytica* is available, as a non-limiting example, from the ATCC under accession numbers 20362, 18944, and 76982.

In some embodiments, the method of producing fatty alcohols may be achieved in a recombinant microorganism by one or two different biosynthetic pathways. These pathways are described as an acyl-CoA independent pathway or an acyl-CoA dependent pathway and reference is made to FIG. 1. Accordingly fatty alcohols can be produced by a recombinant microorganism that lacks a functional endogenous enzyme involved in the biosynthesis of fatty acyl-CoA substrates. Thus in some aspects, fatty alcohols can be produced by a recombinant microorganism that express a gene encoding a improved FAR polypeptide described herein and that lacks a gene encoding a fatty acyl-CoA synthetase (FACS) and/or a gene encoding a fatty acyl-ACP thioesterase (TE). Without being bound to a particular theory, fatty alcohol production may be increased in a microorganism lacking a gene encoding a FACS and/or a TE because silencing or inactivating the FACS and/or TE gene may inactivate a competing biosynthetic pathway.

Accordingly, genetically modified *E. coli* host microorganisms silenced or inactivated in the fatty acyl-CoA synthetase fadD gene and/or the short chain fatty acyl-CA synthetase fadK gene can be used as recombinant hosts for production of fatty alcohols. The *E. coli* host microorganism can be genetically modified to be silenced or inactivated in one or more of the additional genes described above.

Transformation and Cell Culture

Polynucleotides of the invention, encoding FAR variants, may be introduced into host cells for expression of the FAR variant. The polynucleotide may be introduced into the cell as a self-replicating episome (e.g., expression vector) or may be stably integrated into the host cell DNA.

In some embodiments, a host cell is transformed with a polynucleotide encoding a FAR variant. In transformation, the polynucleotide that is introduced into the host cell remains in the genome or on a plasmid or other stably maintained vector in the cell and is capable of being inherited by the progeny thereof. Stable transformation is typically accomplished by transforming the host cell with an expression vector comprising the polynucleotide of interest (e.g., the polynucleotide encoding the FAR variant) along with a selectable marker gene (e.g., a gene that confers resistance to an antibiotic). Only those host cells which have integrated the polynucleotide sequences of the expression vector into their genome will survive selection with the marker (e.g., antibiotic). These stably transformed host cells can then be propagated according to known methods in the art.

Methods, reagents and tools for transforming host cells described herein, such as bacteria, yeast (including oleaginous yeast) and filamentous fungi are known in the art. General methods, reagents and tools for transforming, e.g., bacteria can be found, for example, in Sambrook et al (2001) *Molecular Cloning: A Laboratory Manual*, 3$^{rd}$ ed., Cold Spring Harbor Laboratory Press, New York. Methods, reagents and tools for transforming yeast are described in "Guide to Yeast Genetics and Molecular Biology," C. Guthrie and G. Fink, Eds., *Methods in Enzymology* 350 (Academic Press, San Diego, 2002). Methods, reagents and tools for transforming, culturing, and manipulating *Y. lipolytica* are found in "*Yarrowia lipolytica*," C. Madzak, J. M. Nicaud and C. Gaillardin in "Production of Recombinant Proteins. Novel Microbial and Eucaryotic Expression Systems," G. Gellissen, Ed. 2005, which is incorporated herein by reference for all purposes. In some embodiments, introduction of the DNA construct or vector of the present invention into a host cell can be effected by calcium phosphate transfection, DEAE-Dextran mediated transfection, PEG-mediated transformation, electroporation, or other common techniques (See Davis et al., 1986, *Basic Methods in Molecular Biology*, which is incorporated herein by reference).

The engineered host cells can be cultured in conventional nutrient media modified as appropriate for activating promoters, selecting transformants, or amplifying the FAR polynucleotide. Culture conditions, such as temperature, pH and the like, are those previously used with the host cell selected for expression, and will be apparent to those skilled in the art. As noted, many references are available for the culture and production of many cells, including cells of bacterial, plant, animal (especially mammalian) and archebacterial origin. See e.g., Sambrook, Ausubel, and Berger (all supra), as well as Freshney (1994) *Culture of Animal Cells, a Manual of*

Basic Technique, third edition, Wiley-Liss, New York and the references cited therein; Doyle and Griffiths (1997) *Mammalian Cell Culture: Essential Techniques* John Wiley and Sons, NY; Humason (1979) *Animal Tissue Techniques*, fourth edition W.H. Freeman and Company; and Ricciardelli, et al., (1989) *In Vitro Cell Dev. Biol.* 25:1016-1024, all of which are incorporated herein by reference. For plant cell culture and regeneration, Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture; Fundamental Methods* Springer Lab Manual, Springer-Verlag (Berlin Heidelberg New York); Jones, ed. (1984) *Plant Gene Transfer and Expression Protocols*, Humana Press, Totowa, N.J. and *Plant Molecular Biology* (1993) R. R. D. Croy, Ed. Bios Scientific Publishers, Oxford, U.K. ISBN 0 12 198370 6, all of which are incorporated herein by reference. Cell culture media in general are set forth in Atlas and Parks (eds.) *The Handbook of Microbiological Media* (1993) CRC Press, Boca Raton, Fla., which is incorporated herein by reference. Additional information for cell culture is found in available commercial literature such as the *Life Science Research Cell Culture Catalogue* (1998) from Sigma-Aldrich, Inc (St Louis, Mo.) ("Sigma-LSRCCC") and, for example, *The Plant Culture Catalogue and supplement* (1997) also from Sigma-Aldrich, Inc (St Louis, Mo.) ("Sigma-PCCS"), all of which are incorporated herein by reference.

VII. Production and Recovery of Far Variants

In another aspect, the present invention provides a method of making a polypeptide having improved FAR enzymatic activity. In some embodiments, the method comprises: providing a host cell transformed with any one of the described FAR polynucleotides of the present invention; culturing the transformed host cell in a culture medium under conditions in which the host cell expresses the encoded FAR polypeptide; and optionally recovering or isolating the expressed FAR polypeptide. The method further provides optionally lysing the transformed host cells after expressing the encoded FAR polypeptide and optionally recovering or isolating the expressed FAR polypeptide from the cell lysate. The present invention further provides a method of making an FAR polypeptide, said method comprising cultivating a host cell transformed with a FAR polypeptide under conditions suitable for the production of the FAR polypeptide and recovering the FAR polypeptide.

The FAR polypeptide can be recovered from the host cell using protein recovery techniques that are well known in the art, including those described herein. Cells are typically harvested by centrifugation, disrupted by physical or chemical means, and the resulting crude extract may be retained for further purification. Microbial cells employed in expression of proteins can be disrupted by any convenient method, including freeze-thaw cycling, sonication, mechanical disruption, or use of cell lysing agents, or other methods, which are well known to those skilled in the art.

The resulting polypeptide may be recovered/isolated and optionally purified by any of a number of methods known in the art. For example, the polypeptide may be isolated from the nutrient medium by conventional procedures including, but not limited to, centrifugation, filtration, extraction, spray-drying, evaporation, chromatography (e.g., ion exchange, affinity, hydrophobic interaction, chromatofocusing, and size exclusion), or precipitation. Protein refolding steps can be used, as desired, in completing the configuration of the mature protein. Finally, high performance liquid chromatography (HPLC) can be employed in the final purification steps. See, for example, Parry et al., 2001, *Biochem. J.* 353:117, and Hong et al., 2007, *Appl. Microbiol. Biotechnol.* 73:1331, both incorporated herein by reference. In addition to the references noted supra, a variety of purification methods are well known in the art, including, for example, those set forth in Sandana (1997) *Bioseparation of Proteins*, Academic Press, Inc.; Bollag et al. (1996) *Protein Methods*, 2$^{nd}$ Edition, Wiley-Liss, NY; Walker (1996) *The Protein Protocols Handbook* Humana Press, NJ; Harris and Angal (1990) *Protein Purification Applications: A Practical Approach*, IRL Press at Oxford, Oxford, England; Harris and Angal *Protein Purification Methods: A Practical Approach*, IRL Press at Oxford, Oxford, England; Scopes (1993) *Protein Purification: Principles and Practice* 3$^{rd}$ *Edition*, Springer Verlag, NY; Janson and Ryden (1998) *Protein Purification: Principles, High Resolution Methods and Applications, Second Edition*, Wiley-VCH, NY; and Walker (1998) *Protein Protocols on CD-ROM*, Humana Press, NJ, all of which are incorporated herein by reference.

VIII. Methods of Producing Fatty Alcohols and Fatty Alcohol Compositions

The present disclosure also provides methods of producing fatty alcohols with the improved FAR polypeptides described herein, as well as the resultant fatty alcohol compositions produced by said methods. The methods can be carried out in cell-free systems with isolated improved FAR polypeptides, or in cell-based systems with microorganisms engineered to express one or more improved FAR polypeptides, as described above.

In embodiments in which fatty alcohols are produced in cell-free systems, an isolated improved FAR polypeptide is provided with a substrate (a fatty acyl-ACP and/or a fatty acyl-CoA complex) and NAD(P)H under suitable conditions of temperature, pH, and ionic strength and time sufficient for the production of a fatty alcohol composition. In some embodiments, the improved FAR polypeptide is provided with a composition of a fatty acid, Coenzyme A and a fatty acyl-CoA synthase under suitable conditions of temperature, pH and ionic strength and time sufficient for production of a fatty alcohol composition.

In embodiments employing cell-based systems, a recombinant host cell capable of expressing a gene that encodes an improved FAR polypeptide as described herein above is cultured in an aqueous nutrient medium comprising an assimilable source of carbon under conditions suitable for production of a fatty alcohol composition. Any of the various host microorganisms described herein can be used.

In some particular embodiments, a method of producing a fatty alcohol composition comprises culturing a recombinant microorganism in a suitable culture medium, wherein the recombinant microorganism comprises a gene encoding an improved FAR polypeptide capable of producing at least about 1.5 more fatty alcohol than a wild-type FAR comprising SEQ ID NO:2 when assayed under the same conditions. In some embodiments, a method of producing a fatty alcohol composition comprises culturing a recombinant microorganism in a suitable culture medium, wherein the recombinant microorganism comprises a gene encoding a FAR variant capable of producing an increased amount of C10-C18 fatty alcohols, an increased amount of C12-C16 fatty alcohols, an increased amount of C10-C14 fatty alcohols, an increased amount of C12-C14 fatty alcohols, or an increased amount of C16-018 fatty alcohols as compared to a wild-type FAR comprising SEQ ID NO:2 when assayed under the same conditions. In some embodiments, a method of producing a fatty alcohol composition comprises culturing a recombinant microorganism in a suitable culture medium, wherein the recombinant microorganism comprises a gene encoding a FAR variant capable of producing a fatty alcohol profile having one or more of an increased amount of C16:1 (cis $\Delta^9$-1-hexadecenol), a decreased amount of C18:1 (cis $\Delta^{11}$-1-octadecenol), an increased amount of C14:0 (1-tetradecanol), and a decreased amount of C16:0 (1-hexadecanol) as compared to a wild-type FAR comprising SEQ ID NO:2.

In some embodiments, the method of producing a fatty alcohol composition comprises culturing a recombinant microorganism (for example, but not limited to a strain of E. coli, Yarrowia, or Saccharomyces), in a suitable culture medium, wherein the recombinant microorganism comprises a gene encoding an improved FAR polypeptide comprising a sequence that is at least about 70% (or at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%) identical to SEQ ID NO:2 and comprises one or more amino acid substitutions selected from A2D/F/G/H/I/P/N/Q/T/V/W, T3R, Q4R, Q5S, Q6P, Q7N, N8K/S, G9D/F, A10T, A12T/V, G14N/R/V/W, E17D, Q18I, K22E, V24I, L33V, I42L, G50S/V, L54P, R60H, H61R, P62S, A63R/Y, R65G/Q/Y, L69E/Q, E71K, A73K/V, S74K/P, S76K/N/R, V77A/I, H83R, E87G/V, T91I/R, L93V, H98P/R, T101L, G102C, V104I/M, S107C/L/W, G110D, L111S, T112A, P113D/L, R115A/H, R117D, A120V, G121H/S, Q122R, A125V, N128H, S132G, N134K/R/S, E137L, E138L/Q, D1400, A142V, K144Q, L148E, E151L, V153I, N160S, A162T, N174C, N177Q/R/T, Q180H/R, V185A/I, I186A/G/Y, P188A/I/M/S, T197P, D198Q, E202G, E204G, E205G/P, V207I/L, L209K/N, D212R, K213R, V217L, R2200, K224R, L226A/M, E227A/G/H/R/T, K229R, R236K, E237L, S244A/F/G/H/P, D245N, T246A, L257K, K260R/T, A261D, S263P, G264S, S266A, I269T, S283E/F/K/M/T/V, I287L, E288Q, V290I, A295T/V, A299T, E303G, V305I, S306F/H/N/W, V318I, I328T, L330V, S331V, L332S, A333T, S339G/V, G340P/S/V, Q341K, R342L, G350S, G351C, K359L, L364F/I, M365N, A366T/V, T370A/I, A374K/Y, D376P, Q377C/K/Y, Y380K/N/R, R381C, T384R, A389I/UM/V, D396G, V397I/L, V398Y, V399T, G400A/L, G401A/C/I/US/V, R403C/S, V404A, P405A/C/F/G/US/V/W, L406Y, A409V/W/Y, G410A/C/H/N/Q/R/S, A412C/F/M/V, M413L/R, A416L/V, Q418I/R/V/Y, E421I/L/N/P/R/S/V/Y, N427K, D429E/K/N/Q/R, T430H/I/R, R432C/Q, S433F/H/K/L/N/W, T436D/K/Q, I437V, F440L, A443T, P444S, Y446H, S452A/G/N, S458G/L/M/Q, R459H, L463E/T, D464G, V466E/Q/R, A472V, Q474R, L479Q, I484V, G487R/S/T/Y, N490S, E496A, K498A, L499A/H/I/N/P/R/S, Y500C/G/H/L/N/P/Q/R/S/W, S501 G/R, L502A/P/Q/R/S, A504G/R, A505K, D506G/S, T507A/G/P/R/S, R508D/G/H, K509D/E/G/H/N/R/S/Y, K510A/D/G/P/S/Y, A511G/I/K/P/Q/R/S/T, and A512K/S/T, wherein the amino acid positions are numbered with reference to SEQ ID NO:2; and allowing expression of said gene, wherein said expression results in the production of a composition of fatty alcohols (e.g., a composition comprising an increased amount of an aggregate of the fatty alcohols C14:0 (1-tetradecanol), C16:1 (cis $\Delta^9$-1-hexadecenol), C16:0 (1-hexadecanol), C18:1 (cis $\Delta^{11}$-1-octadecenol), and C18:0 (1-octadecanol), or a composition comprising a fatty alcohol profile having one or more of an increased amount of C16:1 (cis $\Delta^9$-1-hexadecenol), a decreased amount of C18:1 (cis $\Delta^{11}$-1-octadecenol), an increased amount of C14:0 (1-tetradecanol), and a decreased amount of C16:0 (1-hexadecanol) as compared to a wild-type FAR).

In other embodiments, the method of producing a fatty alcohol composition comprises culturing a recombinant microorganism (for example, but not limited to a strain of E. coli, Yarrowia, or Saccharomyces), in a suitable culture medium, wherein the recombinant microorganism comprises a gene encoding an improved FAR polypeptide comprising a sequence that is at least about 80% (at least 85%, at least 90%, at least 95% or at least 97%) identical to SEQ ID NO: 2 and including a substitution at one or more positions 2, 134, 138, 188, 405 and 511 when aligned to SEQ ID NO: 2; and allowing expression of said gene, wherein said expression results in the production of a composition of fatty alcohols. In some embodiments, the substitution at position 2 is H, T, D, F, V, G, Q, P or I; the substitution at position 134 is R, K, or S; the substitution at position 138 is Q or L; substitution at position 188 is S; the substitution at position 405 is V, S, F, G, C, L, S, A, or W; and the substitution at position 511 is T, P, G, S, K, Q, or R.

Fermentation

Fermentation of the recombinant host cell is carried out under suitable conditions and for a time sufficient for production of fatty alcohols. Conditions for the culture and production of cells, including filamentous fungi, bacterial and yeast cells, are readily available. Cell culture media in general are set forth in Atlas and Parks, Eds., *The Handbook of Microbiological Media* (1993) CRC Press, Boca Raton, Fla., which is incorporated herein by reference. The individual components of such media are available from commercial sources, e.g., under the Difco™ and BBL™ trademarks. In one non-limiting example, the aqueous nutrient medium is a "rich medium" comprising complex sources of nitrogen, salts, and carbon, such as YP medium, comprising 10 g/L of peptone and 10 g/L yeast extract of such a medium. In other non-limiting embodiments, the aqueous nutrient medium comprises a mixture of Yeast Nitrogen Base (Difco™) in combination supplemented with an appropriate mixture of amino acids, e.g., SC medium. In particular aspects of this embodiment, the amino acid mixture lacks one or more amino acids, thereby imposing selective pressure for maintenance of an expression vector within the recombinant host cell.

The recombinant microorganisms can be grown under batch or continuous fermentation conditions. Classical batch fermentation is a closed system, wherein the compositions of the medium is set at the beginning of the fermentation and is not subject to artificial alternations during the fermentation. A variation of the batch system is a fed-batch fermentation which also finds use in the present invention. In this variation, the substrate is added in increments as the fermentation progresses. Fed-batch systems are useful when catabolite repression is likely to inhibit the metabolism of the cells and where it is desirable to have limited amounts of substrate in the medium. Batch and fed-batch fermentations are common and well known in the art. Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth. Continuous fermentation systems strive to maintain steady state growth conditions. Methods for modulating nutrients and growth factors for continuous fermentation processes as well as techniques for maximizing the rate of product formation are well known in the art of industrial microbiology.

In some embodiments, fermentations are carried out a temperature within the range of from about 10° C. to about 60° C., from about 15° C. to about 50° C., from about 20° C. to about 45° C., from about 20° C. to about 40° C., from about 20° C. to about 35° C. and from about 25° C. to about 45° C. In a particular aspect, the fermentation is carried out at a temperature of from about 28° C. and also from about 30° C. In other embodiments, the fermentation is carried out for a period of time within the range of from about 8 hours to 240 hours, from about 8 hours to about 168 hours, from about 8 hours to 144 hours, from about 16 hours to about 120 hours, or from about 24 hours to about 72 hours. It will be understood that, in certain embodiments where thermostable host cells are used, fermentations may be carried out at higher temperatures. In other embodiments, the fermentation will be carried out at a pH in the range of 4-8, in the range of 4.5 to 7.5, in the range of 5 to 7, and also in the range of 5.5 to 6.5. As used herein, the terms "culture" and "fermentation" are used interchangeably.

Carbon sources useful in the aqueous fermentation medium or broth of the disclosed process in which the recombinant microorganisms are grown are those assimilable by the recombinant host strain. Assimilable carbon sources are available in many forms and include renewable carbon sources and the cellulosic and starch feedstock substrates obtained there from. Such examples include, for example, depolymerized cellulosic material, monosaccharides, disaccharides, oligosaccharides, saturated and unsaturated fatty acids, succinate, acetate and mixtures thereof. Further carbon sources include, without limitation, glucose, galactose, sucrose, xylose, fructose, glycerol, arabinose, mannose, raffinose, lactose, maltose, and mixtures thereof. In some embodiments, the term "fermentable sugars" is used interchangeably with the term "assimilable carbon source". In one aspect, fermentation is carried out with a mixture of glucose and galactose as the assimilable carbon source. In another aspect, fermentation is carried out with glucose alone to accumulate biomass, after which the glucose is substantially removed and replaced with an inducer, e.g., galactose for induction of expression of one or more heterologous genes involved in fatty alcohol production. In still another aspect, fermentation is carried out with an assimilable carbon source that does not mediate glucose repression, e.g., raffinose, to accumulate biomass, after which the inducer, e.g., galactose, is added to induce expression of one or more heterologous genes involved in fatty alcohol production. In some preferred embodiments, the assimilable carbon source is from cellulosic and starch feedstock derived from but not limited to, wood, wood pulp, paper pulp, grain, corn stover, corn fiber, rice, paper and pulp processing waste, woody or herbaceous plants, fruit or vegetable pulp, distillers grain, grasses, rice hulls, wheat straw, cotton, hemp, flax, sisal, corn cobs, sugar cane bagasse, switch grass and mixtures thereof.

Production Levels

The methods described herein produce fatty alcohols in high yield. Cells expressing FAR variants described herein may yield fatty alcohols in the range of about 0.5 g to at least 35.0 g fatty alcohols per liter of nutrient medium, depending upon the improved FAR polypeptide used. Exemplary culture conditions for E. coli are provided in the examples. Other E. coli culture conditions, as well as culture conditions for other host cells, are known or can be determined. In some embodiments, about 35 g/L to about 50 g/L (e.g., about 35 g/L, about 40 g/L, about 45 g/L, or about 50 g/L), or sometimes about 50 g/L to about 100 g/L (e.g., about 50 g/L, about 60 g/L, about 70 g/L, about 80 g/L, about 90 g/L, or about 100 g/L) are produced. In particular embodiments, the amount of fatty alcohols produced by the methods described herein is at least about 0.5 g/L, such as at least about 1 g/L, such as at least about 1.5 g/L, such as at least about 2.0 g/L, such as at least about 2.5 g/L, such as at least about 3 g/L, such as at least about 3.5 g/L, such as at least about 4 g/L, such as at least about 4.5 g/L, such as at least about 5 g/L, such as at least about 10 g/L of medium. In various embodiments, the amount of fatty alcohols produced by the methods described herein is at least about 20 g/L, such as at least about 30 g/L, such as at least about 40 g/L, such as at least about 50 g/L of medium. In some embodiments fermentation yields at least 0.1, at least 0.15 or at least 0.18 g fatty alcohol/gram glucose. In some embodiments fermentation yields at least 1 gram, at least 1.5 grams or at least 1.8 grams fatty alcohol/gram dry cell weight.

In some embodiments, the methods described herein produce fatty alcohol compositions of particular chain lengths in high yield. In some embodiments, the methods described herein produce fatty alcohol compositions comprising at least about 90% C10-C18 fatty alcohols in an amount that is at least about 0.5 g/L, such as at least about 1 g/L, at least about 1.5 g/L, at least about 2.0 g/L, at least about 2.5 g/L, at least about 3 g/L, at least about 3.5 g/L, at least about 4 g/L, at least about 4.5 g/L, at least about 5 g/L, at least about 10 g/L, at least about 20 g/L, at least about 30 g/L, at least about 40 g/L, or at least about 50 g/L fatty alcohols per liter of medium. In some embodiments, the methods described herein produce fatty alcohol compositions comprising at least about 90% C12-C16 fatty alcohols in an amount that is at least about 0.5 g/L, such as at least about 1 g/L, at least about 1.5 g/L, at least about 2.0 g/L, at least about 2.5 g/L, at least about 3 g/L, at least about 3.5 g/L, at least about 4 g/L, at least about 4.5 g/L, at least about 5 g/L, at least about 10 g/L, at least about 20 g/L, at least about 30 g/L, at least about 40 g/L, or at least about 50 g/L fatty alcohols per liter of medium. In some embodiments, the methods described herein produce fatty alcohol compositions comprising at least about 90% C14-C16 fatty alcohols in an amount that is at least about 0.5 g/L, such as at least about 1 g/L, at least about 1.5 g/L, at least about 2.0 g/L, at least about 2.5 g/L, at least about 3 g/L, at least about 3.5 g/L, at least about 4 g/L, at least about 4.5 g/L, at least about 5 g/L, at least about 10 g/L, at least about 20 g/L, at least about 30 g/L, at least about 40 g/L, or at least about 50 g/L fatty alcohols per liter of medium. In some embodiments, the methods described herein produce fatty alcohol compositions comprising at least about 90% C16-C18 fatty alcohols in an amount that is at least about 0.5 g/L, such as at least about 1 g/L, at least about 1.5 g/L, at least about 2.0 g/L, at least about 2.5 g/L, at least about 3 g/L, at least about 3.5 g/L, at least about 4 g/L, at least about 4.5 g/L, at least about 5 g/L, at least about 10 g/L, at least about 20 g/L, at least about 30 g/L, at least about 40 g/L, or at least about 50 g/L fatty alcohols per liter of medium. In some embodiments, the methods described herein produce an aggregate of the fatty alcohols C14:0 (1-tetradecanol), C16:1 (cis $\Delta^9$-1-hexadecenol), C16:0 (1-hexadecanol), C18:1 (cis $\Delta^{11}$-1-octadecenol), and C18:0 (1-octadecanol) in high yield. In some embodiments, the amount of such an aggregate of fatty alcohols that is produced is at least about 0.5 g/L, such as at least about 1 g/L, at least about 1.5 g/L, at least about 2.0 g/L, at least about 2.5 g/L, at least about 3 g/L, at least about 3.5 g/L, at least about 4 g/L, at least about 4.5 g/L, at least about 5 g/L, at least about 10 g/L, at least about 20 g/L, at least about 30 g/L, at least about 40 g/L, or at least about 50 g/L of medium.

In some embodiments, the amount of fatty alcohols produced by the methods described herein is in the range of about 100 mg/g to about 5 g/g of dry cell weight. In other embodiments, the amount of fatty alcohols produced by the methods described herein is in the range of about 1 g/g to about 4 g/g of dry cell weight, such as in the range of about 2 g/g to about 3 g/g of dry cell weight by routine modification of culturing conditions.

In certain embodiments, the amount of fatty alcohols produced by the methods described herein is in the range of about 10% to about 20% of dry cell weight, such as in the range of about 20% to about 30% of dry cell weight, such as in the range of about 30% to about 40% of dry cell weight, such as in the range of about 40% to about 50% of dry cell weight, such as in the in range of about 50% to about 60% of dry cell weight, such as in the range of about 60% to about 70% of dry cell weight, such as in the range of about 70% to about 80% of dry cell weight by routine modification of culturing conditions.

In some embodiments, host cells of the invention produce fatty alcohol compositions having particular profiles as compared to the fatty alcohol compositions produced by a wild-type FAR enzyme. In some embodiments, the methods of the present invention produce fatty alcohol compositions having an increased amount of C14:0 (1-tetradecanol) and/or an increased amount of C16:1 (cis $\Delta^9$-1-hexadecenol) relative to the wild-type FAR from which the FAR variant is derived. In some embodiments, the methods of the present invention produce fatty alcohol compositions having a decreased amount of 018:0 (1-octadecanol) and/or a decreased amount of C18:1 (cis $\Delta^{11}$-1-octadecenol) relative to the wild-type FAR from which the FAR variant is derived. In some embodiments, the methods of the present invention produce fatty alcohol compositions having an increased amount of C14:0 (1-tetradecanol) and a decreased amount of C18:1 (cis $\Delta^{11}$-1-octadecenol) relative to the wild-type FAR from which the FAR variant is derived. For example, in some embodiments, the methods of the present invention produce fatty alcohol compositions having an increased amount of C16:1 (cis $\Delta^9$-1-hexadecenol) relative to the wild-type FAR from which the FAR variant is derived (e.g., increased by at least about 5%, at least about 10%, at least about 15%, at least about 20%, at least about 25%, at least about 30%, at least about 35%, at least about 40%, at least about 45%, at least about 50%, or more relative to the wild-type FAR enzyme from which the FAR variant is derived). In some embodiments, the methods of the present invention produce fatty alcohol compositions having a decreased amount of C18:1 (cis $\Delta^{11}$-1-octadecenol) relative to the wild-type FAR from which the FAR variant is derived (e.g., decreased by at least about 5%, at least about 10%, at least about 15%, at least about 20%, at least about 25%, at least about 30%, at least about 35%, at least about 40%, at least about 45%, at least about 50%, or more relative to the wild-type FAR enzyme from which the FAR variant is derived). In some embodiments, the methods of the present invention produce fatty alcohol compositions having an increased amount of C14:0 (1-tetradecanol) relative to the wild-type FAR from which the FAR variant is derived (e.g., increased by at least about 5%, at least about 10%, at least about 15%, at least about 20%, at least about 25%, at least about 30%, at least about 35%, at least about 40%, at least about 45%, at least about 50%, or more relative to the wild-type FAR enzyme from which the FAR variant is derived). In some embodiments, the methods of the present invention produce fatty alcohol compositions having a decreased amount of C16:0 (1-hexadecanol) relative to the wild-type FAR from which the FAR variant is derived (e.g., decreased by at least about 5%, at least about 10%, at least about 15%, at least about 20%, at least about 25%, at least about 30%, at least about 35%, at least about 40%, at least about 45%, at least about 50%, or more relative to the wild-type FAR enzyme from which the FAR variant is derived). In some embodiments, the methods of the present invention produce fatty alcohol compositions having a combination of two or more of: an increased amount of C16:1 (cis $\Delta^9$-1-hexadecenol) (e.g., increased by at least about 5%, at least about 10%, at least about 15%, at least about 20%, at least about 25%, at least about 30%, at least about 35%, at least about 40%, at least about 45%, at least about 50%, or more relative to the wild-type FAR enzyme from which the FAR variant is derived); a decreased amount of C18:1 (cis $\Delta^{11}$-1-octadecenol) (e.g., decreased by at least about 5%, at least about 10%, at least about 15%, at least about 20%, at least about 25%, at least about 30%, at least about 35%, at least about 40%, at least about 45%, at least about 50%, or more relative to the wild-type FAR enzyme from which the FAR variant is derived); an increased amount of C14:0 (1-tetradecanol) (e.g., increased by at least about 5%, at least about 10%, at least about 15%, at least about 20%, at least about 25%, at least about 30%, at least about 35%, at least about 40%, at least about 45%, at least about 50%, or more relative to the wild-type FAR enzyme from which the FAR variant is derived); and a decreased amount of C16:0 (1-hexadecanol) (e.g., decreased by at least about 5%, at least about 10%, at least about 15%, at least about 20%, at least about 25%, at least about 30%, at least about 35%, at least about 40%, at least about 45%, at least about 50%, or more relative to the wild-type FAR enzyme from which the FAR variant is derived).

Methods of Producing a Fatty Alcohol Composition

In another aspect, the present invention provides for methods of producing a fatty alcohol composition using a host cell comprising a FAR variant of the present invention. Fatty alcohol compositions can be made by culturing a host cell comprising a FAR variant as described herein in a suitable culture medium under conditions (e.g., time, temperature, and/or pH conditions) suitable for the production of fatty alcohols, and producing the fatty alcohol composition. In some embodiments, the methods further comprise isolating the fatty alcohol compositions from the culture medium. In some embodiments, the host cell comprising the FAR variant is a bacteria (e.g., *E. coli*), a yeast (e.g., *Yarrowia* or *Saccharomyces*), or a fungus. In some embodiments, the FAR variant comprises at least about 70% identity to SEQ ID NO:2 and comprises one or more amino acid substitutions as described herein (e.g., in Table 2, Table 4, Table 5, or Table 6). In some embodiments, the host cell comprising the FAR variant is cultured under temperature conditions of from about 10° C. to about 60° C. (e.g., from about 15° C. to about 50° C., from about 20° C. to about 45° C., from about 20° C. to about 40° C., from about 20° C. to about 35° C., or from about 25° C. to about 45° C.). In some embodiments, the host cell comprising the FAR variant is cultured under time conditions the fermentation of from about 8 hours to 240 hours (e.g., from about 8 hours to about 168 hours, from about 8 hours to about 144 hours, from about 16 hours to about 120 hours, or from about 24 hours to about 72 hours). In some embodiments, the host cell comprising the FAR variant is cultured under pH conditions of about pH 4-8 (e.g., about pH 4.5 to 7.5, about pH 5 to 7, or about pH 5.5 to 6.5).

While not meant to limit the invention in any manner, in some embodiments, the method of producing a fatty alcohol composition comprises a) culturing a recombinant strain of *E. coli*, *Yarrowia*, or *Saccharomyces*, in a suitable culture medium, wherein the recombinant strain comprises a gene encoding an improved FAR polypeptide, b) allowing expression of said gene, and c) producing the fatty alcohol composition, wherein i) the improved FAR polypeptide comprises an amino acid sequence that is at least about 70% identical to SEQ ID NO:2 and comprises one or more amino acid substitutions as described herein (e.g., one or more amino acid substitutions sets listed in Table 2, Table 4, or Table 5); ii) the culturing is carried at a temperature of about 20° C. to about 40° C. and from about 16 to 120 hours, iii) the culture medium comprises a carbon source comprising fermentable sugars obtained from a cellulosic feedstock, and iv) at least about 5 g/L of recoverable fatty alcohols are produced. In some embodiments, fermentable sugars in the culture medium include glucose and/or sucrose.

In some embodiments, the method of producing a fatty alcohol composition comprises a) culturing a recombinant strain of E. coli, Yarrowia, or Saccharomyces, in a suitable culture medium, wherein the recombinant strain comprises a gene encoding an improved FAR polypeptide, b) allowing expression of said gene, and c) producing the fatty alcohol composition, wherein i) the improved FAR polypeptide comprises an amino acid sequence that is at least about 95% identical to SEQ ID NO:2 and comprises a substitution at one or more positions 2, 134, 138, 188, 405 and 511 when aligned to SEQ ID NO:2, ii) the culturing is carried at a temperature of about 20° C. to about 40° C. and from about 16 to 120 hours, iii) the culture medium comprises a carbon source comprising fermentable sugars obtained from a cellulosic feedstock, and iv) at least about 5 g/L of fatty alcohol are produced. In certain embodiments, the substitution at position 2 is H, T, D, F, V, G, Q, P or I; the substitution at position 134 is R, K, or 5; the substitution at position 138 is Q or L; substitution at position 188 is 5; the substitution at position 405 is V, S, F, G, C, L, S, A, or W; and the substitution at position 511 is T, P, G, 5, K, Q, or R, and the improved FAR polypeptide will comprise one or more additional substitutions of an amino acid residue relative to a position corresponding to SEQ ID NO:2.

Recovery of Fatty Alcohols

Fatty alcohols produced by the methods can be isolated to yield fatty alcohol compositions. In some embodiments, recombinant microorganism hosts secrete the fatty alcohols into the nutrient medium. For cell-based methods carried out with recombinant microorganism hosts that secrete the fatty alcohols into the nutrient medium, the fatty alcohols can be isolated by solvent extraction of the aqueous nutrient medium with a suitable water immiscible solvent. Phase separation followed by solvent removal provides the fatty alcohol which may then be further purified and fractionated using methods and equipment known in the art. In other aspects of the disclosure, the secreted fatty alcohols coalesce to form a water immiscible phase that can be directly separated from the aqueous nutrient medium either during the fermentation or after its completion.

In certain embodiments, fatty alcohols are isolated by separating the cells from the aqueous nutrient medium, for example by centrifugation, resuspension and extraction of the fatty alcohols from the recombinant host cells using an organic solvent or solvent mixture. Suitable protocols for recovering fatty alcohols from recombinant host cells and/or culture medium are known to the skilled artisan.

Fatty alcohols produced with microorganism hosts that do not secrete the fatty alcohols into the nutrient medium can be recovered by first lysing the cells to release the fatty alcohols and extracting the fatty alcohols from the lysate using conventional means. Reference is made to Yeast Protocols Handbook, Clontech Laboratories, Inc., A Takara Bio Company, 1290 Terra Bella Ave., Mountain View, Calif. 94043, published July 2009, available online.

In some embodiments, the compositions produced by the methods described herein comprise saturated fatty alcohols, unsaturated fatty alcohols, or both saturated and unsaturated fatty alcohols. In various embodiments, the compositions produced by the methods described herein comprise both saturated and unsaturated fatty alcohols. In certain embodiments, the unsaturated fatty alcohols are monounsaturated fatty alcohols. In some embodiments, the fatty alcohol compositions comprise both saturated and unsaturated fatty alcohols, and the amount of unsaturated fatty alcohols is less than about 30%, such as less than about 20%, such as less than about 10%, such as less than about 5%, such as less than about 1% of the fatty alcohols present in the composition. In other embodiments, the fatty alcohol compositions comprise both saturated and unsaturated fatty alcohols, and the amount of saturated fatty alcohols is less than about 30%, such as less than about 20%, such as less than about 10%, such as less than about 5%, such as less than about 1% of the fatty alcohols present in the composition.

In some embodiments, the fatty alcohol compositions produced by the methods described herein comprise one or more alcohols selected from the group consisting of 1-octanol (C8:0), 1-decanol (C10:0), 1-dodecanol (C12:0), 1-tetradecanol (C14:0), 1-hexadecanol (C16:0), 1-octadecanol (C18:0), 1-icosanol (C20:0), 1-docosanol (C22:0), 1-tetracosanol (C24:0), cis $\Delta^9$-1-hexadecenol (C16:1), and cis $\Delta^{11}$-1-octadecenol (C18:1). In some embodiments, the fatty alcohol compositions produced by the methods described herein comprise 1-tetradecanol (C14:0), 1-hexadecanol (C16:0), 1-octadecanol (C18:0), cis $\Delta^9$-1-hexadecenol (C16:1), and/or cis $\Delta^{11}$-1-octadecenol (C18:1).

In some embodiments, C8 to C20 fatty alcohols comprise at least about 80%, such as at least about 85%, such as at least about 90%, such as at least about 92%, such as at least about 95%, such as at least about 97%, such as at least about 99% by weight of the total isolated fatty alcohols. In certain embodiments, 010 to C18 fatty alcohols comprise about 80%, such as at least about 85%, such as at least about 90%, such as at least about 92%, such as at least about 95%, such as at least about 97%, such as at least about 99% by weight of the total isolated fatty alcohols. In certain embodiments, C14 to C18 fatty alcohols comprise about 80%, such as at least about 85%, such as at least about 90%, such as at least about 92%, such as at least about 95%, such as at least about 97%, such as at least about 99% by weight of the total isolated fatty alcohols. In some embodiments, C16 to C18 fatty alcohols comprise at least about 80%, such as at least about 85%, such as at least about 90%, such as at least about 91%, such as at least about 92%, such as at least about 93%, such as at least about 94%, such as at least about 95%, such as at least about 96%, such as at least about 97%, such as at least about 98%, such as at least about 99% by weight of the total isolated fatty alcohols. In some embodiments, the C16 to C18 fatty alcohols are saturated. In some embodiments, the 016 to C18 fatty alcohols are a mixture of saturated and unsaturated fatty alcohols.

IX. Fatty Alcohol Derivatives

Fatty alcohols produced using the methods disclosed herein can be converted to a variety of commercially useful compounds, referred to as fatty alcohol derivatives. Without limitation, exemplary fatty alcohol derivatives include fatty acids, fatty aldehydes, fatty esters, wax esters, fatty acetates, ethoxylates, sulphates, phosphates, amines, alkanes, and alkenes. The fatty alcohol derivatives may be obtained from fatty alcohols using either enzymatic or chemical methods. In some embodiments, total fatty alcohols produced in a fermentation are derivatized. Sometimes fatty alcohols produced in a fermentation are fractionated, and a fraction(s) is derivatized.

Alkane and/or Alkene Compositions

In some embodiments, the fatty alcohol compositions produced by the methods described herein can be reduced to yield alkanes and/or alkenes having the same carbon chain length as the fatty alcohol starting materials. Without being bound by any particular theory, the hydroxyl group of an alcohol is a poor leaving group, and therefore, in principle a chemical moiety that binds to the oxygen atom of the hydroxyl group to make it a better leaving group can be used to reduce the fatty alcohols described herein. In another embodiment, alkanes can be produced by hydrogenation of fatty alcohols or fatty acids.

Any method known in the art can be used to reduce the fatty alcohols produced according to the methods described herein. In some embodiments, reduction of fatty alcohols can be carried out chemically, for example, by a Barton deoxygenation (or Barton-McCombie deoxygenation), a two-step reaction in which the alcohol is first converted to a methyl xanthate or thioimidazoyl carbamate, and the xanthate or thioimidazoyl carbamate is reduced with a tin hydride or trialkylsilane reagent under radical conditions to produce the alkane and/or alkene. See J. J. Li, C. Limberakis, D. A. *Pflum, Modern Organic Synthesis in the Laboratory* (Oxford University Press, 2007) at pp. 81-83.

In some embodiments, reduction of fatty alcohols to the corresponding alkanes and/or alkenes can be accomplished using a microorganism that has a biosynthetic pathway for reducing fatty alcohols. In certain embodiments, the microorganism is a bacterium. In specific embodiments, the bacterium is *Vibrio furnissii* strain M1. In some embodiments, the fatty alcohol compositions produced by the methods described herein are contacted with the appropriate microorganism for reduction to alkanes and/or alkenes. In other embodiments, the fatty alcohol compositions produced by the methods described herein are contacted with membrane fractions from the appropriate microorganism so that the reduction is carried out in a cell free system. See, e.g., Park, 2005, *J. Bacteriol.* 187(4):1426-1429.

In certain embodiments, alkanes and/or alkenes produced by the reduction of fatty alcohols described herein are isolated from the reaction mixture and unreduced fatty alcohol starting materials to produce a composition that comprises substantially all alkanes and/or alkenes. In some embodiments, the alkanes and/or alkenes produced by the reduction of fatty alcohols described herein and the unreacted fatty alcohol starting materials are isolated from the reaction mixture to produce a composition comprising alkanes and/or alkenes and fatty alcohols.

In certain embodiments, the resulting compositions comprise at least about 60% alkanes and/or alkenes, such as at least about 70% alkanes and/or alkenes, such as at least about 80% alkanes and/or alkenes, such as at least about 85% alkanes and/or alkenes, such as at least about 90% alkanes and/or alkenes, such as at least about 92% alkanes and/or alkenes, such as at least about 95% alkanes and/or alkenes, such as at least about 96% alkanes and/or alkenes, such as at least about 97% alkanes and/or alkenes, such as at least about 98% alkanes and/or alkenes, such as at least about 99% alkanes and/or alkenes by weight of the composition after reduction.

In other embodiments, the resulting compositions comprise at least about 10% alkanes and/or alkenes, such as at least about 20% alkanes and/or alkenes, such as at least about 30% alkanes and/or alkenes, such as at least about 40% alkanes and/or alkenes, such as at least about 50% alkanes and/or alkenes by weight of the composition after reduction.

In some typical embodiments, the compositions produced by the methods described herein comprise one or more alkanes selected from the group consisting of octane, decane, dodecane, tetradecane, hexadecane, octadecane, icosane, docosane, and tetracosane. In other typical embodiments, the compositions produced by the methods described herein comprise one or more alkenes selected from the group consisting of octene, decene, dodecene, tetradecene, hexadecene, octadecene, icosene, docosene, and tetracosene.

In typical embodiments, C8 to C20 alkanes and/or alkenes comprise at least about 80%, such as at least about 85%, such as at least about 90%, such as at least about 92%, such as at least about 95%, such as at least about 97%, such as at least about 99% by weight of the total alkanes and/or alkenes in the composition. In certain embodiments, 010 to C18 alkanes and/or alkenes comprise about 80%, such as at least about 85%, such as at least about 90%, such as at least about 92%, such as at least about 95%, such as at least about 97%, such as at least about 99% by weight of the total alkanes and/or alkenes in the composition.

In some embodiments, the C8 to C20 alkane and/or alkene composition produced by the methods of the disclosure, i.e. using an improved FAR enzyme of the disclosure, preferentially comprises alkanes and/or alkenes of certain chain lengths. In one embodiment, 016:1 fatty alcohol is preferentially produced. In another embodiment, the composition comprises the following fatty alcohols in order of decreasing relative distribution: C16:1, C16:0, C18:1, C14:0, and C18:0. In another embodiment, the composition comprises the following fatty alcohols in order of decreasing relative distribution: C16:1, C16:0, C14:0, C18:1, and C18:0. In yet another embodiment, the composition comprises the following fatty alcohols in order of decreasing relative distribution: C16:1, C14:0, C16:0, C18:1, and C18:0.

In certain embodiments, alkanes and/or alkenes having particular carbon chain lengths can be isolated from longer and/or shorter alkanes and/or alkenes, for example by HPLC. In certain embodiments, alkane and/or alkene compositions that are suitable, e.g., for use in jet fuels, comprise C10 to C14 alkanes and/or alkenes. In other embodiments, alkane and/or alkene compositions that are suitable, e.g., for use in diesel fuels comprise alkanes and/or alkenes that have 16 or more carbons (e.g., C16 or longer-chain alkanes and/or alkenes).

Ester Compositions

In certain embodiments, the fatty alcohols are further processed with a carboxylic acid to form acid esters. Esterification reactions of fatty alcohols are well-known in the art. In certain embodiments, the transesterification reaction is carried out in the presence of a strong catalyst, e.g., a strong alkaline such as sodium hydroxide. In other embodiments, the reaction is carried out enzymatically using an enzyme that catalyzes the conversion of fatty alcohols to acid esters, such as lipoprotein lipase. See, e.g., Tsujita et al., 1999, *J. Biochem.* 126(6):1074-1079.

Sulfate Derivatives

In some embodiments, the fatty alcohols can be reacted with a sulfonic acid group to produce sulfate derivatives.

X. Exemplary Compositions Containing Fatty Alcohols and Fatty Alcohol Derivatives Produced According to the Methods of the Invention In yet another aspect, the present invention relates to the use of FAR variants as described herein and microorganisms expressing the FAR variants as described herein for the production of various compositions, including but not limited to, detergent compositions (e.g., laundry detergents in liquid and powder form, hard surface cleaners, dishwashing liquids, and the like); industrial compositions (e.g., lubricants, solvents; and industrial cleaners); personal care compositions (e.g., soaps, cosmetics, shampoos, and gels); and fuel compositions (e.g., biodiesels and petrodiesels). These compositions may comprise fatty alcohols and/or fatty alcohol derivatives.

Fuel Compositions

The fatty alcohol compositions described herein and compounds derived there from can be used as components of fuel compositions. In certain embodiments, the fatty alcohol compositions produced by the methods described above can be used directly in fuel compositions. Fuel compositions containing fatty alcohols and derivatives produced by the methods of the present invention include any compositions used in powering combustion engines, including but not limited to biodiesel fuels and petrodiesel fuels (e.g., jet fuels and rocket fuels).

In some embodiments, the fuel composition is diesel fuel. Diesel fuel is any fuel used in diesel engines and includes both petrodiesel and biodiesel. Petrodiesel is a specific fractional distillate of fossil fuel oil. It is comprised of about 75% saturated hydrocarbons and 25% aromatic hydrocarbons. Biodiesel is not derived from petroleum but from vegetable oil or animal fats and contains long chain alkyl esters. Biodiesel is made by the transesterification of lipids (e.g., spent vegetable oil from fryers or seed oils) with an alcohol and burns cleaner than petrodiesel. Biodiesel can be used alone or mixed with petrodiesel in any amount for use in modern engines.

In some embodiments, the fuel composition is kerosene. Kerosene is a combustible hydrocarbon that is also a specific fractional distillate of fossil fuel and contains hydrocarbons having 6 to 16 carbon atoms. Kerosene has a heat of combustion comparable to that of petrodiesel and is widely used in jet fuel to power jet engines and for heating in certain countries. Kerosene-based fuels can also be burned with liquid oxygen and used as rocket fuel (e.g., RP-1).

In various embodiments, the fatty alcohols can be reacted with a carboxylic acid to produce acid esters. In particular embodiments, the acid esters are used as components of biodiesel fuel compositions. In other embodiments, the fatty alcohols are reacted with a reducing agent to produce alkanes and/or alkenes. In some embodiments, alkanes and/or alkenes (e.g., C10 to C14) derived from the fatty alcohol compositions are used as components of jet fuel compositions. In other embodiments, alkanes and/or alkenes derived from fatty alcohol compositions are used as components of rocket fuel. In still other embodiments, alkanes and/or alkenes (e.g., C16 to C24) derived from the fatty alcohol compositions are used as components in petrodiesel-like fuel compositions.

In some embodiments, the fuel compositions comprise an alkane and/or alkene derived from the fatty alcohol compositions described herein. In certain embodiments, the alkanes and/or alkenes have from 6 to 16 carbons and the fuel composition is a kerosene-like fuel composition. In various embodiments, the kerosene-like fuel compositions are included in jet fuel compositions. In particular embodiments, the kerosene-like fuel compositions are included in various grades of jet fuel, including but not limited to, grades Avtur, Jet A, Jet A-1, Jet B, JP-4, JP-5, JP-7 and JP-8. In other embodiments, the kerosene-like fuel compositions are included in fuel compositions for heating. In still other embodiments, the kerosene-like fuel compositions derived from the fatty alcohol compositions described above are burned with liquid oxygen to provide rocket fuel. In particular embodiments, the kerosene-like fuel compositions are used in RP-1 rocket fuel.

In some embodiments, the alkanes and/or alkenes derived from the fatty alcohol compositions described herein are used in fuel compositions that are similar to petrodeisel fuel compositions, e.g., that contain saturated and aromatic hydrocarbons. In certain embodiments, the fuel compositions comprise only alkanes and/or alkenes derived from the fatty alcohol compositions described herein. In other embodiments, the fuel compositions comprise alkanes and/or alkenes derived from the fatty alcohol compositions described herein mixed with other components, such as petrodiesel fuel. In some embodiments, the acid esters derived from the fatty alcohol compositions described herein are used as biodiesel fuel without being mixed with other components. In other embodiments, the fatty acid esters derived from the fatty alcohol compositions described herein are mixed with other components, such as petrodiesel fuel.

In certain embodiments, fatty alcohols, or acid esters or alkanes and/or alkenes derived there from, are combined with other fuels or fuel additives to produce compositions having desired properties for their intended use. Exemplary fuels and fuel additives for particular applications are well-known in the art. Exemplary fuels which can be combined with the compositions described herein include, but are not limited to, traditional fuels such as ethanol and petroleum-based fuels. Exemplary fuel additives which can be combined with the compositions described herein include, but are not limited to, cloud point lowering additives, surfactants, antioxidants, metal deactivators, corrosion inhibitors, anti-icing additives, anti-wear additives, deposit-modifying additives and octane enhancers.

Detergent Compositions

In certain embodiments, the fatty alcohol compositions described herein and compounds derived there from can be used as components of detergent compositions. Detergent compositions containing fatty alcohols produced by the methods of the present invention include compositions used in cleaning applications, including, but not limited to, laundry detergents, hand-washing agents, dishwashing detergents, rinse-aid detergents, household detergents, and household cleaners, in liquid, gel, granular, powder, or tablet form. In some embodiments, the fatty alcohol compositions produced by the methods described above can be used directly in detergent compositions. In some embodiments, the fatty alcohols can be reacted with a sulfonic acid group to produce sulfate derivatives that can be used as components of detergent compositions. Detergent compositions that can be generated using the fatty alcohol compositions produced by the methods of the present invention include, but are not limited to, hair shampoos and conditioners, carpet shampoos, light-duty household cleaners, light-duty household detergents, heavy-duty household cleaners, and heavy-duty household detergents. Detergent compositions generally include, in addition to fatty alcohols, one or more or of builders (e.g., sodium carbonate, complexation agents, soap, and zeolites), enzymes (e.g., a protease, a lipase and an amylases); carboxymethyl cellulose, optical brighteners, fabric softeners, colourants and perfumes (e.g., cyclohexyl salicylate).

In some embodiments, sulfate derivatives (e.g., C12-15) derived from the fatty alcohol compositions are used in products such as hair shampoos, carpet shampoos, light-duty household cleaners, and light-duty household detergents. In some embodiments, fatty alcohol compositions (e.g., C16-C18) produced by the methods described herein are used in products such as hair shampoos and conditioners. In some embodiments, sulfate derivatives (e.g., C16-18) derived from the fatty alcohol compositions are used in products such as heavy-duty household cleaners and heavy-duty household detergents.

Personal Care Compositions

In certain embodiments, the fatty alcohol compositions described herein and compounds derived there from can be used as components of personal care compositions. In some embodiments, the fatty alcohol compositions produced by the methods described above can be used directly in personal care compositions. Personal care compositions containing fatty alcohols produced by the methods of the present invention include compositions used for application to the body (e.g., for application to the skin, hair, nails, or oral cavity) for the purposes of grooming, cleaning, beautifying, or caring for the body, including but not limited to lotions, balms, creams, gels, serums, cleansers, toners, masks, sunscreens, soaps, shampoos, conditioners, body washes, styling aids, and cosmetic compositions (e.g., makeup in liquid, cream, solid, anhydrous, or pencil form). In some embodiments, the fatty alcohols can be reacted with a sulfonic acid group to produce sulfate derivatives that can be used as components of said compositions.

In some embodiments, fatty alcohol compositions (e.g., C12) produced by the methods described herein are used in products such as lubricating oils, pharmaceuticals, and as an emollient in cosmetics. In some embodiments, fatty alcohol compositions (e.g., C14) produced by the methods described herein are used in products such as cosmetics (e.g., cold creams) for its emollient properties. In some embodiments, fatty alcohol compositions (e.g., C16) produced by the methods described herein are used in products such as cosmetics (e.g., skin creams and lotions) as an emollient, emulsifier, or thickening agent. In some embodiments, fatty alcohol compositions (e.g., C18) produced by the methods described herein are used in products such as lubricants, resins, perfumes, and cosmetics, e.g., as an emollient, emulsifier, or thickening agent. In some embodiments, sulfate derivatives (e.g., C12-14) derived from the fatty alcohol compositions produced by the methods described herein are used in products such as toothpastes.

Other Compositions

In some instances, fatty alcohols (especially cetyl alcohol, stearyl alcohol and myristyl alcohol) may be used as food additives (e.g., adjuvants and production aids).

XI. EXAMPLES

The following examples are offered to illustrate, but not to limit, the claimed invention.

Example 1

Wild-type *M. algicola* DG893 FAR Gene Acquisition and Vector Construction

Gene acquisition of wild-type *M. algicola* DG893 FAR ("FAR Maa") is described in the published application WO/2011/008535. The genomic sequence of *M. algicola* DG893 can also be found at GenBank Accession No. NZ_ABCP01000001.1. The amino acid sequence of the encoded FAR polypeptide is designated SEQ ID NO:2. The polynucleotide sequences of two different codon-optimized genes encoding the FAR polypeptide of SEQ ID NO: 2 are designated SEQ ID NO:1 and SEQ ID NO:3. The *M. algicola* DG893 FAR gene and genes encoding variants of the *M. algicola* DG893 FAR were cloned into the vector pCK110900 (depicted as FIG. 3 in U.S. Patent Appln. Pub. 2006/0195947) under the control of a lac promoter, as described in WO 2011/008535. The resulting plasmids were introduced into *E. coli* BW25113, BW25113 ΔfadE, or BW25113 ΔtorR (Baba et al., *Molecular Systems Biology*, 2006 doi:10,1038/msb4100050 Article No. 2006.0008), W3110-ΔfhuA and MG1655-7740 by routine transformation methods.

Example 2

Evaluation of *M. algicola* FAR Variants with Improved Activity Using Microtiter Plate Assays FAR Maa Variant Nos. 1-172 were grown in 96-well shallow plates containing 180 μL Luria Bertani (LB) or M9YE medium supplemented with 1% glucose and 30 μg/mL chloramphenicol (CAM), for approximately 16-18 hours (overnight) in a shaker-incubator at 30° C., 200 rpm. A 5% inoculum was used in 96-deep-well plates to initiate fresh 380 μL culture containing 2×YT broth medium supplemented with 30 μg/mL CAM and 0.4% glucose. The culture was incubated for 2 hours at 30° C., 250 rpm to an $OD_{600}$ of 0.6-0.8, at which point expression of the heterologous FAR gene was induced with isopropyl-β-D-thiogalactoside (IPTG) (1 mM final concentration). Incubation was continued for about 24 hours under the same conditions. FAR Maa Variant Nos. 173-423 were grown under the same conditions except M9YE medium was used to inoculate the cells and an additional amount of glucose (0.5% w/v final conc.) was added to the culture at 3 and 6 hrs after induction by IPTG. FAR Maa Variant Nos. 424-527 were grown under the above conditions except M9YE medium containing 5% glucose was used to inoculate the cells and induction by IPTG, the culture was incubated at 30° or 37° C. for 48 hours. FAR Maa Variant Nos. 528-629 were grown under the above conditions except M9YE medium containing 10% glucose was used to inoculate the cells and after induction by IPTG, the culture was incubated at 40° for 24 hours.

Cell cultures were extracted with 1 mL of isopropanol: methyl t-butyl ether (MTBE) (4:6 ratio) for 2 hours. The extracts were centrifuged and the upper organic phase was transferred into polypropylene 96-well plates and analyzed by the following GC-FID method using DB-5MS column (length 30 m, I.D. 0.32 mm, film 0.25 um): start temp. 150° C., increase the temperature at a rate of 25° C./min to 246° C. and hold for 1.81 min. Total run time, 5.65 min. Under the above GC conditions the approximate retention times (min) of produced fatty alcohols and acids were as follows: 3.19, C14:0-OH; 3.48, C14:0-OOH; 3.91, C16:1-OH; 3.98, C16:0-OH; 4.15, C16:0-OOMe (internal standard); 4.21, C16:1-OOH; 4.28, C16:0-OOH; 4.83, C18:1-OH; 4.92, C18:0-OH; 5.31, C18:0-OOH and 5.51, C18:1-OOH. Identification of individual fatty alcohol was done by comparison to commercial standards (Sigma Chemical Company, 6050 Spruce St. Louis, Mo. 63103).

Table 2 provides the relative fatty alcohol production for illustrative variants relative to wild-type *M. algicola* DG893 FAR. Codon-optimized SEQ ID NO:3 was mutated and used to express FAR Maa Variant Nos. 1-172, and codon-optimized SEQ ID NO:1 was mutated and used to express FAR Maa Variants Nos. 173-629. Relative fatty alcohol production is presented as fold improvement over wild-type FAR Maa at 30° C. (for Variant Nos. 1-423); over FAR Maa Variant No. 391 at 37° C. (for Variant Nos. 424-527); or over FAR Maa Variant No. 438 at 40° C. (for Variant Nos. 528-629). In Table 2, the amino acid substitutions listed for each variant correspond to residue positions of SEQ ID NO:2 (e.g., "G410S" means that the residue at position 410 in SEQ ID NO:2 (glycine) is substituted with serine), and the amino acid positions were determined by optimal alignment with SEQ ID NO:2. For Variant Nos. 424-527, the activity of these variants was also tested at 30° C., and the activity of these variants at 30° C. was similar to that obtained from Variant No. 391 at 30° C.

TABLE 2

Variant FAR polypeptides and total relative production of fatty alcohols

| Variant No. | Amino acid substitutions relative to SEQ ID NO: 2 | Relative fold improvement in fatty alcohol production† |
|---|---|---|
| 1 | G410S; | + |
| 2 | S283V; | + |
| 3 | D198Q; | + |
| 4 | S283K; | + |
| 5 | S339V; | + |
| 6 | S458G; | + |
| 7 | L463T; | + |
| 8 | G410R; | ++ |
| 9 | E288Q; | + |
| 10 | G410Q; | + |
| 11 | E138Q; | + |
| 12 | S283M; | + |
| 13 | R236K; | + |
| 14 | L33V; | + |
| 15 | M413L; | + |
| 16 | I287L; | + |
| 17 | A416V; | + |
| 18 | R117D; | + |
| 19 | E138L; K144Q; | + |
| 20 | K359L; A511T; | +++ |
| 21 | N134R; | + |
| 22 | L209N; A412V; | + |
| 23 | S244G; | + |
| 24 | H83R; | + |
| 25 | A412V; | + |
| 26 | E237L; | ++ |
| 27 | L209N; | + |
| 28 | T101L; | + |
| 29 | E151L; | + |
| 30 | L463E; | + |
| 31 | I437V; A511T; | + |
| 32 | E204G; | + |
| 33 | R65Q; | + |
| 34 | G340V; | + |
| 35 | S458M; | + |
| 36 | A443T; | + |
| 37 | L257K; | + |
| 38 | A374K; | + |
| 39 | I42L; | + |
| 40 | S339G; | + |
| 41 | N134K; | ++ |
| 42 | V397L; | + |
| 43 | S458Q; | +++ |
| 44 | G487Y; | + |
| 45 | G340S; P405S; | + |
| 46 | A412F; | + |
| 47 | A412C; | + |
| 48 | R115A; | + |
| 49 | E421R; | +++ |
| 50 | P405S; | + |
| 51 | D140C; | +++ |
| 52 | P405F; | + |
| 53 | G14W; | + |
| 54 | D429Q; | + |
| 55 | S433K; | ++ |
| 56 | N8K; | + |
| 57 | P405G; | + |
| 58 | S501G; | + |
| 59 | K229R; | + |
| 60 | Q377C; | + |

TABLE 2-continued

Variant FAR polypeptides and total relative production of fatty alcohols

| Variant No. | Amino acid substitutions relative to SEQ ID NO: 2 | Relative fold improvement in fatty alcohol production† |
|---|---|---|
| 61 | Y380R; | + |
| 62 | K509S; | + |
| 63 | Q418I; | + |
| 64 | D506S; | + |
| 65 | K510G; | +++ |
| 66 | Y500C; | + |
| 67 | E496A; | + |
| 68 | A2H; | +++ |
| 69 | P405C; | + |
| 70 | A505K; | + |
| 71 | G9F; | + |
| 72 | S306W; | + |
| 73 | E303G; T430I; | + |
| 74 | A504G; | + |
| 75 | Q418V; | + |
| 76 | Y500P; | + |
| 77 | D506G; | + |
| 78 | E421Y; | ++ |
| 79 | S433H; | + |
| 80 | K510P; | ++ |
| 81 | L502Q; | + |
| 82 | A511P; | ++ |
| 83 | A511G; | +++ |
| 84 | L502A; | + |
| 85 | S331V; | + |
| 86 | Q418R; | + |
| 87 | A2W; | +++ |
| 88 | E421I; | ++ |
| 89 | A2D; | +++ |
| 90 | K224R; | + |
| 91 | Q418Y; | + |
| 92 | G401V; | + |
| 93 | L502R; | ++ |
| 94 | K510Y; | + |
| 95 | L502S; | + |
| 96 | Y500L; | + |
| 97 | A504R; | ++ |
| 98 | E137L; | + |
| 99 | S433W; | + |
| 100 | T507G; | + |
| 101 | Q180R; T246A; | + |
| 102 | G401L; | + |
| 103 | G121S; S433L; | + |
| 104 | K510S; | + |
| 105 | T507A; | + |
| 106 | S76K; | + |
| 107 | K509H; | ++ |
| 108 | K510D; | + |
| 109 | A511R; | +++ |
| 110 | G401S; | + |
| 111 | S107L; | ++ |
| 112 | R508G; | + |
| 113 | Q7N; | + |
| 114 | Y500W; | + |
| 115 | Q377Y; | + |
| 116 | G400L; | + |
| 117 | L499P; | + |
| 118 | S74K; | + |
| 119 | T507R; | + |
| 120 | E303G; | + |
| 121 | A511T; | ++++ |
| 122 | P113L; E421P; | ++ |
| 123 | A2T; L332S; | +++ |
| 124 | T3R; | + |
| 125 | L499A; | + |
| 126 | A2F; | +++ |
| 127 | A511S; | +++ |
| 128 | A511K; | +++ |
| 129 | P113D; | + |
| 130 | S501R; | + |
| 131 | L364F; G400A; | + |

TABLE 2-continued

Variant FAR polypeptides and total relative production of fatty alcohols

| Variant No. | Amino acid substitutions relative to SEQ ID NO: 2 | Relative fold improvement in fatty alcohol production† |
|---|---|---|
| 132 | A374Y; | + |
| 133 | Y500G; | + |
| 134 | A511Q; | ++++ |
| 135 | E421S; | ++ |
| 136 | G14N; | + |
| 137 | K509E; | + |
| 138 | G121H; | + |
| 139 | D429K; | ++ |
| 140 | A511I; | + |
| 141 | A2V; | ++ |
| 142 | Y500N; | + |
| 143 | S433F; | ++ |
| 144 | L499H; | + |
| 145 | T436K; | + |
| 146 | A2V; S107C; | ++ |
| 147 | A2G; L148E; | +++ |
| 148 | E205P; A512T; | ++++ |
| 149 | A416L; | + |
| 150 | T384R; | + |
| 151 | A2Q; | +++ |
| 152 | K498A; L502R; | + |
| 153 | Y500Q; | + |
| 154 | Y500S; | + |
| 155 | P405L; | + |
| 156 | T507S; | + |
| 157 | L499S; | + |
| 158 | S306F; | + |
| 159 | L226A; | + |
| 160 | E17D; | + |
| 161 | N8S; | + |
| 162 | K509G; | ++ |
| 163 | A73K; | + |
| 164 | K510A; | + |
| 165 | S433N; | + |
| 166 | Q5S; P405S; | + |
| 167 | L502P; | + |
| 168 | A2P; | + |
| 169 | E421L; | +++ |
| 170 | L499R; | ++ |
| 171 | E421V; | ++ |
| 172 | E421N; | + |
| 173 | G50V; A511T; | + |
| 174 | R381C; A511T; | + |
| 175 | A142V; A511T; | + |
| 176 | P188S; A511T; | + |
| 177 | S74P; | + |
| 178 | A472V; A511T; | ++ |
| 179 | V185A; A511T; | ++ |
| 180 | P444S; A511T; | + |
| 181 | R459H; D464G; L499P; A511T; | + |
| 182 | V77A; A511T; | + |
| 183 | K260T; A511T; | + |
| 184 | H98R; A511T; | + |
| 185 | K22E; A511T; | + |
| 186 | V24I; R403C; A511T; | + |
| 187 | A125V; A511T; | ++ |
| 188 | A299T; A511T; | + |
| 189 | R220C; A511T; | + |
| 190 | V185A; A333T; A511T; | ++ |
| 191 | S458L; A511T; | + |
| 192 | L111S; A511T; | + |
| 193 | E71K; S458L; A511T; | + |
| 194 | L93V; | + |
| 195 | Y446H; A511T; | + |
| 196 | D245N; A511T; | ++ |
| 197 | I328T; A511T; | + |
| 198 | S263P; G410T; A511T; | ++ |
| 199 | N490S; A511T; | ++ |
| 200 | E138Q; P188S; E227G; E237L; | + |
| 201 | N134R; E138Q; P188S; | ++ |
| 202 | E138Q; P188S; | + |
| 203 | A120V; N134K; S458Q; A511T; | + |
| 204 | Q4R; A10T; E138Q; | ++ |
| 205 | T91I; N134R; P188S; K260R; A511T; | + |
| 206 | N134K; E138Q; P188S; S458Q; | ++ |
| 207 | S458Q; I484V; | + |
| 208 | N134K; E227G; | + |
| 209 | N134S; E138Q; P188S; | + |
| 210 | T112A; N134K; P188S; | + |
| 211 | N134S; E138Q; P188S; A511T; | ++ |
| 212 | N134K; P188S; | + |
| 213 | A12V; S458Q; A511T; | ++ |
| 214 | N134R; G410Q; A412C; S458Q; | + |
| 215 | G102C; N134R; E138Q; P188S; | + |
| 216 | N134S; E138Q; E205G; A511T; | + |
| 217 | N134S; E138Q; P188S; F440L; A511T; | + |
| 218 | N134R; E202G; K213R; | + |
| 219 | N134R; P188S; K213R; K260R; I437V; S458Q; | + |
| 220 | N134S; P188S; G410Q; A412V; S458Q; A511T; | + |
| 221 | N134R; P188S; | + |
| 222 | L54P; A366T; G410S; S458Q; A511T; | + |
| 223 | N134S; E227G; | + |
| 224 | G50S; N134K; E138Q; S458Q; | ++ |
| 225 | S458Q; A511T; | ++ |
| 226 | N134S; E138Q; P188S; E227G; | + |
| 227 | E138Q; I269T; A511T; | ++ |
| 228 | D396G; A511T; | ++ |
| 229 | R115H; N134R; P188S; | + |
| 230 | N134R; E138Q; N160S; P188S; E303G; | ++ |
| 231 | R60H; T112A; N134R; E227G; V290I; G410Q; I437V; S458Q; | ++ |
| 232 | E138Q; G350S; A511T; | ++ |
| 233 | P188S; E227G; | + |
| 234 | E138Q; P188S; S306N; | + |
| 235 | N134K; P188S; S458Q; | ++ |
| 236 | N134K; S458L; | ++ |
| 237 | S132G; S458Q; A511T; | + |
| 238 | A2G; N134S; E138Q; P188S; A511T; | +++ |
| 239 | A2I; T112A; N134K; E138Q; P188S; A511T; | + |
| 240 | N134S; E138Q; P188S; E227G; A511T; | +++ |
| 241 | T112A; N134K; E138Q; P188S; A511T; | ++ |
| 242 | A2G; T112A; N134R; E138Q; P188S; K510P; A511R; | + |
| 243 | A2H; T112A; N134S; E138Q; P188S; S458Q; A511T; | + |
| 244 | A2D; T112A; N134R; E138Q; P188S; E421V; K509H; A511Q; A512T; | ++ |
| 245 | N134S; E138Q; P188S; V207I; K510P; A511G; | +++ |
| 246 | N134S; E138Q; P188S; S458Q; K510P; A511K; | +++ |
| 247 | Q122R; N134S; E138Q; P188S; K510P; A511R; | +++ |
| 248 | N134S; E138Q; P188S; S458Q; K510P; A511R; | +++ |
| 249 | N134S; E138Q; P188S; K510P; A511R; A512T; | +++ |
| 250 | N134S; E138Q; P188S; E227G; S458Q; K510P; A511K; | +++ |
| 251 | A2G; T112A; N134K; E138Q; P188S; S458Q; K509H; K510P; A511Q; | ++ |
| 252 | N134S; E138Q; P188S; E421S; S458Q; K509H; K510P; A511R; | +++ |
| 253 | T112A; N134R; E138Q; P188S; E421R; S458Q; K510P; A511S; | ++ |
| 254 | N134S; E138Q; P188S; K510P; A511G; A512T; | +++ |
| 255 | A2H; N134S; E138Q; P188S; K510P; A511S; A512T; | ++ |
| 256 | A2W; T112A; N134R; E138Q; P188S; K509H; K510P; A511G; | ++ |
| 257 | A2N; N134S; E138Q; P188S; E421V; A511T; | + |
| 258 | N134S; E138Q; P188S; E421R; S458Q; K510P; A511S; A512T; | +++ |
| 259 | N134S; E138Q; P188S; E421L; K509H; K510P; A511K; | ++ |
| 260 | A2P; N134S; E138Q; P188S; K510P; A511R; A512T; | +++ |

TABLE 2-continued

Variant FAR polypeptides and total relative production of fatty alcohols

| Variant No. | Amino acid substitutions relative to SEQ ID NO: 2 | Relative fold improvement in fatty alcohol production† |
|---|---|---|
| 261 | N134K; E138Q; P188S; A511T; | ++ |
| 262 | T112A; N134S; E138Q; P188S; A511T; | ++ |
| 263 | N134S; E138Q; P188S; S458Q; A511T; A512T; | +++ |
| 264 | A2G; A73V; T112A; N134S; E138Q; P188S; E227G; A511T; | +++ |
| 265 | E138Q; P188S; A511T; A512T; | +++ |
| 266 | N134R; E138Q; P188S; A511T; | ++ |
| 267 | N134S; E138Q; P188S; E421L; S458Q; A511T; | ++ |
| 268 | N134S; E138Q; P188S; S458Q; A511T; | ++ |
| 269 | N134S; E138Q; P188S; E421R; S458Q; A511T; | ++ |
| 270 | T112A; E138Q; P188S; A511T; | ++ |
| 271 | N134S; E138Q; P188S; E227G; A511T; A512T; | +++ |
| 272 | T112A; N134S; E138Q; P188S; E205P; E421R; A511T; | + |
| 273 | A2G; T112A; E138Q; P188S; A511T; | +++ |
| 274 | N134S; E138Q; P188S; A511T; A512T; | ++ |
| 275 | N134S; E138Q; P188S; D429N; L499S; K509G; A511T; | ++ |
| 276 | N134S; E138Q; P188S; A412V; D429K; L499H; K509E; A511T; | +++ |
| 277 | N134S; E138Q; P188S; D429N; K509N; A511T; | +++ |
| 278 | N134S; E138Q; P188S; A412V; D429K; A511T; | + |
| 279 | N134S; E138Q; P188S; A412V; D429K; L499N; A511T; | ++ |
| 280 | N134S; E138Q; P188S; L499R; K509R; A511T; | ++ |
| 281 | N134S; E138Q; P188S; D429E; L499N; K509G; A511T; | + |
| 282 | N134S; E138Q; P188S; Q180R; S306W; L499R; K509G; A511T; | +++ |
| 283 | G121S; N134S; E138Q; P188S; S306W; A374Y; L499R; K509S; A511T; | +++ |
| 284 | N134S; E138Q; P188S; D429K; L499N; A504G; K509G; A511T; | + |
| 285 | V77I; N134S; E138Q; P188S; S306W; A511T; | +++ |
| 286 | N134S; E138Q; P188S; D429N; L499N; A504G; K509G; A511T; | ++ |
| 287 | N134S; E138Q; P188S; D429E; L499N; A511T; | +++ |
| 288 | N134S; E138Q; P188S; A412V; D429E; L499I; K509D; A511T; | +++ |
| 289 | N134S; E138Q; P188S; S306W; A412V; D429K; L499S; A511T; | +++ |
| 290 | N134S; E138Q; P188S; D429N; L499R; K509S; A511T; | + |
| 291 | N134S; E138Q; P188S; A412V; L499I; K509G; A511T; | +++ |
| 292 | N134S; E138Q; P188S; D429E; L499H; K509G; A511T; | +++ |
| 293 | N134S; E138Q; P188S; A504R; K509N; A511T; | +++ |
| 294 | N134S; E138Q; P188S; A412V; D429E; L499R; K509Q; A511T; | ++ |
| 295 | N134S; E138Q; P188S; D429N; L499I; K509G; A511T; | + |
| 296 | N134S; E138Q; P188S; S306W; A374Y; L499R; A504R; A511T; | ++ |
| 297 | N134S; E138Q; P188S; D429E; K509D; A511T; | +++ |
| 298 | N134S; E138Q; Q180R; P188S; S306W; L499H; K509S; A511T; | +++ |
| 299 | N134E; E138Q; P188S; V397I; A511T; | +++ |
| 300 | G9F; N134S; E138Q; P188S; L502Q; T507A; A511T; | +++ |
| 301 | N134S; E138Q; P188S; G401V; L502S; A511T; | ++++ |
| 302 | N134S; E138Q; P188S; G401S; A511T; | +++ |
| 303 | G9F; P113L; N134S; E138Q; P188S; G401L; L502S; T507A; A511T; | ++++ |
| 304 | N134S; E138Q; P188S; G401L; A511T; | ++++ |
| 305 | G9F; N134S; E138Q; P188S; E288Q; G410R; E421S; A511T; | + |
| 306 | P113L; N134S; E138Q; P188S; K224R; A366V; L502Q; T507R; A511T; | ++ |
| 307 | N134S; E138Q; P188S; G401V; G487Y; L502S; T507A; A511T; | +++ |
| 308 | N134S; E138Q; P188S; S244P; E288Q; G401S; A511T; | ++++ |
| 309 | N134S; E138Q; P188S; G401L; G410R; G487Y; L502S; A511T; | +++ |
| 310 | G9F; E87V; N134S; E138Q; P188S; K224R; E288Q; G401V; G487Y; L502R; A511T; | +++ |
| 311 | N134S; E138Q; P188S; E421N; T507A; A511T; | + |
| 312 | G9F; N134S; E138Q; P188S; K224R; E288Q; G401A; L502S; T507P; A511T; | +++ |
| 313 | P113L; N134S; E138Q; P188S; G487Y; L502S; T507A; A511T; | +++ |
| 314 | G9F; P113L; N134S; E138Q; P188S; E288Q; G401L; A511T; | +++ |
| 315 | P113L; N134S; E138Q; P188S; L502Q; T507R; A511T; | +++ |
| 316 | N134S; E138Q; P188S; V404I; G410R; R508H; A511T; | +++ |
| 317 | G9F; P113L; N134S; E138Q; P188S; G487Y; L502A; A511T; | +++ |
| 318 | N134S; E138Q; P188S; G401S; G410R; A511T; | +++ |
| 319 | N134S; E138Q; P188S; G401V; A511T; | ++++ |
| 320 | G9F; P113L; N134S; E138Q; P188S; G401A; G410R; A511T; | +++ |
| 321 | G9F; P113L; N134S; E138Q; P188S; G401V; T507A; A511T; | +++ |
| 322 | P113L; N134S; E138Q; P188S; K224R; G487Y; L502R; A511T; | +++ |
| 323 | P113L; N134S; E138Q; P188S; E421R; G487Y; L502A; A511T; | +++ |
| 324 | N134S; E138Q; P188S; A409V; A511T; | +++ |
| 325 | S76K; N134S; E138Q; P188S; Y380R; A416L; Y500N; S501R; R508G; A511T; | +++ |
| 326 | S76N; N134S; E138Q; P188S; Y380R; Y500N; S501R; A511T; | ++ |
| 327 | N134S; E138Q; P188S; Y500Q; S501R; A511T; | ++ |
| 328 | N134S; E138Q; P188S; L209N; Y380R; A409V; A416L; T430I; Y500N; S501R; A511T; | +++ |
| 329 | S76R; N134S; E138Q; P188S; E303G; T430I; Y500Q; S501R; R508G; A511T; | +++ |
| 330 | N134S; E138Q; P188S; L209N; E303G; R508G; A511T; | +++ |
| 331 | S76K; N134S; E138Q; P188S; E303G; Y380R; T430I; Y500N; A511T; | ++ |
| 332 | S76N; N134S; E138Q; P188S; Y380R; A416L; Y500Q; R508G; A511T; | +++ |
| 333 | N134S; E138Q; P188S; A416L; T430I; Y500G; S501G; A511T; | +++ |
| 334 | N134S; E138Q; P188S; R508G; A511T; | +++ |
| 335 | N134S; E138Q; P188S; E303G; A511T; | +++ |
| 336 | S76R; N134S; E138Q; P188S; A416L; T430I; Y500N; S501R; R508G; A511T; | +++ |
| 337 | N134S; E138Q; P188S; Y380R; A416L; T430I; Y500G; S501G; R508G; A511T; | +++ |
| 338 | N134S; E138Q; V185I; P188S; A416L; Y500Q; R508G; A511T; | +++ |
| 339 | N134S; E138Q; L148E; P188S; E303G; Y380R; T430I; Y500Q; A511T; | +++ |
| 340 | N134S; E138Q; L148E; P188S; Y500Q ;S501R; A511T; | ++ |
| 341 | N134S; E138Q; P188S; A416L; A511T; | +++ |
| 342 | N134S; E138Q; P188S; A416L; R508G; A511T; | +++ |
| 343 | N134S; E138Q; P188S; Y380R; A511T | ++ |
| 344 | S76K; N134S; E138Q; P188S; E303G; A416L; T430I; Y500Q; A511T; | +++ |
| 345 | N134S; E138Q; P188S; Y380R; Y500Q; R508G; A511T; | +++ |
| 346 | N134S; E138Q; L148E; P188S; E303G; Y380R; Y500N; A511T; | +++ |
| 347 | S76K; N134S; E138Q; P188S; A416L; A511T; | +++ |
| 348 | N134S; E138Q; P188S; Y380R; T430I; Y500Q; A511T; | +++ |

TABLE 2-continued

Variant FAR polypeptides and total relative production of fatty alcohols

| Variant No. | Amino acid substitutions relative to SEQ ID NO: 2 | Relative fold improvement in fatty alcohol production† |
|---|---|---|
| 349 | N134S; E138Q; P188S; Y380R; A416V; R508G; A511T; | +++ |
| 350 | N134S; E138Q; P188S; Y500Q; S501G; R508G; A511T; | +++ |
| 351 | N134S; E138Q; P188S; L332S; P405F; A511T; | +++ |
| 352 | N134S; E138Q; P188S; Q418R; S433N; K510D; A511T; | +++ |
| 353 | N134S; E138Q; P188S; P405L; A511T; | +++ |
| 354 | N134S; E138Q; P188S; P405A; Q418R; K510Y; A511T; | ++++ |
| 355 | A2V; S107C; N134S; E138Q; P188S; T246A; L332S; P405G; Q418V; K510D; A511T; | ++ |
| 356 | N134S; E138Q; P188S; Q418I; S433Y; K510Y; A511T; | +++ |
| 357 | N134S; E138Q; P188S; P405A; Q418V; K510S; A511T; | ++++ |
| 358 | N134S; E138Q; P188S; T246A; P405L; Q418V; S433K; A511T; | ++++ |
| 359 | N134S; E138Q; P188S; Q418I; K510S; A511T; | +++ |
| 360 | S107C; N134S; E138Q; P188S; P405C; A505K; K510Y; A511T; | ++++ |
| 361 | N134S; E138Q; P188S; P405C; Q418I; A505K; K510D; A511T; | ++++ |
| 362 | N134S; E138Q; P188S; L332S; P405F; Q418I; K510D; A511T; | +++ |
| 363 | N134S; E138Q; P188S; P405A; Q418V; A511T; | ++++ |
| 364 | N134S; E138Q; P188S; P405L; Q418R; S433H; K510D; A511T; | ++++ |
| 365 | N134S; E138Q; P188S; P405L; K510S; A511T; | +++ |
| 366 | N134S; E138Q; P188S; S433H; K510D; A511T; | +++ |
| 367 | N134S; E138Q; P188S; P405G; Q418I; S433N; K510Y; A511T; | ++++ |
| 368 | A2V; S107C; N134S; E138Q; P188S; L332S; P405V; Q418R; A511T; | ++ |
| 369 | N134S; E138Q; P188S; P405V; Q418I; S433N; K510S; A511T; | ++++ |
| 370 | N134S; E138Q; P188S; P405V; Q418V; A511T; | ++++ |
| 371 | S107L; N134S; E138Q; P188S; T246A; P405L; Q418V; A505K; K510Y; A511T; | +++ |
| 372 | A2V; S107W; N134S; E138Q; P188S; P405O; Q418R; A511T; | + |
| 373 | N134S; E138Q; P188S; T246A; S433K; K510D; A511T; | +++ |
| 374 | N134S; E138Q; P188S; P405A; A511T; | +++ |
| 375 | A2V; G110D; N134S; E138Q; P188S; P405V; Q418V; A511T; | +++++ |
| 376 | E87G; N134S; E138Q; P188S; P405V; A412V; Q418I; R508G; K509D; A511T; | +++++ |
| 377 | N134S; E138Q; P188S; A295V; P405V; Q418V; A511T; | ++++ |
| 378 | N134S; E138Q; P188S; L209N; P405V; Q418V; L502S; R508H; K509H; A511T; | +++++ |
| 379 | N134S; E138Q; P188S; T370A; P405V; Q418V; L502S; R508D; K509H; A511T; | +++++ |
| 380 | N134S; E138Q; P188S; P405V; Q418V; R508H; K509D; A511T; | +++++ |
| 381 | N134S; E138Q; P188S; P405V; Q418V; R508H; K509H; A511T; | +++++ |
| 382 | N134S; E138Q; P188S; P405V; Q418V; R508G; K509N; A511T; | +++++ |
| 383 | N134S; E138Q; P188S; P405V; Q418V; A511T; | +++++ |
| 384 | N134S; E138Q; P188S; P405W; Q418V; R508H; K509D; A511T; | +++++ |
| 385 | H61R; N134S; E138Q; P188S; P405V; A416L; Q418V; S433N; L502S; K509D; A511T; | ++++ |
| 386 | N134S; E138Q; P188S; P405V; Q418V; K509D; A511T; | +++++ |
| 387 | N134S; E138Q; P188S; A295T; P405V; Q418V; S458Q; R508H; K509D; A511T; | +++++ |
| 388 | N134S; E138Q; P188S; P405V; Q418V; R508D; K509D; A511T; | +++++ |
| 389 | N134S; E138Q; P188S; L209N; P405V; Q418V; A511T; | +++++ |
| 390 | N134S; E138Q; P188S; P405V; Q418V; L502S; R508D; A511T; | +++++ |
| 391 | N134S; E138Q; P188S; L209K; P405V; Q418V; S458Q; L502S; R508D; K509D; A511T; | +++++ |
| 392 | N134S; E138Q; P188S; E303G; G401I; P405A; Q418I; R508G; K509D; A511T; | ++++ |
| 393 | N134S; E138Q; P188S;E303G; 04011; P405A; Q418V; L502S; R508G; K509D; A511T; | ++++ |
| 394 | E114G; N134S; E138Q; P188S; E3030; P405V; Q418V; L502S; R508G; K509D; A511T; | ++++ |
| 395 | N134S; E138Q; P188S; E303G; G401S; P405A; A416L; Q418V; R508G; K509D; A511T; | ++++ |
| 396 | N134S; E138Q; P188S; G401S; P405A; Q418V; L502S; K509H; A511T; | ++++ |
| 397 | N134S; E138Q; P188S; P405V; A416L; Q418V; A511T; | ++++ |
| 398 | N134S; E138Q; P188S; P405A; Q418V; S458Q; R508G; K509H; A511T; | ++++ |
| 399 | N134S; E138Q; A162T; P188S; E303G; G401S; P405A; A416L; Q418I; L502S; R508G; K509Y; A511T; | ++++ |
| 400 | N134S; E138Q; P188S; P405V; Q418V; S458Q; R508G; A511T; | ++++ |
| 401 | N134S; E138Q; P188S; G401V; P405A; A412V; Q418I; L502S; R508G; K509H; A511T; | ++++ |
| 402 | N134S; E138Q; P188S; E303G; G401I; P405A; Q418V; L502S; K509H; A511T; | ++++ |
| 403 | N134S; E138Q; P188S; E303G; P405V; A412V; Q418I; K509D; A511T; | ++++ |
| 404 | N134S; E138Q; P188S; P405V; A416L; Q418V; L502S; R508G; K509H; A511T; | ++++ |
| 405 | N134S; E138Q; P188S; E303G; P405V; Q418V; R508G; K509D; A511T; | ++++ |
| 406 | N134S; E138Q; P188S; P405V; Q418V; L502S; R508G; K509D; A511T; | ++++ |
| 407 | N134S; E138Q; P188S; G401S; P405L; A412V; A416L; Q418V; L502S; K509H; A511T; | ++++ |
| 408 | N134S; E138Q; P188S; P405A; A412V; A416L; Q418V; R508G; K509D; A511T; | ++++ |
| 409 | N134S; E138Q; P188S; P405V; Q418V; L502S; R508G; K509H; A511T; | ++++ |
| 410 | N134S; E138Q; P188S; P405V; Q418I; R508G; K509D; A511T; | ++++ |
| 411 | N134S; E138Q; P188S; G401V; P405V; Q418I; A505K; A511T; | ++++ |
| 412 | N134S; E138Q; P188S; P405V; Q418V; A505K; A511T; | ++++ |
| 413 | N134S; E138Q; P188S; E303G; G401L; P405V; Q418V; A505K; A511T; | ++++ |
| 414 | N134S; E138Q; P188S; E303G; G401V; P405L; Q418I; A505K; A511T; | ++++ |
| 415 | K22R; N134S; E138Q; P188S; E303G; G401V; P405A; Q418V; A511T; | ++++ |
| 416 | N134S; E138Q; P188S; G264S; P405V; Q418V; Y500D; A505K; A511T; | ++++ |
| 417 | N134S; E138Q; P188S; E303G; P405V; 0418I; A511T; | ++++ |
| 418 | N134S; E138Q; P188S; E303G; G401L; P405C; Q418V; A511T; | ++++ |
| 419 | N134S; E138Q; P188S; E303G; G401I; P405W; Q418V; A511T; | ++++ |
| 420 | N134S; E138Q; P188S; E303G; G401L; P405V; Q418I; A505K; A511T; | ++++ |
| 421 | N134S; E138Q; P188S; G401V; P405C; Q418V; A511T; | ++++ |
| 422 | N134S; E138Q; P188S; E303G; P405A; Q418V; A505K; A511T; | ++++ |
| 423 | N134S; E138Q; P188S; P405V; Q418I; A511T; | ++++ |
| 424 | N134S; E138Q; P188S; P405V; Q418V; D429E; | ** |

TABLE 2-continued

Variant FAR polypeptides and total relative production of fatty alcohols

| Variant No. | Amino acid substitutions relative to SEQ ID NO: 2 | Relative fold improvement in fatty alcohol production† |
|---|---|---|
| | S458Q; L502S; R508D; K509D; A511T; | |
| 425 | N134S; E138Q; P188S; D212R; P405V; Q418V; S458Q; G487S; L502S; R508D; K509D; A511T; | ** |
| 426 | N134S; E138Q; P188S; S339G; P405V; Q418V; S458Q; L502S; R508D; K509D; A511T; | * |
| 427 | N134S; E138Q; P188S; P405V; Q418V; N427K; S458Q; L502S; R508D; K509D; A511T; | * |
| 428 | N134S; E138Q; P188S; P405V; Q418V; S458Q; V466Q; L502S; R508D; K509D; A511T; | ** |
| 429 | N134R; E138Q; P188S; P405V; Q418V; S458Q; L502S; R508D; K509D; A511T; | ** |
| 430 | T91R; N134S; E138Q; P188S; P405V; Q418V; S458Q; L502S; R508D; K509D; A511T; | * |
| 431 | G14V; N134S; E138Q; P188S; P405V; Q418V; S458Q; L502S; R508D; K509D; A511T; | *** |
| 432 | L69E; N134S; E138Q; P188S; P405V; Q418V; S458Q; L502S; R508D; K509D; A511T; | ** |
| 433 | N134S; E138Q; P188S; P405V; A409W; Q418V; S458Q; L502S; R508D; K509D; A511T; | * |
| 434 | N134S; E138Q; P188S; S244H; P405V; Q418V; S458Q; L502S; R508D; K509D; A511T; | * |
| 435 | H98P; N134S; E138Q; P188S; P405V; Q418V; S458Q; L502S; R508D; K509D; A511T; | * |
| 436 | N134S; E138Q; P188S; Q377K; P405V; Q418V; S458Q; L502S; R508D; K509D; A511T; | *** |
| 437 | N134S; E138Q; P188S; A389V; P405V; Q418V; S458Q; L502S; R508D; K509D; A511T; | ** |
| 438 | N134S; E138Q; P188S; P405V; Q418V; S433K; S458Q; L502S; R508D; K509D; A511T; | *** |
| 439 | N134S; E138Q; P188S; P405V; Q418V; R432Q; S458Q; L502S; R508D; K509D; A511T; | * |
| 440 | N134S; E138Q; P188S; Y380K; P405V; Q418V; S458Q; L502S; R508D; K509D; A511T; | * |
| 441 | L69Q; N134S; E138Q; P188S; P405V; Q418V; S458Q; L502S; R508D; K509D; A511T; | * |
| 442 | N134S; E138Q; P188S; P405V; L406Y; Q418V; S458Q; L502S; R508D; K509D; A511T; | * |
| 443 | N134S; E138Q; P188S; S283F; P405V; Q418V; S458Q; L502S; R508D; K509D; A511T; | * |
| 444 | N134S; E138Q; P188S; P405V; G410N; Q418V; S458Q; L502S; R508D; K509D; A511T; | * |
| 445 | N134S; E138Q; V153I; P188S; P405V; Q418V; S458Q; L502S; R508D; K509D; A511T; | ** |
| 446 | N134S; E138Q; P188S; T197P; P405V; Q418V; S458Q; L502S; R508D; K509D; A511T; | * |
| 447 | N134S; E138Q; P188S; S244P; P405V; Q418V; S458Q; L502S; R508D; K509D; A511T; | *** |
| 448 | N134S; E138Q; N177R; P188S; P405V; Q418V; S458Q; L502S; R508D; K509D; A511T; | * |
| 449 | N134S; E138Q; P188S; S244G; P405V; Q418V; S458Q; L502S; R508D; K509D; A511T; | * |
| 450 | N134S; E138Q; P188S; V305I; P405V; Q418V; R432C; S458Q; L502S; R508D; K509D; A511T; | * |
| 451 | R65Y; N134S; E138Q; P188S; P405V; Q418V; S458Q; L502S; R508D; K509D; A511T; | * |
| 452 | R65G; N134S; E138Q; P188S; P405V; Q418V; S458Q; L502S; R508D; K509D; A511T; | * |
| 453 | N134S; E138Q; P188S; A412M; Q418V; S458Q; L502S; R508D; K509D; A511T; | * |
| 454 | N134S; E138Q; I186A; P188S; P405V; Q418V; S458Q; L502S; R508D; K509D; A511T; | * |
| 455 | N134S; E138Q; P188S; P405V; Q418I; S458Q; L502S; R508D; K509D; A511T; | * |
| 456 | N134S; E138Q; P188S; R342L; P405V; Q418V; S458Q; L502S; R508D; K509D; A511T; | * |
| 457 | N134S; E138Q; P188S; G340P; P405V; Q418V; S458Q; L502S; R508D; K509D; A511T; | ** |
| 458 | N134S; E138Q; P188S; P405V; Q418V; T436D; S458Q; L502S; R508D; K509D; A511T; | * |
| 459 | N134S; E138Q; P188S; Q180H; P405V; Q418V; S452N; S458Q; L502S; R508D; K509D; A511T; | * |
| 460 | N134S; E138Q; P188S; S283E; P405V; Q418V; S458Q; L502S; R508D; K509D; A511T; | * |
| 461 | N134S; E138Q; P188S; S306W; T370I; P405V; Q418V; S458Q; L502S; R508D; K509D; A511T; | *** |
| 462 | N134S; E138Q; P188S; P405V; G410A; Q418V; S458Q; L502S; R508D; K509D; A511T; | * |
| 463 | N134S; E138Q; P188S; P405V; G410R; Q418V; S458Q; L502S; R508D; K509D; A511T; | * |
| 464 | N134S; E138Q; P188S; P405V; A409Y; Q418V; S458Q; L502S; R508D; K509D; A511T; | * |
| 465 | N134S; E138Q; P188S; P405V; Q418V; S458Q Y500N; L502S; R508D; K509D; A511T; | ** |
| 466 | G14R; N134S; E138Q; P188S; P405V; Q418V; S458Q; L502S; R508D; K509D; A511T; | *** |
| 467 | N134S; E138Q; P188S; V404A; P405V; Q418V; S458Q; L502S; R508D; K509D; A511T; | ** |
| 468 | N134S; E138Q; P188S; P405V; Q418V; E421P; S458Q; L502S; R508D; K509D; A511T; | ** |
| 469 | N134S; E138Q; P188S; A389M; P405V; Q418V; S458Q; L502S; R508D; K509D; A511T; | ** |
| 470 | N134S; E138Q; P188S; E227R; P405V; Q418V; S458Q; L502S; R508D; K509D; A511T; | ** |
| 471 | N134S; E138Q; N174C; P188S; P405V; Q418V; S458Q; L502S; R508D; K509D; A511T; | ** |
| 472 | V104M; N134S; E138Q; P188S; P405V; Q418V; S458Q; L502S; R508D; K509D; A511T; | *** |
| 473 | N134S; E138Q; P188S; G351C; P405V; Q418V; S458Q; L502S; R508D; K509D; A511T; | * |
| 474 | N134S; E138Q; P188S; Y380R; P405V; Q418V; S458Q; L502S; R508D; K509D; A511T; | * |
| 475 | Q18I; N134S; E138Q; P188S; P405V; Q418V; S458Q; L502S; R508D; K509D; A511T; | * |
| 476 | N134S; E138Q; P188S; P405V; Q418V; S458Q; L499R; L502S; R508D; K509D; A511T; | ** |
| 477 | N134S; E138Q; P188M; P405V; Q418V; S458Q; L502S; R508D; K509D; A511T; | * |
| 478 | N134S; E138Q; N177T; P188S; P405V; Q418V; S458Q; L502S; R508D; K509D; A511T; | ** |
| 479 | N134S; E138Q; P188S; P405V; Q418V; D429R; S458Q; L502S; R508D; K509D; A511T; | * |
| 480 | N134S; E138Q; P188S; P405V; Q418V; T436Q; S458Q; L502S; R508D; K509D; A511T; | * |
| 481 | A63Y; N134S; E138Q; P188S; P405V; Q418V; S458Q; L502S; R508D; K509D; A511T; | * |
| 482 | N134S; E138Q; P188S; P405V; Q418V; S452N; S458Q; L502S; R508D; K509D; A511T; | ** |
| 483 | N134S; E138Q; P188S; P405V; G410H; Q418V; S458Q; L502S; R508D; K509D; A511T; | * |
| 484 | N134S; E138Q; P188S; S266A; P405V; Q418V; S458Q; L502S; R508D; K509D; A511T; | * |
| 485 | V104I; N134S; E138Q; P188S; P405V; Q418V; S458Q; L502S; R508D; K509D; A511T; | *** |
| 486 | N134S; E138Q; P188S; S283M; P405V; Q418V; S458Q; L502S; R508D; K509D; A511T; | *** |
| 487 | N134S; E138Q; N177Q; P188S; P405V; G410C; Q418V; S458Q; L502S; R508D; K509D; A511T; | ** |
| 488 | N134S; E138Q; P188S; A389I; P405V; Q418V; S458Q; L502S; R508D; K509D; A511T; | ** |
| 489 | N134S; E138Q; P188S; P405V; Q418V; S458Q; V466R; L502S; R508D; K509D; A511T; | * |
| 490 | N134S; E138Q; P188S; P405V; Q418V; S452A; S458Q; L502S; R508D; K509D; A511T; | * |
| 491 | N134S; E138Q; P188S; S244F; P405V; Q418V; S458Q; L502S; R508D; K509D; A511T; | * |
| 492 | N134S; E138Q; P188S; P405V; A409V; Q418V; S458Q; L479Q; L502S; R508D; 509D; A511T; | * |
| 493 | N134S; E138Q; P188S; P405V; Q418V; S458Q; V466E; L502S; R508D; K509D; A511T; | ** |
| 494 | N134S; E138Q; P188S; V318I; P405V; Q418V; S458Q; L502S; R508D; K509D; A511T; | ** |
| 495 | N134S; E138Q; P188S; A389L; P405V; Q418V; | ** |

TABLE 2-continued

Variant FAR polypeptides and total relative production of fatty alcohols

| Variant No. | Amino acid substitutions relative to SEQ ID NO: 2 | Relative fold improvement in fatty alcohol production† |
|---|---|---|
| | S458Q; L502S; R508D; K509D; A511T; | |
| 496 | N134S; E138Q; P188A; P405V; Q418V; S458Q; L502S; R508D; K509D; A511T; | ** |
| 497 | N134S; E138Q; P188S; E205Q; P405V; Q418V; S458Q; L502S; R508D; K509D; A511T; | ** |
| 498 | N134S; E138Q; P188S; P405V; Q418V; T430H; S458Q; L502S; R508D; K509D; A511T; | ** |
| 499 | A63R; N134S; E138Q; P188S; P405V; Q418V; S458Q; L502S; R508D; K509D; A511T; | * |
| 500 | N134S; E138Q; P188S; P405V; Q418V; S458Q; L502S; R508D; K509D; A511K; | * |
| 501 | N134S; E138Q; P188S; P405V; Q418V; S458Q; Q474R; L502S; R508S; K509D; A511T; | ** |
| 502 | N134S; E138Q; P188S; S306H; P405V; Q418V; S458Q; L502S; R508D; K509D; A511T; | * |
| 503 | N134S; E138Q; P188S; D376P; P405V; Q418V; S458Q; L502S; R508D; K509D; A511T; | *** |
| 504 | N134S; E138Q; P188S; Y380N; P405V; Q418V; S458Q; L502S; R508D; K509D; A511T; | * |
| 505 | N134S; E138Q; P188S; V398Y; P405V; Q418V; S458Q; L502S; R508D; K509D; A511T; | * |
| 506 | G9D; N134S; E138Q; P188S; P405V; Q418V; S458Q; G487T; Y500H; L502S; R508D; K509D; A511T; | * |
| 507 | N134S; E138Q; I186G; P188S; P405V; Q418V; S458Q; L502S; R508D; K509D; A511T; | ** |
| 508 | N128H; N134S; E138Q; P188S; P405V; Q418V; S458Q; L502S; R508D; K509D; A511T; | * |
| 509 | N134S; E138Q; P188S; E227T; P405V; Q418V; S458Q; L502S; R508D; K509D; A511T; | * |
| 510 | N134S; E138Q; P188S; V207L; P405V; Q418V; S458Q; L502S; R508D; K509D; A511T; | ** |
| 511 | N134S; E138Q; P188S; L364I; P405V; Q418V; S458Q; L502S; R508D; K509D; A511T; | *** |
| 512 | N134S; E138Q; P188S; S283T; P405V; Q418V; S458Q; L502S; R508D; K509D; A511T; | ** |
| 513 | N134S; E138Q; P188S; S244A; P405V; M413R; Q418V; S458Q; L502S; R508D; K509D; A511T; | ** |
| 514 | N134S; E138Q; P188S; P405V; Q418V; S458Q; G487R; L502S; R508D; K509D; A511T; | * |
| 515 | N134S; E138Q; P188S; E227A; P405V; Q418V; S458Q; L502S; R508D; K509D; A511T; | * |
| 516 | N134S; E138Q; P188S; V217L; P405V; Q418V; S458Q; L502S; R508D; K509D; A511T; | * |
| 517 | N134S; E138Q; P188S; V399T; P405V; Q418V; S458Q; L502S; R508D; K509D; A511T; | * |
| 518 | H61R; N134S; E138Q; P188S; P405V; G410H; Q418V; S458Q; L502S; R508D; K509D; A511T; | * |
| 519 | N134S; E138Q; P188S; P405V; Q418V; T430R; S458Q; L502S; R508D; K509D; A511T; | ** |
| 520 | N134S; E138Q; P188S; M365N; P405V; Q418V; S458Q; L502S; R508D; K509D; A511T; | ** |
| 521 | N134S; E138Q; P188I; P405V; Q418V; S458Q; L502S; R508D; K509D; A511T; | ** |
| 522 | N134S; E138Q; I186Y; P188S; P405V; Q418V; S458Q; L502S; R508D; K509D; A511T; | * |
| 523 | N134S; E138Q; P188S; L226M; P405V; Q418V; S458Q; L502S; R508D; K509D; A511T; | * |
| 524 | N134S; E138Q; P188S; K224R; P405V; Q418V; S458Q; L502S; R508D; K509D; A511T; | * |
| 525 | N134S; E138Q; P188S; E227H; P405V; Q418V; S458Q; L502S; R508D; K509D; A511T; | * |
| 526 | N134S; E138Q; P188S; G401C; P405V; Q418V; S458Q; L502S; R508D; K509D; A511T; | * |
| 527 | N134S; E138Q; P188S; P405V; Q418V; S458Q; Q474R; L502S; R508D; K509D; A511T; | ** |
| 528 | N134S; E138Q; P188S; Q341K; P405V; Q418V; S433K; S458Q; L502S; R508D; K509D; A511T; | # |
| 529 | V104I; N134S; E138Q; P188S; L330V; P405V; Q418V; S433K; S458Q; V466Q; L502S; R508D; K509D; A511T; | # |
| 530 | N134S; E138Q; P188S; S283T; P405V; Q418V; S433K; S458Q; L502S; R508D; K509D; A511T; | # |
| 531 | N134S; E138Q; P188S; S306H; P405V; Q418V; S433K; S458Q; L502S; R508D; K509D; A511T; | # |
| 532 | R65G; N134S; E138Q; N174C; N177T; P188S; K224R; G351P; P405V; Q418V; S433K; S458Q; L502S; R508D; K509D; A511T; | # |
| 533 | R65G; N134S; E138Q; N174C; N177T; P188S; K224R; V404A; P405V; Q418V; S433K; S458Q; L502S; R508D; K509D; A511T; | # |
| 534 | A63R; R65G; N134S; E138Q; P188S; K224R; L226M; P405V; Q418V; S433K; S458Q; L502S; R508D; K509D; A511T; A512S; | # |
| 535 | Q18I; R65G; N134S; E138Q; P188S; K224R; P405V; Q418V; S433K; S458Q; L502S; R508D; K509D; A511T; | # |
| 536 | A63R; R65G; N134S; E138Q; N174C; P188S; L226M; P405V; Q418V; S433K; S458Q; L502S; R508D; K509D; A511T; | # |
| 537 | R65G; N128H; N134S; E138Q; N174C; P188S; K224R; L226M; G351C; V404A; P405V; Q418V; S433K; S458Q; L502S; R508D; K509D; A511T; | # |
| 538 | A63R; R65G; N134S; E138Q; P188S; G351C; V404A; P405V; Q418V; S433K; S458Q; G487R; L502S; R508D; K509D; A511T; | # |
| 539 | N128H; N134S; E138Q; P188S; G351C; V404A; P405V; Q418V; S433K; S458Q; G487R; L502S; R508D; K509D; A511T; | # |
| 540 | Q18I; N134S; E138Q; N174C; P188S; K224R; L226M; G351C; P405V; Q418V; S433K; S458Q; L502S; R508D; K509D; A511T; | # |
| 541 | R65G; N128H; N134S; E138Q; N174C; N177T; P188S; P405V; L406Y; Q418V; S433K; S458Q; L502S; R508D; K509D; A511T; | # |
| 542 | N128H; N134S; E138Q; N177T; P188S; L226M; P405V; Q418V; S433K; S458Q; L502S; R508D; K509D; A511T; | # |
| 543 | Q18I; A63R; R65G; N134S; E138Q; N174C; P188S; K224R; L226M; P405V; L406Y; Q418V; S433K; S458Q; L502S; R508D; K509D; A511T; | # |
| 544 | A63R; R65G; N134S; E138Q; N174C; N177T; P188S; V404A; P405V; Q418V; S433K; S458Q; L502S; R508D; K509D; A511T; | # |
| 545 | N134S; E138Q; N174C; P188S; K224R; L226M; E227R; G351C; V404A; P405V; Q418V; S433K; S458Q; L502S; R508D; K509D; A511T; | # |
| 546 | Q18I; R65G; N134S; E138Q; N177T; P188S; K224R; V404A; P405V; L406Y; Q418V; S433K; S458Q; L502S; R508D; K509D; A511T; | ## |
| 547 | N128H; N134S; E138Q; N174C; P188S; L226M; G351C; P405V; Q418V; S433K; S458Q; L502S; R508D; K509D; A511T; | ## |
| 548 | Q18I; A63R; N134S; E138Q; N174C; P188S; G351C; P405V; Q418V; S433K; S458Q; G487R; L502S; R508D; K509D; A511T; | # |
| 549 | Q18I; R65G; N128H; N134S; E138Q; N174C; N177T; P188S; K224R; P405V; Q418V; S433K; S458Q; L502S; R508D; K509D; A511T; | # |
| 550 | Q18I; N128H; N134S; E138Q; N174C; N177T; P188S; P405V; Q418V; S433K; S458Q; L502S; R508D; K509D; A511T; | # |
| 551 | Q18I; A63R; R65G; N134S; E138Q; P188S; G351C; P405V; Q418V; S433K; S458Q; L502S; R508D; K509D; A511T; | # |
| 552 | N134S; E138Q; N174C; P188S; K224R; L226M; G351C; P405V; L406Y; Q418V; S433K; S458Q; L502S; R508D; K509D; A511T; | # |
| 553 | A63R; R65G; N134S; E138Q; N174C; P188S; K224R; L226M; P405V; Q418V; S433K; S458Q; L502S; R508D; K509D; A511T; | ## |

TABLE 2-continued

Variant FAR polypeptides and total relative production of fatty alcohols

| Variant No. | Amino acid substitutions relative to SEQ ID NO: 2 | Relative fold improvement in fatty alcohol production† |
|---|---|---|
| 554 | A63R; R65G; N134S; E138Q; N174C; N177T; P188S; L226M; P405V; L406Y; Q418V; S433K; S458Q; G487R; L502S; R508D; K509D; A511T; | ## |
| 555 | Q18I; A63R; R65G; N128H; N134S; E138Q; P188S; P405V; Q418V; S433K; S458Q; G487R; L502S; R508D; K509D; A511T; | ## |
| 556 | Q18I; N128H; N134S; E138Q; N174C; N177T; P188S; L226M; G351C; P405V; Q418V; S433K; S458Q; L502S; R508D; K509D; A511T; | ## |
| 557 | R65G; N134S; E138Q; N174C; P188S; L226M; V404A; P405V; L406Y; Q418V; S433K; S458Q; G487R; L502S; R508D; K509D; A511T; | ## |
| 558 | N134S; E138Q; P188S; V217L; P405V; Q418V; S433K; S458Q; L502S; R508D; K509D; A511T; | # |
| 559 | N134S; E138Q; P188S; A261D; S339G; Y380R; P405V; G410R; Q418V; D429E; S433K; S458Q; Q474R; L502S; R508D; K509D; A511T; | # |
| 560 | N134S; E138Q; P188S; Y380N; P405V; G410A; Q418V; S433K; S458Q; L502S; R508D; K509D; A511T; | # |
| 561 | N134S; E138Q; P188S; S266A; S339G; Y380N; P405V; Q418V; S433K; S458Q; L502S; R508D; K509D; A511T; | # |
| 562 | N134S; E138Q; P188S; V217L; P405V; A409Y; G410N; Q418V; S433K; S458Q; L502S; R508D; K509D; A511T; | # |
| 563 | N134S; E138Q; P188S; P405V; G410N; Q418V; S433K; S458Q; L502S; R508D; K509D; A511T; | # |
| 564 | N134S; E138Q; P188S; P405V; A409W; G410R; Q418V; S433K; S458Q; L502S; R508D; K509D; A511K; | # |
| 565 | N134S; E138Q; P188S; S339G; P405V; Q418V; S433K; S458Q; L502S; R508D; K509D; A511T; | # |
| 566 | N134S; E138Q; P188S; P405V; A409W; G410R; Q418V; S433K; S458Q; L502S; R508D; K509D; A511T; | # |
| 567 | L69E; N134S; E138Q; P188S; S266A; P405V; Q418V; S433K; S458Q; L502S; R508D; K509D; A511T; | # |
| 568 | N134S; E138Q; P188S; S266A; P405V; Q418V; S433K; S458Q; L502S; R508D; K509D; A511T; | # |
| 569 | L69E; N134S; E138Q; P188S; P405V; A409Y; Q418V; D429E; S433K; S458Q; L502S; R508D; K509D; A511T; | # |
| 570 | L69E; N134S; E138Q; P188S; P405V; Q418V; S433K; S458Q; L502S; R508D; K509D; A511T; | # |
| 571 | N134S; E138Q; P188S; S339G; P405V; G410A; Q418V; D429E; S433K; S458Q; L502S; R508D; K509D; A511T; | # |
| 572 | N134S; E138Q; P188S; S339G; P405V; A409W; G410R; Q418V; S433K; S458Q; L502S; R508D; K509D; A511T; | # |
| 573 | N134S; E138Q; P188S; P405V; G410A; Q418V; S433K; S458Q; L502S; R508D; K509D; A511T; | # |
| 574 | N134S; E138Q; P188S; V217L; S266A; P405V; Q418V; S433K; S458Q; L502S; R508D; K509D; A511T; | # |
| 575 | N134S; E138Q; P188S; V399T; G401C; P405V; Q418V; R432Q; S433K; S458Q; L502S; R508D; K509D; A511T; | # |
| 576 | N134S; E138Q; N177R; P188S; V399T; P405V; Q418V; R432Q; S433K; S458Q; L502S; R508D; K509D; A511T; | # |
| 577 | N134S; E138Q; N177R; P188S; V399T; G401C; P405V; Q418V; R432Q; S433K; S458Q; L502S; R508D; K509D; A511T; | # |
| 578 | N134S; E138Q; P188S; V399T; P405V; Q418V; S433K; S458Q; L502S; R508D; K509D; A511T; | # |
| 579 | N134S; E138Q; P188S; V399T; G401C; P405V; Q418V; S433K; S458Q; L502S; R508D; K509D; A511T; | # |
| 580 | N134S; E138Q; P188S; V398Y; G401C; P405V; Q418V; S433K; S458Q; L502S; R508D; K509D; A511T; | # |
| 581 | N134S; E138Q; P188S; V398Y; V399T; G401C; P405V; Q418V; R432Q; S433K; S458Q; L502S; R508D; K509D; A511T; | # |
| 582 | N134S; E138Q; N177R; P188S; V398Y; V399T; P405V; Q418V; R432Q; S433K; S458Q; L502S; R508D; K509D; A511T; | # |
| 583 | N134S; E138Q; P188S; V398Y; V399T; P405V; Q418V; R432Q; S433K; S458Q; L502S; R508D; K509D; A511T; | # |
| 584 | N134S; E138Q; N177R; P188S; V398Y; P405V; Q418V; S433K; S458Q; L502S; R508D; K509D; A511T; | # |
| 585 | N134S; E138Q; P188S; P405V; Q418V; R432Q; S433K; S458Q; L502S; R508D; K509D; A511T; | # |
| 586 | N134S; E138Q; P188S; L364I; G401C; P405V; Q418V; S433K; S458Q; L502S; R508D; K509D; A511T; | # |
| 587 | N134S; E138Q; P188S; S244P; G401C; P405V; Q418V; R432Q; S433K; S458Q; L502S; R508D; K509D; A511T; | # |
| 588 | N134S; E138Q; N177R; P188S; V398Y; P405V; Q418V; R432Q; S433K; S458Q; L502S; R508D; K509D; A511T; | # |
| 589 | N134S; E138Q; P188S; V398Y; P405V; Q418V; S433K; S458Q; L502S; R508D; K509D; A511T; | # |
| 590 | N134S; E138Q; N177R; P188S; V398Y; G401C; P405V; Q418V; R432Q; S433K; S458Q; L502S; R508D; K509D; A511T; | # |
| 591 | N134S; E138Q; N177R; P188S; P405V; Q418V; S433K; S458Q; L502S; R508D; K509D; A511T; | # |
| 592 | N134S; E138Q; P188S; A389M; P405V; Q418V; S458Q; L502S; R508D; K509D; A511T; | # |
| 593 | N134S; E138Q; P188S; D376P; P405V; Q418V; S458Q; L502S; R508D; K509D; A511T; | # |
| 594 | N134S; E138Q; P188S; A389I; P405V; Q418V; S458Q; L502S; R508D; K509D; A511T; | # |
| 595 | N134S; E138Q; P188S; P405V; Q418V; S458Q; Q474R; L502S; R508D; K509D; A511T; | # |
| 596 | N134R; E138Q; P188S; S283F; P405V; Q418V; S458Q; L502S; R508D; K509D; A511T; | ## |
| 597 | N134S; E138Q; P188S; S283M; P405V; Q418V; S458Q; L502S; R508D; K509D; A511T; | # |
| 598 | N134S; E138Q; N177T; P188S; P405V; Q418V; S458Q; L502S; R508D; K509D; A511T; | # |
| 599 | N134S; E138Q; I186G; P188S; P405V; Q418V; S458Q; L502S; R508D; K509D; A511T; | # |
| 600 | N134S; E138Q; P188I; A389L; P405V; Q418V; S458Q; L502S; R508D; K509D; A511T; | # |
| 601 | N134S; E138Q; I74C; P188S; P405V; Q418V; S458Q; Y500R; L502S; R508D; K509D; A511T; | # |
| 602 | V104I; N134S; E138Q; P188S; P405V; Q418V; S458Q; L502S; R508D; K509D; A511T; | # |
| 603 | N134S; E138Q; P188I; P405V; Q418V; S458Q; L502S; R508D; K509D; A511T; | # |
| 604 | N134S; E138Q; P188S; S244H; P405V; Q418V; S458Q; L502S; R508D; K509D; A511T; | # |
| 605 | N134S; E138Q; P188S; M365N; P405V; Q418V; S458Q; L502S; R508D; K509D; A511T; | ## |
| 606 | P62S; N134S; E138Q; P188S; S244A; P405V; L406Y; Q418V; S458Q; L502S; R508D; K509D; A511T; | # |
| 607 | N134S; E138Q; P188S; Q377K; P405V; Q418V; S458Q; L502S; R508D; K509D; A511T; | # |
| 608 | N134S; E138Q; P188S; S283M; P405V; Q418V; S458Q; Y500R; L502S; R508D; K509D; A511T; | # |
| 609 | N134R; E138Q; P188S; V399T; P405V; Q418V; S458Q; L502S; R508D; K509D; A511T; | # |
| 610 | N134S; E138Q; P188S; A389V; P405V; Q418V; | # |

TABLE 2-continued

Variant FAR polypeptides and total relative production of fatty alcohols

| Variant No. | Amino acid substitutions relative to SEQ ID NO: 2 | Relative fold improvement in fatty alcohol production† |
|---|---|---|
| 611 | S458Q; L502S; R508D; K509D; A511T; N134S; E138Q; P188S; D376P; P405V; Q418V; S452G; S458Q; L502S; R508D; K509D; A511T | # |
| 612 | N134S; E138Q; N177Q; P188S; P405V; Q418V; S458Q; Y500R; L502S; R508D; K509D; A511T | # |
| 613 | N134R; E138Q; P188S; P405V; Q418V; S458Q; L502S; R508D; K509D; A511T | # |
| 614 | N134S; E138Q; N177Q; P188S; O377K; P405V; Q418V; S458Q; L502S; R508D; K509D; A511T | # |
| 615 | N134S; E138Q; P188S; P405V; Q418V; S452N; S458Q; L502S; R508D; K509D; A511T | # |
| 616 | N134S; E138Q; P188S; S244F; P405V; Q418V; S458Q; Y500R; L502S; R508D; K509D; A511T | # |
| 617 | Q6P; V104I; N134S; E138Q; P188S; P405V; Q418V; S458Q; L502S; R508D; K509D; A511T | # |
| 618 | N134S; E138Q; P188S; R403S; P405V; Q418V; S458Q; Y500R; L502S; R508D; K509D; A511T | # |
| 619 | N134S; E138Q; P188S; S283T; P405V; Q418V; S458Q; L502S; R508D; K509D; A511T | # |
| 620 | N134S; E138Q; P188S; L364I; P405V; Q418V; S458Q; L502S; R508D; K509D; A511T | # |
| 621 | N134S; E138Q; P188S; S283F; P405V; Q418V; S458Q; L502S; R508D; K509D; A511T | # |
| 622 | A12T; N134R; E138Q; P188S; P405V; Q418V; S458Q; L502S; R508D; K509D; A511T | # |
| 623 | N134S; E138Q; P188S; P405V; Q418V; S458Q; Y500R; L502S; R508D; K509D; A511T | # |
| 624 | N134S; E138Q; P188S; P405V; G410N; Q418V; S458Q; L502S; R508D; K509D; A511T | # |
| 625 | N134S; E138Q; P188S; E227R; P405V; Q418V; S458Q; L502S; R508D; K509D; A511T | # |
| 626 | N134S; E138Q; P188S; P405V; Q418V; S458Q; V466Q; L502S; R508D; K509D; A511T | # |
| 627 | N134S; E138Q; P188S; V318I; P405V; Q418V; S458Q; V466E; L502S; R508D; K509D; A511T | # |
| 628 | N134S; E138Q; P188S; S244P; P405V; Q418V; S458Q; L502S; R508D; K509D; A511T | # |
| 629 | N134S; E138Q; P188S; Y380K; P405V; Q418V; S458Q; L502S; R508D; K509D; A511T | # |

†Fatty alcohols for the relative fatty alcohol measurements include: C14:0 (1-tetradecanol), C16:1 (cis $\Delta^9$-1-hexadecenol), C16:0 (1-hexadecanol), C18:1 (cis $\Delta^{11}$-1-octadecenol), and C18:0 (1-octadecanol).
+ = 1.0 to 1.5 fold improvement over wild-type *M. algicola* FAR at 30° C.
++ = 1.6 to 2.0 fold improvement over wild-type *M. algicola* FAR at 30° C.
+++ = 2.1 to 3.0 fold improvement over wild-type *M. algicola* FAR at 30° C.
++++ = 3.1 to 4.0 fold improvement over wild-type *M. algicola* FAR at 30° C.
+++++ = >4.1 fold improvement over wild-type *M. algicola* FAR at 30° C.
\* = 1.0 to 1.5 fold improvement over Variant No. 391 at 37° C.
\*\* = 1.6 to 2.0 fold improvement over Variant No. 391 at 37° C.
\*\*\* = ≥2.1 fold improvement over Variant No. 391 at 37° C.
# = 1.0 to 1.5 fold improvement over Variant No. 438 at 40° C.
## = ≥1.6 fold improvement over Variant No. 438 at 40° C.

Example 3

Evaluation of *M. algicola* FAR Variants with Improved Activity Using Shake Flasks A subset of FAR Maa Variant Nos. 1-423 were evaluated in shake flasks. Recombinant *E. coli* BW25113 strains (ΔfadE or ΔtorR knockouts) comprising a plasmid containing a heterologous gene encoding *M. algicola* DG893 FAR variants were grown in 5 mL Luria Bertani (LB) or M9YE medium supplemented with 1% glucose and 30 µg/mL chloramphenicol (CAM), for approximately 16-18 hours (overnight) in a shaker-incubator at 30° C., 200 rpm. A 5% inoculum was used to initiate fresh 50 mL culture containing M9YE medium supplemented with 30 µg/mL CAM and 0.4% glucose. The culture was incubated for 2 hours at 30° C., 200 rpm to an $OD_{600}$ of 0.6-0.8, at which point expression of the heterologous FAR gene was induced with isopropyl-β-D-thiogalactoside (IPTG) (1 mM final concentration). Incubation was continued for about 24-48 hours under the same conditions. An additional amount of glucose (0.5% w/v final concentration) was added to the culture at 3, 6, and 9 hours after IPTG induction as needed. Samples were taken at various time points for extraction and analysis.

0.5 mL of cell culture was extracted with 1 mL of isopropanol:methyl t-butyl ether (MTBE) (4:6 ratio) for 2 hours. The extract was centrifuged, the upper organic phase transferred into a GC vial and analyzed by the GC method described in Example 2. The typical shake flask titers at 24 hours for those FAR Maa variants tested under the conditions described herein was in the range of 0.2 g/L to 1.5 g/L. Specifically, FAR Maa Variant No. 370 produced between 0.5 and 1 g/L fatty alcohols and FAR Maa Variant No. 391 produced between 0.8 and 1.2 g/L fatty alcohols.

Example 4

Chain Length Profile of Fatty Alcohols Exhibited by Recombinant *E. coli* Expressing Wild-type FAR Maa or FAR Maa Variants The chain length profile of a subset of FAR Maa variants were evaluated. Table 3 provides the relative chain length distribution of fatty alcohols exhibited by recombinant *E. coli* strains expressing wild-type FAR Maa or FAR Maa variants.

TABLE 3

Relative chain length distribution of fatty alcohols exhibited by recombinant *E. coli* strains expressing wild-type FAR Maa or FAR Maa variants

| *E. coli* strain | Temperature (° C.) | FAR Variant No. | Relative Chain Length Distribution of fatty alcohols[a] | | | | |
|---|---|---|---|---|---|---|---|
| | | | C14:0 | C16:1 | C16:0 | C18:1 | C18:0 |
| BW25113-ΔfadE | 30 | Wild-type | 8 | 30 | 30 | 32 | <1 |
| BW25113-ΔtorR | " | " | 10 | 30 | 30 | 30 | <1 |
| " | " | 370 | 10 | 42 | 29 | 19 | <1 |
| " | " | 391 | 10 | 40 | 29 | 21 | " |
| " | " | 436 | 19 | 46 | 22 | 13 | " |
| " | " | 438 | 21 | 48 | 20 | 11 | " |

TABLE 3-continued

Relative chain length distribution of fatty alcohols exhibited by recombinant
E. coli strains expressing wild-type FAR Maa or FAR Maa variants

| E. coli strain | Temperature (°C.) | FAR Variant No. | Relative Chain Length Distribution of fatty alcohols[a] | | | | |
|---|---|---|---|---|---|---|---|
| | | | C14:0 | C16:1 | C16:0 | C18:1 | C18:0 |
| " | " | 547 | 18 | 45 | 24 | 13 | " |
| " | " | 555 | 27 | 42 | 20 | 11 | " |
| " | " | 556 | 21 | 45 | 24 | 13 | " |
| " | 37 | 436 | 17 | 37 | 34 | 12 | " |
| " | " | 438 | 20 | 40 | 30 | 10 | " |
| " | " | 547 | 26 | 43 | 25 | 6 | " |
| " | " | 555 | 28 | 42 | 24 | 6 | " |
| " | " | 556 | 28 | 43 | 23 | 6 | " |
| " | 40 | 547 | 25 | 38 | 30 | 7 | " |
| " | " | 555 | 23 | 37 | 31 | 9 | " |
| " | " | 556 | 28 | 38 | 28 | 6 | " |
| MG1655-7740 | 30 | 436 | 31 | 33 | 27 | 9 | " |
| " | " | 438 | 35 | 34 | 24 | 7 | " |
| " | 37 | 436 | 32 | 23 | 38 | 7 | " |
| " | " | 438 | 36 | 24 | 34 | 6 | " |
| W3110-10-ΔfhuA | 30 | 436 | 27 | 39 | 26 | 8 | " |
| " | " | 438 | 30 | 41 | 23 | 6 | " |
| " | 37 | 436 | 38 | 31 | 26 | 5 | " |
| " | " | 438 | 39 | 31 | 25 | 5 | " |

[a] The relative chain length distribution is expressed as a % of the total fatty alcohols detected via GC-FID. Fatty alcohols include: C14:0 (1-tetradecanol), C16:1 (cis $\Delta^9$-1-hexadecenol), C16:0 (1-hexadecanol), C18:1 (cis $\Delta^{11}$-1-octadecenol), and C18:0 (1-octadecanol). No C14:1 (1-tetradecanol) was detected.

Example 5

Evaluation of M. algicola FAR Variants with Improved Activity Using Fermentors A. Evaluation of FAR Maa Variants Using a Fed-batch DO-Stat Fermentation Process In an aerated, agitated stirred tank 10 L fermentor, 3.0 L of growth medium containing 33.85 g 5×M9 powder (BD Difco), 6 g Bacto yeast extract (BD), 3 g ammonium phosphate dibasic (Sigma-Aldrich), 15 g ammonium sulfate (EMD), 9 g glucose (Sigma), 1.48 g magnesium sulfate, heptahydrate (Sigma), 44 mg Calcium chloride, Dihydrate (Sigma), 15 ml trace elements solution, 12.6 mg EDTA (Sigma-Aldrich), 150 mg Fe(III) Citrate (Sigma), 6.75 mg Thiamine.HCl (Sigma), and 90 µg chloroamphenicol (Sigma Chemical Co.) was brought to a temperature of 30° C. The fermentor was inoculated with a late exponential culture of E. coli strain containing M. algicola DG893 FAR (FAR Maa) Variant Nos. 370 and 391 to a starting optical density ($OD_{600}$) of about 1.0. The inoculum was grown in a 1000 mL baffled shake flask containing 200 ml of 47.6 g/L terrific broth powder (Difco), 4 ml/L glycerol (Sigma), and 30 11g/ml chloroamphenicol (Sigma Chemical Co.) at 30° C., 250 rpm until the OD600 reached ~8.0-10.0. The fermentor was agitated at 300-1200 rpm and air supplied at 3.0 L/min to maintain a minimum dissolved oxygen level of 30% of saturation. The pH of the culture was controlled at 7.0 by addition of 5 N sodium hydroxide.

After consumption of the 3 g/L initial glucose, an exponential fed-batch growth phase with a specific growth rate of $0.22\,h^{-1}$ was initiated by exponential addition of feed solution containing 500 g/L glucose (Sigma), 13.06 g/L magnesium sulfate, heptahydrate (Sigma), 100 g/L ammonium sulfate (EMD), 10 ml/L trace elements solution, 8.4 mg/L EDTA (Sigma-Aldrich), 100 mg/L Fe(III) Citrate (Sigma), 4.5 mg/L Thiamine.HCl (Sigma), and 30 µg/L chloroamphenicol (Sigma Chemical Co.) to fermentor. After 16 hours of fed-batch culture and 1 hour delay, the expression of FAR Maa Variant Nos. 370 and 391 was induced by the addition of isopropyl-β-D-thiogalactoside (IPTG) (US Biological) to a final concentration of 1 mM. Production of fatty alcohol was maintained by addition of a feed solution containing 650 g/L glucose (Sigma), 5.6 g/L magnesium sulphate, heptahydrate (Sigma), 6.5 g/L ammonium sulfate (EMD), 15 ml/L trace elements solution, 6.3 mg/L EDTA (Sigma-Aldrich), 75 mg/L Fe(III) Citrate (Sigma), 5.6 mg/L Thiamine.HCl (Sigma), 30 µg/L chloroamphenicol (Sigma Chemical Co.), and 1 mM IPTG (US Biological). The addition of feed solution (10 g/L glucose per pulse) was triggered after a 45 minutes delay following dissolved oxygen (DO) spikes above 40%. The culture was grown for another 120 hours at 30° C. Samples were taken at various time points for extraction and analysis. Extraction and quantification of fatty alcohols were performed as described in Examples 2 and 3.

Under the conditions tested, the total production of fatty alcohols was ~45-50 g/L for E. coli BW25113 ΔtorR expressing FAR Maa Variant Nos. 370 and 391 as compared to 12-15 g/L for the same strain expressing the wild-type FAR Maa of SEQ ID NO: 2 under the fermentation conditions reported in WO 2011/100835.

B. Evaluation of FAR Maa Variants at Different Temperatures Using a Short-batch Fermentation Process A short-batch fermentation process was used to more efficiently compare improved FAR Maa variants for relative FOH activity in the presence of excess glucose and under controlled bioreactor conditions. In an aerated, agitated stirred tank 10 L fermentor, 3.0 L of growth medium containing 33.85 g 5x M9 powder (BD Difco), 6 g Bacto yeast extract (BD), 3 g ammonium phosphate dibasic (Sigma-Aldrich), 15 g ammonium sulfate (EMD), 9 g glucose (Sigma), 1.48 g magnesium sulfate, heptahydrate (Sigma), 44 mg calcium chloride dehydrate (Sigma), 15 ml trace elements solution, 12.6 mg EDTA (Sigma-Aldrich), 150 mg Fe(III) citrate (Sigma), 6.75 mg thiamine.HCl (Sigma), and 90 µg chloroamphenicol (Sigma Chemical Co.) was brought to a temperature of 30° C. The fermentor was inoculated with a late exponential culture of E. coli strain containing M. algicola DG893 FAR (FAR Maa) Variant Nos. 370 and 438 to a starting optical density ($OD_{600}$) of about 1.0. The inoculum was grown in a 1000 mL baffled shake flask containing 200 ml of 47.6 g/L terrific broth powder (Difco), 4 ml/L glycerol (Sigma), and 30 µg/ml chloramphenicol (Sigma Chemical Co.) at 30° C., 250 rpm until the $OD_{600}$ reached ~8.0-10.0. The fermentor was agitated at 300-1200 rpm and air supplied at 3.0 L/min to maintain a minimum dissolved oxygen (DO) level of 30% of saturation. The pH of the culture was controlled at 7.0 by addition of 5 N sodium hydroxide.

After consumption of the 3 g/L initial glucose, an exponential fed-batch growth phase with a specific growth rate of $0.22\,h^{-1}$ was initiated by exponential addition of feed solution containing 500 g/L glucose (Sigma), 13.06 g/L magnesium sulfate, heptahydrate (Sigma), 100 g/L ammonium sulfate (EMD), 10 ml/L trace elements solution, 8.4 mg/L EDTA (Sigma-Aldrich), 100 mg/L Fe(III) citrate (Sigma), 4.6 mg/L thiamine.HCl (Sigma), and 30 µg/L chloramphenicol (Sigma Chemical Co.) to the fermentor.

After 16 hours, 0.75-1 L of fed-batch culture was harvested and transferred to a 10 L fermentor containing 3 L production medium (45.13 g 5×M9 powder (BD Difco), 300 g glucose (Sigma), 1.497 g magnesium sulfate, heptahydrate (Sigma), 58.7 mg calcium chloride dehydrate (Sigma), 20 ml trace elements solution, 16.8 mg EDTA (Sigma-Aldrich), 200 mg Fe(III) citrate (Sigma), 9 mg thiamine.HCl (Sigma), and 120 µg chloramphenicol (Sigma Chemical Co.). Deionized water (DIW) was used to adjust the total initial working volume to 4.0 L and the starting $OD_{600}$ to 20. The fatty alcohol production was initiated by induction of the expression of FAR Maa Variant Nos. 370 and 438 via addition of isopropyl-6-D-thiogalactoside (IPTG) (US Biological) to a final concentration of 1 mM. The fermentor was agitated at 300-1200 rpm and air supplied at 3.0 L/min to maintain a minimum dissolved oxygen (DO) level of 30% of saturation. The pH of the culture was controlled at 7.0 by addition of 5 N sodium hydroxide. The production was carried on at the desired temperature (i.e., 30, 34, or 37° C.) for ~30-48 hours. Samples were taken at various time points for extraction and analysis. Extraction and quantification of fatty alcohols were performed as described in Examples 2 and 3.

Under the conditions tested, the total production of fatty alcohols at ~30 hours for Variant No. 370 was 5.6, 3.9, and 1.9 g/L at 30° C., 34° C., and 37° C., respectively. The total production of fatty alcohols at ~30 hours for Variant No. 438 was 7.2, 8.3, and 6.7 g/L at 30° C., 34° C., and 37° C., respectively.

Example 6

Wild-type *M. aquaeolei* FAR Gene Acquisition and Vector Construction

Gene acquisition of wild-type *M. aquaeolei* FAR ("FAR Maq") is described in the published application WO 2011/008535. The amino acid sequence of *M. aquaeolei* FAR can be found at GenBank Accession Number YP_959486, and is designated SEQ ID NO:5. The polynucleotide sequence of the codon-optimized gene encoding the FAR polypeptide of SEQ ID NO:5 is designated SEQ ID NO:4. The *M. aquaeolei* FAR gene and genes encoding variants of the *M. aquaeolei* FAR were cloned into the vector pCK110900 (depicted as FIG. 3 in US Pat. Appln. Pub. 20060195947) under the control of a lac promoter as described in WO/2011/008535. The resulting plasmids were introduced into *E. coli* BW25113 ΔtorR (Baba et al., *Molecular Systems Biology*, 2006 doi:10, 1038/msb4100050 Article No. 2006.0008) by routine transformation methods.

Example 7

Evaluation of Wild-type *M. aquaeolei* FAR in Shake Flask

Recombinant *E. coli* BW25113 ΔtorR strain comprising a plasmid containing a heterologous gene encoding *M. aquaeolei* FAR was grown in 5 mL M9YE media supplemented with 1% glucose and 30 µg/mL chloramphenicol (CAM), for approximately 16-18 hours (overnight) in a shaker-incubator at 30° C. at 200 rpm. A 5% inoculum was used to initiate fresh 50 mL culture using M9YE medium supplemented with 30 µg/mL CAM and 0.4% glucose. The culture was incubated for 2 hours at 30° C., 200 rpm to an $OD_{600}$ of 0.6-0.8, at which point expression of the heterologous FAR gene was induced with isopropyl-β-D-thiogalactoside (IPTG) (1 mM final concentration). An additional amount of glucose (0.5% w/v final conc.) was added to the culture at 3 and 6 hours after IPTG induction. Incubation was continued for about 24 hours under the same conditions.

0.5 mL of cell culture was extracted with 1 mL of isopropanol:methyl t-butyl ether (MTBE) (4:6 ratio) for 2 hours. The extract was centrifuged and the upper organic phase was transferred into a GC vial and analyzed by the following GC-FID method using DB-5MS column (length 30 m, I.D. 0.32 mm, film 0.25 urn): start temp. 150° C., increase the temperature at a rate of 25° C./min to 246° C. and hold for 1.81 min. Total run time, 5.65 min. Under the above GC conditions the approximate retention times (min) of produced fatty alcohols and acids were as follows: 3.19, C14:0-OH; 3.48, C14:0-OOH; 3.91, C16:1-OH; 3.98, C16:0-OH; 4.15, C16:0-OOMe (internal standard); 4.21, C16:1-OOH; 4.28, C16:0-OOH; 4.83, C18:1-OH; 4.92, C18:0-OH; 5.31, C18:0-OOH and 5.51, C18:1-OOH. Identification of individual fatty alcohol was done by comparison to commercial standards (Sigma Chemical Company, 6050 Spruce St. Louis, Mo. 63103). Under the conditions tested, typical shake flask titers at 24 hours for the wild-type *M. aquaeolei* FAR was ~0.2-0.25 g/L. Fatty alcohols include: 2% 014:0-OH (1-tetradecanol), 8% C16:1-OH (cis Δ9-1-hexadecenol), 39% 016:0-OH (1-hexadecanol), 49% 018:1-OH (cis Δ11-1-octadecenol), and <1% 018:0-OH (1-octadecanol).

Example 8

Evaluation of *M. aquaeolei* FAR Variants with Improved Activity Using Microtiter Plates FAR Maq variants were grown in 96-well shallow plates containing 180 µL M9YE medium supplemented with 1% glucose and 30 µg/mL chloramphenicol (CAM), for approximately 16-18 hours (overnight) in a shaker-incubator at 30° C., 200 rpm. A 5% inoculum was used in 96-deep-well plates to initiate fresh 380 µL M9YE medium culture supplemented with 30 µg/mL CAM and 0.5% glucose. The culture was incubated for 2 hours at 30° C., 250 rpm to an $OD_{600}$ of 0.6-0.8, at which point expression of the heterologous FAR gene was induced with isopropyl-β-D-thiogalactoside (IPTG) (1 mM final concentration). Incubation was continued for about 24 hours under the same conditions. An additional amount of glucose (0.5% w/v final conc.) was added to the culture at 6 hours after induction by IPTG. Cell cultures were extracted with 1 mL of isopropanol:methyl t-butyl ether (MTBE) (4:6 ratio) for 2 hours. The extracts were centrifuged and the upper organic phase was transferred into polypropylene 96-well plates and analyzed by the GC-FID method described in Example 7. Identification of individual fatty alcohol was done by comparison to commercial standards (Sigma Chemical Company, 6050 Spruce St. Louis, Mo. 63103).

Table 4 provides the relative fatty alcohol production for illustrative variants relative to wild-type *M. aquaeolei* FAR. Codon-optimized SEQ ID NO:4 was mutated and used to express FAR Maq Variant Nos. 1-89. Relative fatty alcohol production is presented as fold improvement over wild-type FAR Maq at 30° C. In Table 4, the amino acid substitutions listed for each variant correspond to residue positions of SEQ ID NO:5 (e.g., "G402A" means that the residue at position 402 in SEQ ID NO:5 (glycine) is substituted with alanine), and the amino acid positions were determined by optimal alignment with SEQ ID NO:5.

TABLE 4

Variant FAR polypeptides and total relative production of fatty alcohols

| Variant No. | Amino acid substitutions relative to SEQ ID NO: 5 | Relative fold improvement in fatty alcohol production† |
|---|---|---|
| 1 | G402A; | + |
| 2 | N135K; | ++ |
| 3 | E238L; | + |
| 4 | A74K; | ++ |
| 5 | A2T; G113A; | ++ |
| 6 | D141C; | + |
| 7 | Y501N; | ++ |
| 8 | D430K; | ++ |
| 9 | Y501Q; | + |
| 10 | S502R; | + |
| 11 | K230R; Y501G; | + |
| 12 | A2H; E72Q; | ++ |
| 13 | E228G; | ++ |
| 14 | S434K; Y501P; | ++ |
| 15 | S502G; A512K; | +++ |
| 16 | Y381R; | + |
| 17 | A2F; | + |
| 18 | E139Q; | + |
| 19 | L503R; | ++ |
| 20 | S434K; | ++ |
| 21 | I438V; A512G; | ++ |
| 22 | A2T; D116E; | + |
| 23 | Q508G; | + |
| 24 | A108L; D430K; | ++ |
| 25 | A2F; H8N; | + |
| 26 | A45V; A374V; K511D; | + |
| 27 | A512P; | ++ |
| 28 | L503Q; | ++ |
| 29 | A512S; | ++ |
| 30 | A512K; | +++ |
| 31 | A2Q; | ++ |
| 32 | N135K; R412H; | + |
| 33 | A2H; D116A; | ++ |
| 34 | Q508S; R509A; K510G; K511C; A512S; A513L; | ++ |
| 35 | D411R; S434K; | + |
| 36 | A2F; H8N; A108C; | + |
| 37 | A2H; P63S; G113A; D141C; | ++ |
| 38 | A2G; | + |
| 39 | S434F; | + |
| 40 | A2P; A108C; | + |
| 41 | A2Q; G113A; D116A; | ++ |
| 42 | L503R; R509D; | ++ |
| 43 | K511D; | + |
| 44 | Y501G; | ++ |
| 45 | A512R; | ++ |
| 46 | A375Y; | + |
| 47 | P406S; K511D; | + |
| 48 | E72Q; Q508G; | + |

TABLE 4-continued

Variant FAR polypeptides and total relative production of fatty alcohols

| Variant No. | Amino acid substitutions relative to SEQ ID NO: 5 | Relative fold improvement in fatty alcohol production† |
|---|---|---|
| 49 | A512G; | +++ |
| 50 | S434W; | + |
| 51 | T505R; | + |
| 52 | K511G; | ++ |
| 53 | A2H; G113A; | ++ |
| 54 | S502G; | ++ |
| 55 | N459Q; L503Q; | ++ |
| 56 | Y501S; | + |
| 57 | A512Q; | +++ |
| 58 | A2P; | + |
| 59 | A512T; | +++ |
| 60 | Y501W; | + |
| 61 | G111S; Y501P; | + |
| 62 | A2T; | ++ |
| 63 | Y501P; | ++ |
| 64 | L503S; | ++ |
| 65 | A74L; | ++ |
| 66 | P63Q; | + |
| 67 | E205R; | + |
| 68 | R66N; | ++ |
| 69 | D422A; | + |
| 70 | S77G; | ++ |
| 71 | E88Q; | + |
| 72 | H8K; | + |
| 73 | E238C; | + |
| 74 | D199G; | + |
| 75 | Q5F; | + |
| 76 | A513Y; | + |
| 77 | A9L; | + |
| 78 | N459G; | ++ |
| 79 | E72S; | + |
| 80 | E205G; | + |
| 81 | A375Q; | + |
| 82 | Q181D; | ++ |
| 83 | Q4I; | + |
| 84 | E497Y; | ++ |
| 85 | A108R; | ++ |
| 86 | Q5N; | ++ |
| 87 | E497F; | + |
| 88 | T505K; | + |
| 89 | D141G; | + |

†Fatty alcohols for the relative fatty alcohol measurements include: C14:0 (1-tetradecanol), C16:1 (cis Δ$^9$-1-hexadecenol), C16:0 (1-hexadecanol), C18:1 (cis Δ$^{11}$-1-octadecenol), and C18:0 (1-octadecanol).
+ = 1.0 to 1.5 fold improvement over wild-type *M. aquaeolei* FAR at 30° C.
++ = 1.6 to 2.0 fold improvement over wild-type *M. aquaeolei* FAR at 30° C.
+++ = ≥2.1 fold improvement over wild-type *M. aquaeolei* FAR at 30° C.

Table 4A illustrates that many substitutions in SEQ ID NO:5 ("Maq") which improve fatty alcohol yield correspond to beneficial substitutions in SEQ ID NO:2 ("Maa"). "FIOP", or "Fold Improvement Over Parent", is the average observed fold-improvement in fatty alcohol production in *E. coli* expressing a FAR Maq variant relative to *E. coli* expressing the wild-type *M. aquaeolei* FAR.

TABLE 4A

| Maq | FIOP | Maa |
|---|---|---|
| A2G | + | A2G |
| A2T | + | A2T |
| A2P | + | A2P |
| A2F | + | A2F |
| A2Q | + | A2Q |
| A74K | + | A73K |
| N135K | + | N134K |
| E139Q | + | E138Q |
| D141C | + | D140C |
| E205G | + | E204G |

TABLE 4A-continued

| Maq | FIOP | Maa |
|---|---|---|
| E228G | + | E227G |
| E238L | + | E237L |
| A375Y | + | A374Y |
| Y381R | + | Y380R |
| G402A | + | G401A |
| D430K | + | D429K |
| S434W | + | S433W |
| S434F | + | S433F |
| S434K | + | S433K |
| N459G | + | S458G |
| Y501N | + | Y500N |
| Y501S | + | Y500S |
| Y501Q | + | Y500Q |
| Y501G | + | Y500G |
| Y501P | + | Y500P |
| Y501W | + | Y500W |
| S502G | + | S501G |
| S502R | + | S501R |
| L503Q | + | L502Q |
| L503S | + | L502S |
| L503R | + | L502R |
| T505R | + | A504R |
| Q508G | + | T507G |
| Q508R | + | T507R |
| K510D | + | K509D |
| K511D | + | K510D |
| K511P | + | K510P |
| K511G | + | K510G |
| A512S | + | A511S |
| A512G | + | A511G |
| A512R | + | A511R |
| A512K | + | A511K |
| A512P | + | A511P |
| A512Q | + | A511Q |
| A512T | + | A511T |

+ = ≥1.1 fold improvement over wild-type *M. aquaeolei* FAR

Example 9

Substitutions in *M. aquaeolei* FAR

Table 5 is a listing of substitutions that may be introduced into SEQ ID NO:5, or a polypeptide having at least 70% identity to SEQ ID NO:5 as described elsewhere herein, to produce FAR variants. The substitutions and substitution sets are numbered with reference to SEQ NO:5.

As demonstrated in Example 8, numerous substitutions in SEQ ID NO:5 at positions corresponding to beneficial substitutions in SEQ ID NO:2 were shown to result in FARs that support increased fatty alcohol production. Table 5, below, provides contemplated FAR variants of the invention. In Table 5, positions, sets of positions, substitutions and substitution sets are provided with reference to SEQ ID NO:5.

TABLE 5

| Variant No. | Corresponding substitutions in FAR Maq (SEQ ID NO: 5) |
|---|---|
| 1 | D411S |
| 2 | A284V |
| 3 | D199Q |
| 4 | A284K |
| 5 | P340V |
| 6 | N459G |
| 7 | V464T |
| 8 | D411R |
| 9 | E289Q |
| 10 | D411Q |
| 11 | E139Q |
| 12 | A284M |
| 13 | R237K |
| 14 | L34V |
| 15 | L414L |
| 16 | I288L |
| 17 | L417V |
| 18 | R118D |
| 19 | E139L, A145Q |
| 20 | E360L, A512T |
| 21 | N135R |
| 22 | L210N, V413V |
| 23 | S245G |
| 24 | E84R |
| 25 | V413V |
| 26 | E238L |
| 27 | L210N |
| 28 | T102L |
| 29 | R152L |
| 30 | V464E |
| 31 | I438V, A512T |
| 32 | E205G |
| 33 | R66Q |
| 34 | G341V |
| 35 | N459M |
| 36 | A444T |
| 37 | L258K |
| 38 | A375K |
| 39 | I43L |
| 40 | P340G |
| 41 | N135K |
| 42 | L398L |

TABLE 5-continued

| Variant No. | Corresponding substitutions in FAR Maq (SEQ ID NO: 5) |
|---|---|
| 43 | N459Q |
| 44 | A488Y |
| 45 | G341S, P406S |
| 46 | V413F |
| 47 | V413C |
| 48 | D116A |
| 49 | D422R |
| 50 | P406S |
| 51 | D141C |
| 52 | P406F |
| 53 | K15W |
| 54 | D430Q |
| 55 | S434K |
| 56 | A9K |
| 57 | P406G |
| 58 | S502G |
| 59 | K230R |
| 60 | H378C |
| 61 | Y381R |
| 62 | K510S |
| 63 | N419I |
| 64 | R507S |
| 65 | K511G |
| 66 | Y501C |
| 67 | E497A |
| 68 | A2H |
| 69 | P406C |
| 70 | A506K |
| 71 | D10F |
| 72 | T307W |
| 73 | E304G, T431I |
| 74 | T505G |
| 75 | N419V |
| 76 | Y501P |
| 77 | R507G |
| 78 | D422Y |
| 79 | S434H |
| 80 | K511P |
| 81 | L503Q |
| 82 | A512P |
| 83 | A512G |
| 84 | L503A |
| 85 | S332V |
| 86 | N419R |
| 87 | A2W |
| 88 | D422I |
| 89 | A2D |
| 90 | K225R |
| 91 | N419Y |
| 92 | G 402V |
| 93 | L503R |
| 94 | K511Y |
| 95 | L503S |
| 96 | Y501L |
| 97 | T505R |
| 98 | E138L |
| 99 | S434W |
| 100 | Q508G |
| 101 | Q181R, T247A |
| 102 | G402L |
| 103 | T122S, S434L |
| 104 | K511S |
| 105 | Q508A |
| 106 | S77K |
| 107 | K510H |
| 108 | K511D |
| 109 | A512R |
| 110 | G402S |
| 111 | A108L |
| 112 | R509G |
| 113 | H8N |
| 114 | Y501W |
| 115 | H378Y |
| 116 | S401L |
| 117 | V500P |
| 118 | T75K |
| 119 | Q508R |

TABLE 5-continued

| Variant No. | Corresponding substitutions in FAR Maq (SEQ ID NO: 5) |
|---|---|
| 120 | E304G |
| 121 | A512T |
| 122 | Q114L, D422P |
| 123 | A2T, L333S |
| 124 | I3R |
| 125 | V500A |
| 126 | A2F |
| 127 | A512S |
| 128 | A512K |
| 129 | Q114D |
| 130 | S502R |
| 131 | L365F, S401A |
| 132 | A375Y |
| 133 | Y501G |
| 134 | A512Q |
| 135 | D422S |
| 136 | K15N |
| 137 | K510E |
| 138 | T122H |
| 139 | D430K |
| 140 | A512I |
| 141 | A2V |
| 142 | Y501N |
| 143 | S434F |
| 144 | V500H |
| 145 | T437K |
| 146 | A2V, A108C |
| 147 | A2G, L149E |
| 148 | E206P, A513T |
| 149 | L417L |
| 150 | S385R |
| 151 | A2Q |
| 152 | K499A, L503R |
| 153 | Y501Q |
| 154 | Y501S |
| 155 | P406L |
| 156 | Q508S |
| 157 | V500S |
| 158 | T307F |
| 159 | L227A |
| 160 | G18D |
| 161 | A9S |
| 162 | K510G |
| 163 | A74K |
| 164 | K511A |
| 165 | S434N |
| 166 | Q5S, P406S |
| 167 | L503P |
| 168 | A2P |
| 169 | D422L |
| 170 | V500R |
| 171 | D422V |
| 172 | D422N |
| 173 | A51V, A512T |
| 174 | R382C, A512T |
| 175 | A143V, A512T |
| 176 | P189S, A512T |
| 177 | T75P |
| 178 | A473V, A512T |
| 179 | V186A, A512T |
| 180 | P445S, A512T |
| 181 | R460H, D465G, V500P, A512T |
| 182 | V78A, A512T |
| 183 | K261T, A512T |
| 184 | H99R, A512T |
| 185 | K23E, A512T |
| 186 | V25I, R404C, A512T |
| 187 | A126V, A512T |
| 188 | A300T, A512T |
| 189 | R221C, A512T |
| 190 | V186A, A334T, A512T |
| 191 | N459L, A512T |
| 192 | I112S, A512T |
| 193 | E72K, N459L, A512T |
| 194 | L94V |
| 195 | Y447H, A512T |
| 196 | D246N, A512T |

TABLE 5-continued

| Variant No. | Corresponding substitutions in FAR Maq (SEQ ID NO: 5) |
|---|---|
| 197 | I329T, A512T |
| 198 | N264P, D411S, A512T |
| 199 | N491S, A512T |
| 200 | E139Q, P189S, E228G, E238L |
| 201 | N135R, E139Q, P189S |
| 202 | E139Q, P189S |
| 203 | A121V, N135K, N459Q, A512T |
| 204 | Q4R, T11T, E139Q |
| 205 | A92I, N135R, P189S, K261R, A512T |
| 206 | N135K, E139Q, P189S, N459Q |
| 207 | N459Q, I485V |
| 208 | N135K, E228G |
| 209 | N135S, E139Q, P189S |
| 210 | G113A, N135K, P189S |
| 211 | N135S, E139Q, P189S, A512T |
| 212 | N135K, P189S |
| 213 | S13V, N459Q, A512T |
| 214 | N135R, D411Q, V413C, N459Q |
| 215 | G103C, N135R, E139Q, P189S |
| 216 | N135S, E139Q, E206G, A512T |
| 217 | N135S, E139Q, P189S, F441L, A512T |
| 218 | N135R, E203G, K214R |
| 219 | N135R, P189S, K214R, K261R, I438V, N459Q |
| 220 | N135S, P189S, D411Q, V413V, N459Q, A512T |
| 221 | N135R, P189S |
| 222 | L55P, A367T, D411S, N459Q, A512T |
| 223 | N135S, E228G |
| 224 | A51S, N135K, E139Q, N459Q |
| 225 | N459Q, A512T |
| 226 | N135S, E139Q, P189S, E228G |
| 227 | E139Q, I270T, A512T |
| 228 | D397G, A512T |
| 229 | D116H, N135R, P189S |
| 230 | N135R, E139Q, N161S, P189S, E304G |
| 231 | R61H, G113A, N135R, E228G, V291I, D411Q, I438V, N459Q |
| 232 | E139Q, G351S, A512T |
| 233 | P189S, E228G |
| 234 | E139Q, P189S, T307N |
| 235 | N135K, P189S, N459Q |
| 236 | N135K, N459L |
| 237 | S133G, N459Q, A512T |
| 238 | A2G, N135S, E139Q, P189S, A512T |
| 239 | A2I, G113A, N135K, E139Q, P189S, A512T |
| 240 | N135S, E139Q, P189S, E228G, A512T |
| 241 | G113A, N135K, E139Q, P189S, A512T |
| 242 | A2G, G113A, N135R, E139Q, P189S, K511P, A512R |
| 243 | A2H, G113A, N135S, E139Q, P189S, N459Q, A512T |
| 244 | A2D, G113A, N135R, E139Q, P189S, D422V, K510H, A512Q, A513T |
| 245 | N135S, E139Q, P189S, V208I, K511P, A512G |
| 246 | N135S, E139Q, P189S, N459Q, K511P, A512K |
| 247 | E123R, N135S, E139Q, P189S, K511P, A512R |
| 248 | N135S, E139Q, P189S, N459Q, K511P, A512R |
| 249 | N135S, E139Q, P189S, K511P, A512R, A513T |
| 250 | N135S, E139Q, P189S, E228G, N459Q, K511P, A512K |
| 251 | A2G, G113A, N135K, E139Q, P189S, N459Q, K510H, K511P, A512Q |
| 252 | N135S, E139Q, P189S, D422S, N459Q, K510H, K511P, A512R |
| 253 | G113A, N135R, E139Q, P189S, D422R, N459Q, K511P, A512S |
| 254 | N135S, E139Q, P189S, K511P, A512G, A513T |
| 255 | A2H, N135S, E139Q, P189S, K511P, A512S, A513T |
| 256 | A2W, G113A, N135R, E139Q, P189S, K510H, K511P, A512G |
| 257 | A2N, N135S, E139Q, P189S, D422V, A512T |
| 258 | N135S, E139Q, P189S, D422R, N459Q, K511P, A512S, A513T |
| 259 | N135S, E139Q, P189S, D422L, K510H, K511P, A512K |
| 260 | A2P, N135S, E139Q, P189S, K511P, A512R, A513T |
| 261 | N135K, E139Q, P189S, A512T |
| 262 | G113A, N135S, E139Q, P189S, A512T |
| 263 | N135S, E139Q, P189S, N459Q, A512T, A513T |
| 264 | A2G, A74V, G113A, N135S, E139Q, P189S, E228G, A512T |
| 265 | E139Q, P189S, A512T, A513T |
| 266 | N135R, E139Q, P189S, A512T |
| 267 | N135S, E139Q, P189S, D422L, N459Q, A512T |
| 268 | N135S, E139Q, P189S, N459Q, A512T |
| 269 | N135S, E139Q, P189S, D422R, N459Q, A512T |
| 270 | G113A, E139Q, P189S, A512T |
| 271 | N135S, E139Q, P189S, E228G, A512T, A513T |
| 272 | G113A, N135S, E139Q, P189S, E206P, D422R, A512T |
| 273 | A2G, G113A, E139Q, P189S, A512T |

TABLE 5-continued

| Variant No. | Corresponding substitutions in FAR Maq (SEQ ID NO: 5) |
|---|---|
| 274 | N135S, E139Q, P189S, A512T, A513T |
| 275 | N135S, E139Q, P189S, D430N, V500S, K510G, A512T |
| 276 | N135S, E139Q, P189S, V413V, D430K, V500H, K510E, A512T |
| 277 | N135S, E139Q, P189S, D430N, K510N, A512T |
| 278 | N135S, E139Q, P189S, V413V, D430K, A512T |
| 279 | N135S, E139Q, P189S, V413V, D430K, V500N, A512T |
| 280 | N135S, E139Q, P189S, V500R, K510R, A512T |
| 281 | N135S, E139Q, P189S, D430E, V500N, K510G, A512T |
| 282 | N135S, E139Q, Q181R, P189S, T307W, V500R, K510G, A512T |
| 283 | T122S, N135S, E139Q, P189S, T307W, A375Y, V500R, K510S, A512T |
| 284 | N135S, E139Q, P189S, D430K, V500N, T505G, K510G, A512T |
| 285 | V78I, N135S, E139Q, P189S, T307W, A512T |
| 286 | N135S, E139Q, P189S, D430N, V500R, T505G, K510G, A512T |
| 287 | N135S, E139Q, P189S, D430E, V500N, A512T |
| 288 | N135S, E139Q, P189S, V413V, D430E, V500I, K510D, A512T |
| 289 | N135S, E139Q, P189S, T307W, V413V, D430K, V500S, A512T |
| 290 | N135S, E139Q, P189S, D430N, V500R, K510S, A512T |
| 291 | N135S, E139Q, P189S, V413V, V500I, K510G, A512T |
| 292 | N135S, E139Q, P189S, D430E, V500H, K510G, A512T |
| 293 | N135S, E139Q, P189S, T505R, K510N, A512T |
| 294 | N135S, E139Q, P189S, V413V, D430E, V500R, K510G, A512T |
| 295 | N135S, E139Q, P189S, D430N, V500I, K510G, A512T |
| 296 | N135S, E139Q, P189S, T307W, A375Y, V500R, T505R, A512T |
| 297 | N135S, E139Q, P189S, D430E, K510D, A512T |
| 298 | N135S, E139Q, Q181R, P189S, T307W, V500H, K510S, A512T |
| 299 | N135S, E139Q, P189S, L398I, A512T |
| 300 | D10F, N135S, E139Q, P189S, L503Q, Q508A, A512T |
| 301 | N135S, E139Q, P189S, G402V, L503S, A512T |
| 302 | N135S, E139Q, P189S, G402S, A512T |
| 303 | D10F, Q114L, N135S, E139Q, P189S, G402L, L503S, Q508A, A512T |
| 304 | N135S, E139Q, P189S, G402L, A512T |
| 305 | D10F, N135S, E139Q, P189S, E289Q, D411R, D422S, A512T |
| 306 | Q114L, N135S, E139Q, P189S, K225R, A367V, L503Q, Q508R, A512T |
| 307 | N135S, E139Q, P189S, G402V, A488Y, L503S, Q508A, A512T |
| 308 | N135S, E139Q, P189S, S245P, E289Q, G402S, A512T |
| 309 | N135S, E139Q, P189S, G402L, D411R, A488Y, L503S, A512T |
| 310 | D10F, E88V, N135S, E139Q, P189S, K225R, E289Q, G402V, A488Y, L503R, A512T |
| 311 | N135S, E139Q, P189S, D422N, Q508A, A512T |
| 312 | D10F, N135S, E139Q, P189S, K225R, E289Q, G402A, L503S, Q508P, A512T |
| 313 | Q114L, N135S, E139Q, P189S, A488Y, L503S, Q508A, A512T |
| 314 | D10F, Q114L, N135S, E139Q, P189S, E289Q, G402L, A512T |
| 315 | Q114L, N135S, E139Q, P189S, L503Q, Q508R, A512T |
| 316 | N135S, E139Q, P189S, L405I, D411R, R509H, A512T |
| 317 | D10F, Q114L, N135S, E139Q, P189S, A488Y, L503A, A512T |
| 318 | N135S, E139Q, P189S, G402S, D411R, A512T |
| 319 | N135S, E139Q, P189S, G402V, A512T |
| 320 | D10F, Q114L, N135S, E139Q, P189S, G402A, D411R, A512T |
| 321 | D10F, Q114L, N135S, E139Q, P189S, G402V, Q508A, A512T |
| 322 | Q114L, N135S, E139Q, P189S, K225R, A488Y, L503R, A512T |
| 323 | Q114L, N135S, E139Q, P189S, D422S, A488Y, L503A, A512T |
| 324 | N135S, E139Q, P189S, T410V, A512T |
| 325 | S77K, N135S, E139Q, P189S, Y381R, L417L, Y501N, S502R, R509G, A512T |
| 326 | S77N, N135S, E139Q, P189S, Y381R, Y501N, S502R, A512T |
| 327 | N135S, E139Q, P189S, Y501Q, S502R, A512T |
| 328 | N135S, E139Q, P189S, L210N, Y381R, T410V, L417L, T431I, Y501N, S502R, A512T |
| 329 | S77R, N135S, E139Q, P189S, E304G, T431I, Y501Q, S502G, R509G, A512T |
| 330 | N135S, E139Q, P189S, L210N, E304G, R509G, A512T |
| 331 | S77K, N135S, E139Q, P189S, E304G, Y381R, T431I, Y501N, A512T |
| 332 | S77N, N135S, E139Q, P189S, Y381R, L417L, Y501Q, R509G, A512T |
| 333 | N135S, E139Q, P189S, L417L, T431I, Y501G, S502G, A512T |
| 334 | N135S, E139Q, P189S, R509G, A512T |
| 335 | N135S, E139Q, P189S, E304G, A512T |
| 336 | S77R, N135S, E139Q, P189S, L417L, T431I, Y501N, S502R, R509G, A512T |
| 337 | N135S, E139Q, P189S, Y381R, L417L, T431I, Y501Q, S502G, R509G, A512T |
| 338 | N135S, E139Q, V186I, P189S, L417L, Y501Q, R509G, A512T |
| 339 | N135S, E139Q, L149E, P189S, E304G, Y381R, T431I, Y501Q, A512T |
| 340 | N135S, E139Q, L149E, P189S, Y501Q, S502R, A512T |
| 341 | N135S, E139Q, P189S, L417L, A512T |
| 342 | N135S, E139Q, P189S, L417L, R509G, A512T |
| 343 | N135S, E139Q, P189S, Y381R, A512T |
| 344 | S77K, N135S, E139Q, P189S, E304G, L417L, T431I, Y501Q, A512T |
| 345 | N135S, E139Q, P189S, Y381R, Y501Q, R509G, A512T |
| 346 | N135S, E139Q, L149E, P189S, E304G, Y381R, Y501N, A512T |
| 347 | S77K, N135S, E139Q, P189S, L417L, A512T |
| 348 | N135S, E139Q, P189S, Y381R, T431I, Y501Q, A512T |
| 349 | N135S, E139Q, P189S, Y381R, L417V, R509G, A512T |
| 350 | N135S, E139Q, P189S, Y501Q, S502G, R509G, A512T |

TABLE 5-continued

| Variant No. | Corresponding substitutions in FAR Maq (SEQ ID NO: 5) |
|---|---|
| 351 | N135S, E139Q, P189S, L333S, P406F, A512T |
| 352 | N135S, E139Q, P189S, N419R, S434N, K511D, A512T |
| 353 | N135S, E139Q, P189S, P406L, A512T |
| 354 | N135S, E139Q, P189S, P406A, N419R, K511Y, A512T |
| 355 | A2V, A108C, N135S, E139Q, P189S, T247A, L333S, P406G, N419V, K511D, A512T |
| 356 | N135S, E139Q, P189S, N419I, S434Y, K511Y, A512T |
| 357 | N135S, E139Q, P189S, P406A, N419V, K511S, A512T |
| 358 | N135S, E139Q, P189S, T247A, P406L, N419V, S434K, A512T |
| 359 | N135S, E139Q, P189S, N419I, K511S, A512T |
| 360 | A108C, N135S, E139Q, P189S, P406C, A506K, K511Y, A512T |
| 361 | N135S, E139Q, P189S, P406C, N419I, A506K, K511D, A512T |
| 362 | N135S, E139Q, P189S, L333S, P406F, N419I, K511D, A512T |
| 363 | N135S, E139Q, P189S, P406A, N419V, A512T |
| 364 | N135S, E139Q, P189S, P406L, N419R, S434H, K511D, A512T |
| 365 | N135S, E139Q, P189S, P406L, K511S, A512T |
| 366 | N135S, E139Q, P189S, S434H, K511D, A512T |
| 367 | N135S, E139Q, P189S, P406G, N419I, S434N, K511Y, A512T |
| 368 | A2V, A108C, N135S, E139Q, P189S, L333S, P406V, N419R, A512T |
| 369 | N135S, E139Q, P189S, P406V, N419I, S434N, K511S, A512T |
| 370 | N135S, E139Q, P189S, P406V, N419V, A512T |
| 371 | A108L, N135S, E139Q, P189S, T247A, P406L, N419V, A506K, K511Y, A512T |
| 372 | A2V, A108W, N135S, E139Q, P189S, P406G, N419R, A512T |
| 373 | N135S, E139Q, P189S, T247A, S434K, K511D, A512T |
| 374 | N135S, E139Q, P189S, P406A, A512T |
| 375 | A2V, G111D, N135S, E139Q, P189S, P406V, N419V, A512T |
| 376 | E88G, N135S, E139Q, P189S, P406V, V413V, N419I, R509G, K510D, A512T |
| 377 | N135S, E139Q, P189S, A296V, P406V, N419V, A512T |
| 378 | N135S, E139Q, P189S, L210N, P406V, N419V, L503S, R509H, K510H, A512T |
| 379 | N135S, E139Q, P189S, A371A, P406V, N419V, L503S, R509D, K510H, A512T |
| 380 | N135S, E139Q, P189S, P406V, N419V, R509H, K510D, A512T |
| 381 | N135S, E139Q, P189S, P406V, N419V, R509H, K510H, A512T |
| 382 | N135S, E139Q, P189S, P406V, N419V, R509G, K510N, A512T |
| 383 | N135S, E139Q, P189S, P406V, N419V, A512T |
| 384 | N135S, E139Q, P189S, P406W, N419V, R509H, K510D, A512T |
| 385 | H62R, N135S, E139Q, P189S, P406V, L417L, N419V, S434N, L503S, K510D, A512T |
| 386 | N135S, E139Q, P189S, P406V, N419V, K510D, A512T |
| 387 | N135S, E139Q, P189S, A296T, P406V, N419V, N459Q, R509H, K510D, A512T |
| 388 | N135S, E139Q, P189S, P406V, N419V, R509D, K510D, A512T |
| 389 | N135S, E139Q, P189S, L210N, P406V, N419V, A512T |
| 390 | N135S, E139Q, P189S, P406V, N419V, L503S, R509D, A512T |
| 391 | N135S, E139Q, P189S, L210K, P406V, N419V, N459Q, L503S, R509D, K510D, A512T |
| 392 | N135S, E139Q, P189S, E304G, G402I, P406A, N419I, R509G, K510D, A512T |
| 393 | N135S, E139Q, P189S, E304G, G402I, P406A, N419V, L503S, R509G, K510D, A512T |
| 394 | E115G, N135S, E139Q, P189S, E304G, P406V, N419V, L503S, R509G, K510D, A512T |
| 395 | N135S, E139Q, P189S, E304G, G402S, P406A, L417L, N419V, R509G, K510D, A512T |
| 396 | N135S, E139Q, P189S, G402S, P406A, N419V, L503S, K510H, A512T |
| 397 | N135S, E139Q, P189S, P406V, L417L, N419V, A512T |
| 398 | N135S, E139Q, P189S, P406A, N419V, N459Q, R509G, K510H, A512T |
| 399 | N135S, E139Q, K163T, P189S, E304G, G402S, P406A, L417L, N419I, L503S, R509G, K510Y, A512T |
| 400 | N135S, E139Q, P189S, P406V, N419V, N459Q, R509G, A512T |
| 401 | N135S, E139Q, P189S, G402V, P406A, V413V, N419I, L503S, R509G, K510H, A512T |
| 402 | N135S, E139Q, P189S, E304G, G402I, P406A, N419V, L503S, K510H, A512T |
| 403 | N135S, E139Q, P189S, E304G, P406V, V413V, N419I, K510D, A512T |
| 404 | N135S, E139Q, P189S, P406V, L417L, N419V, L503S, R509G, K510H, A512T |
| 405 | N135S, E139Q, P189S, E304G, P406V, N419V, R509G, K510D, A512T |
| 406 | N135S, E139Q, P189S, P406V, N419V, L503S, R509G, K510D, A512T |
| 407 | N135S, E139Q, P189S, G402S, P406L, V413V, L417L, N419V, L503S, K510H, A512T |
| 408 | N135S, E139Q, P189S, P406A, V413V, L417L, N419V, R509G, K510D, A512T |
| 409 | N135S, E139Q, P189S, P406V, N419V, L503S, R509G, K510H, A512T |
| 410 | N135S, E139Q, P189S, P406V, N419I, R509G, K510D, A512T |
| 411 | N135S, E139Q, P189S, G402V, P406V, N419I, A506K, A512T |
| 412 | N135S, E139Q, P189S, P406V, N419V, A506K, A512T |
| 413 | N135S, E139Q, P189S, E304G, G402L, P406V, N419V, A506K, A512T |
| 414 | N135S, E139Q, P189S, E304G, G402V, P406L, N419I, A506K, A512T |
| 415 | K23R, N135S, E139Q, P189S, E304G, G402V, P406A, N419V, A512T |
| 416 | N135S, E139Q, P189S, G265S, P406V, N419V, Y501D, A506K, A512T |
| 417 | N135S, E139Q, P189S, E304G, P406V, N419I, A512T |
| 418 | N135S, E139Q, P189S, E304G, G402L, P406C, N419V, A512T |
| 419 | N135S, E139Q, P189S, E304G, G402I, P406W, N419V, A512T |
| 420 | N135S, E139Q, P189S, E304G, G402L, P406V, N419I, A506K, A512T |
| 421 | N135S, E139Q, P189S, G402V, P406C, N419V, A512T |
| 422 | N135S, E139Q, P189S, E304G, P406A, N419V, A506K, A512T |
| 423 | N135S, E139Q, P189S, P406V, N419I, A512T |
| 424 | N135S, E139Q, P189S, P406V, N419V, D430E, N459Q, L503S, R509D, K510D, A512T |
| 425 | N135S, E139Q, P189S, D213R, P406V, N419V, N459Q, A488S, L503S, R509D, K510D, A512T |

TABLE 5-continued

| Variant No. | Corresponding substitutions in FAR Maq (SEQ ID NO: 5) |
|---|---|
| 426 | N135S, E139Q, P189S, P340G, P406V, N419V, N459Q, L503S, R509D, K510D, A512T |
| 427 | N135S, E139Q, P189S, P406V, N419V, N428K, N459Q, L503S, R509D, K510D, A512T |
| 428 | N135S, E139Q, P189S, P406V, N419V, N459Q, G467Q, L503S, R509D, K510D, A512T |
| 429 | N135R, E139Q, P189S, P406V, N419V, N459Q, L503S, R509D, K510D, A512T |
| 430 | A92R, N135S, E139Q, P189S, P406V, N419V, N459Q, L503S, R509D, K510D, A512T |
| 431 | K15V, N135S, E139Q, P189S, P406V, N419V, N459Q, L503S, R509D, K510D, A512T |
| 432 | L70E, N135S, E139Q, P189S, P406V, N419V, N459Q, L503S, R509D, K510D, A512T |
| 433 | N135S, E139Q, P189S, P406V, T410W, N419V, N459Q, L503S, R509D, K510D, A512T |
| 434 | N135S, E139Q, P189S, S245H, P406V, N419V, N459Q, L503S, R509D, K510D, A512T |
| 435 | H99P, N135S, E139Q, P189S, P406V, N419V, N459Q, L503S, R509D, K510D, A512T |
| 436 | N135S, E139Q, P189S, H378K, P406V, N419V, N459Q, L503S, R509D, K510D, A512T |
| 437 | N135S, E139Q, P189S, A390V, P406V, N419V, N459Q, L503S, R509D, K510D, A512T |
| 438 | N135S, E139Q, P189S, P406V, N419V, S434K, N459Q, L503S, R509D, K510D, A512T |
| 439 | N135S, E139Q, P189S, P406V, N419V, Q433Q, N459Q, L503S, R509D, K510D, A512T |
| 440 | N135S, E139Q, P189S, Y381K, P406V, N419V, N459Q, L503S, R509D, K510D, A512T |
| 441 | L70Q, N135S, E139Q, P189S, P406V, N419V, N459Q, L503S, R509D, K510D, A512T |
| 442 | N135S, E139Q, P189S, P406V, L407Y, N419V, N459Q, L503S, R509D, K510D, A512T |
| 443 | N135S, E139Q, P189S, A284F, P406V, N419V, N459Q, L503S, R509D, K510D, A512T |
| 444 | N135S, E139Q, P189S, P406V, D411N, N419V, N459Q, L503S, R509D, K510D, A512T |
| 445 | N135S, E139Q, I154I, P189S, P406V, N419V, N459Q, L503S, R509D, K510D, A512T |
| 446 | N135S, E139Q, P189S, P198P, P406V, N419V, N459Q, L503S, R509D, K510D, A512T |
| 447 | N135S, E139Q, P189S, S245P, P406V, N419V, N459Q, L503S, R509D, K510D, A512T |
| 448 | N135S, E139Q, N178R, P189S, P406V, N419V, N459Q, L503S, R509D, K510D, A512T |
| 449 | N135S, E139Q, P189S, S245G, P406V, N419V, N459Q, L503S, R509D, K510D, A512T |
| 450 | N135S, E139Q, P189S, V306I, P406V, N419V, Q433C, N459Q, L503S, R509D, K510D, A512T |
| 451 | R66Y, N135S, E139Q, P189S, P406V, N419V, N459Q, L503S, R509D, K510D, A512T |
| 452 | R66G, N135S, E139Q, P189S, P406V, N419V, N459Q, L503S, R509D, K510D, A512T |
| 453 | N135S, E139Q, P189S, P406V, V413M, N419V, N459Q, L503S, R509D, K510D, A512T |
| 454 | N135S, E139Q, I187A, P189S, P406V, N419V, N459Q, L503S, R509D, K510D, A512T |
| 455 | N135S, E139Q, P189S, P406V, N419I, N459Q, L503S, R509D, K510D, A512T |
| 456 | N135S, E139Q, P189S, R343L, P406V, N419V, N459Q, L503S, R509D, K510D, A512T |
| 457 | N135S, E139Q, P189S, G341P, P406V, N419V, N459Q, L503S, R509D, K510D, A512T |
| 458 | N135S, E139Q, P189S, P406V, N419V, T437D, N459Q, L503S, R509D, K510D, A512T |
| 459 | N135S, E139Q, Q181H, P189S, P406V, N419V, E453N, N459Q, L503S, R509D, K510D, A512T |
| 460 | N135S, E139Q, P189S, A284E, P406V, N419V, N459Q, L503S, R509D, K510D, A512T |
| 461 | N135S, E139Q, P189S, T307W, A371I, P406V, N419V, N459Q, L503S, R509D, K510D, A512T |
| 462 | N135S, E139Q, P189S, P406V, D411A, N419V, N459Q, L503S, R509D, K510D, A512T |
| 463 | N135S, E139Q, P189S, P406V, D411R, N419V, N459Q, L503S, R509D, K510D, A512T |
| 464 | N135S, E139Q, P189S, P406V, T410Y, N419V, N459Q, L503S, R509D, K510D, A512T |
| 465 | N135S, E139Q, P189S, P406V, N419V, N459Q, Y501R, L503S, R509D, K510D, A512T |
| 466 | K15R, N135S, E139Q, P189S, P406V, N419V, N459Q, L503S, R509D, K510D, A512T |
| 467 | N135S, E139Q, P189S, L405A, P406V, N419V, N459Q, L503S, R509D, K510D, A512T |
| 468 | N135S, E139Q, P189S, P406V, N419V, D422P, N459Q, L503S, R509D, K510D, A512T |
| 469 | N135S, E139Q, P189S, A390M, P406V, N419V, N459Q, L503S, R509D, K510D, A512T |
| 470 | N135S, E139Q, P189S, E228R, P406V, N419V, N459Q, L503S, R509D, K510D, A512T |
| 471 | N135S, E139Q, N175C, P189S, P406V, N419V, N459Q, L503S, R509D, K510D, A512T |
| 472 | V105M, N135S, E139Q, P189S, P406V, N419V, N459Q, L503S, R509D, K510D, A512T |
| 473 | N135S, E139Q, P189S, G352C, P406V, N419V, N459Q, L503S, R509D, K510D, A512T |
| 474 | N135S, E139Q, P189S, Y381R, P406V, N419V, N459Q, L503S, R509D, K510D, A512T |
| 475 | Q19I, N135S, E139Q, P189S, P406V, N419V, N459Q, L503S, R509D, K510D, A512T |
| 476 | N135S, E139Q, P189S, P406V, N419V, N459Q, V500R, L503S, R509D, K510D, A512T |
| 477 | N135S, E139Q, P189M, P406V, N419V, N459Q, L503S, R509D, K510D, A512T |
| 478 | N135S, E139Q, N178T, P189S, P406V, N419V, N459Q, L503S, R509D, K510D, A512T |
| 479 | N135S, E139Q, P189S, P406V, N419V, D430R, N459Q, L503S, R509D, K510D, A512T |
| 480 | N135S, E139Q, P189S, P406V, N419V, T437Q, N459Q, L503S, R509D, K510D, A512T |
| 481 | D64Y, N135S, E139Q, P189S, P406V, N419V, N459Q, L503S, R509D, K510D, A512T |
| 482 | N135S, E139Q, P189S, P406V, N419V, E453N, N459Q, L503S, R509D, K510D, A512T |
| 483 | N135S, E139Q, P189S, P406V, D411H, N419V, N459Q, L503S, R509D, K510D, A512T |
| 484 | N135S, E139Q, P189S, T267A, P406V, N419V, N459Q, L503S, R509D, K510D, A512T |
| 485 | V105I, N135S, E139Q, P189S, P406V, N419V, N459Q, L503S, R509D, K510D, A512T |
| 486 | N135S, E139Q, P189S, A284M, P406V, N419V, N459Q, L503S, R509D, K510D, A512T |
| 487 | N135S, E139Q, N178Q, P189S, P406V, D411C, N419V, N459Q, L503S, R509D, K510D, A512T |
| 488 | N135S, E139Q, P189S, A390I, P406V, N419V, N459Q, L503S, R509D, K510D, A512T |
| 489 | N135S, E139Q, P189S, P406V, N419V, N459Q, G467R, L503S, R509D, K510D, A512T |
| 490 | N135S, E139Q, P189S, P406V, N419V, E453A, N459Q, L503S, R509D, K510D, A512T |
| 491 | N135S, E139Q, P189S, S245F, P406V, N419V, N459Q, L503S, R509D, K510D, A512T |
| 492 | N135S, E139Q, P189S, P406V, T410V, N419V, N459Q, L480Q, L503S, R509D, K510O, A512T |
| 493 | N135S, E139Q, P189S, P406V, N419V, N459Q, G467E, L503S, R509D, K510D, A512T |
| 494 | N135S, E139Q, P189S, V319I, P406V, N419V, N459Q, L503S, R509D, K510D, A512T |
| 495 | N135S, E139Q, P189S, A390L, P406V, N419V, N459Q, L503S, R509D, K510D, A512T |
| 496 | N135S, E139Q, P189A, P406V, N419V, N459Q, L503S, R509D, K510D, A512T |
| 497 | N135S, E139Q, P189S, E206G, P406V, N419V, N459Q, L503S, R509D, K510D, A512T |

TABLE 5-continued

| Variant No. | Corresponding substitutions in FAR Maq (SEQ ID NO: 5) |
|---|---|
| 498 | N135S, E139Q, P189S, P406V, N419V, T431H, N459Q, L503S, R509D, K510D, A512T |
| 499 | D64R, N135S, E139Q, P189S, P406V, N419V, N459Q, L503S, R509D, K510D, A512T |
| 500 | N135S, E139Q, P189S, P406V, N419V, N459Q, L503S, R509D, K510D, A512K |
| 501 | N135S, E139Q, P189S, P406V, N419V, N459Q, L475R, L503S, R509S, K510D, A512T |
| 502 | N135S, E139Q, P189S, T307H, P406V, N419V, N459Q, L503S, R509D, K510D, A512T |
| 503 | N135S, E139Q, P189S, D377P, P406V, N419V, N459Q, L503S, R509D, K510D, A512T |
| 504 | N135S, E139Q, P189S, Y381N, P406V, N419V, N459Q, L503S, R509D, K510D, A512T |
| 505 | N135S, E139Q, P189S, V399Y, P406V, N419V, N459Q, L503S, R509D, K510D, A512T |
| 506 | D10D, N135S, E139Q, P189S, P406V, N419V, N459Q, A488T, Y501H, L503S, R509D, K510D, A512T |
| 507 | N135S, E139Q, I187G, P189S, P406V, N419V, N459Q, L503S, R509D, K510D, A512T |
| 508 | N129H, N135S, E139Q, P189S, P406V, N419V, N459Q, L503S, R509D, K510D, A512T |
| 509 | N135S, E139Q, P189S, E228T, P406V, N419V, N459Q, L503S, R509D, K510D, A512T |
| 510 | N135S, E139Q, P189S, V208L, P406V, N419V, N459Q, L503S, R509D, K510D, A512T |
| 511 | N135S, E139Q, P189S, L365I, P406V, N419V, N459Q, L503S, R509D, K510D, A512T |
| 512 | N135S, E139Q, P189S, A284T, P406V, N419V, N459Q, L503S, R509D, K510D, A512T |
| 513 | N135S, E139Q, P189S, S245A, P406V, L414R, N419V, N459Q, L503S, R509D, K510D, A512T |
| 514 | N135S, E139Q, P189S, P406V, N419V, N459Q, A488R, L503S, R509D, K510D, A512T |
| 515 | N135S, E139Q, P189S, E228A, P406V, N419V, N459Q, L503S, R509D, K510D, A512T |
| 516 | N135S, E139Q, P189S, V218L, P406V, N419V, N459Q, L503S, R509D, K510D, A512T |
| 517 | N135S, E139Q, P189S, I400T, P406V, N419V, N459Q, L503S, R509D, K510D, A512T |
| 518 | H62R, N135S, E139Q, P189S, P406V, D411H, N419V, N459Q, L503S, R509D, K510D, A512T |
| 519 | N135S, E139Q, P189S, P406V, N419V, T431R, N459Q, L503S, R509D, K510D, A512T |
| 520 | N135S, E139Q, P189S, M366N, P406V, N419V, N459Q, L503S, R509D, K510D, A512T |
| 521 | N135S, E139Q, P189I, P406V, N419V, N459Q, L503S, R509D, K510D, A512T |
| 522 | N135S, E139Q, I187Y, P189S, P406V, N419V, N459Q, L503S, R509D, K510D, A512T |
| 523 | N135S, E139Q, P189S, L227M, P406V, N419V, N459Q, L503S, R509D, K510D, A512T |
| 524 | N135S, E139Q, P189S, K225R, P406V, N419V, N459Q, L503S, R509D, K510D, A512T |
| 525 | N135S, E139Q, P189S, E228H, P406V, N419V, N459Q, L503S, R509D, K510D, A512T |
| 526 | N135S, E139Q, P189S, G402C, P406V, N419V, N459Q, L503S, R509D, K510D, A512T |
| 527 | N135S, E139Q, P189S, P406V, N419V, N459Q, L475R, L503S, R509D, K510D, A512T |
| 528 | N135S, E139Q, P189S, R342K, P406V, N419V, S434K, N459Q, L503S, R509D, K510D, A512T |
| 529 | V105I, N135S, E139Q, P189S, L331V, P406V, N419V, S434K, N459Q, G467Q, L503S, R509D, K510D, A512T |
| 530 | N135S, E139Q, P189S, A284T, P406V, N419V, S434K, N459Q, L503S, R509D, K510D, A512T |
| 531 | N135S, E139Q, P189S, T307H, P406V, N419V, S434K, N459Q, L503S, R509D, K510D, A512T |
| 532 | R66G, N135S, E139Q, N175C, N178T, P189S, K225R, G352C, P406V, N419V, S434K, N459Q, L503S, R509D, K510D, A512T |
| 533 | R66G, N135S, E139Q, N175C, N178T, P189S, K225R, L405A, P406V, N419V, S434K, N459Q, L503S, R509D, K510D, A512T |
| 534 | D64R, R66G, N135S, E139Q, P189S, K225R, L227M, P406V, N419V, S434K, N459Q, L503S, R509D, K510D, A512T, A513S |
| 535 | Q19I, R66G, N135S, E139Q, P189S, K225R, P406V, N419V, S434K, N459Q, L503S, R509D, K510D, A512T |
| 536 | D64R, R66G, N135S, E139Q, N175C, P189S, L227M, P406V, N419V, S434K, N459Q, L503S, R509D, K510D, A512T |
| 537 | R66G, N129H, N135S, E139Q, N175C, P189S, K225R, L227M, G352C, L405A, P406V, N419V, S434K, N459Q, L503S, R509D, K510D, A512T |
| 538 | D64R, R66G, N135S, E139Q, P189S, G352C, L405A, P406V, N419V, S434K, N459Q, A488R, L503S, R509D, K510D, A512T |
| 539 | N129H, N135S, E139Q, P189S, G352C, L405A, P406V, N419V, S434K, N459Q, A488R, L503S, R509D, K510D, A512T |
| 540 | Q19I, N135S, E139Q, N175C, P189S, K225R, L227M, G352C, P406V, N419V, S434K, N459Q, L503S, R509D, K510D, A512T |
| 541 | R66G, N129H, N135S, E139Q, N175C, N178T, P189S, P406V, L407Y, N419V, S434K, N459Q, L503S, R509D, K510D, A512T |
| 542 | N129H, N135S, E139Q, N178T, P189S, L227M, P406V, N419V, S434K, N459Q, L503S, R509D, K510D, A512T |
| 543 | Q19I, D64R, R66G, N135S, E139Q, N175C, P189S, K225R, L227M, P406V, L407Y, N419V, S434K, N459Q, L503S, R509D, K510D, A512T |
| 544 | D64R, R66G, N135S, E139Q, N175C, N178T, P189S, L405A, P406V, N419V, S434K, N459Q, L503S, R509D, K510D, A512T |
| 545 | N135S, E139Q, N175C, P189S, K225R, L227M, E228R, G352C, L405A, P406V, N419V, S434K, N459Q, L503S, R509D, K510D, A512T |
| 546 | Q19I, R66G, N135S, E139Q, N178T, P189S, K225R, L405A, P406V, L407Y, N419V, S434K, N459Q, L503S, R509D, K510D, A512T |
| 547 | N129H, N135S, E139Q, N175C, P189S, L227M, G352C, P406V, N419V, S434K, N459Q, L503S, R509D, K510D, A512T |
| 548 | Q19I, D64R, N135S, E139Q, N175C, P189S, G352C, P406V, N419V, S434K, N459Q, A488R, L503S, R509D, K510D, A512T |
| 549 | Q19I, R66G, N129H, N135S, E139Q, N175C, N178T, P189S, K225R, P406V, N419V, S434K, N459Q, L503S, R509D, K510D, A512T |

TABLE 5-continued

| Variant No. | Corresponding substitutions in FAR Maq (SEQ ID NO: 5) |
|---|---|
| 550 | Q19I, N129H, N135S, E139Q, N175C, N178T, P189S, P406V, N419V, S434K, N459Q, L503S, R509D, K510D, A512T |
| 551 | Q19I, D64R, R66G, N135S, E139Q, P189S, G352C, P406V, N419V, S434K, N459Q, L503S, R509D, K510D, A512T |
| 552 | N135S, E139Q, N175C, P189S, K225R, L227M, G352C, P406V, L407Y, N419V, S434K, N459Q, L503S, R509D, K510D, A512T |
| 553 | D64R, R66G, N135S, E139Q, N175C, P189S, K225R, L227M, P406V, N419V, S434K, N459Q, L503S, R509D, K510D, A512T |
| 554 | D64R, R66G, N135S, E139Q, N175C, N178T, P189S, L227M, P406V, L407Y, N419V, S434K, N459Q, A488R, L503S, R509D, K510D, A512T |
| 555 | Q19I, D64R, R66G, N129H, N135S, E139Q, P189S, P406V, N419V, S434K, N459Q, A488R, L503S, R509D, K510D, A512T |
| 556 | Q19I, N129H, N135S, E139Q, N175C, N178T, P189S, L227M, G352C, P406V, N419V, S434K, N459Q, L503S, R509D, K510D, A512T |
| 557 | R66G, N135S, E139Q, N175C, P189S, L227M, L405A, P406V, L407Y, N419V, S434K, N459Q, A488R, L503S, R509D, K510D, A512T |
| 558 | N135S, E139Q, P189S, V218L, P406V, N419V, S434K, N459Q, L503S, R509D, K510D, A512T |
| 559 | N135S, E139Q, P189S, A262D, P340G, Y381R, P406V, D411R, N419V, D430E, S434K, N459Q, L475R, L503S, R509D, K510D, A512T |
| 560 | N135S, E139Q, P189S, Y381N, P406V, D411A, N419V, S434K, N459Q, L503S, R509D, K510D, A512T |
| 561 | N135S, E139Q, P189S, T267A, P340G, Y381N, P406V, N419V, S434K, N459Q, L503S, R509D, K510D, A512T |
| 562 | N135S, E139Q, P189S, V218L, P406V, T410Y, D411N, N419V, S434K, N459Q, L503S, R509D, K510D, A512T |
| 563 | N135S, E139Q, P189S, P406V, D411N, N419V, S434K, N459Q, L503S, R509D, K510D, A512T |
| 564 | N135S, E139Q, P189S, P406V, T410W, D411A, N419V, S434K, N459Q, L503S, R509D, K510D, A512K |
| 565 | N135S, E139Q, P189S, P340G, P406V, N419V, S434K, N459Q, L503S, R509D, K510D, A512T |
| 566 | N135S, E139Q, P189S, P406V, T410W, D411R, N419V, S434K, N459Q, L503S, R509D, K510D, A512T |
| 567 | L70E, N135S, E139Q, P189S, T267A, P406V, N419V, S434K, N459Q, L503S, R509D, K510D, A512T |
| 568 | N135S, E139Q, P189S, T267A, P406V, N419V, S434K, N459Q, L503S, R509D, K510D, A512T |
| 569 | L70E, N135S, E139Q, P189S, P406V, T410Y, N419V, D430E, S434K, N459Q, L503S, R509D, K510D, A512T |
| 570 | L70E, N135S, E139Q, P189S, P406V, N419V, S434K, N459Q, L503S, R509D, K510D, A512T |
| 571 | N135S, E139Q, P189S, P340G, P406V, D411A, N419V, D430E, S434K, N459Q, L503S, R509D, K510D, A512T |
| 572 | N135S, E139Q, P189S, P340G, P406V, T410W, D411R, N419V, S434K, N459Q, L503S, R509D, K510D, A512T |
| 573 | N135S, E139Q, P189S, P406V, D411A, N419V, S434K, N459Q, L503S, R509D, K510D, A512T |
| 574 | N135S, E139Q, P189S, V218L, T267A, P406V, N419V, S434K, N459Q, L503S, R509D, K510D, A512T |
| 575 | N135S, E139Q, P189S, I400T, G402C, P406V, N419V, Q433Q, S434K, N459Q, L503S, R509D, K510D, A512T |
| 576 | N135S, E139Q, N178R, P189S, I400T, P406V, N419V, Q433Q, S434K, N459Q, L503S, R509D, K510D, A512T |
| 577 | N135S, E139Q, N178R, P189S, I400T, G402C, P406V, N419V, Q433Q, S434K, N459Q, L503S, R509D, K510D, A512T |
| 578 | N135S, E139Q, P189S, I400T, P406V, N419V, S434K, N459Q, L503S, R509D, K510D, A512T |
| 579 | N135S, E139Q, P189S, I400T, G402C, P406V, N419V, S434K, N459Q, L503S, R509D, K510D, A512T |
| 580 | N135S, E139Q, P189S, V399Y, G402C, P406V, N419V, S434K, N459Q, L503S, R509D, K510D, A512T |
| 581 | N135S, E139Q, P189S, V399Y, I400T, G402C, P406V, N419V, Q433Q, S434K, N459Q, L503S, R509D, K510D, A512T |
| 582 | N135S, E139Q, N178R, P189S, V399Y, I400T, P406V, N419V, Q433Q, S434K, N459Q, L503S, R509D, K510D, A512T |
| 583 | N135S, E139Q, P189S, V399Y, I400T, P406V, N419V, Q433Q, S434K, N459Q, L503S, R509D, K510D, A512T |
| 584 | N135S, E139Q, N178R, P189S, V399Y, P406V, N419V, S434K, N459Q, L503S, R509D, K510D, A512T |
| 585 | N135S, E139Q, P189S, P406V, N419V, Q433Q, S434K, N459Q, L503S, R509D, K510D, A512T |
| 586 | N135S, E139Q, P189S, L365I, G402C, P406V, N419V, S434K, N459Q, L503S, R509D, K510D, A512T |
| 587 | N135S, E139Q, P189S, S245P, G402C, P406V, N419V, Q433Q, S434K, N459Q, L503S, R509D, K510D, A512T |

TABLE 5-continued

| Variant No. | Corresponding substitutions in FAR Maq (SEQ ID NO: 5) |
|---|---|
| 588 | N135S, E139Q, N178R, P189S, V399Y, P406V, N419V, Q433Q, S434K, N459Q, L503S, R509D, K510D, A512T |
| 589 | N135S, E139Q, P189S, V399Y, P406V, N419V, S434K, N459Q, L503S, R509D, K510D, A512T |
| 590 | N135S, E139Q, N178R, P189S, V399Y, G402C, P406V, N419V, Q433Q, S434K, N459Q, L503S, R509D, K510D, A512T |
| 591 | N135S, E139Q, N178R, P189S, P406V, N419V, S434K, N459Q, L503S, R509D, K510D, A512T |
| 592 | N135S, E139Q, P189S, A390M, P406V, N419V, N459Q, L503S, R509D, K510D, A512T |
| 593 | N135S, E139Q, P189S, D377P, P406V, N419V, N459Q, L503S, R509D, K510D, A512T |
| 594 | N135S, E139Q, P189S, A390I, P406V, N419V, N459Q, L503S, R509D, K510D, A512T |
| 595 | N135S, E139Q, P189S, P406V, N419V, N459Q, L475R, L503S, R509D, K510D, A512T |
| 596 | N135R, E139Q, P189S, A284F, P406V, N419V, N459Q, L503S, R509D, K510D, A512T |
| 597 | N135S, E139Q, P189S, A284M, P406V, N419V, N459Q, L503S, R509D, K510D, A512T |
| 598 | N135S, E139Q, N178T, P189S, P406V, N419V, N459Q, L503S, R509D, K510D, A512T |
| 599 | N135S, E139Q, I187G, P189S, P406V, N419V, N459Q, L503S, R509D, K510D, A512T |
| 600 | N135S, E139Q, P189I, A390L, P406V, N419V, N459Q, L503S, R509D, K510D, A512T |
| 601 | N135S, E139Q, N175O, P189S, P406V, N419V, N459Q, Y501R, L503S, R509D, K510D, A512T |
| 602 | V105I, N135S, E139Q, P189S, P406V, N419V, N459Q, L503S, R509D, K510D, A512T |
| 603 | N135S, E139Q, P189I, P406V, N419V, N459Q, L503S, R509D, K510D, A512T |
| 604 | N135S, E139Q, P189S, S245H, P406V, N419V, N459Q, L503S, R509D, K510D, A512T |
| 605 | N135S, E139Q, P189S, M366N, P406V, N419V, N459Q, L503S, R509D, K510D, A512T |
| 606 | P63S, N135S, E139Q, P189S, S245A, P406V, L407Y, N419V, N459Q, L503S, R509D, K510D, A512T |
| 607 | N135S, E139Q, P189S, H378K, P406V, N419V, N459Q, L503S, R509D, K510D, A512T |
| 608 | N135S, E139Q, P189S, A284M, P406V, N419V, N459Q, Y501R, L503S, R509D, K510D, A512T |
| 609 | N135R, E139Q, P189S, I400T, P406V, N419V, N459Q, L503S, R509D, K510D, A512T |
| 610 | N135S, E139Q, P189S, A390V, P406V, N419V, N459Q, L503S, R509D, K510D, A512T |
| 611 | N135S, E139Q, P189S, D377P, P406V, N419V, E453G, N459Q, L503S, R509D, K510D, A512T |
| 612 | N135S, E139Q, N178Q, P189S, P406V, N419V, N459Q, Y501R, L503S, R509D, K510D, A512T |
| 613 | N135R, E139Q, P189S, P406V, N419V, N459Q, L503S, R509D, K510D, A512T |
| 614 | N135S, E139Q, N178Q, P189S, H378K, P406V, N419V, N459Q, L503S, R509D, K510D, A512T |
| 615 | N135S, E139Q, P189S, P406V, N419V, E453N, N459Q, L503S, R509D, K510D, A512T |
| 616 | N135S, E139Q, P189S, S245F, P406V, N419V, N459Q, Y501R, L503S, R509D, K510D, A512T |
| 617 | V6P, V105I, N135S, E139Q, P189S, P406V, N419V, N459Q, L503S, R509D, K510D, A512T |
| 618 | N135S, E139Q, P189S, R404S, P406V, N419V, N459Q, Y501R, L503S, R509D, K510D, A512T |
| 619 | N135S, E139Q, P189S, A284T, P406V, N419V, N459Q, L503S, R509D, K510D, A512T |
| 620 | N135S, E139Q, P189S, L365I, P406V, N419V, N459Q, L503S, R509D, K510D, A512T |
| 621 | N135S, E139Q, P189S, A284F, P406V, N419V, N459Q, L503S, R509D, K510D, A512T |
| 622 | S13T, N135R, E139Q, P189S, P406V, N419V, N459Q, L503S, R509D, K510D, A512T |
| 623 | N135S, E139Q, P189S, P406V, N419V, N459Q, Y501R, L503S, R509D, K510D, A512T |
| 624 | N135S, E139Q, P189S, P406V, D411N, N419V, N459Q, L503S, R509D, K510D, A512T |
| 625 | N135S, E139Q, P189S, E228R, P406V, N419V, N459Q, L503S, R509D, K510D, A512T |
| 626 | N135S, E139Q, P189S, P406V, N419V, N459Q, G467Q, L503S, R509D, K510D, A512T |
| 627 | N135S, E139Q, P189S, V319I, P406V, N419V, N459Q, G467E, L503S, R509D, K510D, A512T |
| 628 | N135S, E139Q, P189S, S245P, P406V, N419V, N459Q, L503S, R509D, K510D, A512T |
| 629 | N135S, E139Q, P189S, Y381K, P406V, N419V, N459Q, L503S, R509D, K510D, A512T |

All publications, patents, patent applications and other documents cited in this application are hereby incorporated by reference in their entireties for all purposes to the same extent as if each individual publication, patent, patent application or other document were individually indicated to be incorporated by reference for all purposes.

The entire contents of U.S. provisional application No. 61/221,934, filed Jun. 30, 2009, U.S. provisional application No. 61/315,380, filed Mar. 18, 2010, U.S. patent application Ser. No. 12/825,939, filed on Jun. 29, 2010 and published as US 2011/0000125, are hereby incorporated by reference in their entireties for all purposes.

While various specific embodiments have been illustrated and described, it will be appreciated that various changes can be made without departing from the spirit and scope of the invention(s).

SEQUENCE LISTING

SEQ ID NO: 1
M. algicola DG893 FAR DNA (codon optimized)
ATGGCTACTCAACAACAACAGAACGGTGCATCTGCATCCGGCGTCTTGGAACAACTTCGTGGAA

AGCACGTTCTTATCACAGGTACTACCGGATTTTTGGGCAAAGTGGTTCTGGAAAAGTTGATTCG

```
TACTGTTCCGGATATTGGAGGTATTCATCTGCTGATTCGTGGCAATAAACGTCATCCAGCCGCT

CGTGAACGTTTCCTGAACGAAATTGCGTCCTCCTCCGTCTTCGAACGTTTGCGTCACGATGATA

ATGAAGCCTTCGAGACCTTCTTGGAAGAACGTGTTCACTGTATTACCGGTGAGGTTACTGAATC

CCGTTTTGGTTTGACACCTGAACGTTTTCGTGCTTTGGCCGGTCAGGTTGACGCTTTTATTAAC

AGCGCTGCAAGCGTGAACTTTCGTGAGGAATTGGATAAAGCCCTGAAAATCAACACCTTGTGTC

TTGAAAATGTTGCTGCTCTTGCAGAATTGAACTCCGCTATGGCGGTCATTCAGGTTTCCACTTG

TTACGTTAACGGTAAAAACTCCGGTCAAATTACCGAATCCGTCATTAAACCTGCTGGCGAATCC

ATTCCCCGTTCCACTGACGGTTACTACGAGATCGAAGAATTGGTCCATCTGTTGCAAGACAAGA

TTTCCGATGTTAAAGCTCGTTACTCCGGCAAAGTTCTGGAGAAAAAATTGGTTGATTTGGGTAT

TCGTGAGGCCAATAATTACGGATGGTCCGACACCTACACATTCACCAAATGGTTGGGTGAACAA

CTGCTGATGAAGGCCTTGTCTGGTCGTTCTTTGACTATTGTGCGTCCCTCTATTATTGAGTCCG

CTTTGGAAGAACCTTCCCCTGGTTGGATCGAAGGCGTTAAAGTTGCCGATGCCATTATCTTGGC

TTATGCCCGTGAAAAAGTTAGCCTGTTCCCTGGAAAACGTTCCGGCATTATTGATGTTATTCCT

GTCGATTTGGTTGCGAACTCCATCATCTTGTCTCTGGCTGAGGCGTTGTCTGGTTCTGGTCAAC

GTCGTATTTATCAATGTTGCAGCGGTGGTTCTAATCCAATCTCCCTGGGTAAGTTCATTGATTA

TTTGATGGCCGAGGCTAAGACCAACTATGCTGCCTACGATCAACTGTTTTATCGTCGTCCTACT

AAACCTTTCGTCGCCGTGAACCGTAAATTGTTTGACGTTGTTGTTGGTGGTATGCGTGTTCCTC

TTTCTATTGCCGGTAAAGCTATGCGTTTGGCTGGTCAAAATCGTGAGTTGAAAGTGCTTAAGAA

CCTTGATACGACCCGTTCCCTTGCAACCATTTTTGGCTTCTATACTGCTCCCGACTATATCTTC

CGTAACGATAGCTTGATGGCCCTGGCTTCTCGTATGGGTGAATTGGATCGTGTTCTTTTCCCAG

TTGATGCTCGTCAAATTGATTGGCAGTTGTACTTGTGTAAAATTCATTTGGGTGGTCTGAACCG

TTACGCTTTGAAGGAACGTAAACTGTATCTTTGCGTGCTGCTGATACTCGTAAAAAGCTGCC

TAA

SEQ ID NO: 2
M. algicola DG893 FAR polypeptide
MATQQQQNGASASGVLEQLRGKHVLITGTTGFLGKVVLEKLIRTVPDIGGIHLLIRGNKRHPAA

RERFLNEIASSSVFERLRHDDNEAFETFLEERVHCITGEVTESRFGLTPERFRALAGQVDAFIN

SAASVNFREELDKALKINTLCLENVAALAELNSAMAVIQVSTCYVNGKNSGQITESVIKPAGES

IPRSTDGYYEIEELVHLLQDKISDVKARYSGKVLEKKLVDLGIREANNYGWSDTYTFTKWLGEQ

LLMKALSGRSLTIVRPSIIESALEEPSPGWIEGVKVADAIILAYAREKVSLFPGKRSGIIDVIP

VDLVANSIILSLAEALSGSGQRRIYQCCSGGSNPISLGKFIDYLMAEAKTNYAAYDQLFYRRPT

KPFVAVNRKLFDVVVGGMRVPLSIAGKAMRLAGQNRELKVLKNLDTTRSLATIFGFYTAPDYIF

RNDSLMALASRMGELDRVLFPVDARQIDWQLYLCKIHLGGLNRYALKERKLYSLRAADTRKKAA

SEQ ID NO: 3
M. algicola DG893 FAR DNA (codon optimized)
ATGGCCACCCAGCAGCAGCAGAACGGTGCATCCGCTTCGGGCGTTCTGGAGCAGCTTAGAGGCA

AGCATGTCTTGATTACCGGTACTACAGGATTTCTGGGAAAGGTGGTTCTGGAGAAGCTGATCCG

AACCGTGCCTGACATCGGTGGTATTCATCTGCTGATTAGAGGCAACAAGAGACATCCTGCTGCC

AGAGAAAGATTCTTGAACGAAATCGCCTCTTCCTCTGTGTTCGAGCGGCTTAGACATGACGACA

ACGAAGCCTTTGAGACTTTCCTGGAGGAGCGTGTGCACTGCATCACCGGAGAAGTGACCGAGTC
```

SEQUENCE LISTING

GAGATTTGGCCTTACTCCTGAGCGGTTCCGAGCCCTTGCTGGCCAAGTGGATGCCTTCATCAAT

TCCGCCGCCTCTGTTAACTTCAGAGAGGAGCTGGACAAGGCACTCAAGATCAACACCCTGTGTC

TGGAGAACGTGGCTGCTCTGGCCGAACTTAACTCCGCTATGGCAGTGATCCAAGTTTCCACCTG

TTACGTGAACGGCAAGAACTCTGGACAGATCACCGAGTCCGTTATCAAGCCCGCTGGCGAATCC

ATCCCCAGATCCACAGATGGCTACTACGAGATCGAGGAGCTGGTCCACCTTCTGCAAGACAAGA

TCTCCGACGTGAAGGCTCGATACTCTGGCAAGGTGTTGGAGAAGAAGCTGGTGGACCTGGGCAT

CCGAGAGGCGAACAACTACGGCTGGTCTGACACCTACACCTTCACCAAATGGCTCGGAGAGCAG

CTTCTGATGAAAGCTCTGTCCGGAAGATCCCTGACTATCGTGCGGCCTTCCATCATCGAGTCGG

CTCTTGAAGAGCCTTCTCCAGGTTGGATCGAGGGCGTGAAGGTTGCTGACGCCATCATCCTTGC

GTACGCCAGAGAGAAGGTTTCGTTGTTCCCCGGCAAGCGATCTGGCATCATCGACGTTATCCCC

GTGGATCTGGTGGCCAACTCTATCATTCTCTCTCTTGCTGAAGCCCTTTCTGGATCTGGCCAGC

GTAGAATCTACCAATGTTGTTCTGGCGGTTCTAACCCGATTTCTCTGGGCAAGTTCATCGACTA

CCTTATGGCCGAAGCCAAGACCAACTATGCTGCCTACGACCAGCTCTTCTACCGACGACCCACC

AAGCCCTTCGTCGCTGTGAACCGAAAGCTGTTCGATGTTGTCGTGGGAGGAATGCGAGTGCCTC

TTTCCATTGCTGGCAAGGCCATGAGATTGGCGGGTCAGAATCGAGAATTGAAGGTTCTCAAGAA

CCTTGACACTACTCGATCGCTCGCTACTATCTTTGGATTCTACACTGCTCCTGACTACATCTTC

CGGAATGACTCTCTGATGGCTCTTGCTTCCCGAATGGGAGAACTCGATCGTGTGCTGTTCCCTG

TTGACGCTCGACAGATCGACTGGCAGCTCTACTTGTGTAAGATCCACCTGGGCGGCCTGAACCG

ATATGCTCTGAAAGAACGAAAGCTGTACAGCCTTAGAGCCGCTGATACCCGAAAGAAGGCTGCT

TAA

SEQ ID NO: 4
*M. aquaeolei* FAR DNA (codon optimized)
ATGGCTATCCAGCAGGTTCATCACGCCGACACATCCTCCTCTAAAGTCCTGGGTCAACTTCGTG

GTAAACGTGTCTTGATTACCGGCACTACTGGATTCTTGGGTAAAGTCGTCTTGGAACGTTTGAT

TCGTGCCGTTCCTGACATCGGTGCTATCTACCTGCTGATTCGTGGTAACAAGCGTCACCCGGAT

GCTCGTTCTCGTTTCTTGGAGGAGATTGCTACCTCCTCTGTCTTTGATCGTTTGCGTGAAGCTG

ATTCCGAAGGTTTCGATGCTTTCCTGGAAGAACGTATTCACTGTGTTACTGGTGAAGTTACTGA

AGCTGGTTTCGGTATTGGTCAAGAGGACTATCGTAAGTTGGCCACCGAATTGGACGCAGTCATC

AATTCTGCTGCCTCCGTCAACTTCCGTGAGGAGTTGGATAAGGCTCTGGCCATCAACACTCTGT

GTTTGCGTAACATCGCTGGTATGGTGGATCTTAACCCTAAGCTGGCCGTTCTTCAAGTCTCTAC

GTGTTACGTCAACGGTATGAACTCTGGTCAAGTTACTGAATCCGTCATCAAACCAGCTGGTGAA

GCTGTTCCTCGTTCTCCTGATGGATTCTACGAGATCGAGGAATTGGTTCGTCTGCTGCAAGACA

AGATTGAAGACGTTCAAGCACGTTACTCTGGTAAGGTGTTGGAGCGTAAGTTGGTTGATTTGGG

TATTCGTGAGGCTAATCGTTACGGTTGGTCTGATACATACACCTTCACGAAATGGTTGGGTGAA

CAACTTCTGATGAAAGCCTTGAATGGTCGTACCTTGACTATTCTGCGTCCTAGCATCATTGAAT

CTGCTTTGGAAGAACCAGCACCTGGTTGGATTGAAGGCGTGAAAGTTGCAGATGCGATCATCTT

GGCTTATGCTCGTGAGAAGGTTACTTTGTTTCCGGGTAAACGTTCTGGTATCATTGATGTGATT

CCTGTTGACTTGGTTGCCAATTCCATCATCTTGTCTTTGGCTGAGGCTCTGGGCGAACCTGGTC

GTCGTCGTATCTACCAATGTTGTTCTGGTGGTGGTAATCCTATCTCCCTGGGCGAGTTCATTGA

TCACCTGATGGCTGAATCCAAAGCCAACTATGCCGCATACGATCATCTGTTCTACCGTCAACCC

SEQUENCE LISTING

```
TCCAAGCCTTTCCTTGCTGTCAACCGTGCTTTGTTCGACTTGGTTATCTCTGGTGTCCGTCTGC

CTTTGTCTTTGACCGACCGTGTCTTGAAGCTGCTGGGCAACTCCCGTGACCTGAAGATGCTGCG

TAACCTGGATACTACGCAATCCCTGGCTACTATCTTTGGCTTCTACACAGCCCCCGACTACATC

TTCCGTAATGACGAGTTGATGGCCCTGGCTAACCGTATGGGCGAGGTTGATAAGGGTTTGTTCC

CCGTTGATGCTCGTCTGATTGATTGGGAATTGTACCTGCGTAAGATTCACCTGGCTGGTTTGAA

CCGTTACGCCTTGAAGGAGCGTAAGGTTTACTCTTTGAAGACAGCCCGTCAGCGTAAGAAGGCA

GCTTAA
```

SEQ ID NO: 5
M. aquaeolei FAR polypeptide
MAIQQVHHADTSSSKVLGQLRGKRVLITGTTGFLGKVVLERLIRAVPDIGAIYLLIRGNKRHPD
ARSRFLEEIATSSVFDRLREADSEGFDAFLEERIHCVTGEVTEAGFGIGQEDYRKLATELDAVI
NSAASVNFREELDKALAINTLCLRNIAGMVDLNPKLAVLQVSTCYVNGMNSGQVTESVIKPAGE
AVPRSPDGFYEIEELVRLLQDKIEDVQARYSGKVLERKLVDLGIREANRYGWSDTYTFTKWLGE
QLLMKALNGRTLTILRPSIIESALEEPAPGWIEGVKVADAIILAYAREKVTLFPGKRSGIIDVI
PVDLVANSIILSLAEALGEPGRRRIYQCCSGGGNPISLGEFIDHLMAESKANYAAYDHLFYRQP
SKPFLAVNRALFDLVISGVRLPLSLTDRVLKLLGNSRDLKMLRNLDTTQSLATIFGFYTAPDYI
FRNDELMALANRMGEVDKGLFPVDARLIDWELYLRKIHLAGLNRYALKERKVYSLKTARQRKKA
A SEQ ID NO: 6
FAR Maa variant 370 polypeptide
MATQQQQNGASASGVLEQLRGKHVLITGTTGFLGKVVLEKLIRTVPDIGGIHLLIRGNKRHPAA
RERFLNEIASSSVFERLRHDDNEAFETFLEERVHCITGEVTESRFGLTPERFRALAGQVDAFIN
SAASVSFREQLDKALKINTLCLENVAALAELNSAMAVIQVSTCYVNGKNSGQITESVIKSAGES
IPRSTDGYYEIEELVHLLQDKISDVKARYSGKVLEKKLVDLGIREANNYGWSDTYTFTKWLGEQ
LLMKALSGRSLTIVRPSIIESALEEPSPGWIEGVKVADAIILAYAREKVSLFPGKRSGIIDVIP
VDLVANSIILSLAEALSGSGQRRIYQCCSGGSNPISLGKFIDYLMAEAKTNYAAYDQLFYRRPT
KPFVAVNRKLFDVVVGGMRVVLSIAGKAMRLAGVNRELKVLKNLDTTRSLATIFGFYTAPDYIF
RNDSLMALASRMGELDRVLFPVDARQIDWQLYLCKIHLGGLNRYALKERKLYSLRAADTRKKTA SEQ ID NO: 7
FAR Maa variant 391 polypeptide
MATQQQQNGASASGVLEQLRGKHVLITGTTGFLGKVVLEKLIRTVPDIGGIHLLIRGNKRHPAA
RERFLNEIASSSVFERLRHDDNEAFETFLEERVHCITGEVTESRFGLTPERFRALAGQVDAFIN
SAASVSFREQLDKALKINTLCLENVAALAELNSAMAVIQVSTCYVNGKNSGQITESVIKSAGES
IPRSTDGYYEIEELVHLLQDKISDVKARYSGKVLEKKLVDLGIREANNYGWSDTYTFTKWLGEQ
LLMKALSGRSLTIVRPSIIESALEEPSPGWIEGVKVADAIILAYAREKVSLFPGKRSGIIDVIP
VDLVANSIILSLAEALSGSGQRRIYQCCSGGSNPISLGKFIDYLMAEAKTNYAAYDQLFYRRPT
KPFVAVNRKLFDVVVGGMRVVLSIAGKAMRLAGVNRELKVLKNLDTTRSLATIFGFYTAPDYIF
RNDSLMALAQRMGELDRVLFPVDARQIDWQLYLCKIHLGGLNRYALKERKLYSSRAADTDDKTA SEQ ID NO: 8
FAR Maa variant 436 polypeptide
MATQQQQNGASASGVLEQLRGKHVLITGTTGFLGKVVLEKLIRTVPDIGGIHLLIRGNKRHPAA
RERFLNEIASSSVFERLRHDDNEAFETFLEERVHCITGEVTESRFGLTPERFRALAGQVDAFIN

```
SAASVSFREQLDKALKINTLCLENVAALAELNSAMAVIQVSTCYVNGKNSGQITESVIKSAGES

IPRSTDGYYEIEELVHLLQDKISDVKARYSGKVLEKKLVDLGIREANNYGWSDTYTFTKWLGEQ

LLMKALSGRSLTIVRPSIIESALEEPSPGWIEGVKVADAIILAYAREKVSLFPGKRSGIIDVIP

VDLVANSIILSLAEALSGSGQRRIYQCCSGGSNPISLGKFIDYLMAEAKTNYAAYDKLFYRRPT

KPFVAVNRKLFDVVVGGMRVVLSIAGKAMRLAGVNRELKVLKNLDTTRSLATIFGFYTAPDYIF

RNDSLMALAQRMGELDRVLFPVDARQIDWQLYLCKIHLGGLNRYALKERKLYSSRAADTDDKTA

SEQ ID NO: 9
FAR Maa variant 438 polypeptide
MATQQQQNGASASGVLEQLRGKHVLITGTTGFLGKVVLEKLIRTVPDIGGIHLLIRGNKRHPAA

RERFLNEIASSSVFERLRHDDNEAFETFLEERVHCITGEVTESRFGLTPERFRALAGQVDAFIN

SAASVSFREQLDKALKINTLCLENVAALAELNSAMAVIQVSTCYVNGKNSGQITESVIKSAGES

IPRSTDGYYEIEELVHLLQDKISDVKARYSGKVLEKKLVDLGIREANNYGWSDTYTFTKWLGEQ

LLMKALSGRSLTIVRPSIIESALEEPSPGWIEGVKVADAIILAYAREKVSLFPGKRSGIIDVIP

VDLVANSIILSLAEALSGSGQRRIYQCCSGGSNPISLGKFIDYLMAEAKTNYAAYDQLFYRRPT

KPFVAVNRKLFDVVVGGMRVVLSIAGKAMRLAGVNRELKVLKNLDTTRKLATIFGFYTAPDYIF

RNDSLMALAQRMGELDRVLFPVDARQIDWQLYLCKIHLGGLNRYALKERKLYSSRAADTDDKTA

SEQ ID NO: 10
FAR Maa variant 547 polypeptide
MATQQQQNGASASGVLEQLRGKHVLITGTTGFLGKVVLEKLIRTVPDIGGIHLLIRGNKRHPAA

RERFLNEIASSSVFERLRHDDNEAFETFLEERVHCITGEVTESRFGLTPERFRALAGQVDAFIH

SAASVSFREQLDKALKINTLCLENVAALAELNSAMAVIQVSTCYVCGKNSGQITESVIKSAGES

IPRSTDGYYEIEELVHLLQDKISDVKARYSGKVMEKKLVDLGIREANNYGWSDTYTFTKWLGEQ

LLMKALSGRSLTIVRPSIIESALEEPSPGWIEGVKVADAIILAYAREKVSLFPGKRSGIIDVIP

VDLVANSIILSLAEALSGSGQRRIYQCCSGCSNPISLGKFIDYLMAEAKTNYAAYDQLFYRRPT

KPFVAVNRKLFDVVVGGMRVVLSIAGKAMRLAGVNRELKVLKNLDTTRKLATIFGFYTAPDYIF

RNDSLMALAQRMGELDRVLFPVDARQIDWQLYLCKIHLGGLNRYALKERKLYSSRAADTDDKTA

SEQ ID NO: 11
FAR Maa variant 555 polypeptide
MATQQQQNGASASGVLEILRGKHVLITGTTGFLGKVVLEKLIRTVPDIGGIHLLIRGNKRHPRA

GERFLNEIASSSVFERLRHDDNEAFETFLEERVHCITGEVTESRFGLTPERFRALAGQVDAFIH

SAASVSFREQLDKALKINTLCLENVAALAELNSAMAVIQVSTCYVNGKNSGQITESVIKSAGES

IPRSTDGYYEIEELVHLLQDKISDVKARYSGKVLEKKLVDLGIREANNYGWSDTYTFTKWLGEQ

LLMKALSGRSLTIVRPSIIESALEEPSPGWIEGVKVADAIILAYAREKVSLFPGKRSGIIDVIP

VDLVANSIILSLAEALSGSGQRRIYQCCSGGSNPISLGKFIDYLMAEAKTNYAAYDQLFYRRPT

KPFVAVNRKLFDVVVGGMRVVLSIAGKAMRLAGVNRELKVLKNLDTTRKLATIFGFYTAPDYIF

RNDSLMALAQRMGELDRVLFPVDARQIDWQLYLCKIHLRGLNRYALKERKLYSSRAADTDDKT

SEQ ID NO: 12
FAR Maa variant 556 polypeptide
MATQQQQNGASASGVLEILRGKHVLITGTTGFLGKVVLEKLIRTVPDIGGIHLLIRGNKRHPAA

RERFLNEIASSSVFERLRHDDNEAFETFLEERVHCITGEVTESRFGLTPERFRALAGQVDAFIH

SAASVSFREQLDKALKINTLCLENVAALAELNSAMAVIQVSTCYVCGKTSGQITESVIKSAGES

IPRSTDGYYEIEELVHLLQDKISDVKARYSGKVMEKKLVDLGIREANNYGWSDTYTFTKWLGEQ

LLMKALSGRSLTIVRPSIIESALEEPSPGWIEGVKVADAIILAYAREKVSLFPGKRSGIIDVIP
```

VDLVANSIILSLAEALSGSGQRRIYQCCSGCSNPISLGKFIDYLMAEAKTNYAAYDQLFYRRPT

KPFVAVNRKLFDVVVGGMRVVLSIAGKAMRLAGVNRELKVLKNLDTTRKLATIFGFYTAPDYIF

RNDSLMALAQRMGELDRVLFPVDARQIDWQLYLCKIHLGGLNRYALKERKLYSSRAADTDDKTA

SEQ ID NO: 13
*Marinobacter algicola* DG893 (FAR Maa) wild-type cDNA sequence
ATGGCAACACAGCAGCAACAAAACGGAGCGTCAGCGTCCGGTGTTCTTGAGCAACTACGTGGTA

AACACGTGCTGATCACCGGCACCACCGGGTTTCTTGGTAAGGTGGTACTGGAAAAATTGATTCG

CACGGTGCCGGATATTGGCGGGATCCATCTTCTTATCCGTGGTAACAAAAGGCATCCTGCAGCA

CGGGAACGATTCCTCAACGAGATCGCCAGTTCTTCCGTGTTCGAACGCCTTCGGCACGATGACA

ACGAGGCGTTTGAAACCTTTCTTGAGGAACGCGTTCACTGCATCACCGGCGAAGTGACAGAGTC

GCGTTTCGGGCTCACGCCGGAGCGGTTCCGTGCACTTGCCGGGCAGGTCGATGCGTTTATAAAT

TCCGCAGCCAGTGTGAACTTCCGGGAGGAACTCGACAAGGCGCTGAAGATTAACACCCTGTGCC

TGGAGAACGTTGCCGCTCTGGCGGAGCTCAATAGCGCCATGGCGGTTATCCAGGTGTCCACCTG

CTACGTCAATGGCAAGAATTCCGGCCAGATCACGGAGTCCGTCATCAAGCCGGCGGGCGAGTCT

ATTCCCCGCAGCACCGACGGCTACTATGAAATCGAAGAGCTTGTGCATTTGCTGCAGGACAAAA

TTTCCGACGTGAAAGCCCGATACTCCGGCAAAGTACTTGAAAAAAAGCTGGTGGACCTGGGGAT

TCGAGAGGCCAACAACTACGGCTGGAGTGACACCTACACGTTTACCAAATGGCTGGGTGAGCAA

CTCCTGATGAAAGCCCTTTCCGGGCGTTCACTTACGATTGTTCGCCCTTCCATCATTGAAAGTG

CACTGGAAGAGCCTTCGCCAGGATGGATTGAAGGTGTGAAGGTGGCAGACGCCATTATCCTTGC

CTATGCCCGTGAGAAGGTCTCCCTGTTCCCAGGCAAGCGTAGCGGCATTATCGATGTGATCCCG

GTGGACCTGGTGGCCAACAGTATCATCTTGTCCCTGGCAGAAGCCCTTTCCGGGTCAGGGCAGC

GCCGCATCTATCAATGCTGCAGTGGCGGTTCTAATCCGATTTCGCTGGGCAAGTTCATTGACTA

CCTGATGGCCGAAGCCAAGACCAACTATGCAGCGTATGACCAGTTGTTCTACCGACGGCCCACG

AAACCGTTTGTGGCGGTCAATCGCAAGCTGTTTGATGTTGTGGTTGGCGGCATGCGCGTGCCGT

TGTCGATTGCTGGCAAGGCAATGAGGCTGGCTGGCCAGAACCGTGAGCTCAAGGTTCTCAAAAA

CCTCGATACCACGCGTTCACTGGCCACCATCTTTGGTTTCTACACGGCACCGGATTACATCTTC

CGTAACGATTCGCTGATGGCCCTGGCTTCGCGCATGGGTGAACTGGACCGTGTCCTGTTCCCGG

TGGATGCGCGTCAGATTGACTGGCAGCTGTACTTGTGCAAGATCCACCTGGGAGGTCTCAACCG

CTACGCTCTGAAGGAGCGAAAACTGTACAGCCTGCGGGCCGCCGACACCCGCAAAAAAGCCGCC

SEQ ID NO: 14
*Marinobacter aquaeolei* VT8 (FAR Maq) wild-type cDNA sequence
ATGGCAATACAGCAGGTACATCACGCTGACACTTCATCATCAAAGGTGCTCGGACAGCTCCGTG

GCAAGCGGGTTCTGATCACCGGTACCACTGGCTTTCTGGGCAAGGTGGTCCTCGAAAGGCTGAT

TCGGGCGGTGCCTGATATCGGCGCAATTTACCTGCTGATCCGGGCAATAAACGGCATCCGGAT

GCTCGTTCCCGTTTCCTGGAAGAAATTGCCACCTCCTCGGTGTTTGACCGTCTTCGCGAGGCCG

ATTCAGAGGGATTTGACGCCTTTCTGGAAGAGCGCATTCACTGCGTGACCGGTGAGGTGACCGA

AGCGGGTTTCGGGATAGGGCAGGAAGACTATCGCAAACTCGCCACCGAACTGGATGCGGTGATC

AACTCCGCTGCAAGCGTGAATTTCCGTGAAGAGCTCGACAAGGCGCTGGCCATCAACACCCTGT

GCCTTCGGAATATTGCCGGCATGGTGGATTTGAATCCGAAGCTTGCGGTCCTGCAGGTCTCCAC

CTGCTATGTCAATGGCATGAACTCGGGGCAGGTAACCGAATCGGTGATCAAGCCGGCAGGCGAG

```
GCCGTGCCGCGTTCCCCGGACGGCTTCTATGAGATAGAAGAGCTTGTTCGCCTGCTTCAGGATA

AAATTGAAGACGTTCAGGCCCGTTATTCCGGCAAAGTGCTGGAGAGGAAGCTGGTGGACCTGGG

GATTCGGGAAGCCAACCGCTATGGCTGGAGCGATACCTACACCTTTACCAAGTGGCTGGGCGAA

CAGTTGCTGATGAAGGCGTTAAACGGGCGCACGCTGACCATTCTGCGTCCTTCGATTATCGAAA

GTGCCCTGGAGGAACCAGCGCCCGGCTGGATTGAGGGGGTGAAGGTGGCAGATGCCATCATCCT

GGCTTACGCACGGGAAAAGTCACCCTCTTCCCGGGCAAACGCTCCGGTATCATCGATGTGATT

CCAGTGGACCTGGTGGCCAACTCCATCATCCTTTCCCTGGCGGAAGCTCTTGGAGAACCCGGTC

GACGTCGCATCTATCAATGTTGCAGCGGGGCGGCAATCCAATCTCCCTGGGTGAGTTCATCGA

TCATCTCATGGCGGAATCAAAAGCCAATTACGCTGCCTACGATCACCTGTTCTACCGGCAGCCC

AGCAAGCCGTTTCTGGCGGTTAACCGGGCGCTGTTTGATTTGGTGATCAGTGGTGTTCGCTTAC

CGCTCTCCCTGACGGACCGTGTGCTCAAATTACTGGGAAATTCCCGGGACCTGAAAATGCTCAG

GAATCTGGATACCACCCAGTCGCTGGCAACCATTTTTGGTTTCTACACCGCGCCGGATTATATC

TTCCGGAACGATGAGCTGATGGCGCTGGCGAACCGGATGGGTGAGGTCGATAAAGGGCTGTTCC

CGGTGGATGCCCGCCTGATTGACTGGGAGCTCTACCTGCGCAAGATTCACCTGGCCGGGCTCAA

TCGCTATGCCCTGAAAGAACGAAAGGTGTACAGTCTGAAAACCGCGCGCCAGCGCAAAAAGCT

GCC
```

What is claimed is:

1. A fatty alcohol forming acyl-CoA reductase (FAR) variant that has at least 90% sequence identity to SEQ ID NO:5, wherein the variant comprises a substitution at one or more positions selected from position 512, position 2, position 508, position 511, position 503, position 434, position 501, position 459, position 135, and position 139, wherein the position is numbered with reference to SEQ ID NO:5, and wherein a cell in which the FAR variant is expressed produces more fatty alcohol than a corresponding cell of the same type in which the wild-type FAR from which the FAR variant is derived is expressed, wherein the cell is a yeast cell or a bacterial cell.

2. The FAR variant of claim 1, wherein the cell is a bacterial cell.

3. The FAR variant of claim 1, wherein the wild-type FAR is *Marinobacter aquaeolei* FAR having the amino acid sequence of SEQ ID NO:5.

4. A recombinant polynucleotide encoding the FAR variant of claim 1.

5. The polynucleotide of claim 4 operably linked to a promoter.

6. An expression vector comprising the recombinant polynucleotide of claim 4.

7. A host cell comprising the recombinant polynucleotide of claim 4, wherein the host cell is a yeast cell or a bacterial cell.

8. A host cell comprising a recombinant polynucleotide sequence encoding a fatty alcohol forming acyl-CoA reductase (FAR) variant that has at least 90% sequence identity to SEQ ID NO:5, wherein the host cell is a yeast cell or a bacterial cell and wherein the variant comprises a substitution at one or more positions selected from position 512, position 2, position 508, position 511, position 503, position 434, position 501, position 459, position 135, and position 139, wherein the position is numbered with reference to SEQ ID NO:5.

9. The host cell of claim 8 that is *E. coli*.

10. The host cell of claim 8, wherein the FAR variant comprises at least 95% sequence identity to SEQ ID NO:5.

11. The host cell of claim 10, wherein the FAR variant protein has 100% identity to SEQ ID NO:5 except for the substitutions present in any individual FAR variant selected from variant numbers 1-629 in Table 5.

12. The host cell of claim 8, wherein the variant comprises a substitution at one or both of positions 512 and 2, and wherein:
(a) the amino acid at position 512 is glycine, lysine, proline, glutamine, serine, or threonine; or
(b) the amino acid at position 2 is glycine, proline, threonine, phenylalanine, or glutamine.

13. The host cell of claim 12, wherein the FAR variant further comprises a substitution at one or both of positions 508 and 511, wherein:

(a) the amino acid at position 508 is glycine or serine; or
(b) the amino acid at position 511 is aspartic acid, glycine, or proline.

14. The host cell of claim 12, wherein the FAR variant further comprises a substitution at one or more of positions 503, 434, and 501, and wherein:
   (a) the amino acid at position 503 is glutamine, arginine, or serine;
   (b) the amino acid at position 434 is phenylalanine, lysine, or tryptophan; or
   (c) the amino acid at position 501 is glycine, asparagine, proline, glutamine, serine, or tryptophan.

15. The host cell of claim 12, wherein the FAR variant further comprises a substitution at one or more of positions 459, 135, and 139, wherein:
   (a) the amino acid at position 459 is glycine;
   (b) the amino acid at position 135 is lysine; or
   (c) the amino acid at position 139 is glutamine.

16. The host cell of claim 8 that produces at least 1.5 times more fatty alcohol than a corresponding cell of the same type expressing a wild-type FAR from which the FAR variant is derived.

17. The host cell of claim 8, wherein:
   (a) at least 30% of the fatty alcohol produced is C12-C14 fatty alcohols; or
   (b) at least 55% of the fatty alcohol produced is C16-C18 fatty alcohols; or
   (c) at least 90% of the fatty alcohol produced is C14-C18 fatty alcohols.

18. The host cell of claim 8 that produces a fatty alcohol profile comprising an increased amount of C14:0 (1-tetradecanol) fatty alcohol and a decreased amount of C18:1 (cis $\Delta^{11}$-1-octadecenol) fatty alcohol relative to a corresponding cell of the same type expressing a wild-type FAR from which the FAR variant is derived.

19. The host cell of claim 8, wherein at least 5 g/L of recoverable fatty alcohols are produced.

20. A method of producing fatty alcohols, the method comprising culturing the host cell of claim 8 in a culture medium under conditions in which the fatty alcohols are produced.

21. A method of producing a detergent composition, the method comprising: combining the fatty alcohols produced by the method of claim 20, or a fraction thereof, with a detergent component selected from sodium carbonate, a complexation agent, zeolites, a protease, a lipase, amylase, carboxymethyl cellulose, optical brighteners, colorants and perfumes, thereby producing the detergent composition.

22. A method of producing a composition comprising alkanes or alkenes, the method comprising reducing fatty alcohols produced by the method of claim 20, or a fraction thereof, to produce alkanes or alkenes.

23. A method of producing a composition comprising fatty esters, the method comprising modifying fatty alcohols produced by the method of claim 20, or a fraction thereof, to produce fatty esters.

24. A method of producing a fuel composition, the method comprising reducing or esterifying the fatty alcohols produced by the method of claim 20, or a fraction thereof, to yield the fuel composition.

25. A method of producing fuel comprising (a) producing fatty alcohols according to the method of claim 20, and (b) subjecting the fatty alcohols, or a fraction thereof, to one or more chemical reactions to generate alkanes, whereby fuel is produced.

26. The method of claim 25 wherein the fatty alcohols comprise at least 90% C14-C18 fatty alcohols and optionally contain less than 1% C18:0 fatty alcohols.

27. An *E. coli* cell comprising a recombinant polynucleotide sequence encoding a fatty alcohol forming acyl-CoA reductase (FAR) variant that has at least 90% sequence identity to SEQ ID NO:5, wherein the FAR variant comprises a substitution at one or more positions selected from position 512, position 2, position 508, position 511, position 503, position 434, position 501, position 459, position 135, and position 139, wherein the position is numbered with reference to SEQ ID NO:5.

28. The cell of claim 27 that produces more fatty alcohol than a corresponding cell of the same type in which a FAR polypeptide having 100% identity to SEQ ID NO:5 is expressed.

29. A composition comprising:
   (a) fatty alcohols produced by the method of claim 20; or
   (b) a fatty alcohol derivative prepared by subjecting the fatty alcohols in (a), or a fraction thereof, to one or more chemical reactions that produce a fatty alcohol derivative.

* * * * *

SEQUENCE LISTING

<160> NUMBER OF SEQ ID NOS: 14

<210> SEQ ID NO 1
<211> LENGTH: 1539
<212> TYPE: DNA
<213> ORGANISM: Artificial Sequence
<220> FEATURE:
<223> OTHER INFORMATION: Synthetic DNA encoding M. algicola DG893 FAR
      codon optimized for expression in E. coli

<400> SEQUENCE: 1

```
atggctactc aacaacaaca gaacggtgca tctgcatccg gcgtcttgga caacttcgt      60 ggaaagcacg ttcttatcac aggtactacc ggattttttgg gcaaagtggt tctggaaaag   120
ttgattcgta ctgttccgga tattggaggt attcatctgc tgattcgtgg caataaacgt    180
catccagccg ctcgtgaacg tttcctgaac gaaattgcgt cctcctccgt cttcgaacgt    240
ttgcgtcacg atgataatga agccttcgag accttcttgg aagaacgtgt tcactgtatt    300
accggtgagg ttactgaatc ccgttttggt ttgacacctg aacgttttcg tgctttggcc    360
ggtcaggttg acgcttttat taacagcgct gcaagcgtga actttcgtga ggaattggat    420
aaagccctga aaatcaacac cttgtgtctt gaaatgttg ctgctcttgc agaattgaac    480
tccgctatgg cggtcattca ggtttccact tgttacgtta acggtaaaaa ctccggtcaa    540
attaccgaat ccgtcattaa acctgctggc gaatccattc ccgttccac tgacggttac    600 tacgagatcg aagaattggt ccatctgttg caagacaaga tttccgatgt taaagctcgt    660
tactccggca agttctgga gaaaaattg gttgatttgg gtattcgtga ggccaataat    720 tacgatggt ccgacaccta cacattcacc aaatggttgg gtgaacaact gctgatgaag   780
gccttgtctg gtcgttcttt gactattgtg cgtccctcta ttattgagtc cgctttggaa   840
```

```
gaaccttccc ctggttggat cgaaggcgtt aaagttgccg atgccattat cttggcttat    900
gcccgtgaaa aagttagcct gttccctgga aaacgttccg gcattattga tgttattcct    960
gtcgatttgg ttgcgaactc catcatcttg tctctggctg aggcgttgtc tggttctggt   1020
caacgtcgta tttatcaatg ttgcagcggt ggttctaatc caatctccct gggtaagttc   1080
attgattatt tgatggccga ggctaagacc aactatgctg cctacgatca actgttttat   1140
cgtcgtccta ctaaaccttt cgtcgccgtg aaccgtaaat tgtttgacgt tgttgttggt   1200
ggtatgcgtg ttcctctttc tattgccggt aaagctatgc gtttggctgg tcaaaatcgt   1260
gagttgaaag tgcttaagaa ccttgatacg acccgttccc ttgcaaccat ttttggcttc   1320
tatactgctc ccgactatat cttccgtaac gatagcttga tggccctggc ttctcgtatg   1380
ggtgaattgg atcgtgttct tttcccagtt gatgctcgtc aaattgattg gcagttgtac   1440
ttgtgtaaaa ttcatttggg tggtctgaac cgttacgctt gaaggaacg taaactgtat   1500
tctttgcgtg ctgctgatac tcgtaaaaaa gctgcctaa                          1539

<210> SEQ ID NO 2
<211> LENGTH: 512
<212> TYPE: PRT
<213> ORGANISM: Marinobacter algicola

<400> SEQUENCE: 2

Met Ala Thr Gln Gln Gln Asn Gly Ala Ser Ala Ser Gly Val Leu
1               5                   10                  15

Glu Gln Leu Arg Gly Lys His Val Leu Ile Thr Gly Thr Thr Gly Phe
            20                  25                  30

Leu Gly Lys Val Val Leu Glu Lys Leu Ile Arg Thr Val Pro Asp Ile
        35                  40                  45

Gly Gly Ile His Leu Leu Ile Arg Gly Asn Lys Arg His Pro Ala Ala
    50                  55                  60

Arg Glu Arg Phe Leu Asn Glu Ile Ala Ser Ser Val Phe Glu Arg
65                  70                  75                  80

Leu Arg His Asp Asp Asn Glu Ala Phe Glu Thr Phe Leu Glu Arg
                85                  90                  95

Val His Cys Ile Thr Gly Glu Val Thr Glu Ser Arg Phe Gly Leu Thr
            100                 105                 110

Pro Glu Arg Phe Arg Ala Leu Ala Gly Gln Val Asp Ala Phe Ile Asn
        115                 120                 125

Ser Ala Ala Ser Val Asn Phe Arg Glu Glu Leu Asp Lys Ala Leu Lys
    130                 135                 140

Ile Asn Thr Leu Cys Leu Glu Asn Val Ala Ala Leu Ala Glu Leu Asn
145                 150                 155                 160

Ser Ala Met Ala Val Ile Gln Val Ser Thr Cys Tyr Val Asn Gly Lys
                165                 170                 175

Asn Ser Gly Gln Ile Thr Glu Ser Val Ile Lys Pro Ala Gly Glu Ser
            180                 185                 190

Ile Pro Arg Ser Thr Asp Gly Tyr Tyr Glu Ile Glu Glu Leu Val His
        195                 200                 205

Leu Leu Gln Asp Lys Ile Ser Asp Val Lys Ala Arg Tyr Ser Gly Lys
    210                 215                 220

Val Leu Glu Lys Lys Leu Val Asp Leu Gly Ile Arg Glu Ala Asn Asn
225                 230                 235                 240

Tyr Gly Trp Ser Asp Thr Tyr Thr Phe Thr Lys Trp Leu Gly Glu Gln
```

```
                 245                 250                 255
Leu Leu Met Lys Ala Leu Ser Gly Arg Ser Leu Thr Ile Val Arg Pro
            260                 265                 270

Ser Ile Ile Glu Ser Ala Leu Glu Glu Pro Ser Pro Gly Trp Ile Glu
        275                 280                 285

Gly Val Lys Val Ala Asp Ala Ile Ile Leu Ala Tyr Ala Arg Glu Lys
    290                 295                 300

Val Ser Leu Phe Pro Gly Lys Arg Ser Gly Ile Ile Asp Val Ile Pro
305                 310                 315                 320

Val Asp Leu Val Ala Asn Ser Ile Ile Leu Ser Leu Ala Glu Ala Leu
                325                 330                 335

Ser Gly Ser Gly Gln Arg Arg Ile Tyr Gln Cys Cys Ser Gly Gly Ser
            340                 345                 350

Asn Pro Ile Ser Leu Gly Lys Phe Ile Asp Tyr Leu Met Ala Glu Ala
        355                 360                 365

Lys Thr Asn Tyr Ala Ala Tyr Asp Gln Leu Phe Tyr Arg Arg Pro Thr
    370                 375                 380

Lys Pro Phe Val Ala Val Asn Arg Lys Leu Phe Asp Val Val Gly
385                 390                 395                 400

Gly Met Arg Val Pro Leu Ser Ile Ala Gly Lys Ala Met Arg Leu Ala
                405                 410                 415

Gly Gln Asn Arg Glu Leu Lys Val Leu Lys Asn Leu Asp Thr Thr Arg
            420                 425                 430

Ser Leu Ala Thr Ile Phe Gly Phe Tyr Thr Ala Pro Asp Tyr Ile Phe
        435                 440                 445

Arg Asn Asp Ser Leu Met Ala Leu Ala Ser Arg Met Gly Glu Leu Asp
    450                 455                 460

Arg Val Leu Phe Pro Val Asp Ala Arg Gln Ile Asp Trp Gln Leu Tyr
465                 470                 475                 480

Leu Cys Lys Ile His Leu Gly Gly Leu Asn Arg Tyr Ala Leu Lys Glu
                485                 490                 495

Arg Lys Leu Tyr Ser Leu Arg Ala Ala Asp Thr Arg Lys Lys Ala Ala
            500                 505                 510

<210> SEQ ID NO 3
<211> LENGTH: 1539
<212> TYPE: DNA
<213> ORGANISM: Artificial Sequence
<220> FEATURE:
<223> OTHER INFORMATION: Synthetic DNA encoding M. algicola DG893 FAR
      codon optimized for expression in Yarrowia lipolytia

<400> SEQUENCE: 3
atggccaccc agcagcagca gaacggtgca tccgcttcgg gcgttctgga gcagcttaga      60
ggcaagcatg tcttgattac cggtactaca ggatttctgg aaaggtggt tctggagaag     120 ctgatccgaa ccgtgcctga catcggtggt attcatctgc tgattagagg caacaagaga     180
catcctgctg ccagagaaag attcttgaac gaaatcgcct cttcctctgt gttcgagcgg     240
cttagacatg acgacaacga agcctttgag actttcctgg aggagcgtgt gcactgcatc     300
accggagaag tgaccgagtc gagatttggc cttactcctg agcggttccg agcccttgct     360
ggccaagtgg atgccttcat caattccgcc gcctctgtta acttcagaga ggagctggac     420
aaggcactca gatcaacac cctgtgtctg gagaacgtgg ctgctctggc cgaacttaac     480
tccgctatgg cagtgatcca gtttccacc tgttacgtga acggcaagaa ctctggacag     540
```

```
atcaccgagt ccgttatcaa gcccgctggc gaatccatcc ccagatccac agatggctac    600
tacgagatcg aggagctggt ccaccttctg caagacaaga tctccgacgt gaaggctcga    660
tactctggca aggtgttgga gaagaagctg gtggacctgg gcatccgaga ggcgaacaac    720
tacggctggt ctgacaccta caccttcacc aaatggctcg gagagcagct tctgatgaaa    780
gctctgtccg gaagatccct gactatcgtg cggccttcca tcatcgagtc ggctcttgaa    840
gagccttctc caggttggat cgagggcgtg aaggttgctg acgccatcat ccttgcgtac    900
gccagagaga aggtttcgtt gttccccggc aagcgatctg gcatcatcga cgttatcccc    960
gtggatctgg tggccaactc tatcattctc tctcttgctg aagccctttc tggatctggc   1020
cagcgtagaa tctaccaatg ttgttctggc ggttctaacc cgatttctct gggcaagttc   1080
atcgactacc ttatggccga agccaagacc aactatgctg cctacgacca gctcttctac   1140
cgacgaccca ccaagccctt cgtcgctgtg aaccgaaagc tgttcgatgt tgtcgtggga   1200
ggaatgcgag tgcctctttc cattgctggc aaggccatga gattggcggg tcagaatcga   1260
gaattgaagg ttctcaagaa ccttgacact actcgatcgc tcgctactat ctttggattc   1320
tacactgctc ctgactacat cttccggaat gactctctga tggctcttgc ttcccgaatg   1380
ggagaactcg atcgtgtgct gttccctgtt gacgctcgac agatcgactg gcagctctac   1440
ttgtgtaaga tccacctggg cggcctgaac cgatatgctc tgaaagaacg aaagctgtac   1500
agccttagag ccgctgatac ccgaaagaag gctgcttaa                          1539
```

<210> SEQ ID NO 4
<211> LENGTH: 1542
<212> TYPE: DNA
<213> ORGANISM: Artificial Sequence
<220> FEATURE:
<223> OTHER INFORMATION: Synthetic DNA encoding M. aquaeolei FAR codon optimized for expression

<400> SEQUENCE: 4

```
atggctatcc agcaggttca tcacgccgac acatcctcct ctaaagtcct gggtcaactt     60
cgtggtaaac gtgtcttgat taccggcact actggattct tgggtaaagt cgtcttggaa    120
cgtttgattc gtgccgttcc tgacatcggt gctatctacc tgctgattcg tggtaacaag    180
cgtcacccgg atgctcgttc tcgtttcttg gaggagattg ctacctcctc tgtctttgat    240
cgtttgcgtg aagctgattc cgaaggtttc gatgctttcc tggaagaacg tattcactgt    300
gttactggtg aagttactga agctggtttc ggtattggtc aagaggacta tcgtaagttg    360
gccaccgaat tggacgcagt catcaattct gctgcctccg tcaacttccg tgaggagttg    420
gataaggctc tggccatcaa cactctgtgt ttgcgtaaca tcgctggtat ggtggatctt    480
aaccctaagc tggccgttct tcaagtctct acgtgttacg tcaacggtat gaactctggt    540
caagttactg aatccgtcat caaaccagct ggtgaagctg ttcctcgttc tcctgatgga    600
ttctacgaga tcgaggaatt ggttcgtctg ctgcaagaca agattgaaga cgttcaagca    660
cgttactctg gtaaggtgtt ggagcgtaag ttggttgatt tgggtattcg tgaggctaat    720
cgttacggtt ggtctgatac atacaccttc acgaaatggt tgggtgaaca acttctgatg    780
aaagccttga atggtcgtac cttgactatt ctgcgtccta gcatcattga atctgctttg    840
gaagaaccag cacctggttg gattgaaggc gtgaaagttg cagatgcgat catcttggct    900
tatgctcgtg agaaggttac tttgtttccg ggtaaacgtt ctggtatcat tgatgtgatt    960
cctgttgact tggttgccaa ttccatcatc ttgtctttgg ctgaggctct gggcgaacct   1020
```

```
ggtcgtcgtc gtatctacca atgttgttct ggtggtggta atcctatctc cctgggcgag   1080
ttcattgatc acctgatggc tgaatccaaa gccaactatg ccgcatacga tcatctgttc   1140
taccgtcaac cctccaagcc tttccttgct gtcaaccgtg ctttgttcga cttggttatc   1200
tctggtgtcc gtctgccttt gtctttgacc gaccgtgtct tgaagctgct gggcaactcc   1260
cgtgacctga agatgctgcg taacctggat actacgcaat cctggctac tatctttggc   1320 ttctacacag cccccgacta catcttccgt aatgacgagt tgatggccct ggctaaccgt   1380
atgggcgagg ttgataaggg tttgttcccc gttgatgctc gtctgattga ttgggaattg   1440
tacctgcgta agattcacct ggctggtttg aaccgttacg ccttgaagga gcgtaaggtt   1500
tactctttga agacagcccg tcagcgtaag aaggcagctt aa                      1542
```

<210> SEQ ID NO 5
<211> LENGTH: 513
<212> TYPE: PRT
<213> ORGANISM: Marinobacter aquaeolei

<400> SEQUENCE: 5

```
Met Ala Ile Gln Gln Val His His Ala Asp Thr Ser Ser Ser Lys Val
1               5                   10                  15

Leu Gly Gln Leu Arg Gly Lys Arg Val Leu Ile Thr Gly Thr Thr Gly
                20                  25                  30

Phe Leu Gly Lys Val Val Leu Glu Arg Leu Ile Arg Ala Val Pro Asp
            35                  40                  45

Ile Gly Ala Ile Tyr Leu Leu Ile Arg Gly Asn Lys Arg His Pro Asp
        50                  55                  60

Ala Arg Ser Arg Phe Leu Glu Glu Ile Ala Thr Ser Ser Val Phe Asp
65                  70                  75                  80

Arg Leu Arg Glu Ala Asp Ser Glu Gly Phe Asp Ala Phe Leu Glu Glu
                85                  90                  95

Arg Ile His Cys Val Thr Gly Glu Val Thr Glu Ala Gly Phe Gly Ile
            100                 105                 110

Gly Gln Glu Asp Tyr Arg Lys Leu Ala Thr Glu Leu Asp Ala Val Ile
        115                 120                 125

Asn Ser Ala Ala Ser Val Asn Phe Arg Glu Glu Leu Asp Lys Ala Leu
    130                 135                 140

Ala Ile Asn Thr Leu Cys Leu Arg Asn Ile Ala Gly Met Val Asp Leu
145                 150                 155                 160

Asn Pro Lys Leu Ala Val Leu Gln Val Ser Thr Cys Tyr Val Asn Gly
                165                 170                 175

Met Asn Ser Gly Gln Val Thr Glu Ser Val Ile Lys Pro Ala Gly Glu
            180                 185                 190

Ala Val Pro Arg Ser Pro Asp Gly Phe Tyr Glu Ile Glu Glu Leu Val
        195                 200                 205

Arg Leu Leu Gln Asp Lys Ile Glu Asp Val Gln Ala Arg Tyr Ser Gly
    210                 215                 220

Lys Val Leu Glu Arg Lys Leu Val Asp Leu Gly Ile Arg Glu Ala Asn
225                 230                 235                 240

Arg Tyr Gly Trp Ser Asp Thr Tyr Thr Phe Thr Lys Trp Leu Gly Glu
                245                 250                 255

Gln Leu Leu Met Lys Ala Leu Asn Gly Arg Thr Leu Thr Ile Leu Arg
            260                 265                 270

Pro Ser Ile Ile Glu Ser Ala Leu Glu Glu Pro Ala Pro Gly Trp Ile
        275                 280                 285
```

Glu Gly Val Lys Val Ala Asp Ala Ile Ile Leu Ala Tyr Ala Arg Glu
        290                 295                 300

Lys Val Thr Leu Phe Pro Gly Lys Arg Ser Gly Ile Ile Asp Val Ile
305                 310                 315                 320

Pro Val Asp Leu Val Ala Asn Ser Ile Ile Leu Ser Leu Ala Glu Ala
                325                 330                 335

Leu Gly Glu Pro Gly Arg Arg Arg Ile Tyr Gln Cys Cys Ser Gly Gly
                340                 345                 350

Gly Asn Pro Ile Ser Leu Gly Glu Phe Ile Asp His Leu Met Ala Glu
                355                 360                 365

Ser Lys Ala Asn Tyr Ala Ala Tyr Asp His Leu Phe Tyr Arg Gln Pro
        370                 375                 380

Ser Lys Pro Phe Leu Ala Val Asn Arg Ala Leu Phe Asp Leu Val Ile
385                 390                 395                 400

Ser Gly Val Arg Leu Pro Leu Ser Leu Thr Asp Arg Val Leu Lys Leu
                405                 410                 415

Leu Gly Asn Ser Arg Asp Leu Lys Met Leu Arg Asn Leu Asp Thr Thr
                420                 425                 430

Gln Ser Leu Ala Thr Ile Phe Gly Phe Tyr Thr Ala Pro Asp Tyr Ile
        435                 440                 445

Phe Arg Asn Asp Glu Leu Met Ala Leu Ala Asn Arg Met Gly Glu Val
450                 455                 460

Asp Lys Gly Leu Phe Pro Val Asp Ala Arg Leu Ile Asp Trp Glu Leu
465                 470                 475                 480

Tyr Leu Arg Lys Ile His Leu Ala Gly Leu Asn Arg Tyr Ala Leu Lys
                485                 490                 495

Glu Arg Lys Val Tyr Ser Leu Lys Thr Ala Arg Gln Arg Lys Lys Ala
                500                 505                 510

Ala

<210> SEQ ID NO 6
<211> LENGTH: 512
<212> TYPE: PRT
<213> ORGANISM: Artificial Sequence
<220> FEATURE:
<223> OTHER INFORMATION: Synthetic polypeptide of FAR Maa variant 370

<400> SEQUENCE: 6

Met Ala Thr Gln Gln Gln Asn Gly Ala Ser Ala Ser Gly Val Leu
1               5                   10                  15

Glu Gln Leu Arg Gly Lys His Val Leu Ile Thr Gly Thr Thr Gly Phe
                20                  25                  30

Leu Gly Lys Val Val Leu Glu Lys Leu Ile Arg Thr Val Pro Asp Ile
        35                  40                  45

Gly Gly Ile His Leu Leu Ile Arg Gly Asn Lys Arg His Pro Ala Ala
    50                  55                  60

Arg Glu Arg Phe Leu Asn Glu Ile Ala Ser Ser Ser Val Phe Glu Arg
65                  70                  75                  80

Leu Arg His Asp Asp Asn Glu Ala Phe Glu Thr Phe Leu Glu Glu Arg
                85                  90                  95

Val His Cys Ile Thr Gly Glu Val Thr Glu Ser Arg Phe Gly Leu Thr
                100                 105                 110

Pro Glu Arg Phe Arg Ala Leu Ala Gly Gln Val Asp Ala Phe Ile Asn
        115                 120                 125

```
Ser Ala Ala Ser Val Ser Phe Arg Glu Gln Leu Asp Lys Ala Leu Lys
    130                 135                 140
Ile Asn Thr Leu Cys Leu Glu Asn Val Ala Ala Leu Ala Glu Leu Asn
145                 150                 155                 160
Ser Ala Met Ala Val Ile Gln Val Ser Thr Cys Tyr Val Asn Gly Lys
                165                 170                 175
Asn Ser Gly Gln Ile Thr Glu Ser Val Ile Lys Ser Ala Gly Glu Ser
            180                 185                 190
Ile Pro Arg Ser Thr Asp Gly Tyr Tyr Glu Ile Glu Leu Val His
        195                 200                 205
Leu Leu Gln Asp Lys Ile Ser Asp Val Lys Ala Arg Tyr Ser Gly Lys
    210                 215                 220
Val Leu Glu Lys Lys Leu Val Asp Leu Gly Ile Arg Glu Ala Asn Asn
225                 230                 235                 240
Tyr Gly Trp Ser Asp Thr Tyr Thr Phe Thr Lys Trp Leu Gly Glu Gln
                245                 250                 255
Leu Leu Met Lys Ala Leu Ser Gly Arg Ser Leu Thr Ile Val Arg Pro
            260                 265                 270
Ser Ile Ile Glu Ser Ala Leu Glu Glu Pro Ser Pro Gly Trp Ile Glu
    275                 280                 285
Gly Val Lys Val Ala Asp Ala Ile Leu Ala Tyr Ala Arg Glu Lys
290                 295                 300
Val Ser Leu Phe Pro Gly Lys Arg Ser Gly Ile Ile Asp Val Ile Pro
305                 310                 315                 320
Val Asp Leu Val Ala Asn Ser Ile Ile Leu Ser Leu Ala Glu Ala Leu
                325                 330                 335
Ser Gly Ser Gly Gln Arg Arg Ile Tyr Gln Cys Cys Ser Gly Gly Ser
            340                 345                 350
Asn Pro Ile Ser Leu Gly Lys Phe Ile Asp Tyr Leu Met Ala Glu Ala
    355                 360                 365
Lys Thr Asn Tyr Ala Ala Tyr Asp Gln Leu Phe Tyr Arg Arg Pro Thr
370                 375                 380
Lys Pro Phe Val Ala Val Asn Arg Lys Leu Phe Asp Val Val Gly
385                 390                 395                 400
Gly Met Arg Val Val Leu Ser Ile Ala Gly Lys Ala Met Arg Leu Ala
                405                 410                 415
Gly Val Asn Arg Glu Leu Lys Val Leu Lys Asn Leu Asp Thr Thr Arg
            420                 425                 430
Ser Leu Ala Thr Ile Phe Gly Phe Tyr Thr Ala Pro Asp Tyr Ile Phe
    435                 440                 445
Arg Asn Asp Ser Leu Met Ala Leu Ala Ser Arg Met Gly Glu Leu Asp
450                 455                 460
Arg Val Leu Phe Pro Val Asp Ala Arg Gln Ile Asp Trp Gln Leu Tyr
465                 470                 475                 480
Leu Cys Lys Ile His Leu Gly Gly Leu Asn Arg Tyr Ala Leu Lys Glu
                485                 490                 495
Arg Lys Leu Tyr Ser Leu Arg Ala Ala Asp Thr Arg Lys Lys Thr Ala
            500                 505                 510

<210> SEQ ID NO 7
<211> LENGTH: 512
<212> TYPE: PRT
<213> ORGANISM: Artificial Sequence
<220> FEATURE:
<223> OTHER INFORMATION: Synthetic polypeptide of FAR Ma

<400> SEQUENCE: 7

```
Met Ala Thr Gln Gln Gln Gln Asn Gly Ala Ser Ala Ser Gly Val Leu
1               5                   10                  15

Glu Gln Leu Arg Gly Lys His Val Leu Ile Thr Gly Thr Thr Gly Phe
            20                  25                  30

Leu Gly Lys Val Val Leu Glu Lys Leu Ile Arg Thr Val Pro Asp Ile
        35                  40                  45

Gly Gly Ile His Leu Leu Ile Arg Gly Asn Lys Arg His Pro Ala Ala
    50                  55                  60

Arg Glu Arg Phe Leu Asn Glu Ile Ala Ser Ser Val Phe Glu Arg
65              70                  75                  80

Leu Arg His Asp Asp Asn Glu Ala Phe Glu Thr Phe Leu Glu Glu Arg
                85                  90                  95

Val His Cys Ile Thr Gly Glu Val Thr Glu Ser Arg Phe Gly Leu Thr
                100                 105                 110

Pro Glu Arg Phe Arg Ala Leu Ala Gly Gln Val Asp Ala Phe Ile Asn
            115                 120                 125

Ser Ala Ala Ser Val Ser Phe Arg Glu Gln Leu Asp Lys Ala Leu Lys
    130                 135                 140

Ile Asn Thr Leu Cys Leu Glu Asn Val Ala Ala Leu Ala Glu Leu Asn
145                 150                 155                 160

Ser Ala Met Ala Val Ile Gln Val Ser Thr Cys Tyr Val Asn Gly Lys
                165                 170                 175

Asn Ser Gly Gln Ile Thr Glu Ser Val Ile Lys Ser Ala Gly Glu Ser
            180                 185                 190

Ile Pro Arg Ser Thr Asp Gly Tyr Tyr Glu Ile Glu Glu Leu Val His
        195                 200                 205

Leu Leu Gln Asp Lys Ile Ser Asp Val Lys Ala Arg Tyr Ser Gly Lys
    210                 215                 220

Val Leu Glu Lys Lys Leu Val Asp Leu Gly Ile Arg Glu Ala Asn Asn
225                 230                 235                 240

Tyr Gly Trp Ser Asp Thr Tyr Thr Phe Thr Lys Trp Leu Gly Glu Gln
                245                 250                 255

Leu Leu Met Lys Ala Leu Ser Gly Arg Ser Leu Thr Ile Val Arg Pro
            260                 265                 270

Ser Ile Ile Glu Ser Ala Leu Glu Glu Pro Ser Pro Gly Trp Ile Glu
        275                 280                 285

Gly Val Lys Val Ala Asp Ala Ile Ile Leu Ala Tyr Ala Arg Glu Lys
    290                 295                 300

Val Ser Leu Phe Pro Gly Lys Arg Ser Gly Ile Ile Asp Val Ile Pro
305                 310                 315                 320

Val Asp Leu Val Ala Asn Ser Ile Ile Leu Ser Leu Ala Glu Ala Leu
                325                 330                 335

Ser Gly Ser Gly Gln Arg Arg Ile Tyr Gln Cys Cys Ser Gly Gly Ser
            340                 345                 350

Asn Pro Ile Ser Leu Gly Lys Phe Ile Asp Tyr Leu Met Ala Glu Ala
        355                 360                 365

Lys Thr Asn Tyr Ala Ala Tyr Asp Gln Leu Phe Tyr Arg Arg Pro Thr
    370                 375                 380

Lys Pro Phe Val Ala Val Asn Arg Lys Leu Phe Asp Val Val Val Gly
385                 390                 395                 400

Gly Met Arg Val Val Leu Ser Ile Ala Gly Lys Ala Met Arg Leu Ala
```

```
            405                 410                 415
Gly Val Asn Arg Glu Leu Lys Val Leu Lys Asn Leu Asp Thr Thr Arg
            420                 425                 430

Ser Leu Ala Thr Ile Phe Gly Phe Tyr Thr Ala Pro Asp Tyr Ile Phe
            435                 440                 445

Arg Asn Asp Ser Leu Met Ala Leu Ala Gln Arg Met Gly Glu Leu Asp
    450                 455                 460

Arg Val Leu Phe Pro Val Asp Ala Arg Gln Ile Asp Trp Gln Leu Tyr
465                 470                 475                 480

Leu Cys Lys Ile His Leu Gly Gly Leu Asn Arg Tyr Ala Leu Lys Glu
                485                 490                 495

Arg Lys Leu Tyr Ser Ser Arg Ala Ala Asp Thr Asp Lys Thr Ala
            500                 505                 510
```

<210> SEQ ID NO 8
<211> LENGTH: 512
<212> TYPE: PRT
<213> ORGANISM: Artificial Sequence
<220> FEATURE:
<223> OTHER INFORMATION: Synthetic polypeptide of FAR Maa variant 436

<400> SEQUENCE: 8

```
Met Ala Thr Gln Gln Gln Asn Gly Ala Ser Ala Ser Gly Val Leu
1               5                   10                  15

Glu Gln Leu Arg Gly Lys His Val Leu Ile Thr Gly Thr Thr Gly Phe
                20                  25                  30

Leu Gly Lys Val Val Leu Glu Lys Leu Ile Arg Thr Val Pro Asp Ile
            35                  40                  45

Gly Gly Ile His Leu Leu Ile Arg Gly Asn Lys Arg His Pro Ala Ala
    50                  55                  60

Arg Glu Arg Phe Leu Asn Glu Ile Ala Ser Ser Val Phe Glu Arg
65                  70                  75                  80

Leu Arg His Asp Asp Asn Glu Ala Phe Glu Thr Phe Leu Glu Glu Arg
                85                  90                  95

Val His Cys Ile Thr Gly Glu Val Thr Glu Ser Arg Phe Gly Leu Thr
            100                 105                 110

Pro Glu Arg Phe Arg Ala Leu Ala Gly Gln Val Asp Ala Phe Ile Asn
            115                 120                 125

Ser Ala Ala Ser Val Ser Phe Arg Glu Gln Leu Asp Lys Ala Leu Lys
    130                 135                 140

Ile Asn Thr Leu Cys Leu Glu Asn Val Ala Ala Leu Ala Glu Leu Asn
145                 150                 155                 160

Ser Ala Met Ala Val Ile Gln Val Ser Thr Cys Tyr Val Asn Gly Lys
                165                 170                 175

Asn Ser Gly Gln Ile Thr Glu Ser Val Ile Lys Ser Ala Gly Glu Ser
            180                 185                 190

Ile Pro Arg Ser Thr Asp Gly Tyr Tyr Glu Ile Glu Glu Leu Val His
    195                 200                 205

Leu Leu Gln Asp Lys Ile Ser Asp Val Lys Ala Arg Tyr Ser Gly Lys
    210                 215                 220

Val Leu Glu Lys Lys Leu Val Asp Leu Gly Ile Arg Glu Ala Asn Asn
225                 230                 235                 240

Tyr Gly Trp Ser Asp Thr Tyr Thr Phe Thr Lys Trp Leu Gly Glu Gln
                245                 250                 255

Leu Leu Met Lys Ala Leu Ser Gly Arg Ser Leu Thr Ile Val Arg Pro
```

-continued

```
                260                 265                 270
Ser Ile Ile Glu Ser Ala Leu Glu Glu Pro Ser Pro Gly Trp Ile Glu
            275                 280                 285

Gly Val Lys Val Ala Asp Ala Ile Ile Leu Ala Tyr Ala Arg Glu Lys
        290                 295                 300

Val Ser Leu Phe Pro Gly Lys Arg Ser Gly Ile Ile Asp Val Ile Pro
305                 310                 315                 320

Val Asp Leu Val Ala Asn Ser Ile Ile Leu Ser Leu Ala Glu Ala Leu
                325                 330                 335

Ser Gly Ser Gly Gln Arg Arg Ile Tyr Gln Cys Cys Ser Gly Gly Ser
            340                 345                 350

Asn Pro Ile Ser Leu Gly Lys Phe Ile Asp Tyr Leu Met Ala Glu Ala
        355                 360                 365

Lys Thr Asn Tyr Ala Ala Tyr Asp Lys Leu Phe Tyr Arg Arg Pro Thr
    370                 375                 380

Lys Pro Phe Val Ala Val Asn Arg Lys Leu Phe Asp Val Val Val Gly
385                 390                 395                 400

Gly Met Arg Val Val Leu Ser Ile Ala Gly Lys Ala Met Arg Leu Ala
                405                 410                 415

Gly Val Asn Arg Glu Leu Lys Val Leu Lys Asn Leu Asp Thr Thr Arg
            420                 425                 430

Ser Leu Ala Thr Ile Phe Gly Phe Tyr Thr Ala Pro Asp Tyr Ile Phe
        435                 440                 445

Arg Asn Asp Ser Leu Met Ala Leu Ala Gln Arg Met Gly Glu Leu Asp
    450                 455                 460

Arg Val Leu Phe Pro Val Asp Ala Arg Gln Ile Asp Trp Gln Leu Tyr
465                 470                 475                 480

Leu Cys Lys Ile His Leu Gly Gly Leu Asn Arg Tyr Ala Leu Lys Glu
                485                 490                 495

Arg Lys Leu Tyr Ser Ser Arg Ala Ala Asp Thr Asp Lys Thr Ala
            500                 505                 510
```

<210> SEQ ID NO 9
<211> LENGTH: 512
<212> TYPE: PRT
<213> ORGANISM: Artificial Sequence
<220> FEATURE:
<223> OTHER INFORMATION: Synthetic polypeptide of FAR Maa variant 438

<400> SEQUENCE: 9

```
Met Ala Thr Gln Gln Gln Gln Asn Gly Ala Ser Ala Ser Gly Val Leu
1               5                   10                  15

Glu Gln Leu Arg Gly Lys His Val Leu Ile Thr Gly Thr Thr Gly Phe
            20                  25                  30

Leu Gly Lys Val Val Leu Glu Lys Leu Ile Arg Thr Val Pro Asp Ile
        35                  40                  45

Gly Gly Ile His Leu Leu Ile Arg Gly Asn Lys Arg His Pro Ala Ala
    50                  55                  60

Arg Glu Arg Phe Leu Asn Glu Ile Ala Ser Ser Val Phe Glu Arg
65                  70                  75                  80

Leu Arg His Asp Asp Asn Glu Ala Phe Glu Thr Phe Leu Glu Glu Arg
                85                  90                  95

Val His Cys Ile Thr Gly Glu Val Thr Glu Ser Arg Phe Gly Leu Thr
            100                 105                 110

Pro Glu Arg Phe Arg Ala Leu Ala Gly Gln Val Asp Ala Phe Ile Asn
```

```
            115                 120                 125
Ser Ala Ala Ser Val Ser Phe Arg Glu Gln Leu Asp Lys Ala Leu Lys
130                 135                 140

Ile Asn Thr Leu Cys Leu Glu Asn Val Ala Ala Leu Ala Glu Leu Asn
145                 150                 155                 160

Ser Ala Met Ala Val Ile Gln Val Ser Thr Cys Tyr Val Asn Gly Lys
                165                 170                 175

Asn Ser Gly Gln Ile Thr Glu Ser Val Ile Lys Ser Ala Gly Glu Ser
            180                 185                 190

Ile Pro Arg Ser Thr Asp Gly Tyr Tyr Glu Ile Glu Glu Leu Val His
        195                 200                 205

Leu Leu Gln Asp Lys Ile Ser Asp Val Lys Ala Arg Tyr Ser Gly Lys
    210                 215                 220

Val Leu Glu Lys Lys Leu Val Asp Leu Gly Ile Arg Glu Ala Asn Asn
225                 230                 235                 240

Tyr Gly Trp Ser Asp Thr Tyr Thr Phe Thr Lys Trp Leu Gly Glu Gln
                245                 250                 255

Leu Leu Met Lys Ala Leu Ser Gly Arg Ser Leu Thr Ile Val Arg Pro
            260                 265                 270

Ser Ile Ile Glu Ser Ala Leu Glu Glu Pro Ser Pro Gly Trp Ile Glu
        275                 280                 285

Gly Val Lys Val Ala Asp Ala Ile Ile Leu Ala Tyr Ala Arg Glu Lys
    290                 295                 300

Val Ser Leu Phe Pro Gly Lys Arg Ser Gly Ile Ile Asp Val Ile Pro
305                 310                 315                 320

Val Asp Leu Val Ala Asn Ser Ile Ile Leu Ser Leu Ala Glu Ala Leu
                325                 330                 335

Ser Gly Ser Gly Gln Arg Arg Ile Tyr Gln Cys Cys Ser Gly Gly Ser
            340                 345                 350

Asn Pro Ile Ser Leu Gly Lys Phe Ile Asp Tyr Leu Met Ala Glu Ala
        355                 360                 365

Lys Thr Asn Tyr Ala Ala Tyr Asp Gln Leu Phe Tyr Arg Arg Pro Thr
    370                 375                 380

Lys Pro Phe Val Ala Val Asn Arg Lys Leu Phe Asp Val Val Gly
385                 390                 395                 400

Gly Met Arg Val Val Leu Ser Ile Ala Gly Lys Ala Met Arg Leu Ala
                405                 410                 415

Gly Val Asn Arg Glu Leu Lys Val Leu Lys Asn Leu Asp Thr Thr Arg
            420                 425                 430

Lys Leu Ala Thr Ile Phe Gly Phe Tyr Thr Ala Pro Asp Tyr Ile Phe
        435                 440                 445

Arg Asn Asp Ser Leu Met Ala Leu Ala Gln Arg Met Gly Glu Leu Asp
    450                 455                 460

Arg Val Leu Phe Pro Val Asp Ala Arg Gln Ile Asp Trp Gln Leu Tyr
465                 470                 475                 480

Leu Cys Lys Ile His Leu Gly Gly Leu Asn Arg Tyr Ala Leu Lys Glu
                485                 490                 495

Arg Lys Leu Tyr Ser Ser Arg Ala Ala Asp Thr Asp Lys Thr Ala
            500                 505                 510

<210> SEQ ID NO 10
<211> LENGTH: 512
<212> TYPE: PRT
<213> ORGANISM: Artificial Sequence
```

<220> FEATURE:
<223> OTHER INFORMATION: Synthetic polypeptide of FAR Maa variant 547

<400> SEQUENCE: 10

```

```
Gly Met Arg Val Val Leu Ser Ile Ala Gly Lys Ala Met Arg Leu Ala
                405                 410                 415
Gly Val Asn Arg Glu Leu Lys Val Leu Lys Asn Leu Asp Thr Thr Arg
            420                 425                 430
Lys Leu Ala Thr Ile Phe Gly Phe Tyr Thr Ala Pro Asp Tyr Ile Phe
        435                 440                 445
Arg Asn Asp Ser Leu Met Ala Leu Ala Gln Arg Met Gly Glu Leu Asp
450                 455                 460
Arg Val Leu Phe Pro Val Asp Ala Arg Gln Ile Asp Trp Gln Leu Tyr
465                 470                 475                 480
Leu Cys Lys Ile His Leu Gly Gly Leu Asn Arg Tyr Ala Leu Lys Glu
                485                 490                 495
Arg Lys Leu Tyr Ser Ser Arg Ala Ala Asp Thr Asp Asp Lys Thr Ala
                500                 505                 510

<210> SEQ ID NO 11
<211> LENGTH: 511
<212> TYPE: PRT
<213> ORGANISM: Artificial Sequence
<220> FEATURE:
<223> OTHER INFORMATION: Synthetic polypeptide of FAR Maa variant 555

<400> SEQUENCE: 11

Met Ala Thr Gln Gln Gln Gln Asn Gly Ala Ser Ala Ser Gly Val Leu
1               5                   10                  15
Glu Ile Leu Arg Gly Lys His Val Leu Ile Thr Gly Thr Thr Gly Phe
            20                  25                  30
Leu Gly Lys Val Val Leu Glu Lys Leu Ile Arg Thr Val Pro Asp Ile
        35                  40                  45
Gly Gly Ile His Leu Leu Ile Arg Gly Asn Lys Arg His Pro Arg Ala
    50                  55                  60
Gly Glu Arg Phe Leu Asn Glu Ile Ala Ser Ser Val Phe Glu Arg
65                  70                  75                  80
Leu Arg His Asp Asp Asn Glu Ala Phe Glu Thr Phe Leu Glu Glu Arg
                85                  90                  95
Val His Cys Ile Thr Gly Glu Val Thr Glu Ser Arg Phe Gly Leu Thr
            100                 105                 110
Pro Glu Arg Phe Arg Ala Leu Ala Gly Gln Val Asp Ala Phe Ile His
        115                 120                 125
Ser Ala Ala Ser Val Ser Phe Arg Glu Gln Leu Asp Lys Ala Leu Lys
    130                 135                 140
Ile Asn Thr Leu Cys Leu Glu Asn Val Ala Ala Leu Ala Glu Leu Asn
145                 150                 155                 160
Ser Ala Met Ala Val Ile Gln Val Ser Thr Cys Tyr Val Asn Gly Lys
                165                 170                 175
Asn Ser Gly Gln Ile Thr Glu Ser Val Ile Lys Ser Ala Gly Glu Ser
            180                 185                 190
Ile Pro Arg Ser Thr Asp Gly Tyr Tyr Glu Ile Glu Glu Leu Val His
        195                 200                 205
Leu Leu Gln Asp Lys Ile Ser Asp Val Lys Ala Arg Tyr Ser Gly Lys
    210                 215                 220
Val Leu Glu Lys Lys Leu Val Asp Leu Gly Ile Arg Glu Ala Asn Asn
225                 230                 235                 240
Tyr Gly Trp Ser Asp Thr Tyr Thr Phe Thr Lys Trp Leu Gly Glu Gln
                245                 250                 255
```

Leu Leu Met Lys Ala Leu Ser Gly Arg Ser Leu Thr Ile Val Arg Pro
            260                 265                 270

Ser Ile Ile Glu Ser Ala Leu Glu Glu Pro Ser Pro Gly Trp Ile Glu
        275                 280                 285

Gly Val Lys Val Ala Asp Ala Ile Ile Leu Ala Tyr Ala Arg Glu Lys
    290                 295                 300

Val Ser Leu Phe Pro Gly Lys Arg Ser Gly Ile Ile Asp Val Ile Pro
305                 310                 315                 320

Val Asp Leu Val Ala Asn Ser Ile Ile Leu Ser Leu Ala Glu Ala Leu
                325                 330                 335

Ser Gly Ser Gly Gln Arg Arg Ile Tyr Gln Cys Cys Ser Gly Gly Ser
            340                 345                 350

Asn Pro Ile Ser Leu Gly Lys Phe Ile Asp Tyr Leu Met Ala Glu Ala
        355                 360                 365

Lys Thr Asn Tyr Ala Ala Tyr Asp Gln Leu Phe Tyr Arg Arg Pro Thr
    370                 375                 380

Lys Pro Phe Val Ala Val Asn Arg Lys Leu Phe Asp Val Val Val Gly
385                 390                 395                 400

Gly Met Arg Val Val Leu Ser Ile Ala Gly Lys Ala Met Arg Leu Ala
                405                 410                 415

Gly Val Asn Arg Glu Leu Lys Val Leu Lys Asn Leu Asp Thr Thr Arg
            420                 425                 430

Lys Leu Ala Thr Ile Phe Gly Phe Tyr Thr Ala Pro Asp Tyr Ile Phe
        435                 440                 445

Arg Asn Asp Ser Leu Met Ala Leu Ala Gln Arg Met Gly Glu Leu Asp
    450                 455                 460

Arg Val Leu Phe Pro Val Asp Ala Arg Gln Ile Asp Trp Gln Leu Tyr
465                 470                 475                 480

Leu Cys Lys Ile His Leu Arg Gly Leu Asn Arg Tyr Ala Leu Lys Glu
                485                 490                 495

Arg Lys Leu Tyr Ser Ser Arg Ala Ala Asp Thr Asp Lys Thr
            500                 505                 510

<210> SEQ ID NO 12
<211> LENGTH: 512
<212> TYPE: PRT
<213> ORGANISM: Artificial Sequence
<220> FEATURE:
<223> OTHER INFORMATION: Synthetic polypeptide of FAR Maa variant 556

<400> SEQUENCE: 12

Met Ala Thr Gln Gln Gln Asn Gly Ala Ser Ala Ser Gly Val Leu
1               5                   10                  15

Glu Ile Leu Arg Gly Lys His Val Leu Ile Thr Gly Thr Thr Gly Phe
            20                  25                  30

Leu Gly Lys Val Val Leu Glu Lys Leu Ile Arg Thr Val Pro Asp Ile
        35                  40                  45

Gly Gly Ile His Leu Leu Ile Arg Gly Asn Lys Arg His Pro Ala Ala
    50                  55                  60

Arg Glu Arg Phe Leu Asn Glu Ile Ala Ser Ser Val Phe Glu Arg
65                  70                  75                  80

Leu Arg His Asp Asp Asn Glu Ala Phe Glu Thr Phe Leu Glu Glu Arg
                85                  90                  95

Val His Cys Ile Thr Gly Glu Val Thr Glu Ser Arg Phe Gly Leu Thr
            100                 105                 110

```
Pro Glu Arg Phe Arg Ala Leu Ala Gly Gln Val Asp Ala Phe Ile His
    115                 120                 125

Ser Ala Ala Ser Val Ser Phe Arg Glu Gln Leu Asp Lys Ala Leu Lys
130                 135                 140

Ile Asn Thr Leu Cys Leu Glu Asn Val Ala Ala Leu Ala Glu Leu Asn
145                 150                 155                 160

Ser Ala Met Ala Val Ile Gln Val Ser Thr Cys Tyr Val Cys Gly Lys
                165                 170                 175

Thr Ser Gly Gln Ile Thr Glu Ser Val Ile Lys Ser Ala Gly Glu Ser
            180                 185                 190

Ile Pro Arg Ser Thr Asp Gly Tyr Tyr Glu Ile Glu Leu Val His
        195                 200                 205

Leu Leu Gln Asp Lys Ile Ser Asp Val Lys Ala Arg Tyr Ser Gly Lys
210                 215                 220

Val Met Glu Lys Lys Leu Val Asp Leu Gly Ile Arg Glu Ala Asn Asn
225                 230                 235                 240

Tyr Gly Trp Ser Asp Thr Tyr Thr Phe Thr Lys Trp Leu Gly Glu Gln
                245                 250                 255

Leu Leu Met Lys Ala Leu Ser Gly Arg Ser Leu Thr Ile Val Arg Pro
            260                 265                 270

Ser Ile Ile Glu Ser Ala Leu Glu Glu Pro Ser Pro Gly Trp Ile Glu
        275                 280                 285

Gly Val Lys Val Ala Asp Ala Ile Ile Leu Ala Tyr Ala Arg Glu Lys
    290                 295                 300

Val Ser Leu Phe Pro Gly Lys Arg Ser Gly Ile Ile Asp Val Ile Pro
305                 310                 315                 320

Val Asp Leu Val Ala Asn Ser Ile Ile Leu Ser Leu Ala Glu Ala Leu
                325                 330                 335

Ser Gly Ser Gly Gln Arg Arg Ile Tyr Gln Cys Cys Ser Gly Cys Ser
            340                 345                 350

Asn Pro Ile Ser Leu Gly Lys Phe Ile Asp Tyr Leu Met Ala Glu Ala
        355                 360                 365

Lys Thr Asn Tyr Ala Ala Tyr Asp Gln Leu Phe Tyr Arg Arg Pro Thr
    370                 375                 380

Lys Pro Phe Val Ala Val Asn Arg Lys Leu Phe Asp Val Val Gly
385                 390                 395                 400

Gly Met Arg Val Val Leu Ser Ile Ala Gly Lys Ala Met Arg Leu Ala
                405                 410                 415

Gly Val Asn Arg Glu Leu Lys Val Leu Lys Asn Leu Asp Thr Thr Arg
            420                 425                 430

Lys Leu Ala Thr Ile Phe Gly Phe Tyr Thr Ala Pro Asp Tyr Ile Phe
        435                 440                 445

Arg Asn Asp Ser Leu Met Ala Leu Ala Gln Arg Met Gly Glu Leu Asp
    450                 455                 460

Arg Val Leu Phe Pro Val Asp Ala Arg Gln Ile Asp Trp Gln Leu Tyr
465                 470                 475                 480

Leu Cys Lys Ile His Leu Gly Gly Leu Asn Arg Tyr Ala Leu Lys Glu
                485                 490                 495

Arg Lys Leu Tyr Ser Ser Arg Ala Ala Asp Thr Asp Lys Thr Ala
            500                 505                 510

<210> SEQ ID NO 13
<211> LENGTH: 1536
```

```
<212> TYPE: DNA
<213> ORGANISM: Artificial Sequence
<220> FEATURE:
<223> OTHER INFORMATION: Synthetic DNA which is cDNA of wild-type
      Marinobacter algicola DG893 (FAR Maa)

<400> SEQUENCE: 13
atggcaacac agcagcaaca aaacggagcg tcagcgtccg gtgttcttga gcaactacgt      60
ggtaaacacg tgctgatcac cggcaccacc gggtttcttg gtaaggtggt actggaaaaa    120
ttgattcgca cggtgccgga tattggcggg atccatcttc ttatccgtgg taacaaaagg    180
catcctgcag cacgggaacg attcctcaac gagatcgcca gttcttccgt gttcgaacgc    240
cttcggcacg atgacaacga ggcgtttgaa acctttcttg aggaacgcgt tcactgcatc    300
accggcgaag tgacagagtc gcgtttcggg ctcacgccgg agcggttccg tgcacttgcc    360
gggcaggtcg atgcgtttat aaattccgca gccagtgtga acttccggga ggaactcgac    420
aaggcgctga agattaacac cctgtgcctg agaacgttg ccgctctggc ggagctcaat    480
agcgccatgg cggttatcca ggtgtccacc tgctacgtca atggcaagaa ttccggccag    540
atcacggagt ccgtcatcaa gccggcgggc gagtctattc cccgcagcac cgacggctac    600
tatgaaatcg aagagcttgt gcatttgctg caggacaaaa tttccgacgt gaaagcccga    660
tactccggca agtacttga aaaaaagctg gtggacctgg ggattcgaga ggccaacaac    720
tacggctgga gtgacaccta cacgtttacc aaatggctgg gtgagcaact cctgatgaaa    780
gccctttccg ggcgttcact acgattgtt cgccccttcca tcattgaaag tgcactggaa    840
gagccttcgc caggatggat tgaaggtgtg aaggtggcag acgccattat ccttgcctat    900
gcccgtgaga aggtctccct gttcccaggc aagcgtagcg cattatcga tgtgatcccg    960
gtggacctgg tggccaacag tatcatcttg tccctggcag aagccctttc cgggtcaggg   1020
cagcgccgca tctatcaatg ctgcagtggc ggttctaatc cgatttcgct gggcaagttc   1080
attgactacc tgatggccga agccaagacc aactatgcag cgtatgacca gttgttctac   1140
cgacggccca cgaaaccgtt tgtggcggtc aatcgcaagc tgtttgatgt tgtggttggc   1200
ggcatgcgcg tgccgttgtc gattgctggc aaggcaatga ggctggctgg ccagaaccgt   1260
gagctcaagg ttctcaaaaa cctcgatacc acgcgttcac tggccaccat ctttggtttc   1320
tacacggcac cggattacat cttccgtaac gattcgctga tggccctggc ttcgcgcatg   1380
ggtgaactgg accgtgtcct gttcccggtg gatgcgcgtc agattgactg gcagctgtac   1440
ttgtgcaaga tccacctggg aggtctcaac cgctacgctc tgaaggagcg aaaactgtac   1500
agcctgcggg ccgccgacac ccgcaaaaaa gccgcc                              1536

<210> SEQ ID NO 14
<211> LENGTH: 1539
<212> TYPE: DNA
<213> ORGANISM: Artificial Sequence
<220> FEATURE:
<223> OTHER INFORMATION: Synthetic DNA which is cDNA of wild-type
      Marinobacter aquaeolei VT8 (FAR Maq)

<400> SEQUENCE: 14
atggcaatac agcaggtaca tcacgctgac acttcatcat caaaggtgct cggacagctc      60
cgtggcaagc gggttctgat caccggtacc actggctttc tgggcaaggt ggtcctcgaa    120
aggctgattc gggcggtgcc tgatatcggc gcaatttacc tgctgatccg gggcaataaa    180
cggcatccgg atgctcgttc ccgtttcctg gaagaaattg ccacctcctc ggtgtttgac    240
```

```
cgtcttcgcg aggccgattc agagggattt gacgcctttc tggaagagcg cattcactgc    300
gtgaccggtg aggtgaccga agcgggtttc gggatagggc aggaagacta tcgcaaactc    360
gccaccgaac tggatgcggt gatcaactcc gctgcaagcg tgaatttccg tgaagagctc    420
gacaaggcgc tggccatcaa caccctgtgc cttcggaata ttgccggcat ggtggatttg    480
aatccgaagc ttgcggtcct gcaggtctcc acctgctatg tcaatggcat gaactcgggg    540
caggtaaccg aatcggtgat caagccggca ggcgaggccg tgccgcgttc cccggacggc    600
ttctatgaga tagaagagct tgttcgcctg cttcaggata aaattgaaga cgttcaggcc    660
cgttattccg gcaaagtgct ggagaggaag ctggtggacc tggggattcg ggaagccaac    720
cgctatggct ggagcgatac ctacaccttt accaagtggc tgggcgaaca gttgctgatg    780
aaggcgttaa acgggcgcac gctgaccatt ctgcgtcctt cgattatcga aagtgccctg    840
gaggaaccag cgcccggctg gattgagggg gtgaaggtgg cagatgccat catcctggct    900
tacgcacggg aaaaagtcac cctcttcccg ggcaaacgct ccggtatcat cgatgtgatt    960
ccagtggacc tggtggccaa ctccatcatc ctttccctgg cggaagctct tggagaaccc    1020
ggtcgacgtc gcatctatca atgttgcagc ggggcggca atccaatctc cctgggtgag    1080
ttcatcgatc atctcatggc ggaatcaaaa gccaattacg ctgcctacga tcacctgttc    1140
taccggcagc ccagcaagcc gtttctggcg gttaaccggg cgctgtttga tttggtgatc    1200
agtggtgttc gcttaccgct ctccctgacg gaccgtgtgc tcaaattact gggaaattcc    1260
cgggacctga aaatgctcag gaatctggat accacccagt cgctggcaac cattttggt     1320 ttctacaccg cgccggatta tatcttccgg aacgatgagc tgatgcgct ggcgaaccgg     1380 atgggtgagg tcgataaagg gctgttcccg gtggatgccc gcctgattga ctgggagctc    1440
tacctgcgca agattcacct ggccgggctc aatcgctatg ccctgaaaga acgaaaggtg    1500
tacagtctga aaaccgcgcg ccagcgcaaa aaagctgcc                          1539
```